United States Patent
Cha et al.

(10) Patent No.: US 11,778,905 B2
(45) Date of Patent: *Oct. 3, 2023

(54) COMPOUND AND ORGANIC LIGHT EMITTING DEVICE COMPRISING SAME

(71) Applicant: LG CHEM, LTD., Seoul (KR)

(72) Inventors: Yongbum Cha, Daejeon (KR); Sung Kil Hong, Daejeon (KR); Seong So Kim, Daejeon (KR); Minseung Chun, Daejeon (KR); Sang Duk Suh, Daejeon (KR)

(73) Assignee: LG Chem, Ltd., Seoul (KR)

( * ) Notice: Subject to any disclaimer, the term of this patent is extended or adjusted under 35 U.S.C. 154(b) by 414 days.

This patent is subject to a terminal disclaimer.

(21) Appl. No.: 16/760,598

(22) PCT Filed: Jan. 25, 2019

(86) PCT No.: PCT/KR2019/001114
§ 371 (c)(1),
(2) Date: Apr. 30, 2020

(87) PCT Pub. No.: WO2019/156405
PCT Pub. Date: Aug. 15, 2019

(65) Prior Publication Data
US 2021/0119137 A1 Apr. 22, 2021

(30) Foreign Application Priority Data
Feb. 9, 2018 (KR) .......... 10-2018-0016458

(51) Int. Cl.
*H01L 51/00* (2006.01)
*H10K 85/60* (2023.01)
(Continued)

(52) U.S. Cl.
CPC ......... *H10K 85/654* (2023.02); *C07D 251/24* (2013.01); *C07D 405/10* (2013.01);
(Continued)

(58) Field of Classification Search
CPC .. C07D 251/24; C07D 405/10; C07D 409/10; C07D 239/26; C09K 11/06;
(Continued)

(56) References Cited

U.S. PATENT DOCUMENTS

2004/0251816 A1 12/2004 Leo et al.
2008/0176041 A1* 7/2008 Sato .................... H01L 51/5275
428/161
(Continued)

FOREIGN PATENT DOCUMENTS

KR 10-20000051826 8/2000
KR 10-20120021203 3/2012
(Continued)

*Primary Examiner* — Alexander C Kollias
(74) *Attorney, Agent, or Firm* — Bryan Cave Leighton Paisner LLP

(57) ABSTRACT

Provided is a compound of Chemical Formula 1:

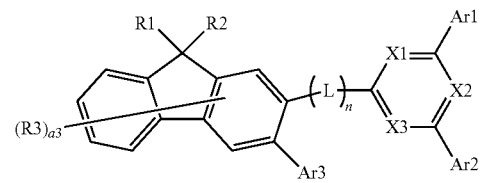

wherein X1 is N or CRa, X2 is N or CRb, X3 is N or CRc, and one or more of X1 to X3 are N;
Ar1 and Ar2 each independently is a substituted or unsubstituted alkyl, aryl group, or heteroaryl group;
Ar3 is a substituted or unsubstituted aryl or heteroaryl group;

(Continued)

L is a substituted or unsubstituted arylene group;

R1 and R2 each independently is hydrogen, deuterium, or a substituted or unsubstituted alkyl or aryl group, or bond to each other to form a ring;

R3 and Ra to Rc each independently is a hydrogen, deuterium, halogen, nitrile, nitro, hydroxyl, or a substituted or unsubstituted group selected from among a silyl, boron, alkyl, cycloalkyl, alkoxy, aryloxy, alkylthioxy, arylthioxy, alkylsulfoxy, arylsulfoxy, alkenyl, aralkyl, aralkenyl, alkylaryl, arylphosphine, phosphine oxide, aryl, or a heteroaryl group, or bond to adjacent groups to form a ring;

a3 is 1 to 6; and n is 1 to 5, and an organic light emitting device comprising the same.

9 Claims, 1 Drawing Sheet

(51) Int. Cl.

| | | |
|---|---|---|
| *C07D 251/24* | (2006.01) | |
| *C07D 405/10* | (2006.01) | |
| *C07D 409/10* | (2006.01) | |
| *C09K 11/06* | (2006.01) | |
| *H10K 50/11* | (2023.01) | |
| *H10K 50/18* | (2023.01) | |

(52) U.S. Cl.
CPC ............ *C07D 409/10* (2013.01); *C09K 11/06* (2013.01); *H10K 85/615* (2023.02); *H10K 85/626* (2023.02); *H10K 85/6574* (2023.02); *H10K 85/6576* (2023.02); *C09K 2211/1018* (2013.01); *H10K 50/11* (2023.02); *H10K 50/18* (2023.02)

(58) Field of Classification Search
CPC .... C09K 2211/1018; C09K 2211/1059; H01L 51/0052; H01L 51/0058; H01L 51/0073; H01L 51/0074; H01L 51/5012; H01L 51/5096; H01L 51/5024; H01L 51/5048; H01L 51/5088; H01L 51/0067; H10K 85/654; H10K 85/6574; H10K 85/6576

See application file for complete search history.

(56) References Cited

U.S. PATENT DOCUMENTS

| | | | |
|---|---|---|---|
| 2018/0053900 A1* | 2/2018 | Eum | .................. H01L 51/0072 |
| 2019/0051839 A1 | 2/2019 | Jang et al. | |
| 2020/0010433 A1 | 1/2020 | Jung et al. | |
| 2020/0048232 A1* | 2/2020 | Cha | ...................... C07D 209/88 |
| 2021/0020848 A1* | 1/2021 | Yang | .................... C07D 239/74 |
| 2021/0163452 A1* | 6/2021 | Yoo | ......................... H10K 59/00 |

FOREIGN PATENT DOCUMENTS

| | | |
|---|---|---|
| KR | 10-20150115622 | 10/2015 |
| KR | 10-20160095667 | 8/2016 |
| KR | 10-20170103574 | 9/2017 |
| KR | 10-20170126691 | 11/2017 |
| KR | 10-20170141144 | 12/2017 |
| KR | 10-20180010132 | 1/2018 |
| KR | 10-20180115217 | 10/2018 |
| WO | 2003012890 | 2/2003 |
| WO | 2016105141 | 6/2016 |
| WO | 2017179883 | 10/2017 |
| WO | 2017179911 | 10/2017 |

* cited by examiner

【FIG. 1】
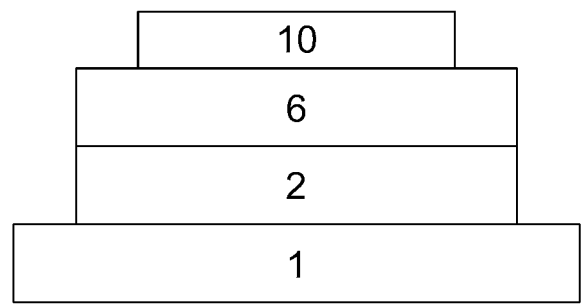
【FIG. 2】
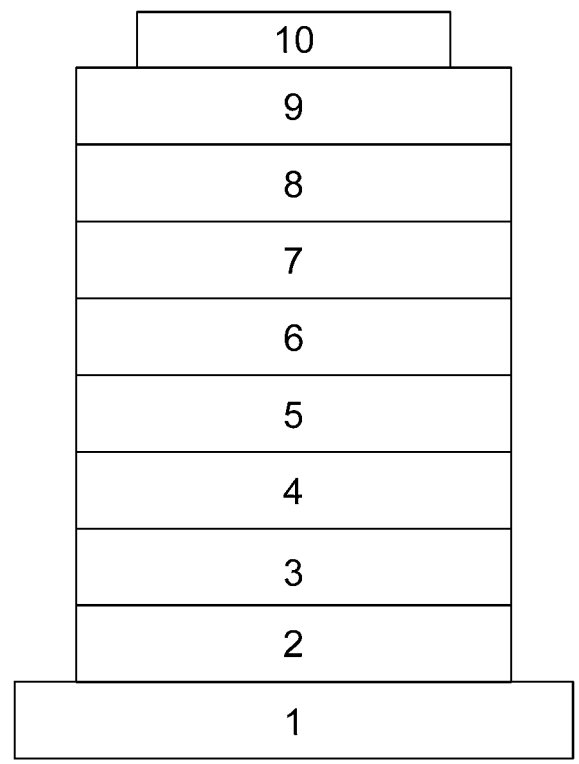

COMPOUND AND ORGANIC LIGHT EMITTING DEVICE COMPRISING SAME

CROSS-REFERENCE TO RELATED APPLICATIONS

This application is a National Stage Application of International Application No. PCT/KR2019/001114 filed on Jan. 25, 2019, which claims priority to and the benefits of Korean Patent Application No. 10-2018-0016458, filed with the Korean Intellectual Property Office on Feb. 9, 2018, the entire contents of which are incorporated herein by reference.

TECHNICAL FIELD

The present specification relates to a compound and an organic light emitting device comprising same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

BRIEF DESCRIPTION

Technical Problem

The present specification is directed to providing a compound and an organic light emitting device comprising same.

Technical Solution

One embodiment of the present disclosure provides a compound of Chemical Formula 1:

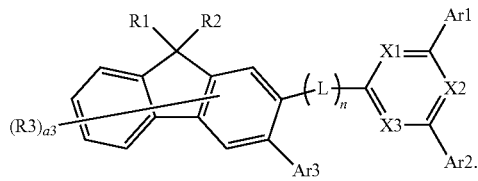

Chemical Formula 1

In Chemical Formula 1:

X1 is N or CRa, X2 is N or CRb, X3 is N or CRc, and one or more of X1 to X3 are N;

Ar1 and Ar2 are the same as or different from each other, and each independently is a substituted or unsubstituted alkyl group, a substituted or unsubstituted aryl group, or a substituted or unsubstituted heteroaryl group;

Ar3 is a substituted or unsubstituted aryl group or a substituted or unsubstituted heteroaryl group;

L is a substituted or unsubstituted arylene group;

R1 and R2 are the same as or different from each other, and each independently is hydrogen, deuterium, a substituted or unsubstituted alkyl group, or a substituted or unsubstituted aryl group, or bond to each other to form a substituted or unsubstituted ring;

R3 and Ra to Rc are the same as or different from each other, and each independently is hydrogen, deuterium, a halogen group, a nitrile group, a nitro group, a hydroxyl group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted arylphosphine group, a substituted or unsubstituted phosphine oxide group, a substituted or unsubstituted aryl group, or a substituted or unsubstituted heteroaryl group, or can bond to adjacent groups to form a substituted or unsubstituted ring;

a3 is an integer of 1 to 6;

n is an integer of 1 to 5;

when a3 is 2 or greater, the R3s are the same as or different from each other; and when n is 2 or greater, the Ls are the same as or different from each other.

Another embodiment of the present specification provides an organic light emitting device comprising a first electrode, a second electrode, and one or more organic material layers provided between the first electrode and the second electrode, wherein one or more layers of the organic material layers comprise the above-described compound.

Advantageous Effects

A compound described in the present specification can be used as a material of an organic material layer of an organic light emitting device. In one embodiment, the compound described in the present specification can be used as a light emitting, electron transfer or electron injection material, and can be preferably used in a hole blocking layer, an electron transfer layer or an electron injection layer.

In one embodiment, an organic light emitting device comprising the compound of the present disclosure is capable of enhancing efficiency.

In one embodiment, an organic light emitting device comprising the compound of the present disclosure is capable of lowering a driving voltage.

In one embodiment, an organic light emitting device comprising the compound of the present disclosure is capable of enhancing lifetime properties.

DESCRIPTION OF DRAWINGS

FIG. 1 illustrates an example of an organic light emitting device formed with a substrate (1), an anode (2), a light emitting layer (6) and a cathode (10).

FIG. 2 illustrates an example of an organic light emitting device formed with a substrate (1), an anode (2), a hole injection layer (3), a hole transfer layer (4), an electron blocking layer (5), a light emitting layer (6), a hole blocking layer (7), an electron transfer layer (8), an electron injection layer (9) and a cathode (10).

DETAILED DESCRIPTION

Hereinafter, the present disclosure will be described in more detail.

One embodiment of the present specification provides a compound of Chemical Formula 1, and an organic light emitting device comprising same.

By including both a nitrogen-containing 6-membered heteroring readily receiving electrons and a fluorene structure readily receiving holes, the compound of Chemical Formula 1 forms a bipolar structure. Due to the bipolar structure, the compound of Chemical Formula 1 controls hole and electron flows (charge balance), and can lower a driving voltage and improve efficiency of an organic light emitting device.

The compound of Chemical Formula 1 has a structure in which substituents substitute No. 2 and No. 3 carbons among the substitutable carbon positions of the fluorene core. Specifically, in the compound according to one embodiment of the present application, substituents having favorable electron injection properties such as triazine, pyrimidine or pyridine bond to the No. 2 position of the fluorene core, and additionally, a substituent bond at the adjacent No. 3 position.

The substituents bond at adjacent positions of the fluorene core causing steric hindrance, and due to the steric hindrance, the compounds of the present disclosure have a distorted molecular structure. This increases structural stability, and therefore, when using the compounds of the present disclosure in a device, a lifetime of the device is enhanced and efficiency of the device increases.

Examples of the substituents are described below, however, the substituents are not limited thereto.

In the present specification,

means a site bonding to other substituents or bonding sites.

In the present specification, the term "substituted or unsubstituted" means being substituted with one or more substituents selected from the group consisting of deuterium, a halogen group, a nitrile group, a nitro group, a hydroxyl group, a silyl group, a boron group, an alkyl group, a cycloalkyl group, an aralkyl group, an alkoxy group, an alkenyl group, an aralkenyl group, a phosphine oxide group, an arylphosphine group, an aryloxy group, an alkylthioxy group, an arylthioxy group, an alkylsulfoxy group, an arylsulfoxy group, an aryl group, an alkylaryl group, and a heteroaryl group or being unsubstituted, or being substituted with a substituent linking two or more substituents of the above-illustrated substituents or being unsubstituted. For example, the heteroarylaryl group can be an aryl group, or can be interpreted as a substituent linking a heteroaryl group and an aryl group. Examples of a group linking three substituents include an aryl group substituted with a heteroaryl group substituted with an aryl group, an aryl group substituted with an aryl group substituted with a heteroaryl group, a heteroaryl group substituted with an aryl group substituted with a heteroaryl group, and the like.

In one embodiment of the present specification, the term "substituted or unsubstituted" means being substituted with one or more substituents selected from the group consisting of deuterium, a nitrile group, a halogen group, an alkyl group, a cycloalkyl group, an aralkyl group, an alkenyl group, an aralkenyl group, an aryl group, and an arylalkyl group or being unsubstituted, or being substituted with a substituent linking two or more substituents of the above-illustrated substituents or being unsubstituted.

In the present specification, examples of the halogen group include fluorine, chlorine, bromine or iodine.

In the present specification, the silyl group can have a chemical formula of $-SiR_xR_yR_z$, and Rx, Ry and Rz each independently can be hydrogen, a substituted or unsubstituted alkyl group, or a substituted or unsubstituted aryl group. Specific examples of the silyl group can include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group can have a chemical formula of $-BR_{100}R_{101}$, and $R_{100}$ and $R_{101}$ each independently can be hydrogen, a substituted or unsubstituted alkyl group, or a substituted or unsubstituted aryl group. Specific examples of the boron group can include a dimethylboron group, a diethylboron group, a t-butylethylboron group, a diphenylboron group, a phenylboron group and the like, but are not limited thereto.

In the present specification, the alkoxy group means a group in which an alkyl group bonds to an oxygen atom, and although not particularly limited thereto, the number of carbon atoms is preferably from 1 to 40. According to one embodiment, the number of carbon atoms of the alkoxy group is from 1 to 10. According to another embodiment, the number of carbon atoms of the alkoxy group is from 1 to 6. Specific examples of the alkoxy group can include a methoxy group, an ethoxy group, a propoxy group, an isobutyloxy group, a sec-butyloxy group, a pentyloxy group, an iso-amyloxy group, a hexyloxy group and the like, but are not limited thereto.

In the present specification, the alkyl group can be linear or branched, and although not particularly limited thereto, the number of carbon atoms is preferably from 1 to 40. According to one embodiment, the number of carbon atoms of the alkyl group is from 1 to 20. According to another embodiment, the number of carbon atoms of the alkyl group is from 1 to 10. According to another embodiment, the number of carbon atoms of the alkyl group is from 1 to 6. Specific examples of the alkyl group can include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 3,3-dimethylbutyl, 2-ethylbutyl, heptyl, n-heptyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 4-methylhexyl, 5-methylhexyl and the like, but are not limited thereto.

In the present specification, the cycloalkyl group means a cyclic hydrocarbon group, and although not particularly limited thereto, the number of carbons is preferably from 3 to 60. According to one embodiment, the number of carbon atoms of the cycloalkyl group is from 3 to 30. According to another embodiment, the number of carbon atoms of the cycloalkyl group is from 3 to 20. According to another embodiment, the number of carbon atoms of the cycloalkyl group is from 3 to 6. Specific examples thereof can include cyclopropyl, cyclobutyl, cyclopentyl, 3-methyl-cyclopentyl, 2,3-dimethylcyclopentyl, cyclohexyl, 3-methyl-cyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkenyl group represents a linear or branched unsaturated hydrocarbon group, and although not particularly limited thereto, the number of carbon atoms is preferably from 2 to 30. According to one embodiment, the number of carbon atoms of the alkenyl group is from 2 to 20. Specific examples thereof can include ethenyl, vinyl, propenyl, allyl, isopropenyl, butenyl, isobutenyl, n-pentenyl and n-hexenyl, but are not limited thereto.

In the present specification, the aralkenyl group means an alkenyl group substituted with an aryl group.

In the present specification, the aryl group means totally or partially unsaturated substituted or unsubstituted monocyclic or polycyclic. Although not particularly limited thereto, the number of carbon atoms is preferably from 6 to 60, and the aryl group can be a monocyclic aryl group or a polycyclic aryl group. According to one embodiment, the number of carbon atoms of the aryl group is from 6 to 40. According to one embodiment, the number of carbon atoms of the aryl group is from 6 to 30. The aryl group can be a monocyclic aryl group or a polycyclic aryl group. Examples of the monocyclic aryl group can include a phenyl group, a biphenyl group, a terphenyl group and the like, but are not limited thereto. Examples of the polycyclic aryl group can include a naphthyl group, an anthracenyl group, a phenanthrenyl group, a perylenyl group, a fluoranthenyl group, a triphenylenyl group, a phenalenyl group, a pyrenyl group, a tetracenyl group, a chrysenyl group, a pentacenyl group, a fluorenyl group, an indenyl group, an acenaphthylenyl group, a benzofluorenyl group, a spirofluorenyl group and the like, but are not limited thereto.

In the present specification, the fluorenyl group can be substituted, and two substituents bond to each other to form a spiro structure.

Examples of the substituted fluorenyl group include

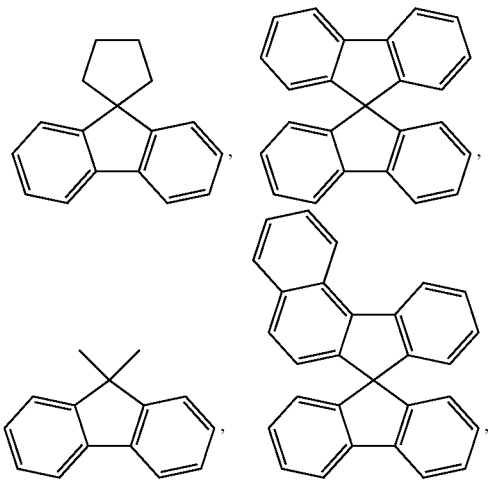

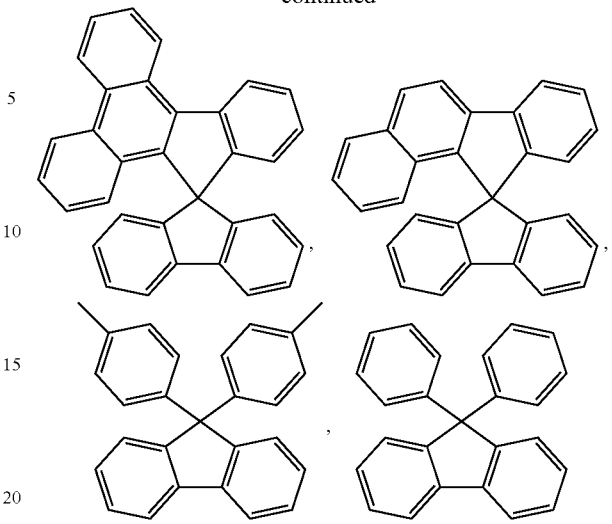

and the like, but are not limited thereto.

In the present specification, the heteroaryl group is a cyclic group including one or more of N, O and S as a heteroatom, and although not particularly limited thereto, the number of carbon atoms is preferably from 2 to 40. According to one embodiment, the number of carbon atoms of the heteroaryl group is from 2 to 30. According to another embodiment, the number of carbon atoms of the heteroaryl group is from 2 to 20. Examples of the heteroaryl group can include a thiophenyl group, a furanyl group, a pyrrolyl group, an imidazolyl group, a thiazolyl group, an oxazolyl group, an oxadiazolyl group, a triazolyl group, a pyridinyl group, a bipyridinyl group, a pyrimidinyl group, a triazinyl group, a triazolyl group, an acridinyl group, a carbolinyl group, an acenaphthoquinoxalinyl group, an indenoquinazolinyl group, an indenoisoquinolinyl group, an indenoquinolinyl group, a pyridoindolyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a dibenzofuranyl group, a phenanthrolinyl group, a thiazolyl group, an isoxazolyl group, an oxadiazolyl group, a thiadiazolyl group, a benzothiazolyl group, a phenoxazinyl group, a phenothiazinyl group, a dibenzofuranyl group and the like, but are not limited thereto. The heteroaryl group includes an aliphatic heteroaryl group and an aromatic heteroaryl group.

In the present specification, the alkylaryl group means an aryl group substituted with an alkyl group.

Descriptions on the alkyl group provided above can apply to the alkyl group in the alkylthioxy group, the alkylsulfoxy group and the alkylaryl group.

Descriptions on the aryl group provided above can apply to the aryl group in the aralkenyl group, the arylphosphine group, the aryloxy group, the arylthioxy group and the arylsulfoxy group.

In the present specification, the "adjacent" group can mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring can be interpreted as groups "adjacent" to each other.

In the present specification, the meaning of bonding to adjacent groups to form a ring means bonding to adjacent groups to form a substituted or unsubstituted aliphatic hydrocarbon ring, a substituted or unsubstituted aromatic hydrocarbon ring, a substituted or unsubstituted aliphatic heteroring, a substituted or unsubstituted aromatic heteroring, or a fused ring thereof. The hydrocarbon ring means a ring formed only with carbon and hydrogen atoms, and the hydrocarbon ring can be an aliphatic hydrocarbon ring or an aromatic hydrocarbon ring. The heteroring means a ring including one or more of heteroatoms, and the heteroring can be an aliphatic heteroring or an aromatic heteroring. In the present specification, the aliphatic hydrocarbon ring, the aromatic hydrocarbon ring, the aliphatic heteroring and the aromatic heteroring can be monocyclic or polycyclic.

The aliphatic hydrocarbon ring means a ring formed only with carbon and hydrogen atoms as a ring that is not aromatic. Examples of the aliphatic hydrocarbon ring include cyclopropane, cyclobutane, cyclobutene, cyclopentane, cyclopentene, cyclohexane, cyclohexene, 1,4-cyclohexadiene, cycloheptane, cycloheptene, cyclooctane, cyclooctene and the like, but are not limited thereto.

The aromatic hydrocarbon ring means an aromatic ring formed only with carbon and hydrogen atoms. Examples of the aromatic hydrocarbon ring include benzene, naphthalene, anthracene, phenanthrene, perylene, fluoranthene, triphenylene, phenalene, pyrene, tetracene, chrysene, pentacene, fluorene, indene, acenaphthalene, benzofluorene, spirofluorene and the like, but are not limited thereto.

The aliphatic heteroring means an aliphatic ring including one or more of heteroatoms. Examples of the aliphatic heteroring include oxirane, tetrahydrofuran, 1,4-dioxane, pyrrolidine, piperidine, morpholine, oxepane, azocane, thiocane and the like, but are not limited thereto.

The aromatic heteroring means an aromatic ring including one or more of heteroatoms. Examples of the aromatic heteroring include pyridine, pyrrole, pyrimidine, pyridazine, furan, thiophene, imidazole, pyrazole, oxazole, isoxazole, thiazole, isothiazole, triazole, oxadiazole, thiadiazole, dithiazole, tetrazole, pyran, thiopyran, diazine, oxazine, thiazine, dioxin, triazine, tetrazine, isoquinoline, quinoline, quinol, quinazoline, quinoxaline, naphthridine, acridine, phenanthridine, diazanaphthalene, triazaindene, indole, indolizine, benzothiazole, benzoxazole, benzimidazole, benzothiophene, benzofuran, dibenzothiophene, dibenzofuran, carbazole, benzocarbazole, dibenzocarbazole, phenazine, imidazopyridine, phenoxazine, phenanthridine, indolocarbazole, indenocarbazole and the like, but are not limited thereto.

According to one embodiment of the present specification, R1 and R2 are the same as or different from each other, and each independently is hydrogen, deuterium, a substituted or unsubstituted alkyl group having 1 to 30 carbon atoms, or a substituted or unsubstituted aryl group having 6 to 30 carbon atoms.

According to one embodiment of the present specification, R1 and R2 are the same as or different from each other, and each independently is hydrogen, deuterium, a substituted or unsubstituted alkyl group having 1 to 20 carbon atoms, or a substituted or unsubstituted aryl group having 6 to 20 carbon atoms.

According to one embodiment of the present specification, R1 and R2 are the same as or different from each other, and each independently is hydrogen, deuterium, a substituted or unsubstituted alkyl group having 1 to 10 carbon atoms, or a substituted or unsubstituted aryl group having 6 to 10 carbon atoms.

According to one embodiment of the present specification, R1 and R2 are the same as or different from each other, and each independently is hydrogen, deuterium, an alkyl group having 1 to 10 carbon atoms, or an aryl group having 6 to 10 carbon atoms.

According to one embodiment of the present specification, R1 and R2 are the same as or different from each other, and each independently is a substituted or unsubstituted methyl group, or a substituted or unsubstituted phenyl group, or bond to each other to form a substituted or unsubstituted fluorene ring. When R1 and R2 bond to each other to form a substituted or unsubstituted fluorene group, the linking sites of R1 and R2 are each a single bond site of the fluorene pentagonal ring.

According to one embodiment of the present specification, R1 and R2 are the same as or different from each other, and each independently is a methyl group, or a phenyl group, or bond to each other to form a fluorene ring.

According to one embodiment of the present specification, R3 is hydrogen or deuterium.

According to one embodiment of the present specification, X1 is N, X2 is CRb, and X3 is CRc.

According to one embodiment of the present specification, X1 is CRa, X2 is N, and X3 is CRc.

According to one embodiment of the present specification, X1 is CRa, X2 is CRb, and X3 is N.

According to one embodiment of the present specification, X1 is N, X2 is N, and X3 is CRc.

According to one embodiment of the present specification, X1 is N, X2 is CRb, and X3 is N.

According to one embodiment of the present specification, X1 is CRa, X2 is N, and X3 is N.

According to one embodiment of the present specification, X1 is N, X2 is N, and X3 is N.

As the number of N included in the heteroring including X1 to X3 increases, hole injection properties of the compound of the present disclosure can be enhanced. Accordingly, in the compound of the present disclosure, X1 to X3 being all N is most preferred.

According to one embodiment of the present specification, Ra is hydrogen or deuterium.

According to one embodiment of the present specification, Rb is hydrogen or deuterium.

According to one embodiment of the present specification, Rc is hydrogen or deuterium.

According to one embodiment of the present specification, L is a substituted or unsubstituted arylene group having 6 to 30 carbon atoms.

According to one embodiment of the present specification, L is an arylene group having 6 to 30 carbon atoms unsubstituted or substituted with deuterium, an alkyl group or an aryl group.

According to one embodiment of the present specification, L is a substituted or unsubstituted arylene group having 6 to 24 carbon atoms.

According to one embodiment of the present specification, L is a substituted or unsubstituted arylene group having 6 to 12 carbon atoms.

According to one embodiment of the present specification, L is a substituted or unsubstituted phenylene group, a substituted or unsubstituted biphenylene group, a substituted or unsubstituted terphenylene group, a substituted or unsubstituted quaterphenylene group, a substituted or unsubstituted naphthylene group, a substituted or unsubstituted anthracenylene group, a substituted or unsubstituted pyrenylene group, a substituted or unsubstituted phenanthrenylene group, a substituted or unsubstituted perylenylene group, a substituted or unsubstituted tetracenylene group, a substituted or unsubstituted triphenylene group, a substituted or unsubstituted fluoranthenylene group, or a substituted or unsubstituted fluorenylene group.

According to one embodiment of the present specification, L is a phenylene group unsubstituted or substituted with deuterium, an alkyl group or an aryl group; a biphenylene group unsubstituted or substituted with deuterium, an alkyl group or an aryl group; a terphenylene group unsubstituted or substituted with deuterium, an alkyl group or an aryl group; a quaterphenylene group unsubstituted or substituted with deuterium, an alkyl group or an aryl group; a naphthylene group unsubstituted or substituted with deuterium, an alkyl group or an aryl group; an anthracenylene group unsubstituted or substituted with deuterium, an alkyl group or an aryl group; a pyrenylene group unsubstituted or substituted with deuterium, an alkyl group or an aryl group; a phenanthrenylene group unsubstituted or substituted with deuterium, an alkyl group or an aryl group; a perylenylene group unsubstituted or substituted with deuterium, an alkyl group or an aryl group; a tetracenylene group unsubstituted or substituted with deuterium, an aryl group or an alkyl group; a triphenylene group unsubstituted or substituted with deuterium, an alkyl group or an aryl group; a fluoranthenylene group unsubstituted or substituted with deuterium, an alkyl group or an aryl group; or a fluorenylene group unsubstituted or substituted with deuterium, an alkyl group or an aryl group.

According to one embodiment of the present specification, L is a substituted or unsubstituted phenylene group or a substituted or unsubstituted biphenylene group.

According to one embodiment of the present specification, L is a phenylene group unsubstituted or substituted with deuterium, an alkyl group or an aryl group; or a biphenylene group unsubstituted or substituted with deuterium, an alkyl group or an aryl group.

According to one embodiment of the present specification, L is a phenylene group or a biphenylene group.

According to one embodiment of the present specification, L is a p-phenylene group.

According to one embodiment of the present specification, L is an m-phenylene group.

According to one embodiment of the present specification, L is

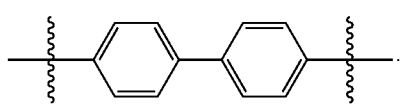

According to one embodiment of the present specification, L is

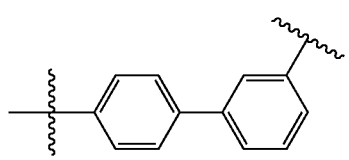

According to one embodiment of the present specification, L is

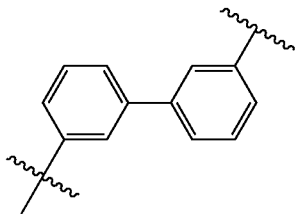

According to one embodiment of the present specification, n is 2 or greater, and at least one of the two or more Ls is a substituted or unsubstituted m-phenylene group.

According to one embodiment of the present specification, n is 2 or greater, and at least one of the two or more Ls is an m-phenylene group unsubstituted or substituted with deuterium, an alkyl group or an aryl group.

According to one embodiment of the present specification, Chemical Formula 1 is any one of the following Chemical Formulae 1-A to 1-C:

Chemical Formula 1-A

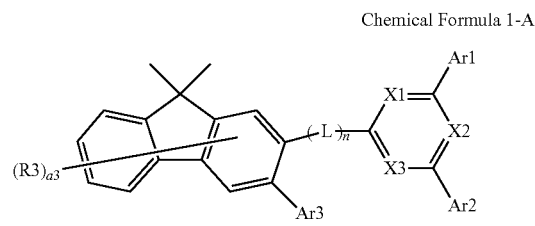

Chemical Formula 1-B

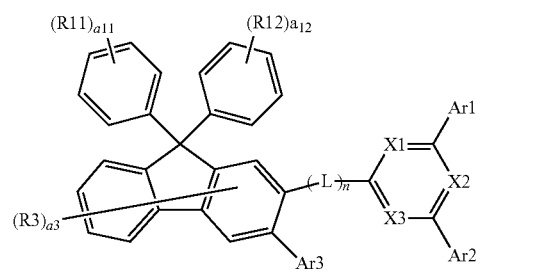

Chemical Formula 1-C

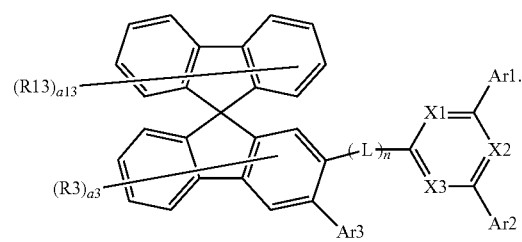

In Chemical Formulae 1-A to 1-C:

R3, Ar1 to Ar3, X1 to X3, L, n and a3 have the same definitions as in Chemical Formula 1;

R11 to R13 are the same as or different from each other, and each independently is hydrogen, deuterium, a halogen group, a nitrile group, a nitro group, a hydroxyl group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted arylphosphine group, a substituted or unsubstituted phosphine oxide group, a substituted or unsubstituted aryl group, or a substituted or unsubstituted heteroaryl group;

a11 and a12 are each an integer of 1 to 5;

a13 is an integer of 1 to 8; and when a11 to a13 are 2 or greater, two or more substituents in the parentheses are the same as or different from each other.

According to one embodiment of the present specification, R11 is hydrogen.

According to one embodiment of the present specification, R12 is hydrogen.

According to one embodiment of the present specification, R13 is hydrogen.

According to one embodiment of the present specification, Chemical Formula 1 is Chemical Formula 2:

Chemical Formula 2

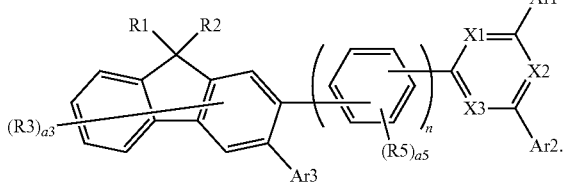

In Chemical Formula 2, R1, R2, R3, X1, X2, X3, Ar1, Ar2, a3 and n have the same definitions as in Chemical Formula 1;

R5 is hydrogen, deuterium, a halogen group, a nitrile group, a nitro group, a hydroxyl group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted arylphosphine group, a substituted or unsubstituted phosphine oxide group, a substituted or unsubstituted aryl group, or a substituted or unsubstituted heteroaryl group, or can bond to adjacent groups to form a substituted or unsubstituted hydrocarbon ring;

a5 is an integer of 1 to 4; and when a5 is 2 or greater, the R5s are the same as or different from each other.

According to one embodiment of the present specification, n is an integer of 1 to 4.

According to one embodiment of the present specification, n is an integer of 1 to 3.

According to one embodiment of the present specification, n is 1.

According to one embodiment of the present specification, n is 2.

According to one embodiment of the present specification, Ar1 and Ar2 are the same as or different from each other, and each independently is a substituted or unsubstituted alkyl group having 1 to 30 carbon atoms, a substituted or unsubstituted aryl group having 6 to 30 carbon atoms, or a substituted or unsubstituted heteroaryl group having 2 to 30 carbon atoms.

According to one embodiment of the present specification, Ar1 and Ar2 are the same as or different from each other, and each independently is a substituted or unsubstituted alkyl group having 1 to 20 carbon atoms, a substituted or unsubstituted aryl group having 6 to 24 carbon atoms, or a substituted or unsubstituted heteroaryl group having 2 to 24 carbon atoms.

According to one embodiment of the present specification, Ar1 and Ar2 are the same as or different from each other, and each independently is a substituted or unsubstituted alkyl group having 1 to 10 carbon atoms, a substituted or unsubstituted aryl group having 6 to 20 carbon atoms, or a substituted or unsubstituted heteroaryl group having 2 to 20 carbon atoms.

According to one embodiment of the present specification, Ar1 and Ar2 are the same as or different from each other, and each independently is a substituted or unsubstituted aryl group having 6 to 30 carbon atoms.

According to one embodiment of the present specification, Ar1 and Ar2 are the same as or different from each other, and each independently is a substituted or unsubstituted aryl group having 6 to 24 carbon atoms.

According to one embodiment of the present specification, Ar1 and Ar2 are the same as or different from each other, and each independently is a substituted or unsubstituted aryl group having 6 to 20 carbon atoms.

According to one embodiment of the present specification, Ar1 and Ar2 are the same as or different from each other, and each independently is an aryl group unsubstituted or substituted with a nitrile group or an aryl group.

According to one embodiment of the present specification, at least one of Ar1 and Ar2 is an aryl group substituted with a nitrile group.

According to one embodiment of the present specification, Ar1 and Ar2 are the same as or different from each other, and each independently is a substituted or unsubstituted phenyl group, or a substituted or unsubstituted biphenyl group.

According to one embodiment of the present specification, Ar1 and Ar2 are the same as or different from each other, and each independently is a phenyl group unsubstituted or substituted with a nitrile group or an aryl group, or a biphenyl group unsubstituted or substituted with an aryl group.

According to one embodiment of the present specification, Ar1 and Ar2 are the same as or different from each other, and each independently is a phenyl group unsubstituted or substituted with a nitrile group, or a biphenyl group.

According to one embodiment of the present specification, Ar1 and Ar2 are the same as or different from each other, and each independently is a phenyl group, a 4-nitrilephenyl group or a biphenyl group.

According to one embodiment of the present specification, Ar3 is a substituted or unsubstituted aryl group having 6 to 30 carbon atoms, or a substituted or unsubstituted heteroaryl group having 2 to 30 carbon atoms.

According to one embodiment of the present specification, Ar3 is an aryl group having 6 to 30 carbon atoms unsubstituted or substituted with an aryl group, or a heteroaryl group having 2 to 30 carbon atoms unsubstituted or substituted with an aryl group.

According to one embodiment of the present specification, Ar3 is a substituted or unsubstituted aryl group having 6 to 24 carbon atoms, or a substituted or unsubstituted heteroaryl group having 2 to 24 carbon atoms.

According to one embodiment of the present specification, Ar3 is a substituted or unsubstituted aryl group having 6 to 18 carbon atoms, or a substituted or unsubstituted heteroaryl group having 2 to 20 carbon atoms.

According to one embodiment of the present specification, Ar3 is a substituted or unsubstituted aryl group having 6 to 18 carbon atoms, or a substituted or unsubstituted heteroaryl group having 2 to 20 carbon atoms and comprising O or S.

According to one embodiment of the present specification, Ar3 is a substituted or unsubstituted phenyl group, a substituted or unsubstituted biphenyl group, a substituted or unsubstituted naphthyl group, a substituted or unsubstituted dibenzofuranyl group, or a substituted or unsubstituted dibenzothiophenyl group.

According to one embodiment of the present specification, Ar3 is a phenyl group unsubstituted or substituted with a nitrile group or an aryl group, a biphenyl group unsubstituted or substituted with an aryl group, a naphthyl group unsubstituted or substituted with an aryl group, a dibenzofuranyl group unsubstituted or substituted with an aryl group, or a dibenzothiophenyl group unsubstituted or substituted with an aryl group.

According to one embodiment of the present specification, Ar3 is a phenyl group, a 4-nitrilephenyl group, a biphenyl group, a naphthyl group, a dibenzofuranyl group, or a dibenzothiophenyl group.

According to one embodiment of the present specification, Chemical Formula 1 can be the following Chemical Formula 3:

Chemical Formula 3

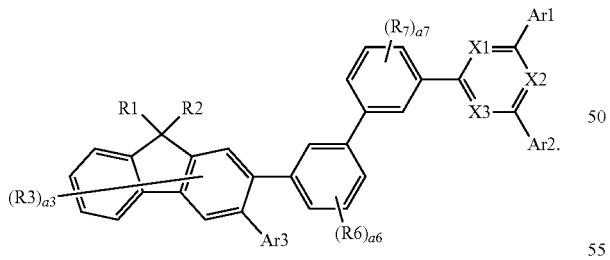

In Chemical Formula 3:
R1 to R3, Ar1 to Ar3, X1 to X3 and a3 have the same definitions as in Chemical Formula 1;
R6 and R7 are the same as or different from each other, and each independently is deuterium, a halogen group, a nitrile group, a nitro group, a hydroxyl group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted arylphosphine group, a substituted or unsubstituted phosphine oxide group, a substituted or unsubstituted aryl group, or a substituted or unsubstituted heteroaryl group;

a6 and a7 are each an integer of 1 to 4; and when a6 and a7 are 2 or greater, two or more substituents in the parentheses are the same as or different from each other.

According to one embodiment of the present specification, R6 is hydrogen.

According to one embodiment of the present specification, R7 is hydrogen.

When L is a biphenyl group, the nitrogen-containing 6-membered heteroring and the fluorene are localized, and electron and hole flows can be more controlled. The compound in which L is a biphenyl group has excellent bipolar properties, and a device lifetime can be more improved.

In addition, when L is

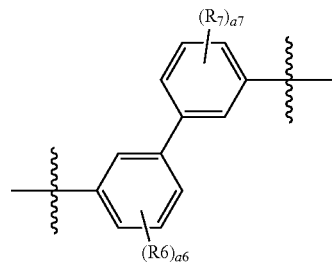

in Chemical Formula 1, stacking of compounds is more effectively prevented compared to the structure in which L is

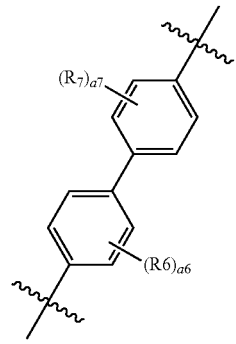

and a proper level of solubility is obtained readily achieving a synthesis process and decreasing a deposition temperature as well.

Accordingly, when using the compound in which L is

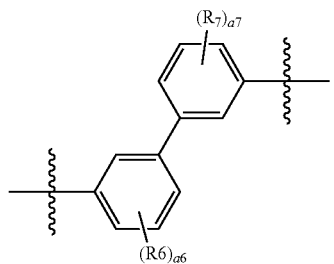

in a device, a driving voltage is low, device efficiency is high and a lifetime is enhanced compared to devices using compounds in which L is other biphenyl groups.

According to one embodiment of the present specification, the compound of Chemical Formula 1 is any one compound selected from among the following compounds:

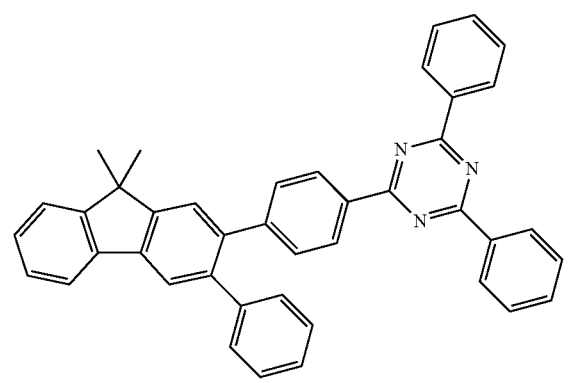

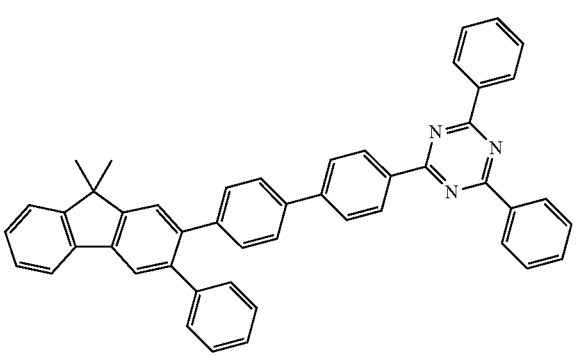

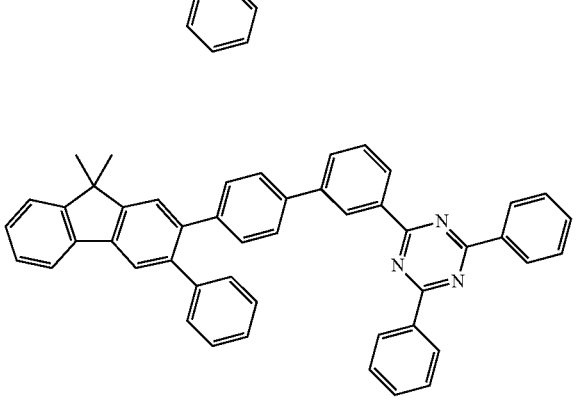

-continued

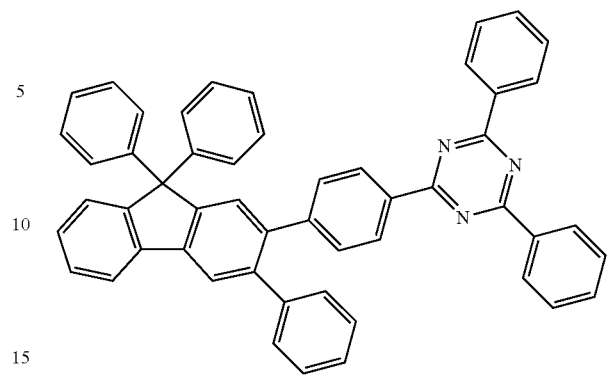

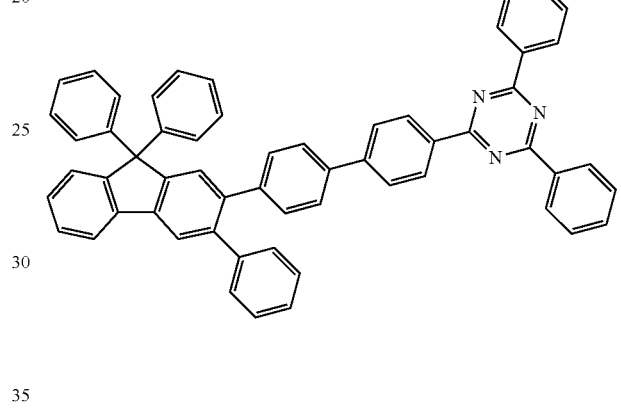

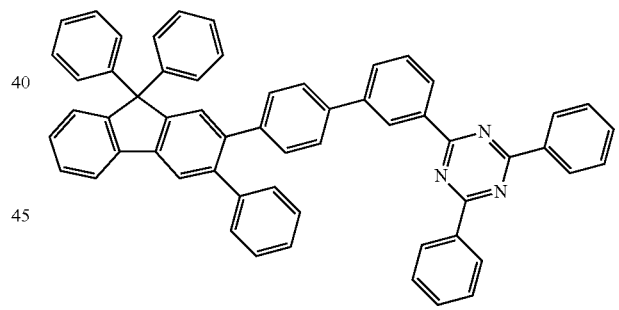

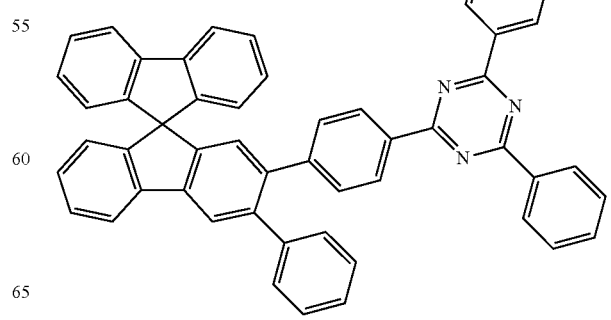

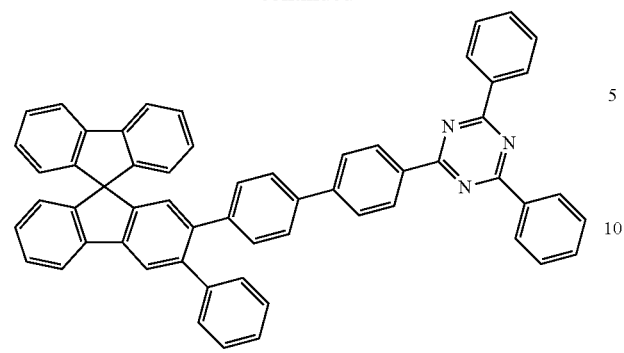
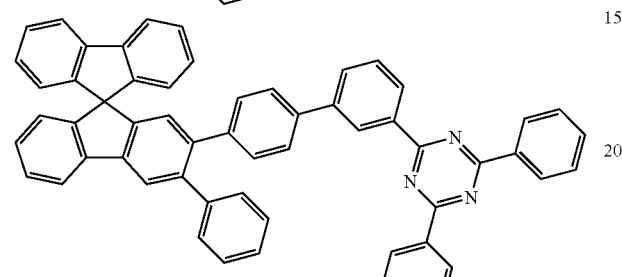
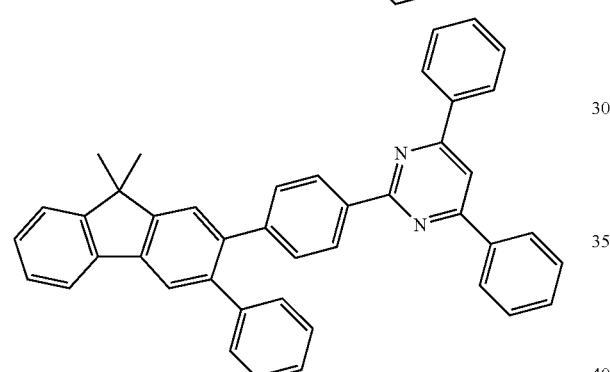
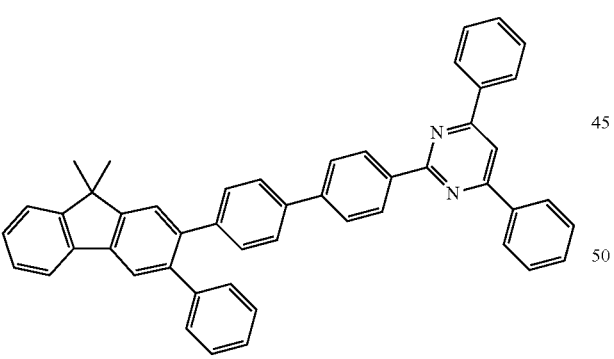
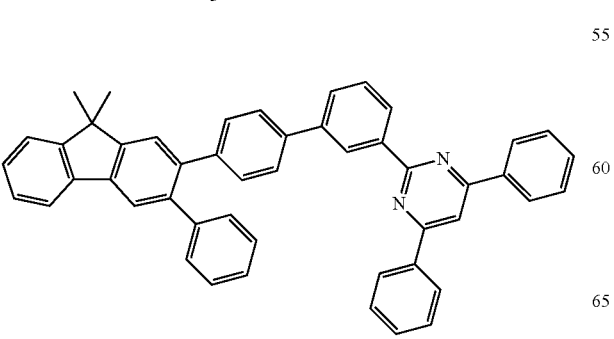
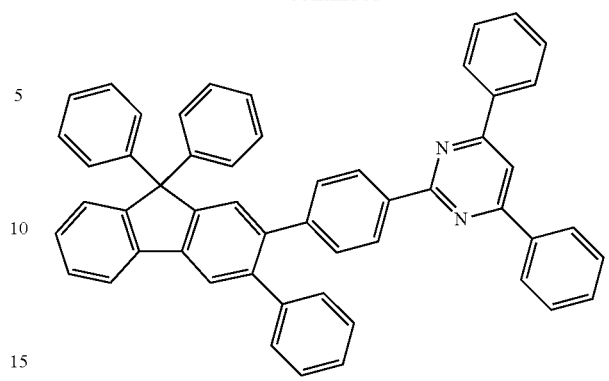
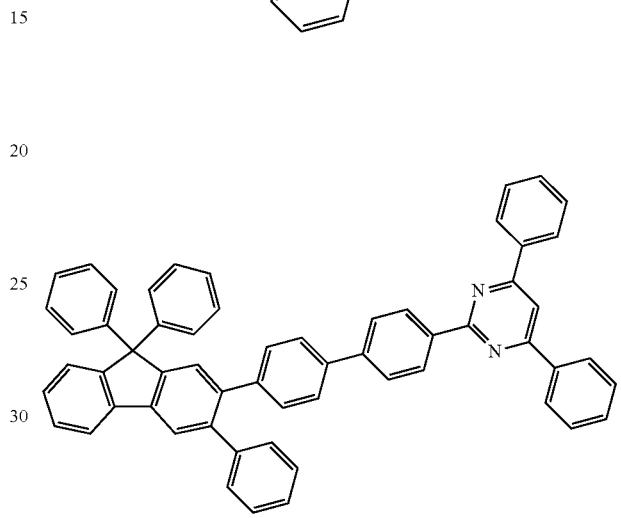
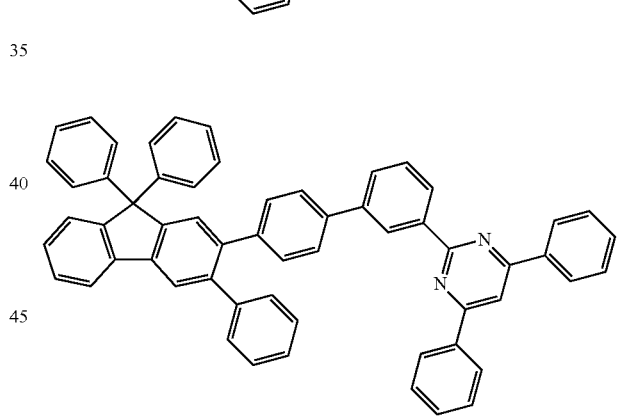
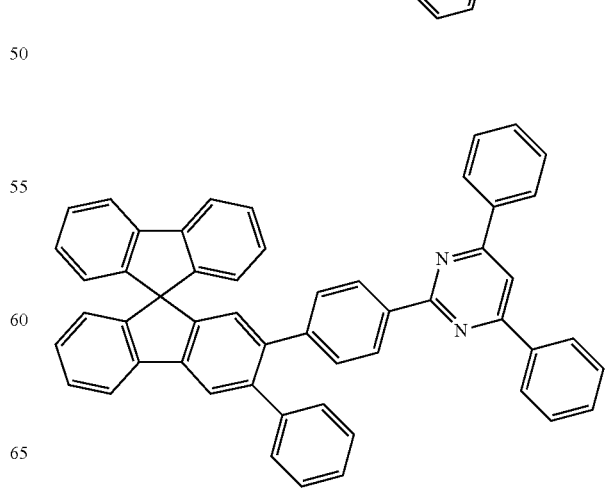

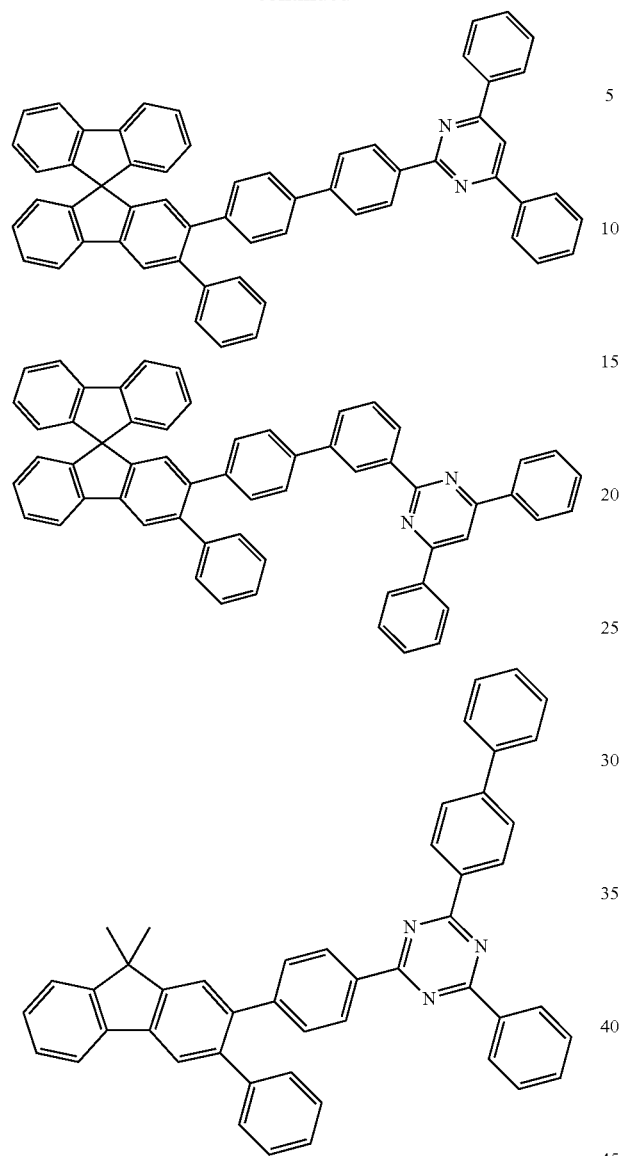
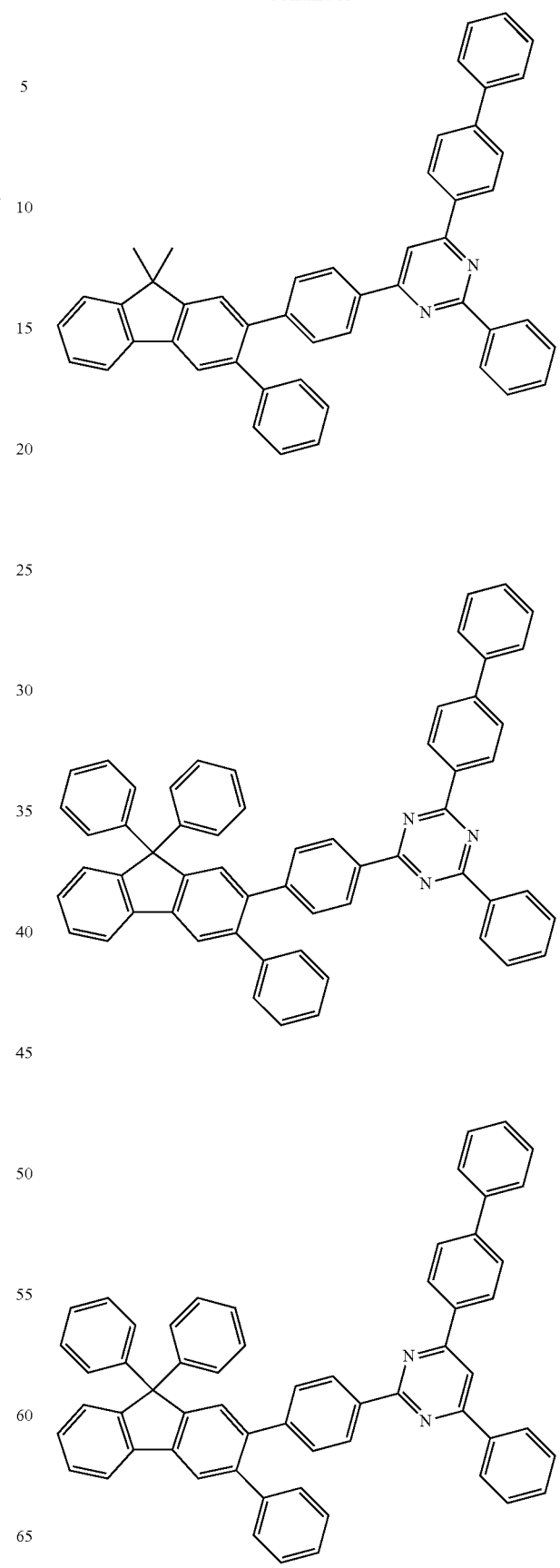

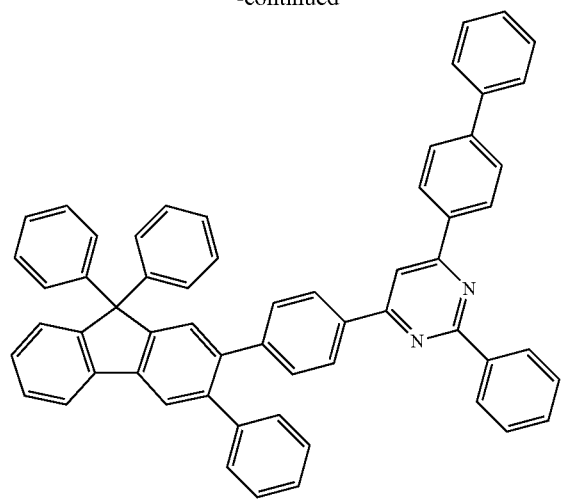
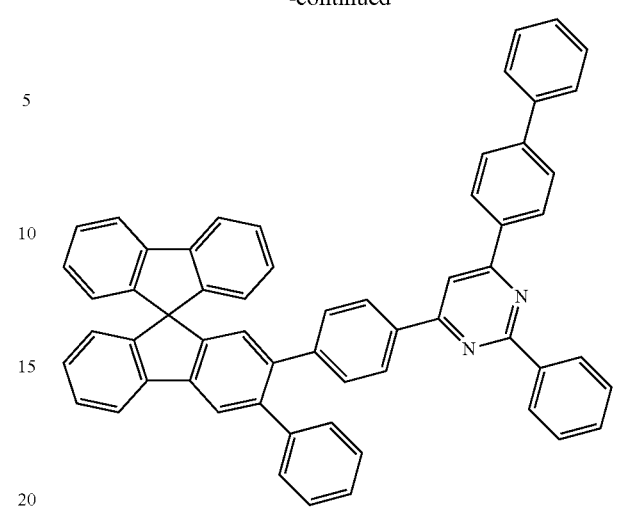
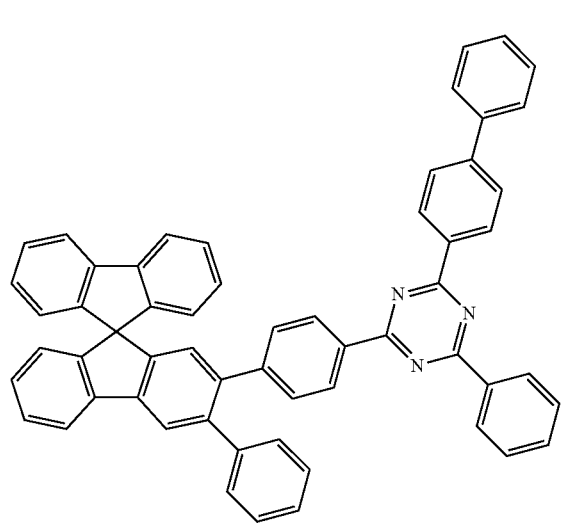
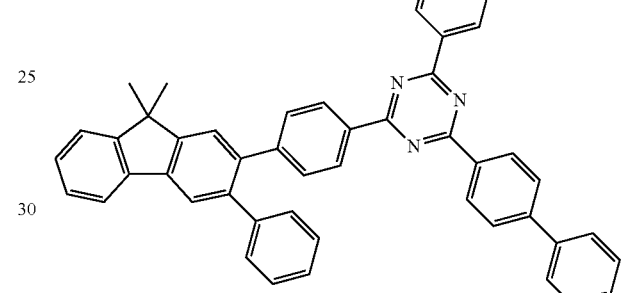
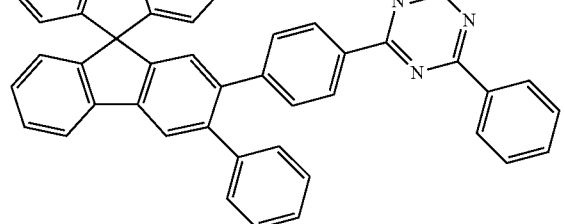
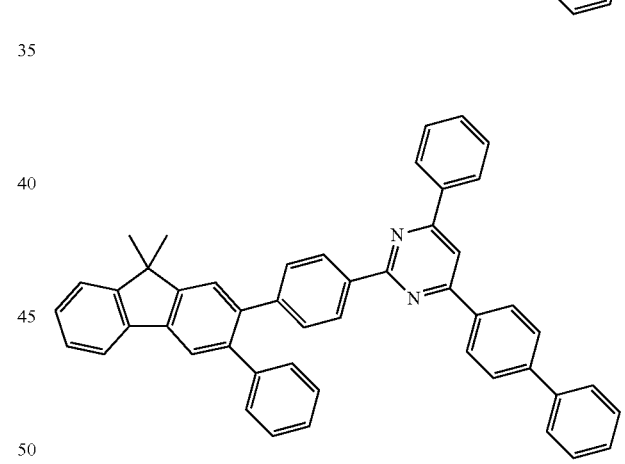
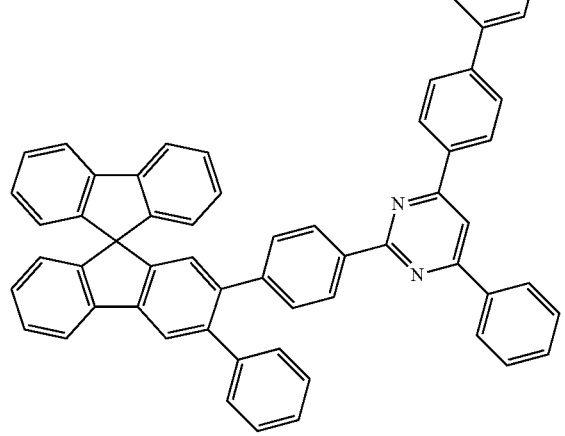
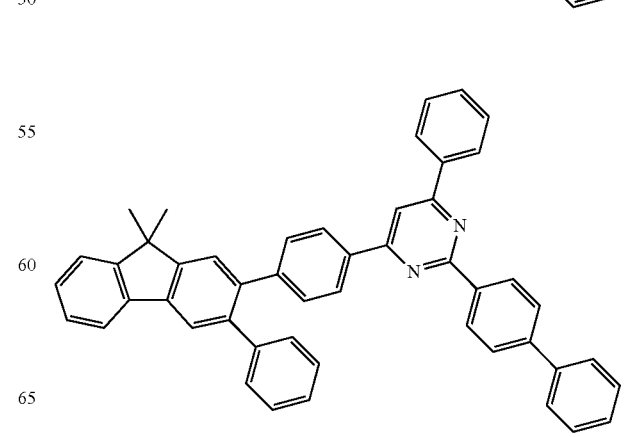

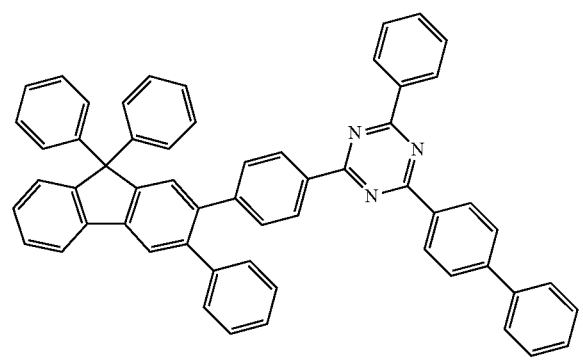
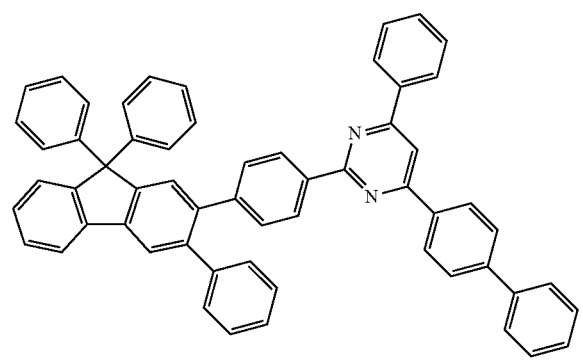
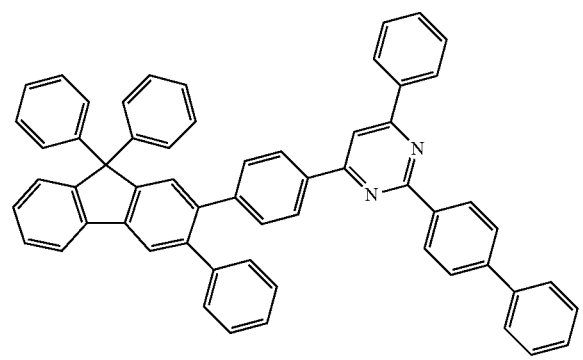
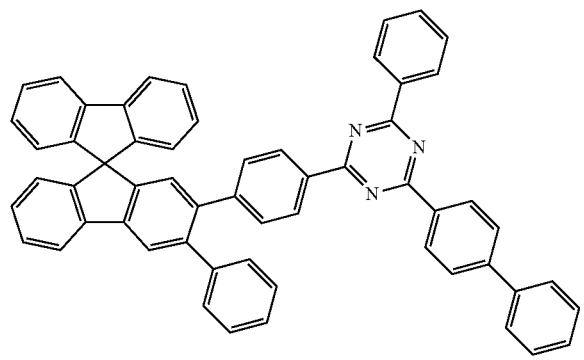
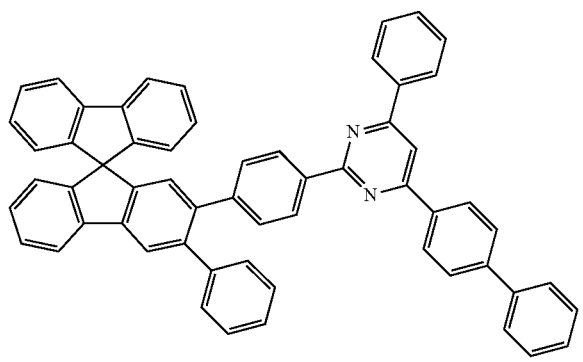
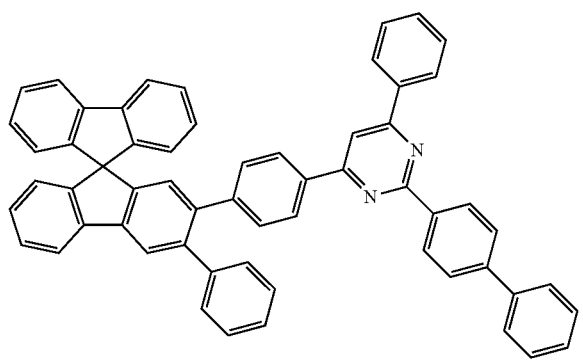
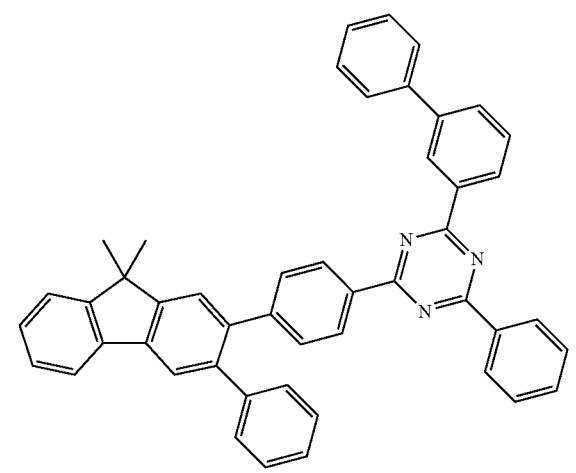
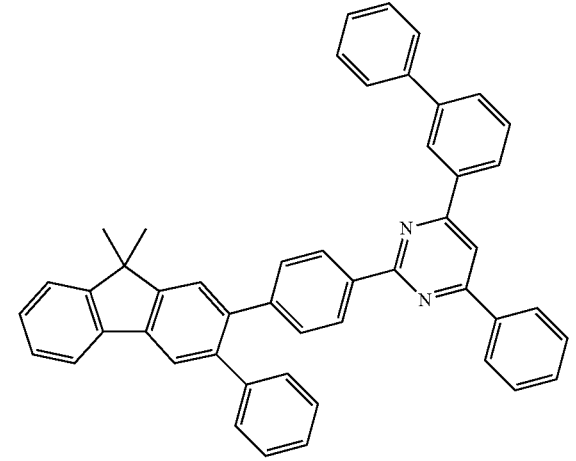

25
-continued
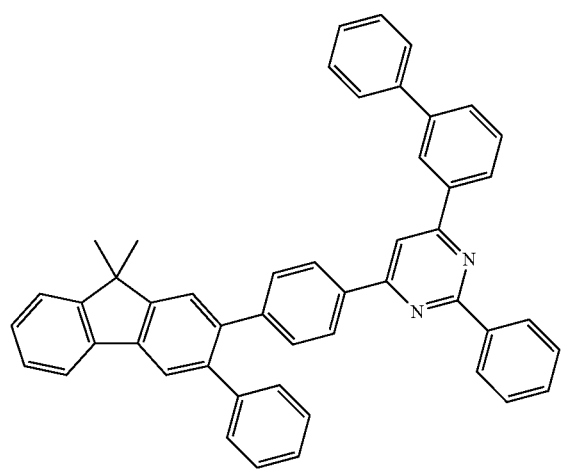
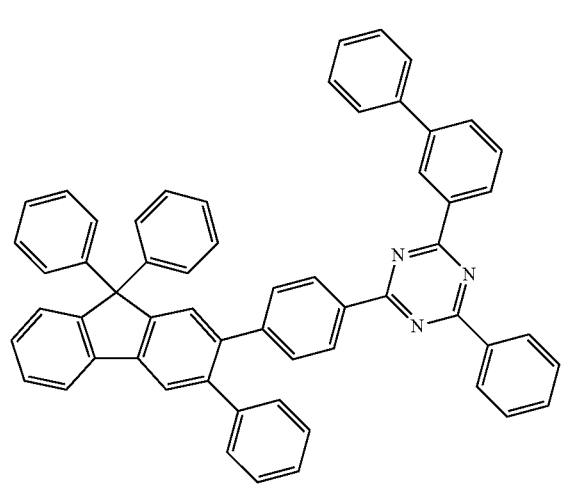
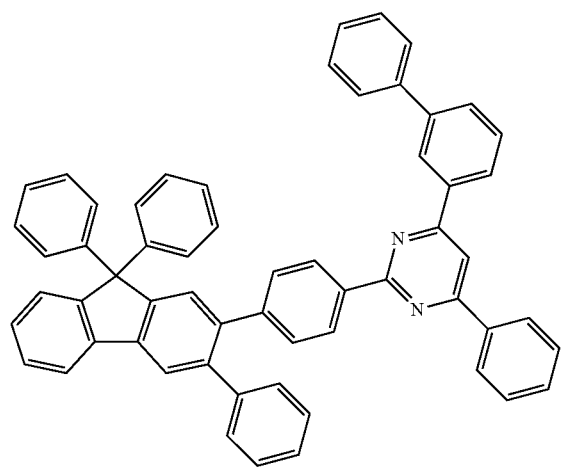
26
-continued
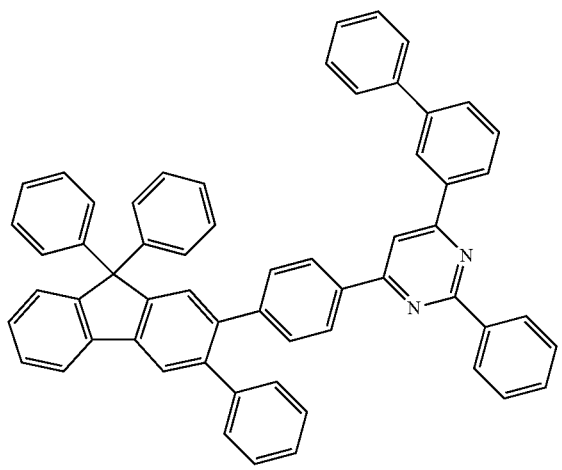
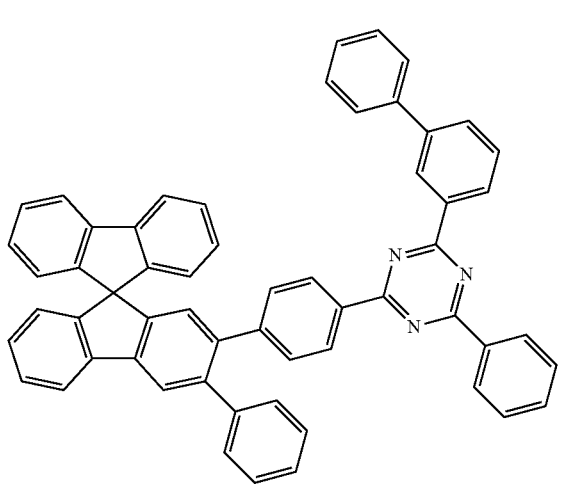
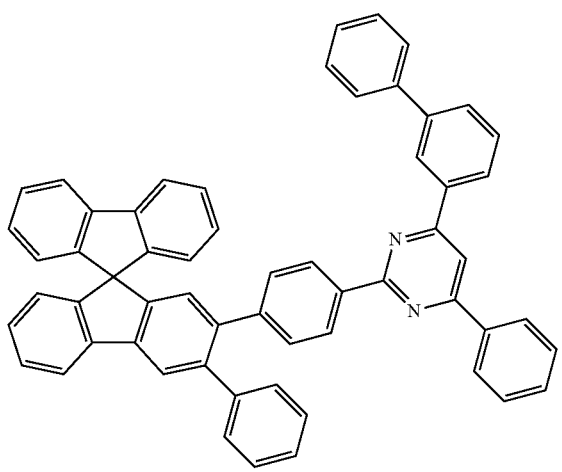

-continued
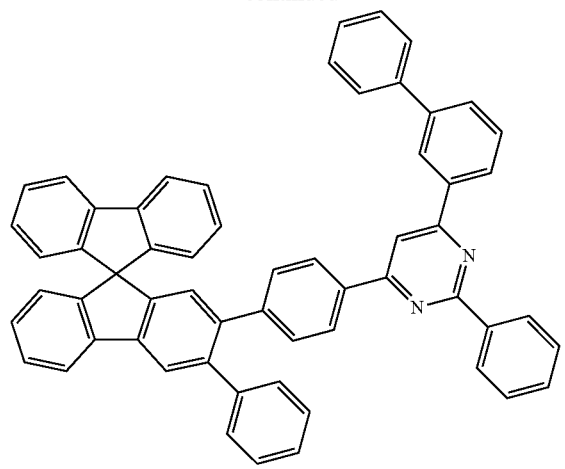
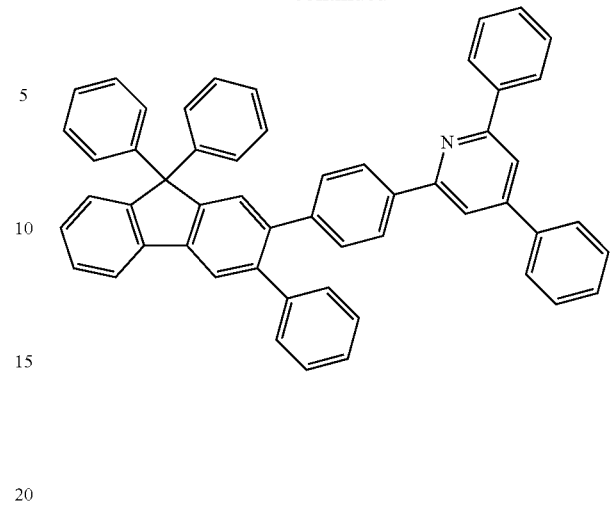
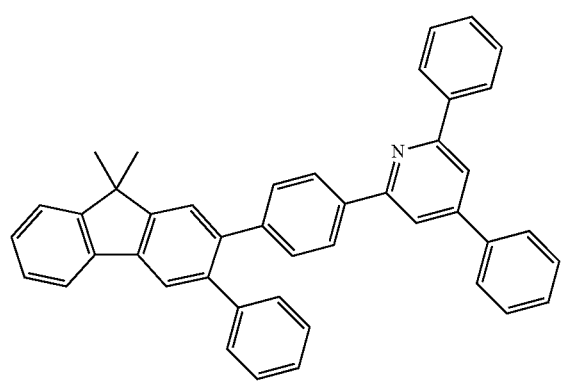
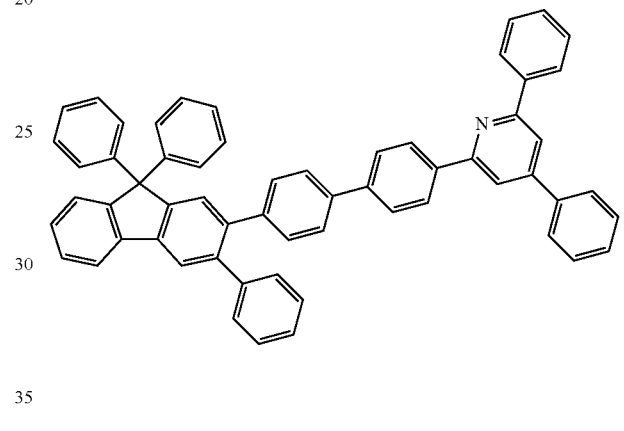
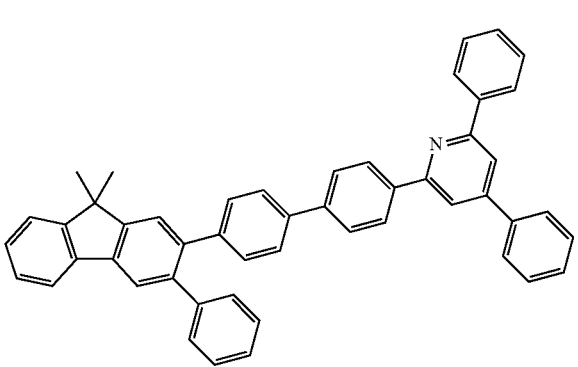
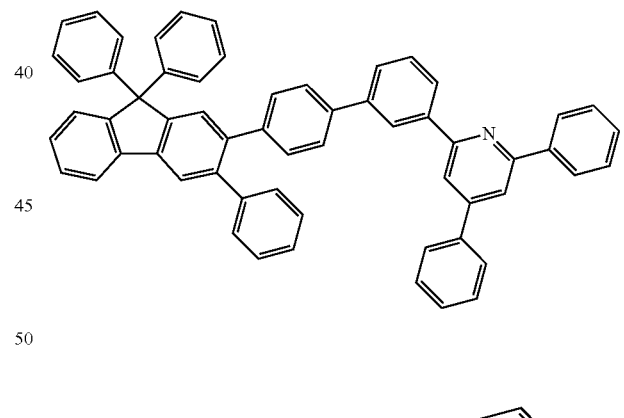
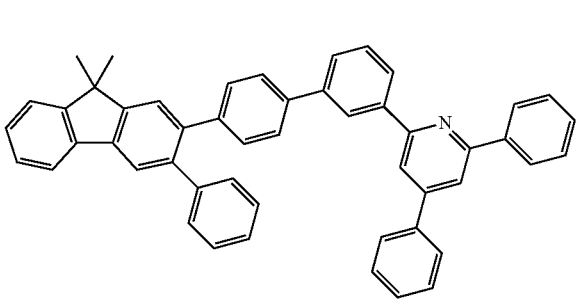
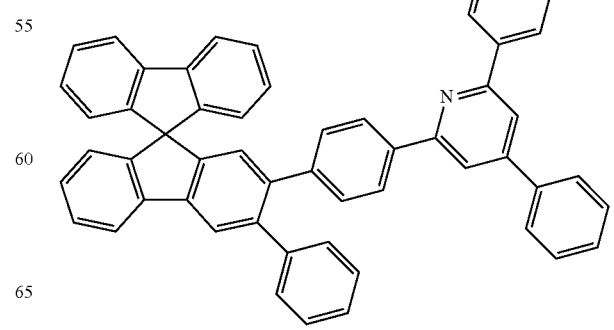

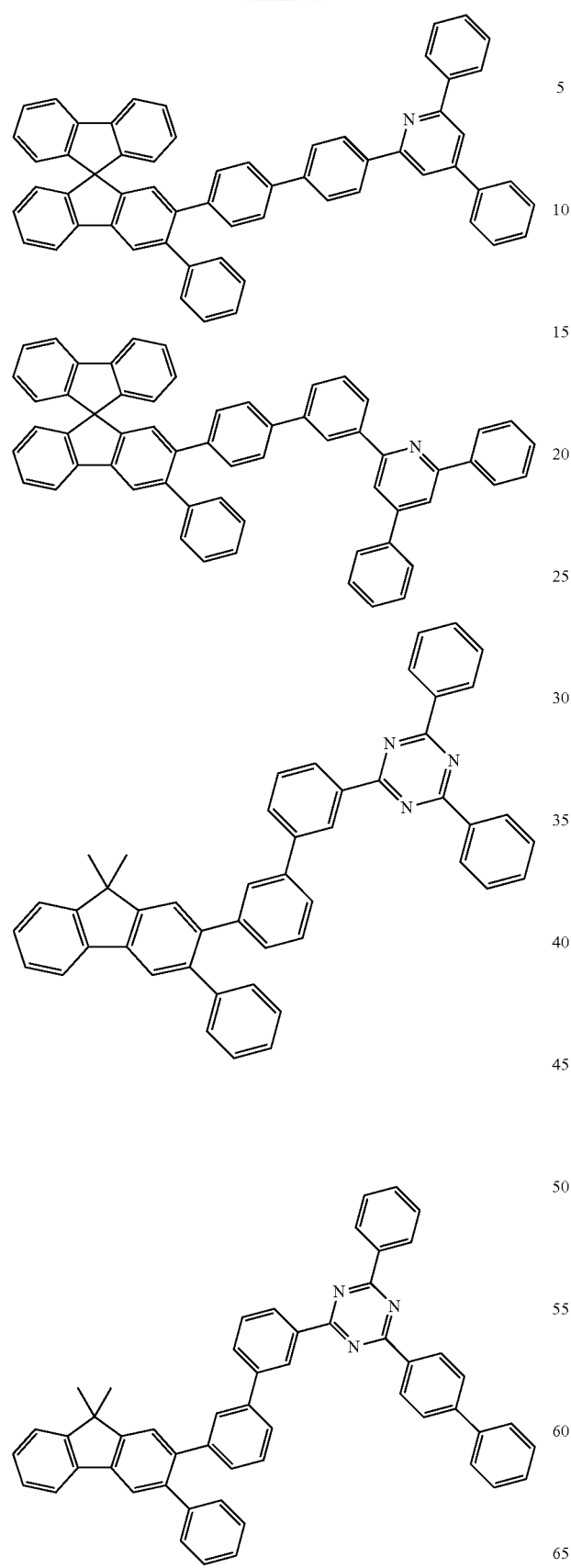
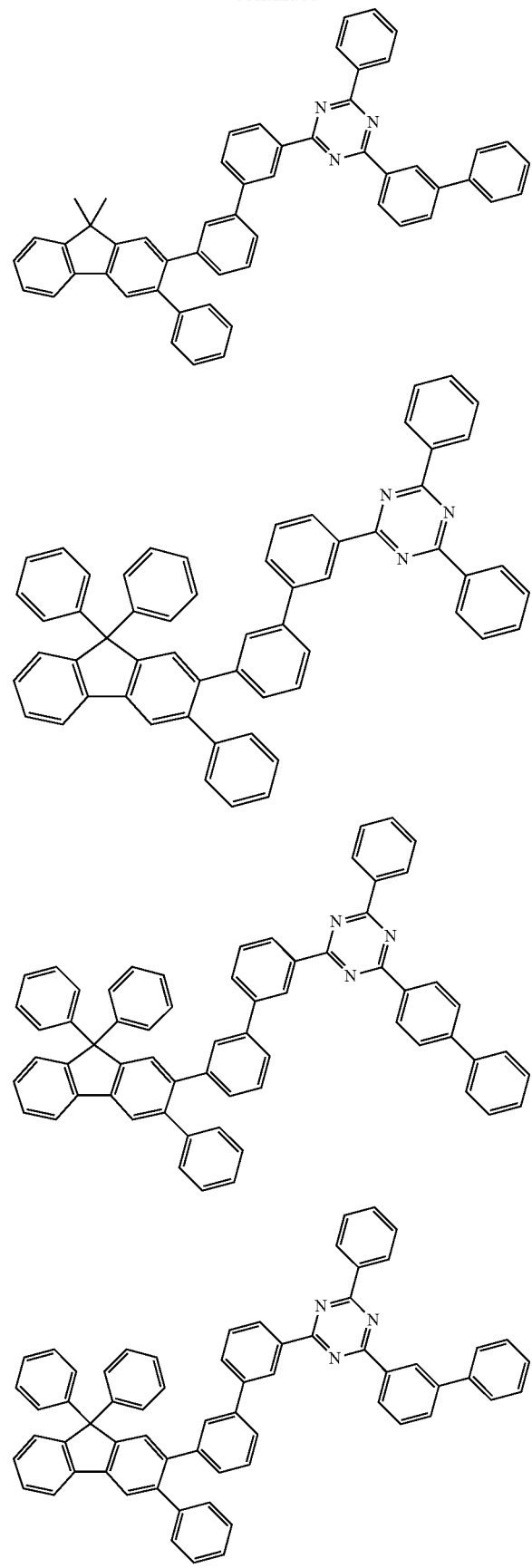

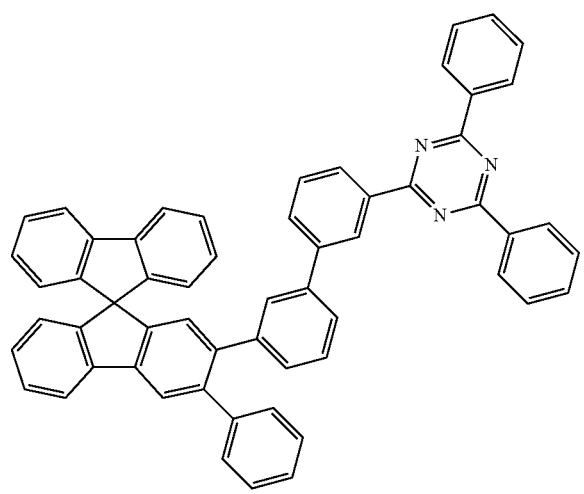
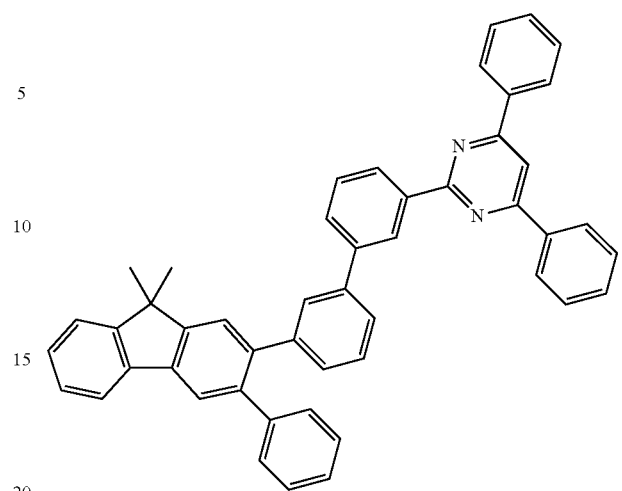
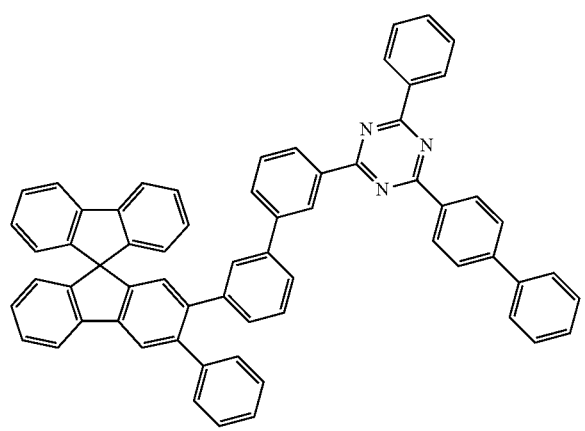
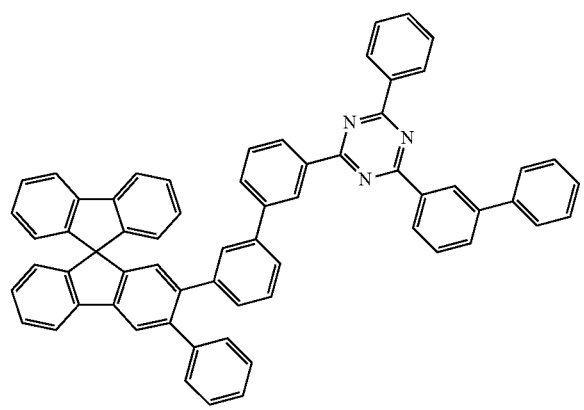
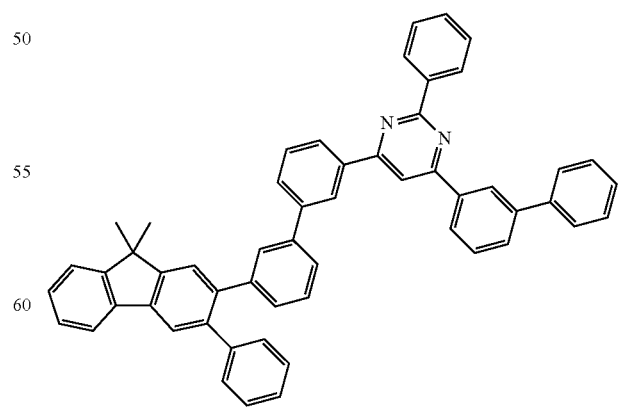

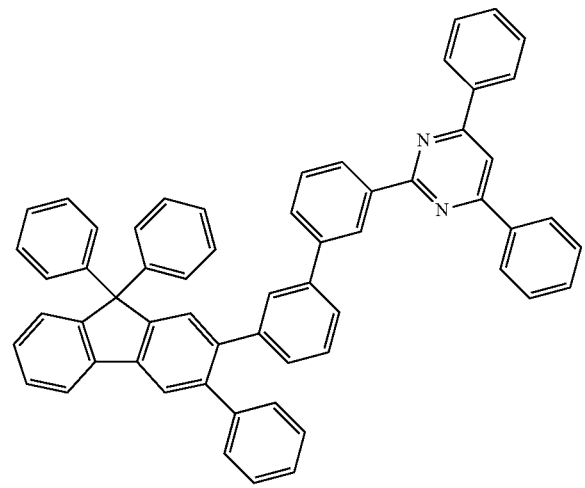
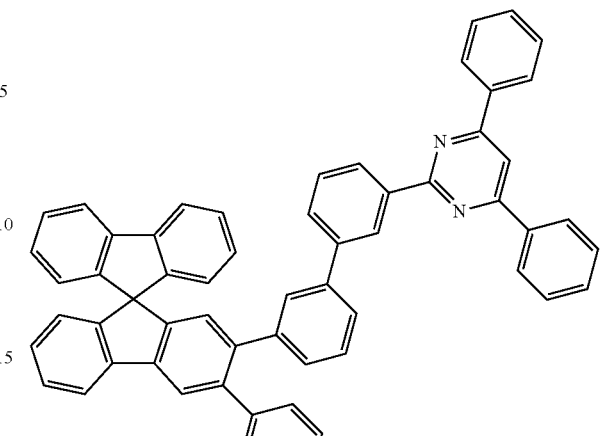
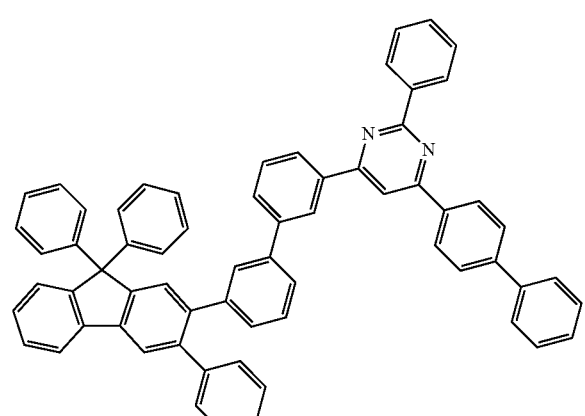
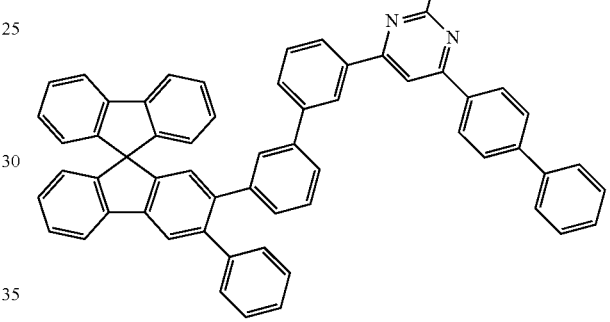
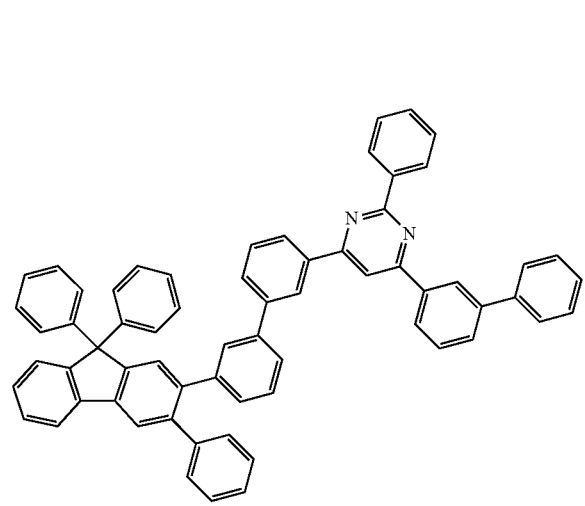
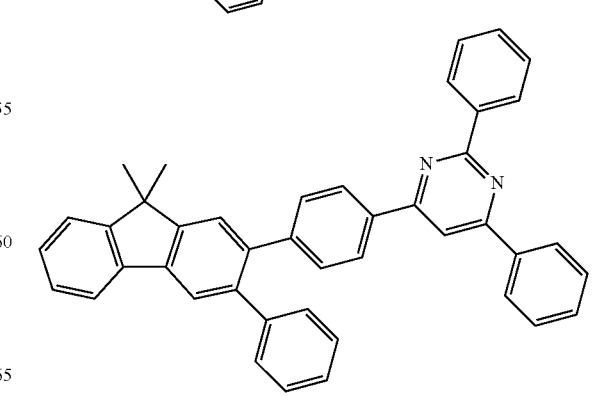

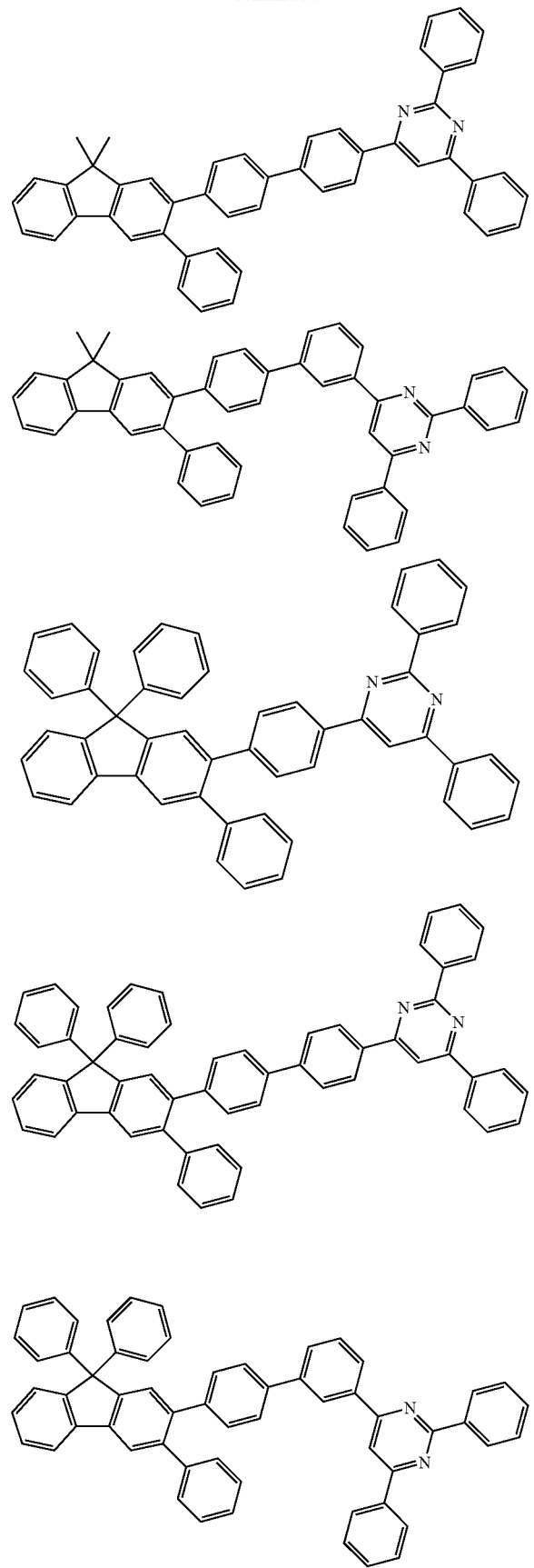
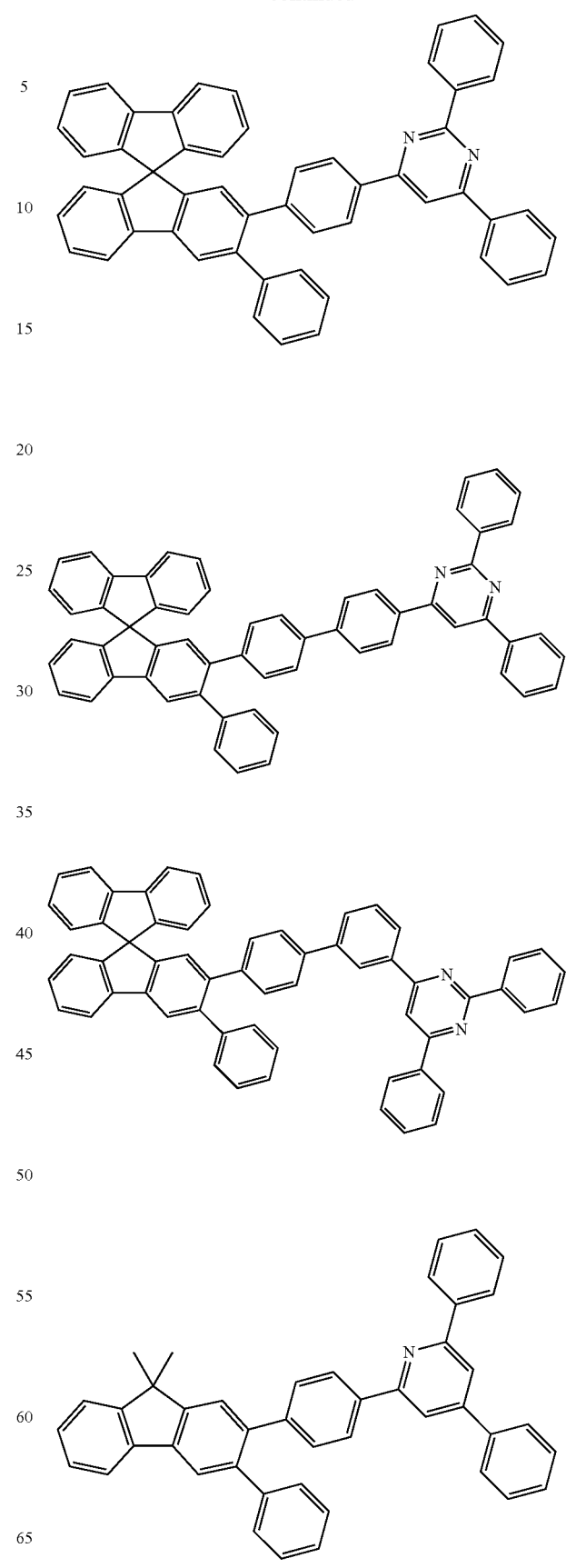

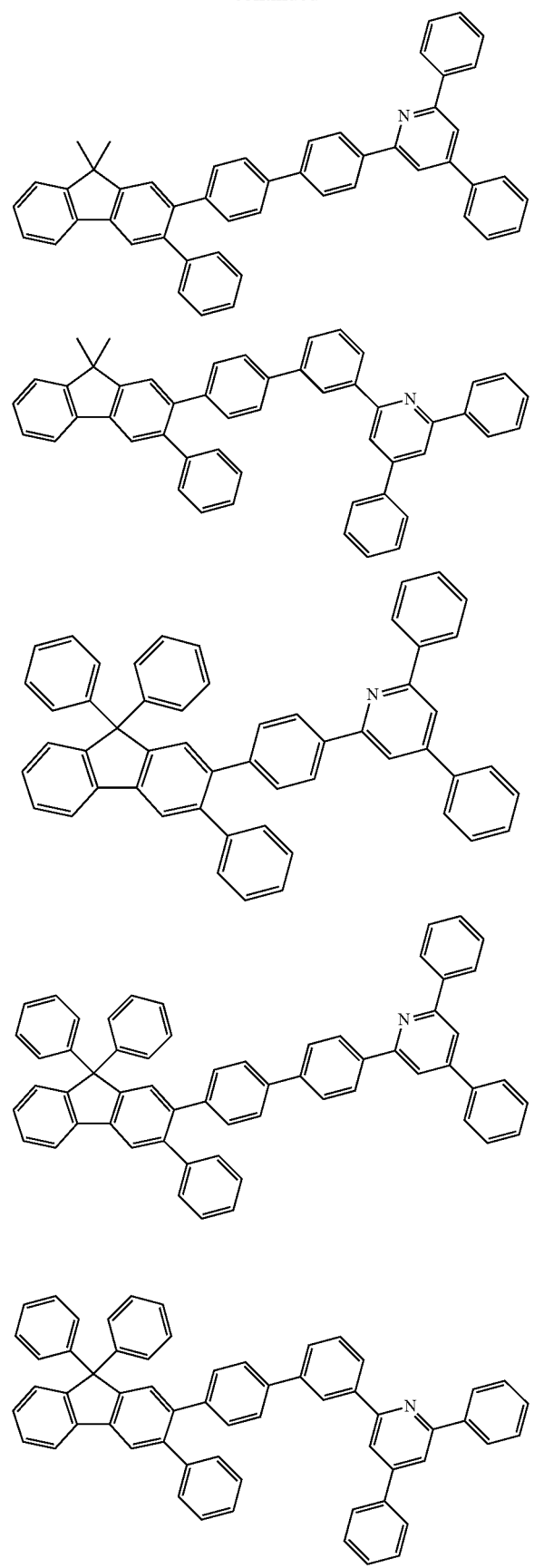
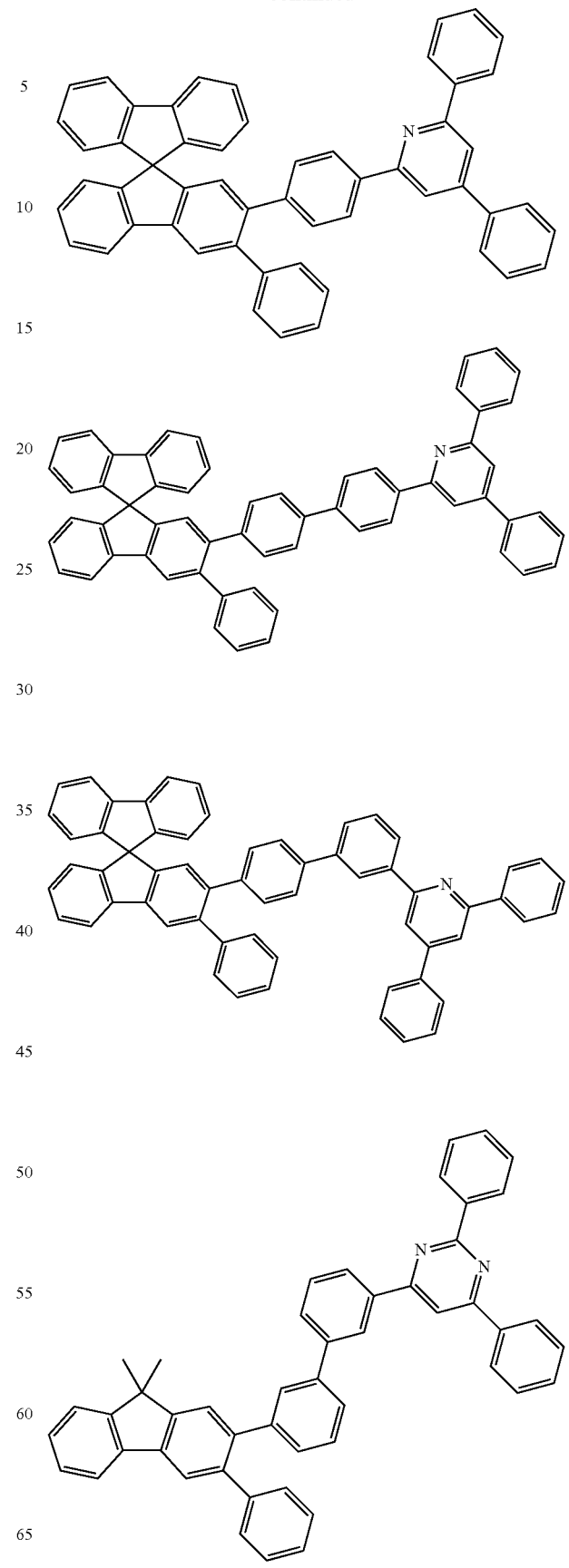

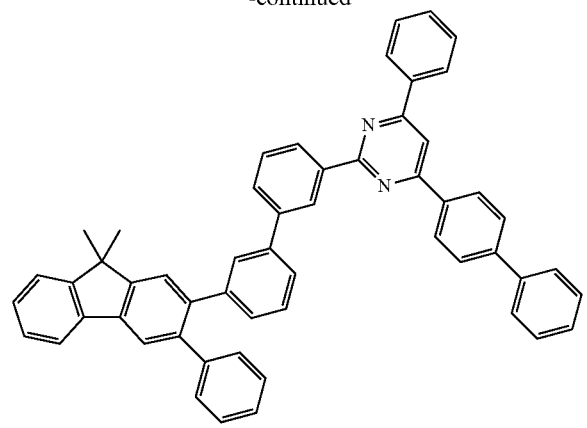
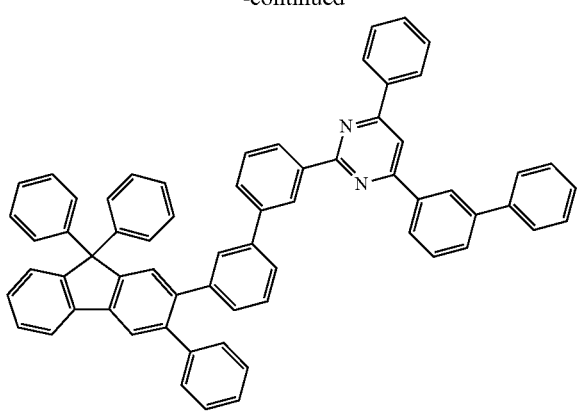
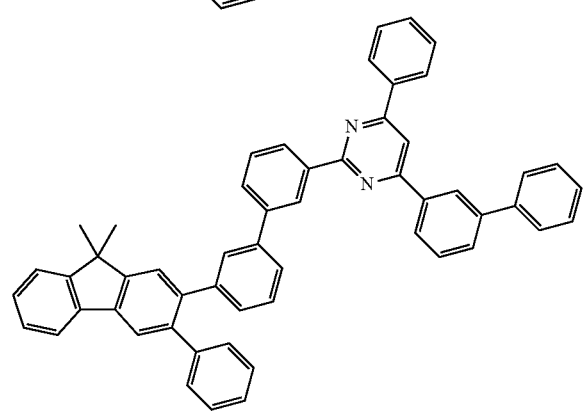
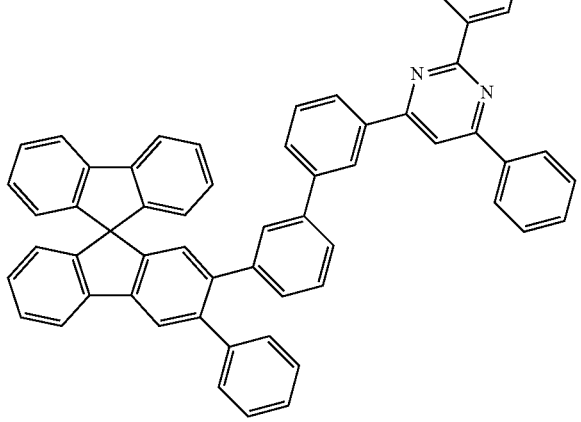
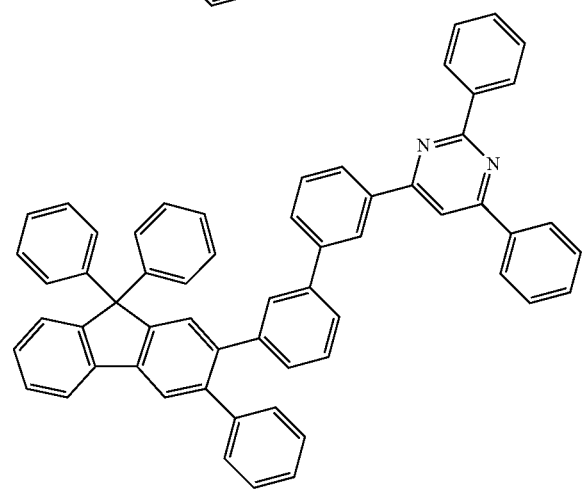
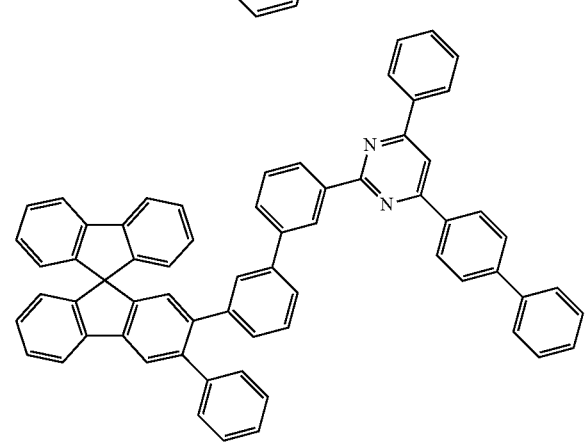
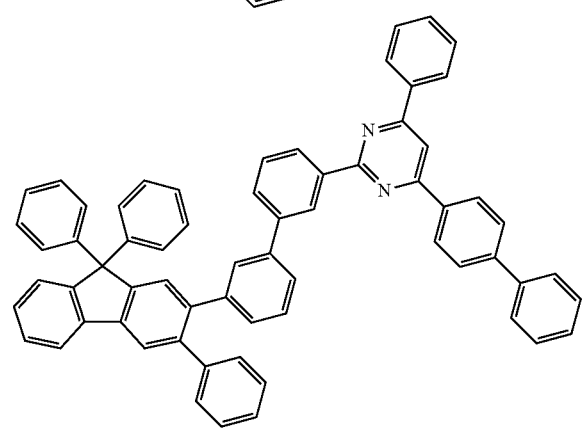
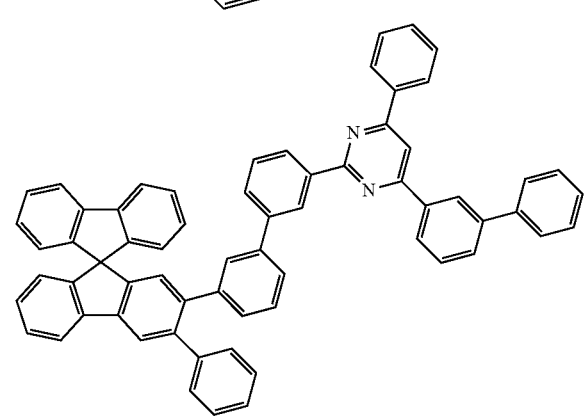

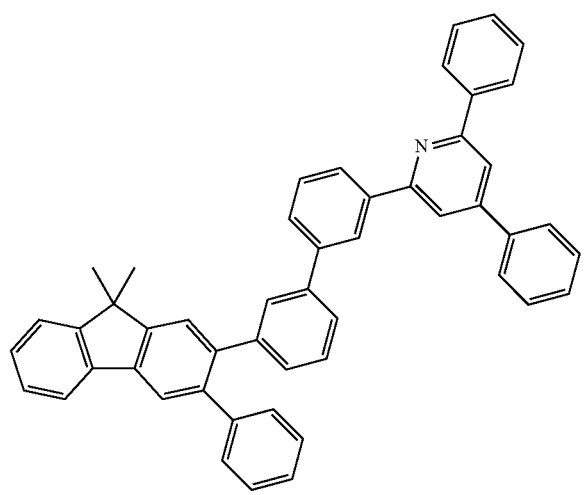
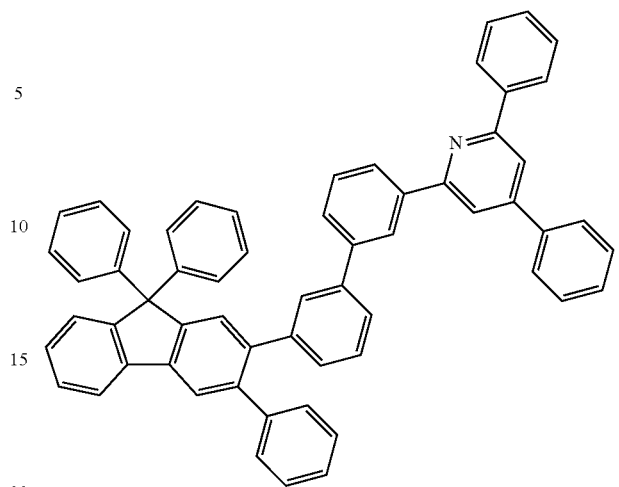
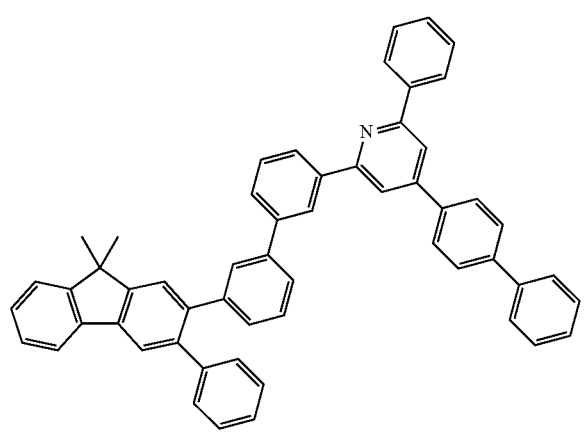
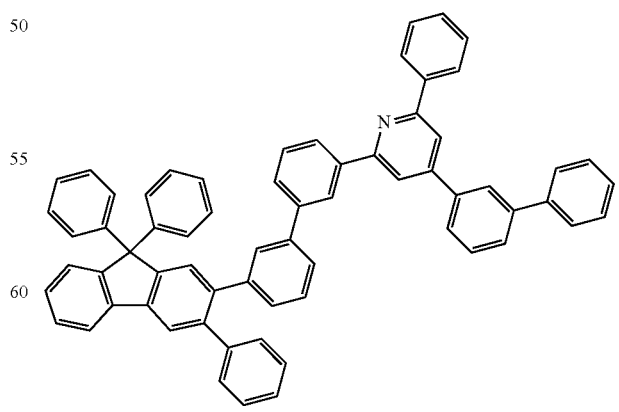
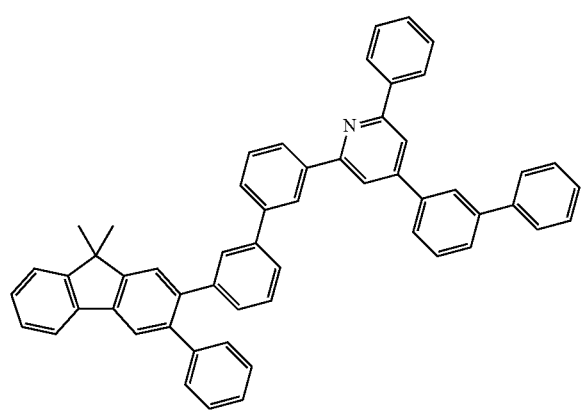

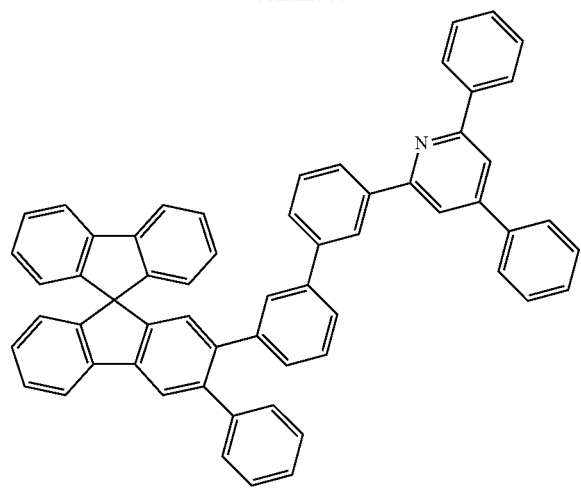
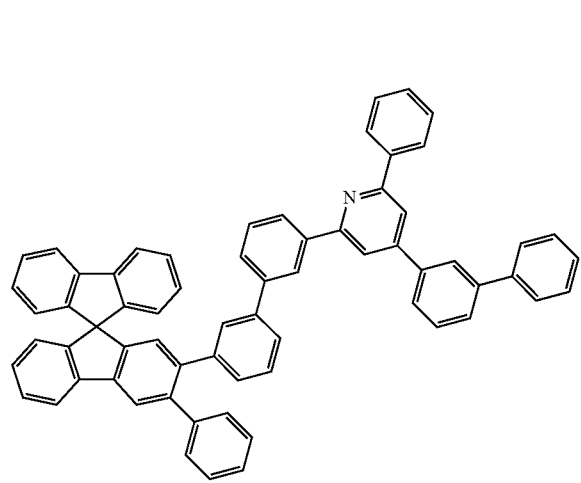
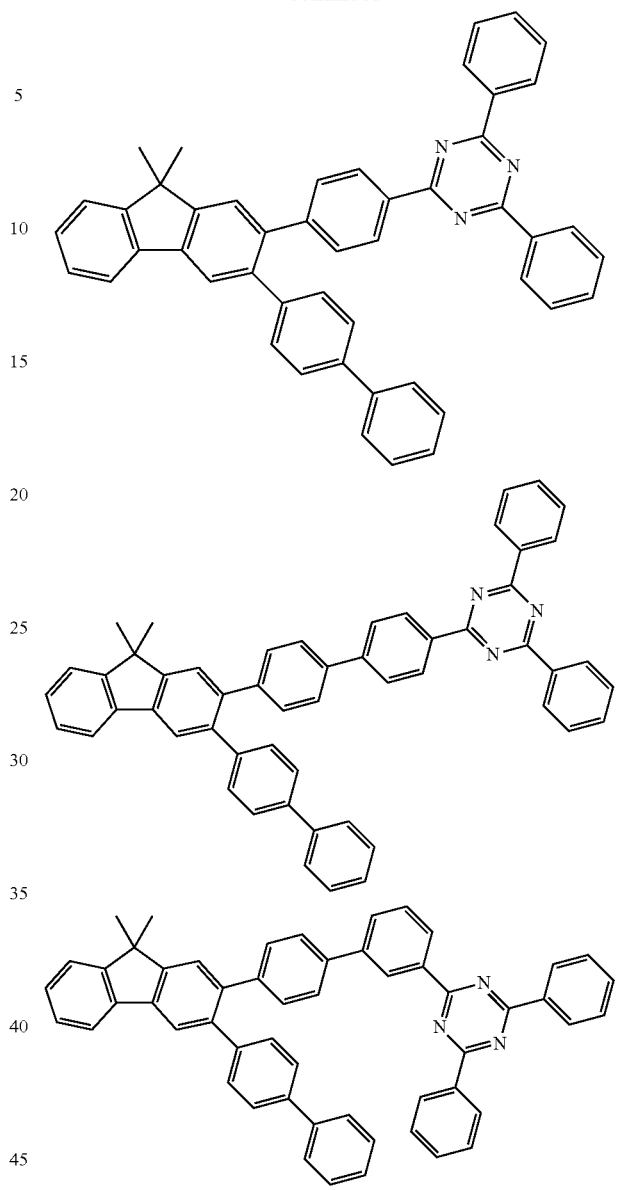

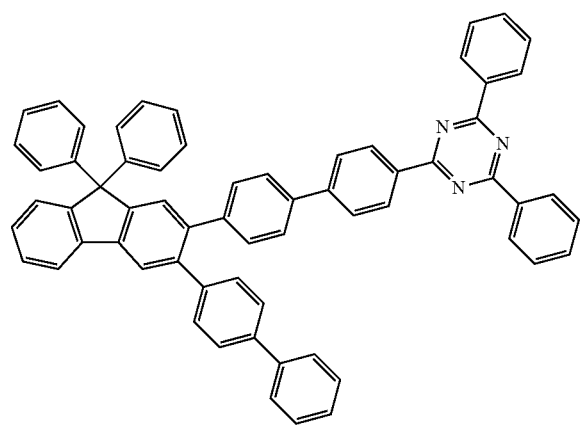
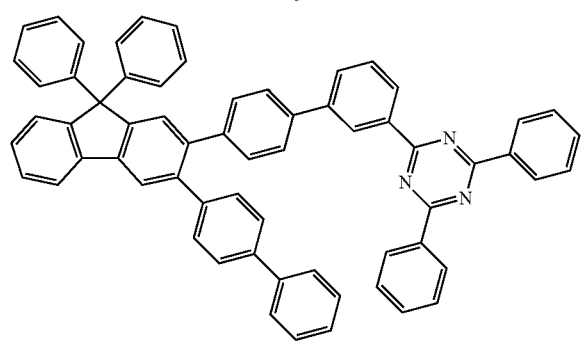
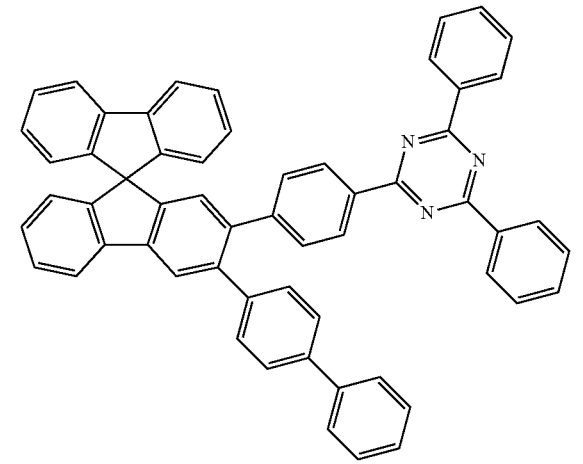
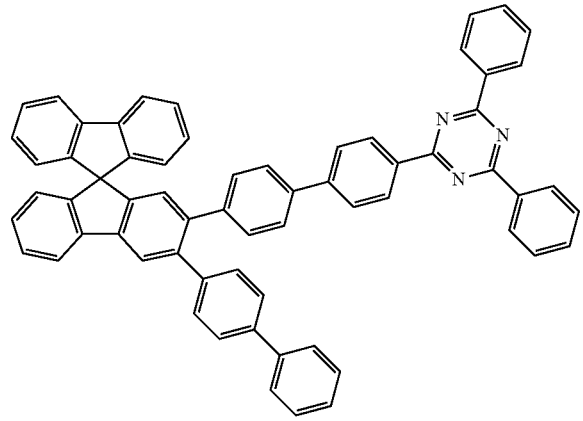
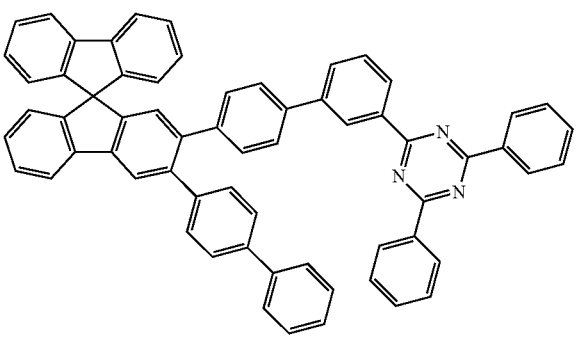
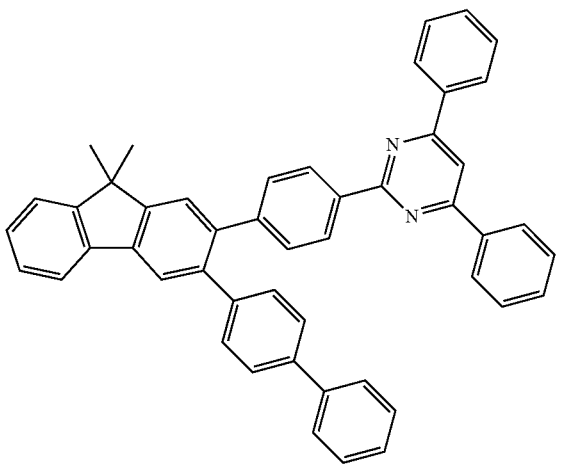
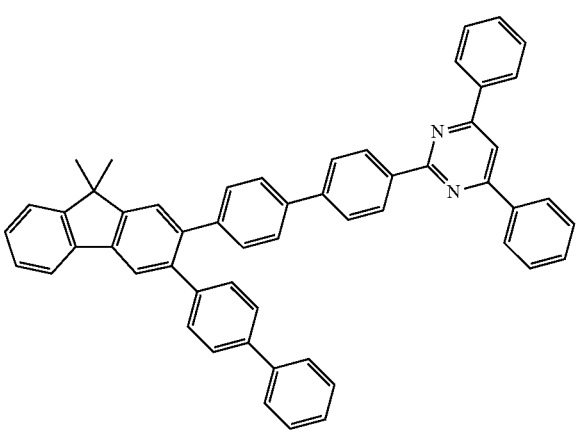
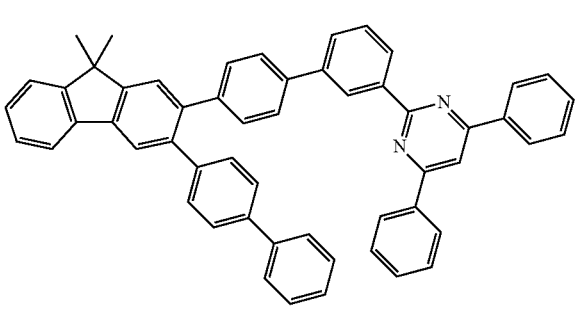

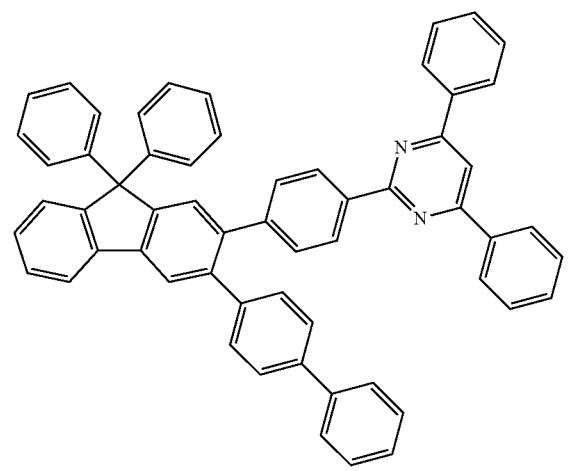
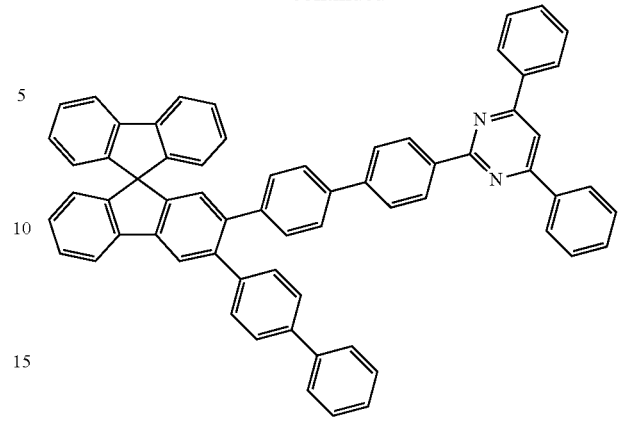
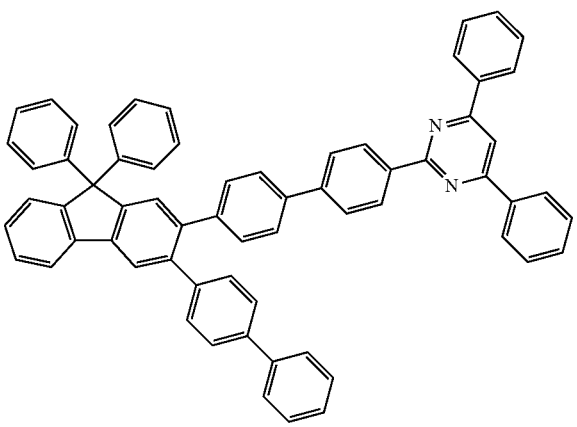
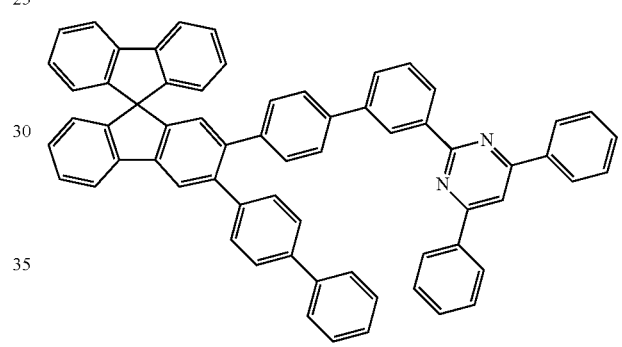
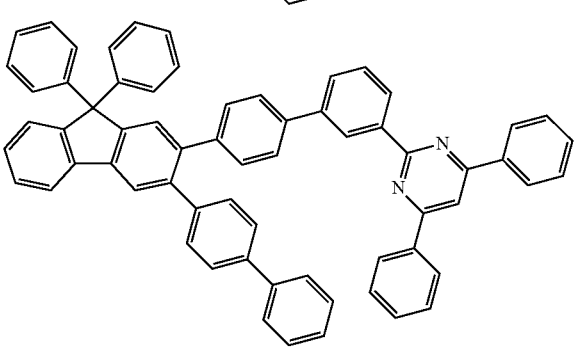
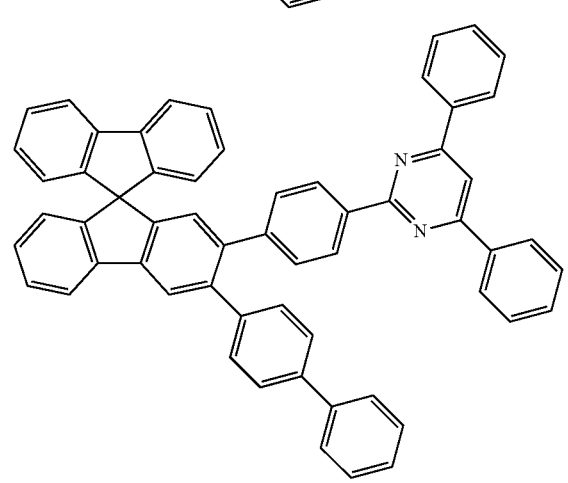
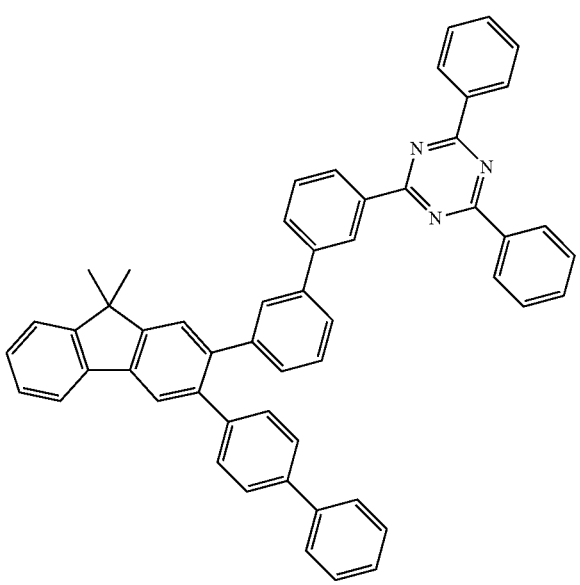

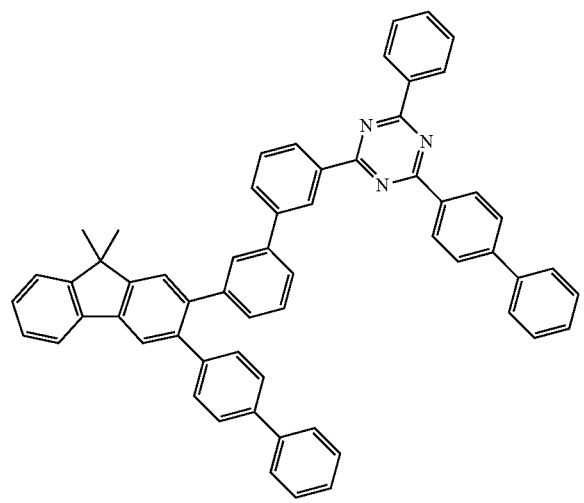
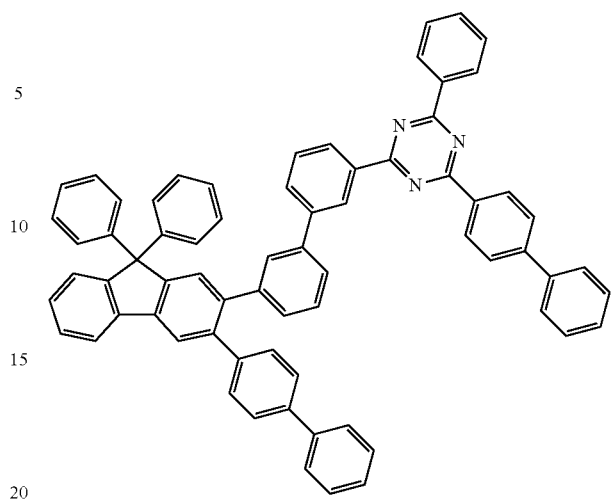
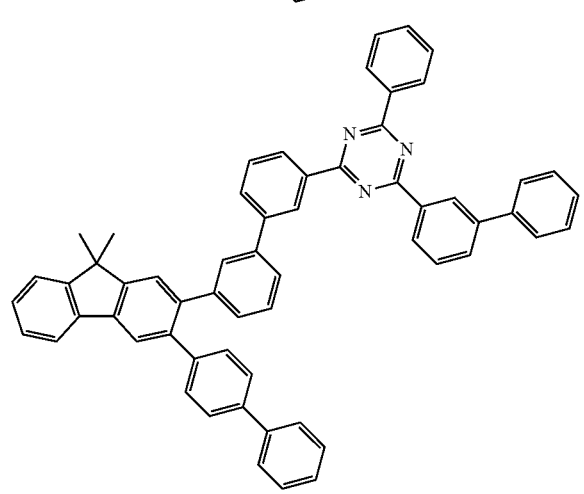
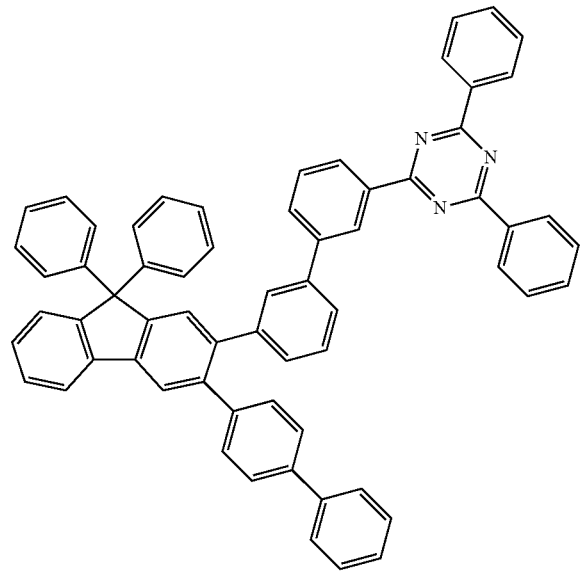
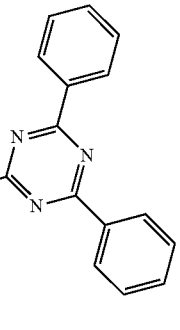

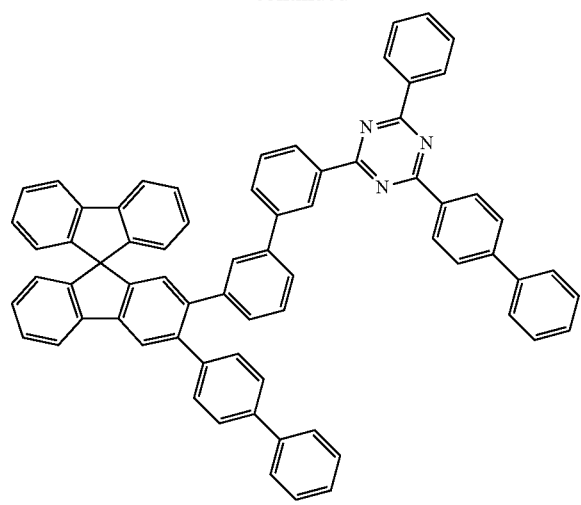
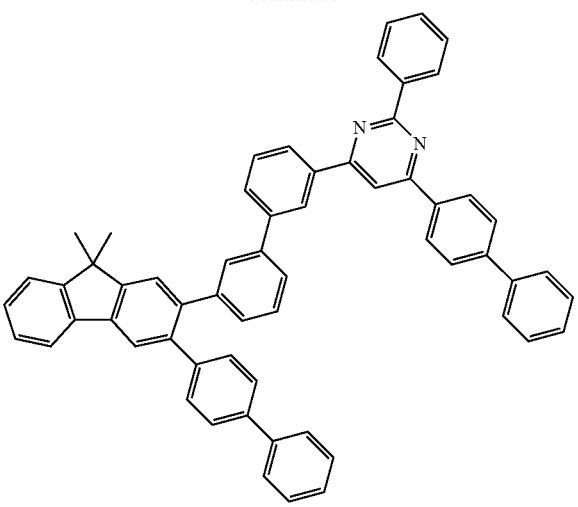
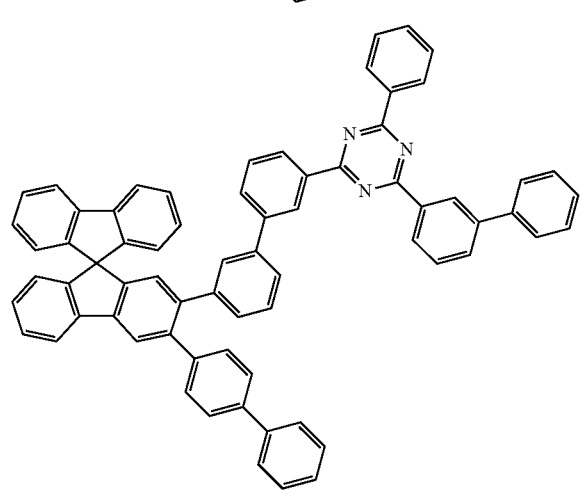
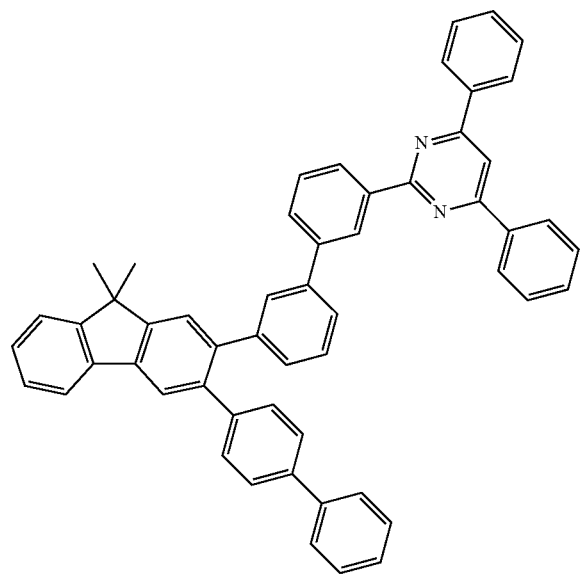
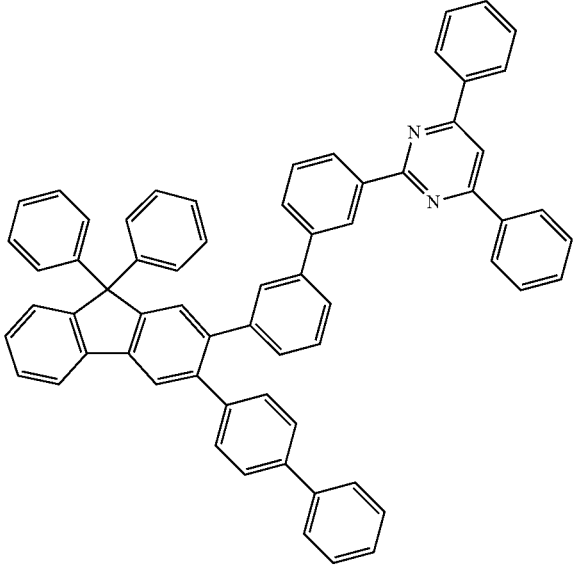

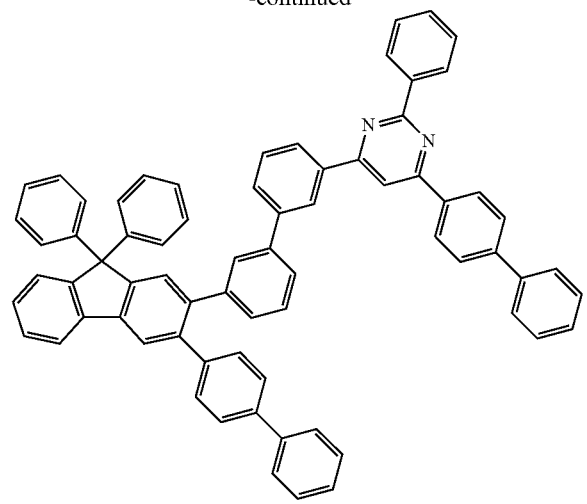
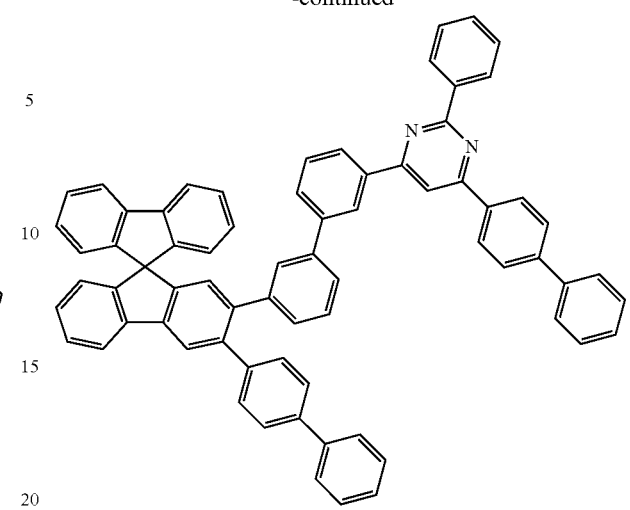
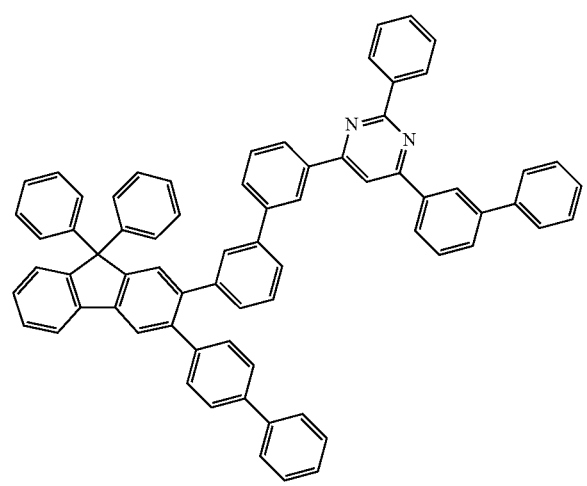
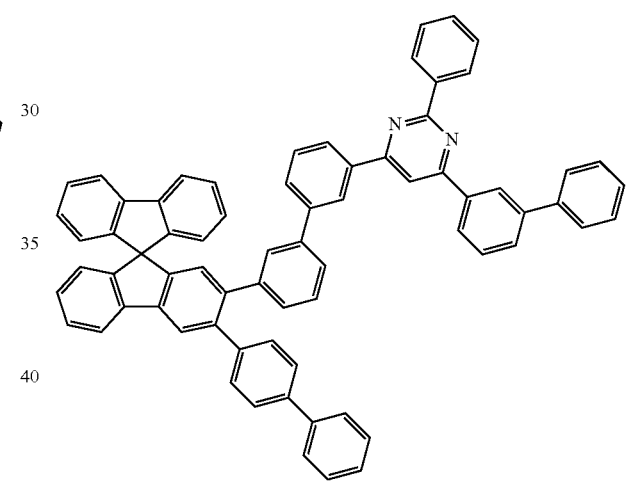
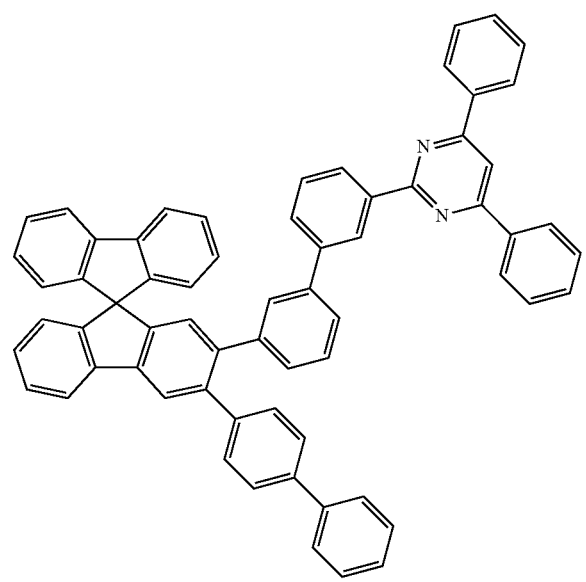
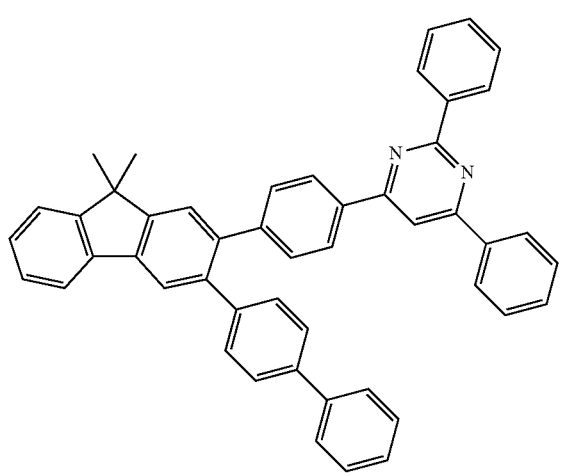

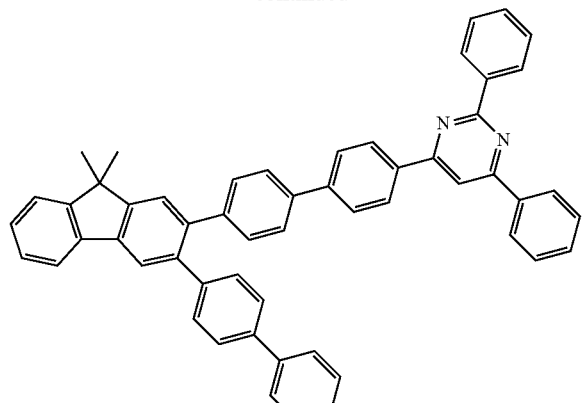
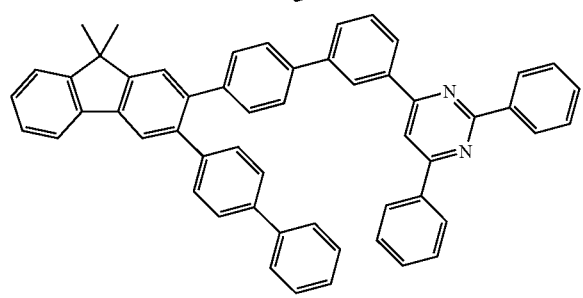
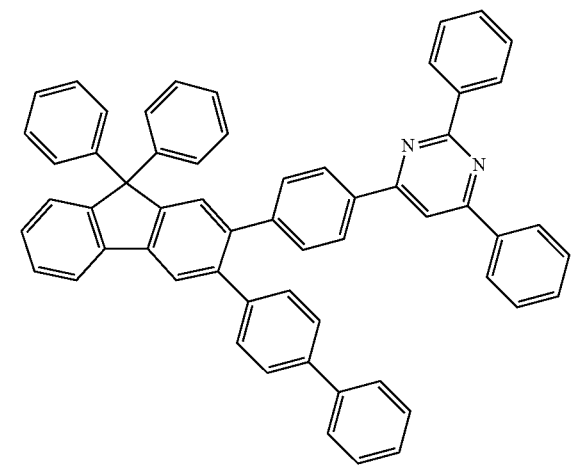
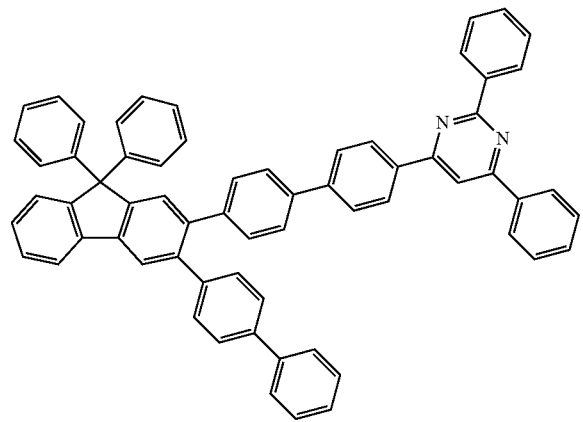
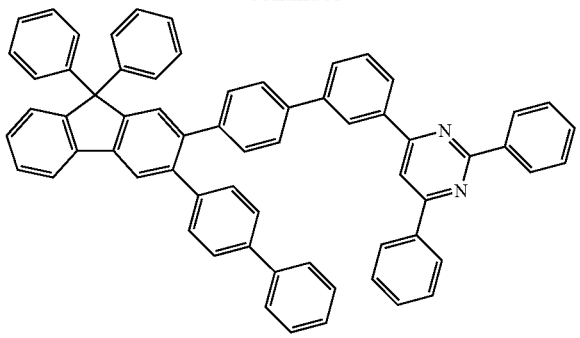
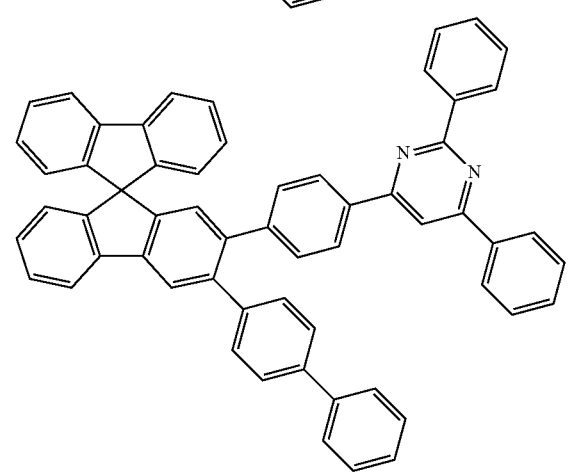
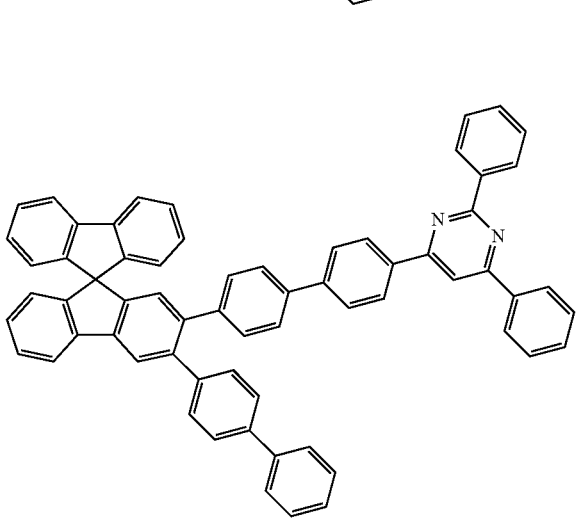
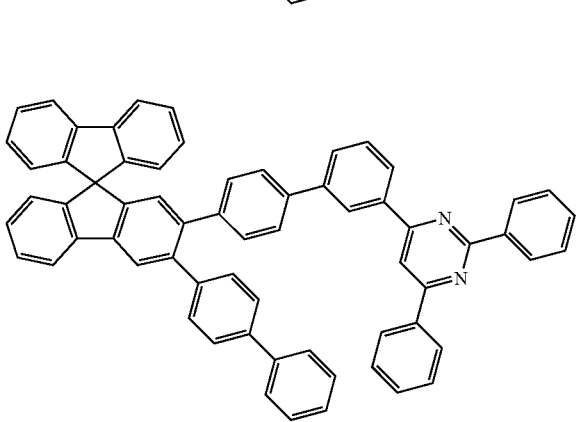

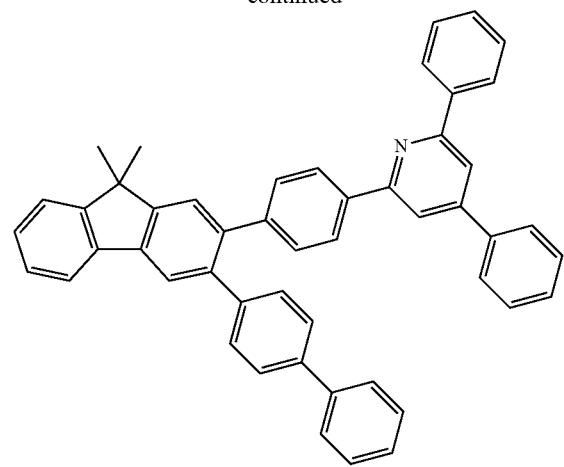
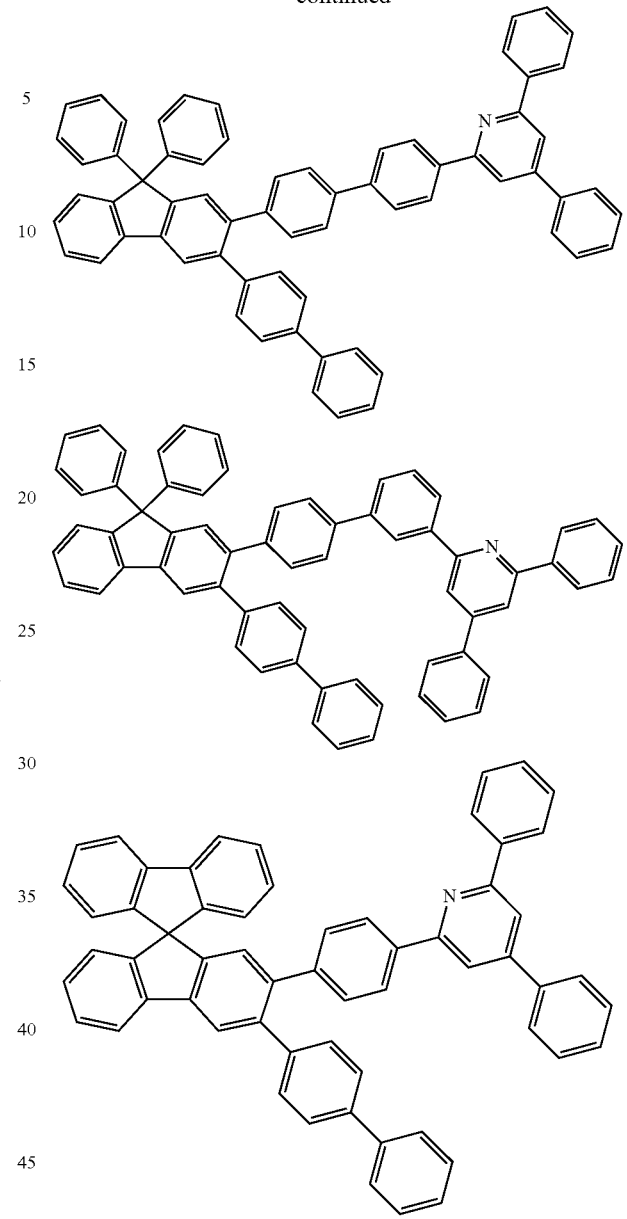
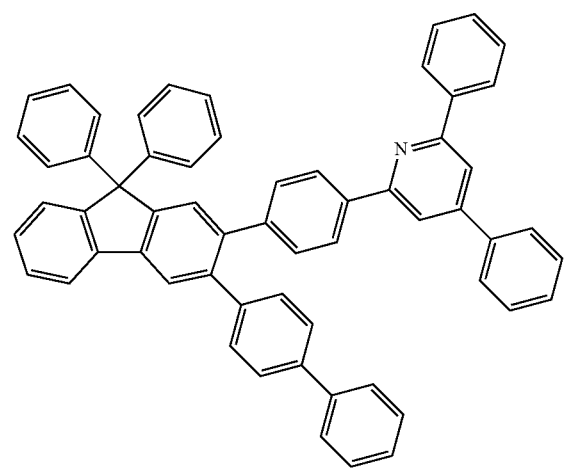
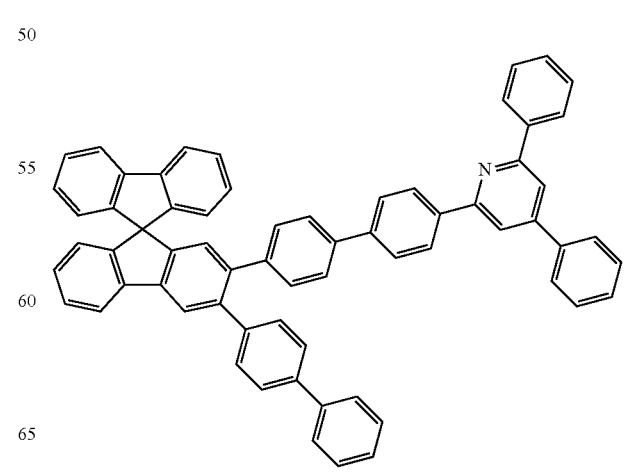

59
-continued
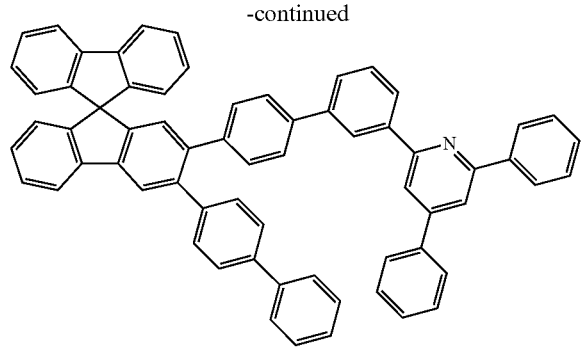
60
-continued
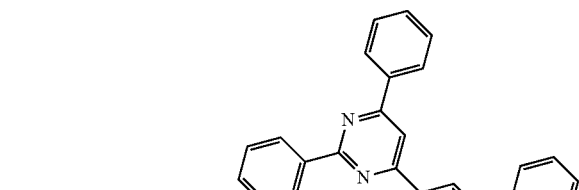
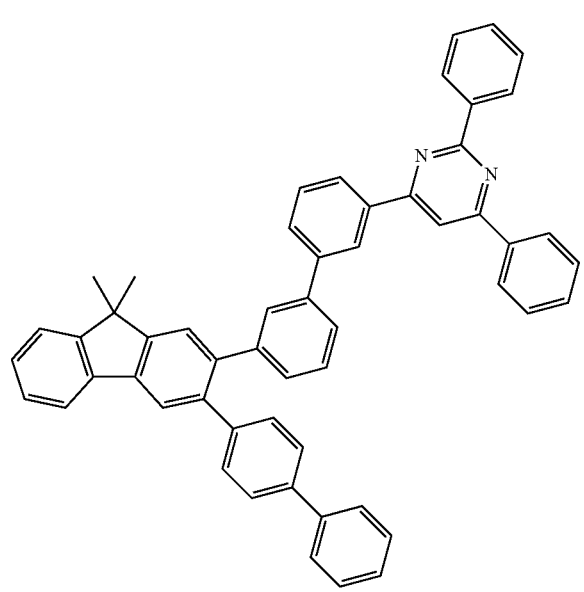
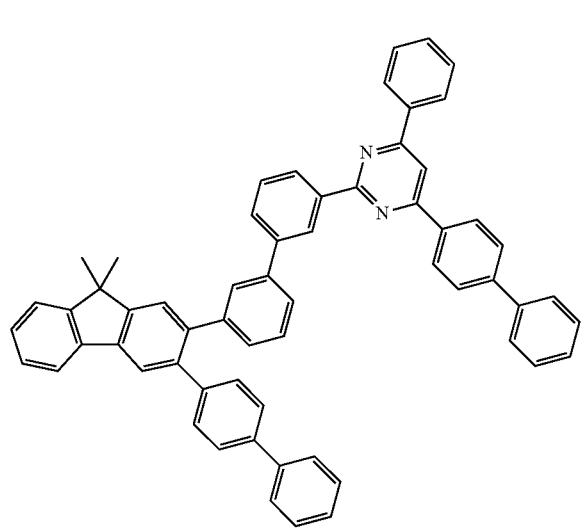
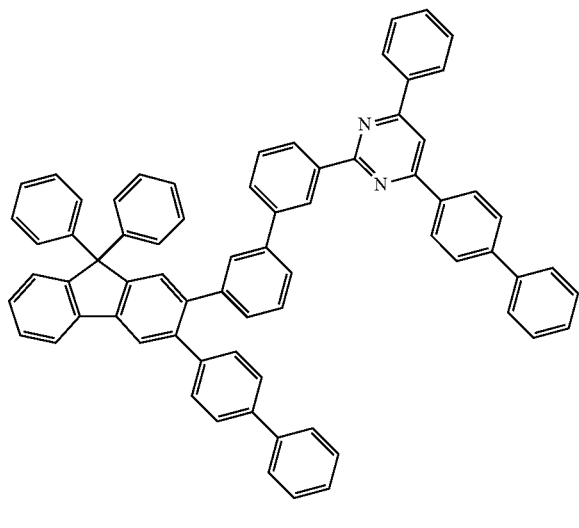

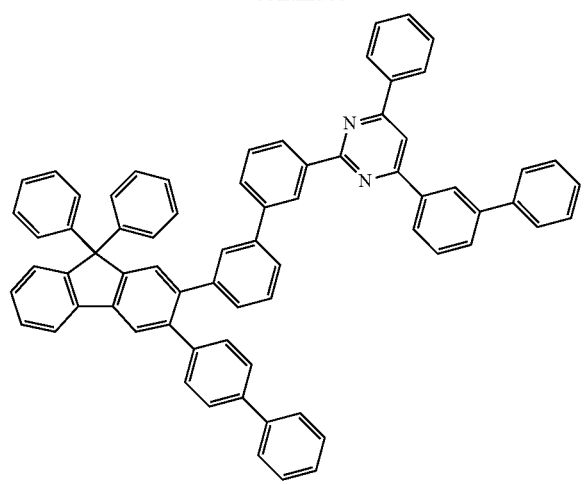
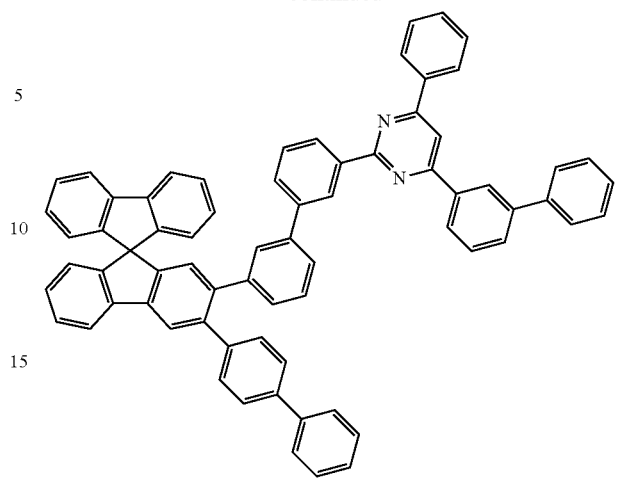
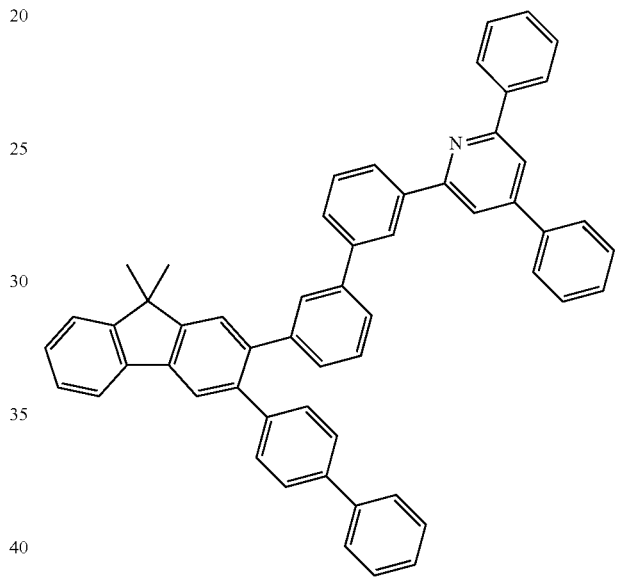
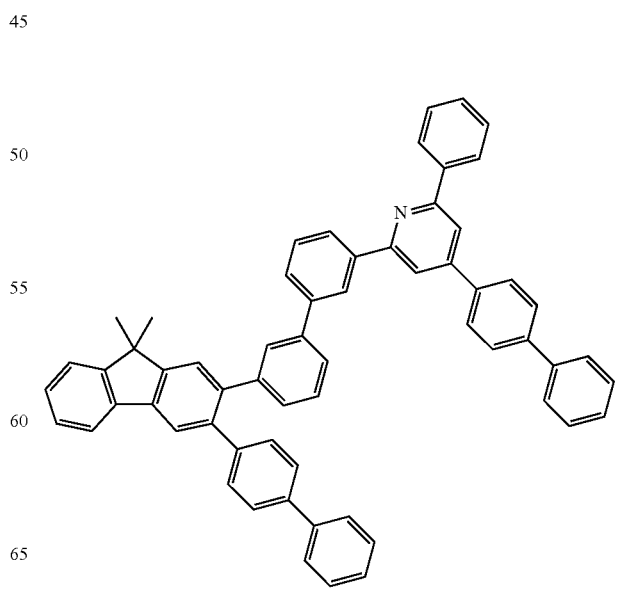

-continued
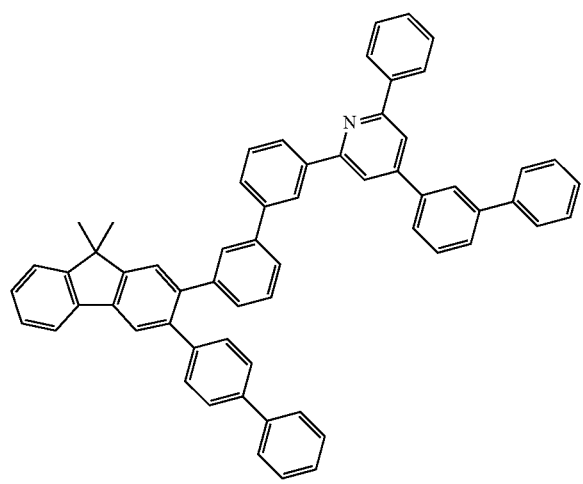
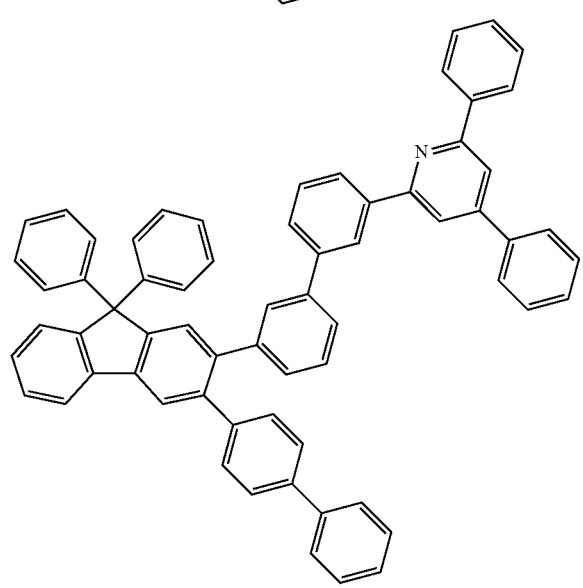
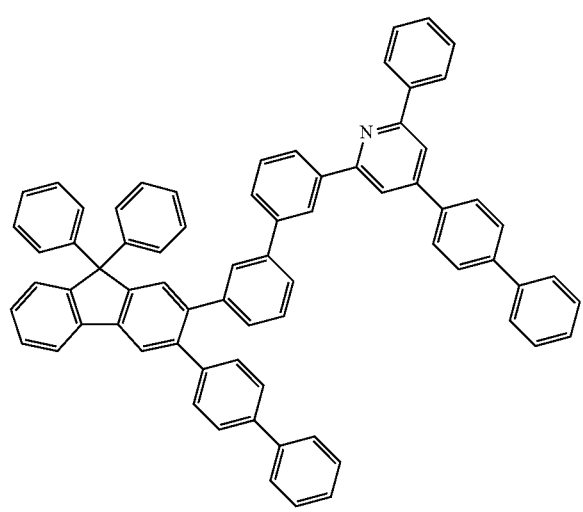
-continued
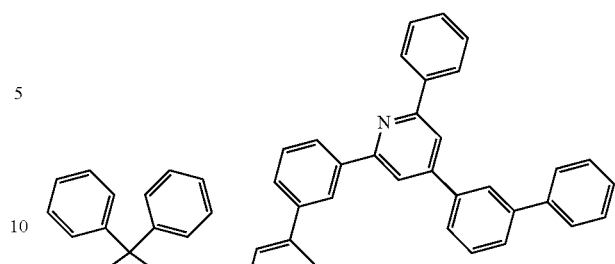
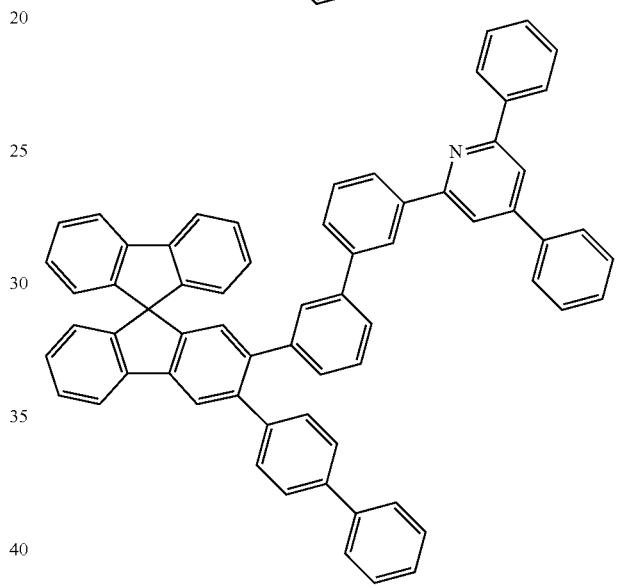
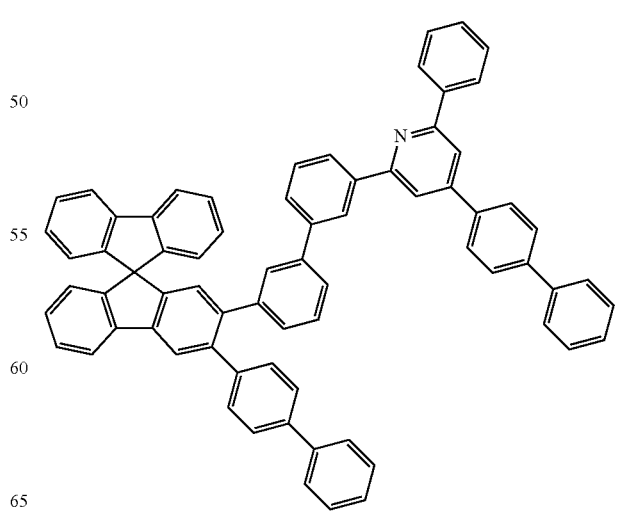

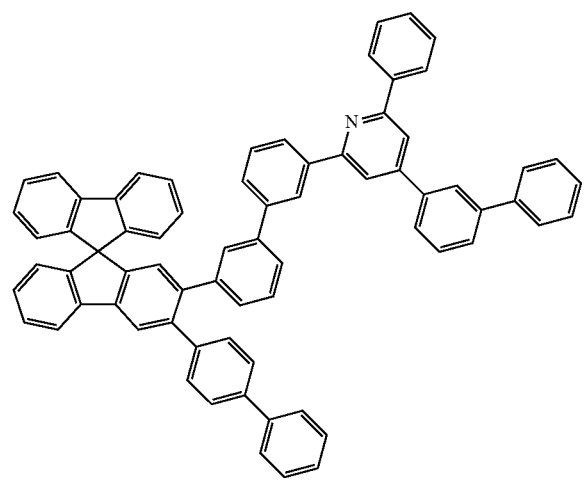
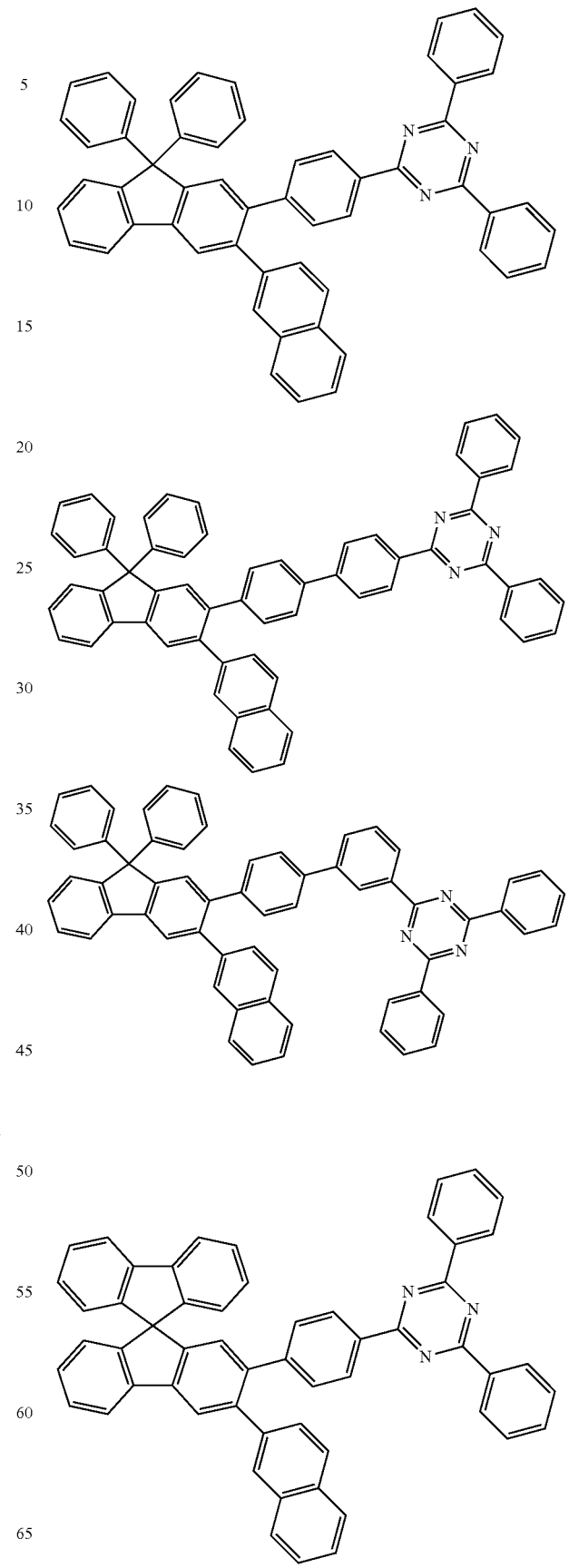

67
-continued
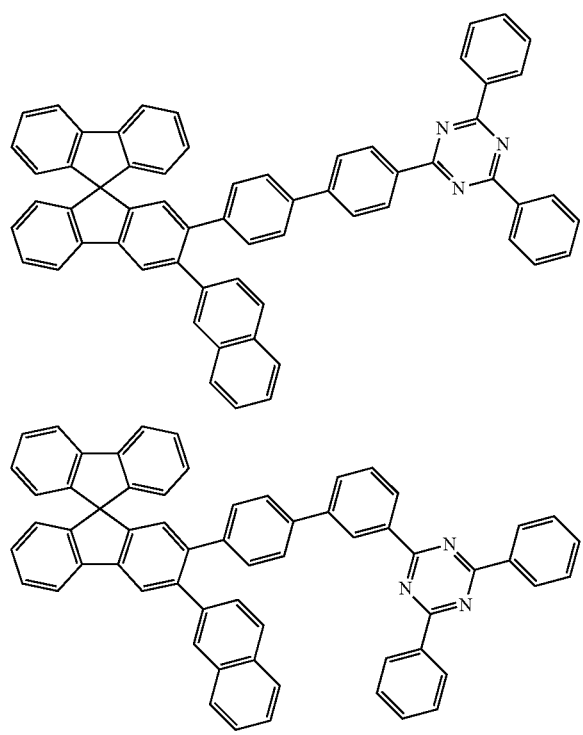
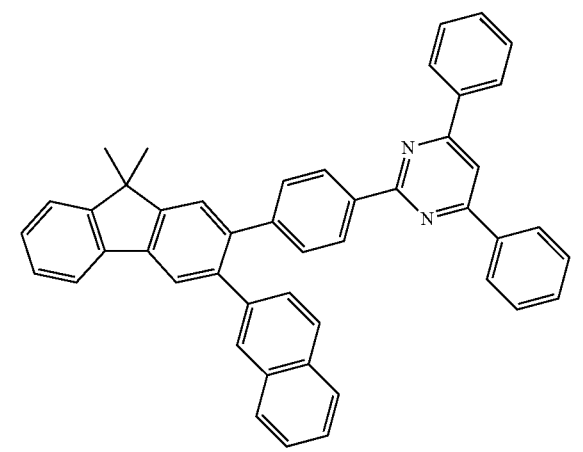
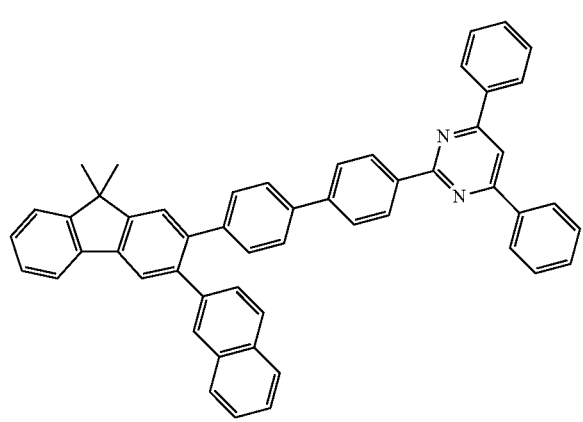
68
-continued
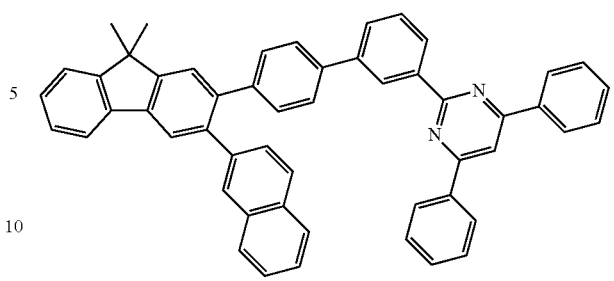
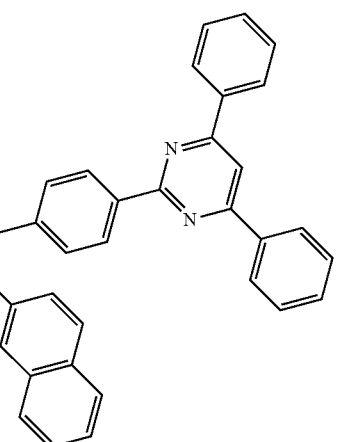
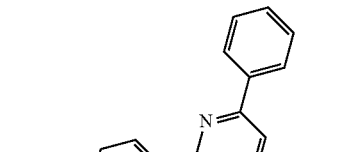
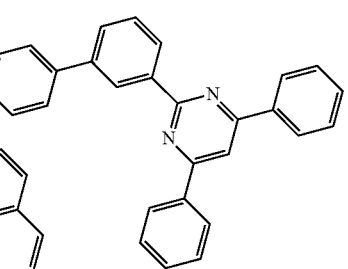

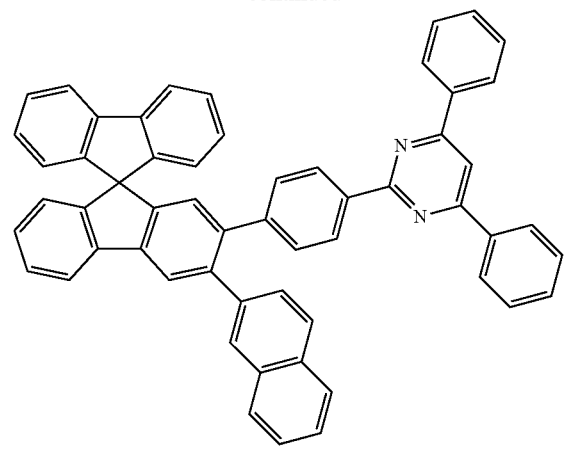
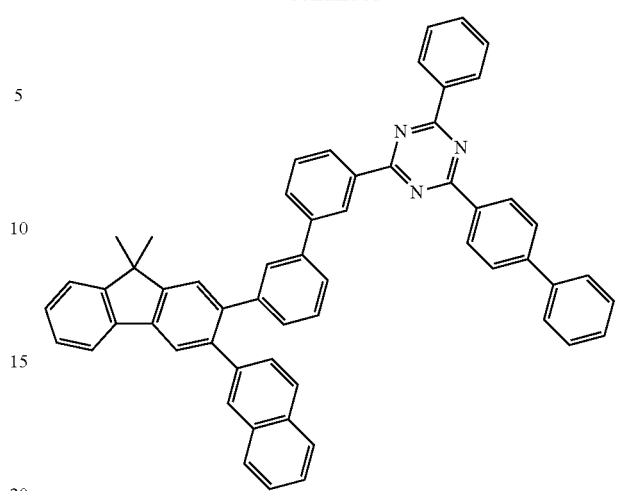
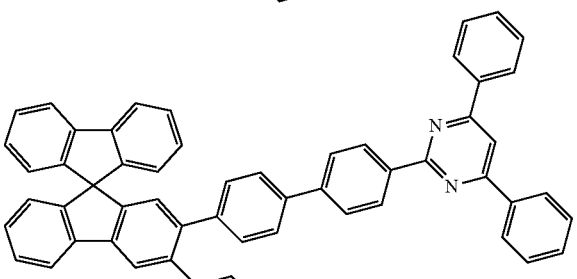
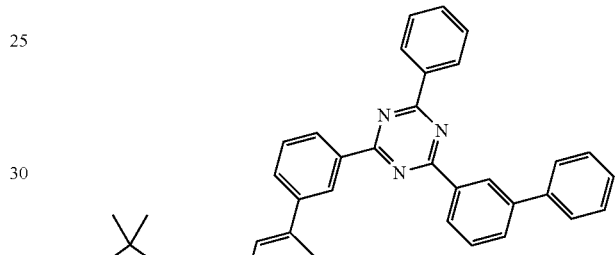
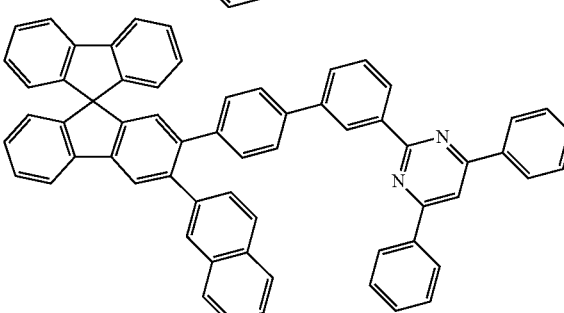
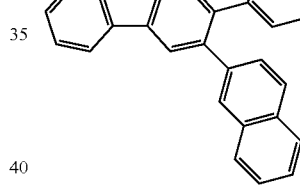
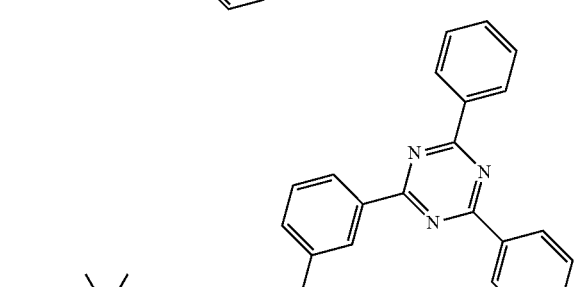
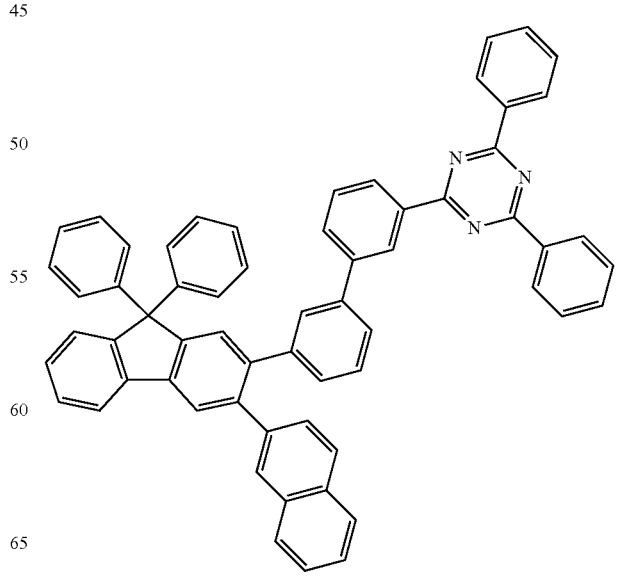

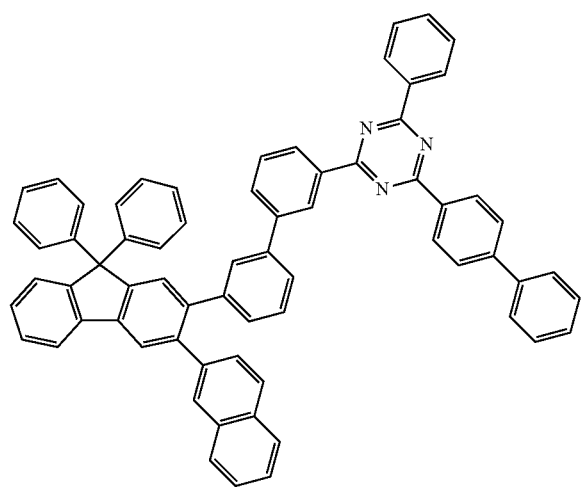
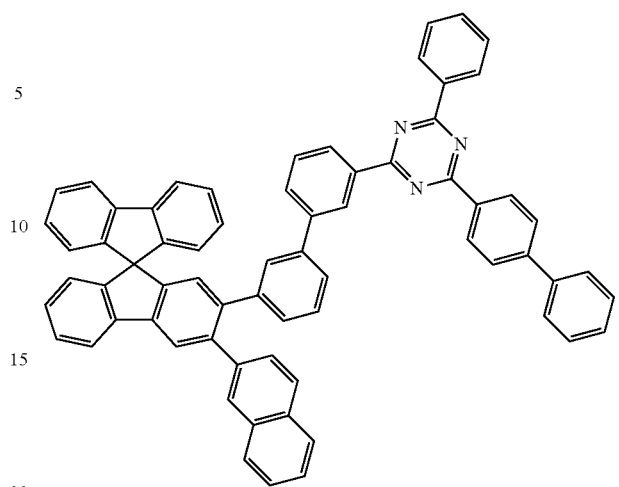
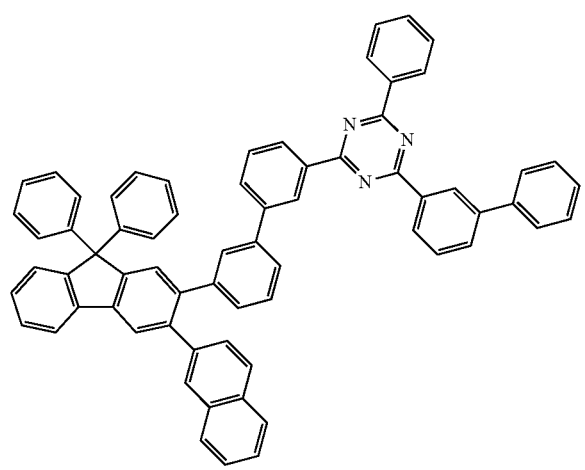
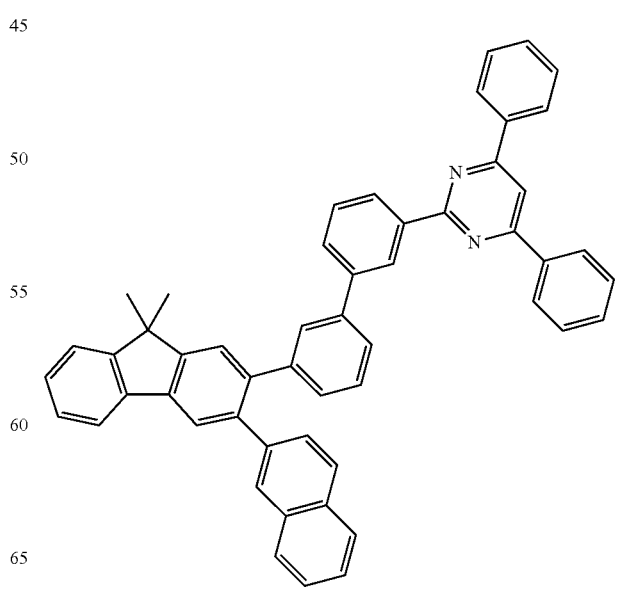

73
-continued
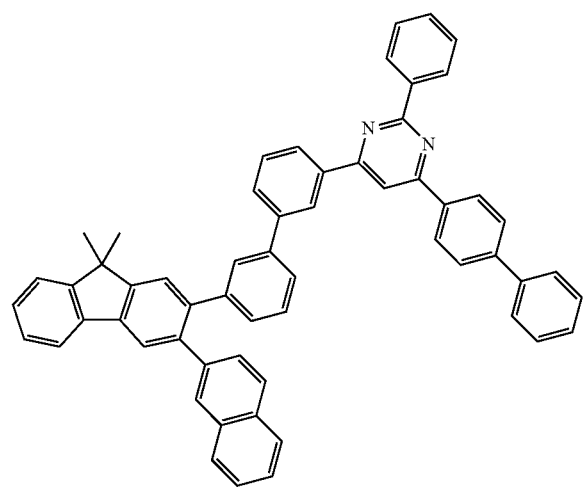
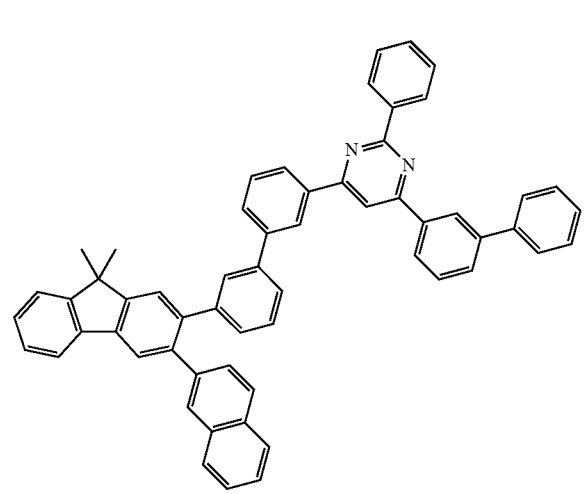
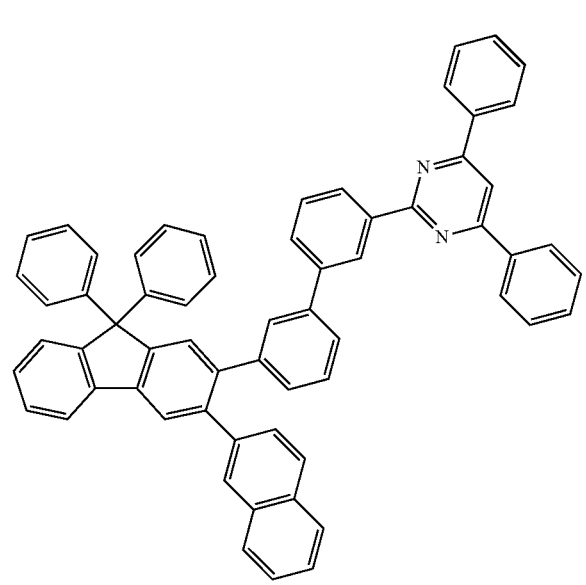
74
-continued
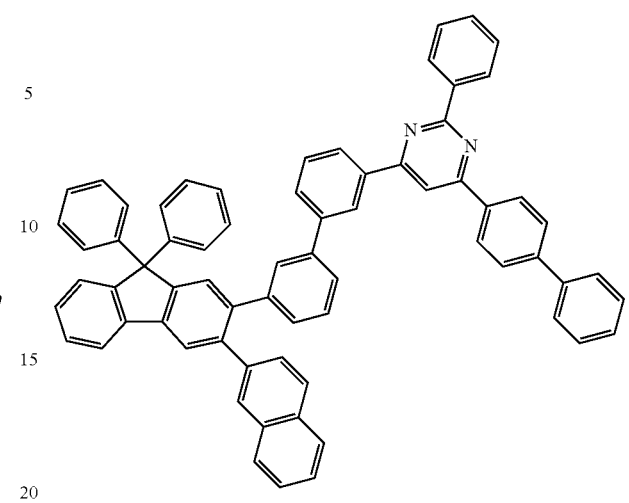
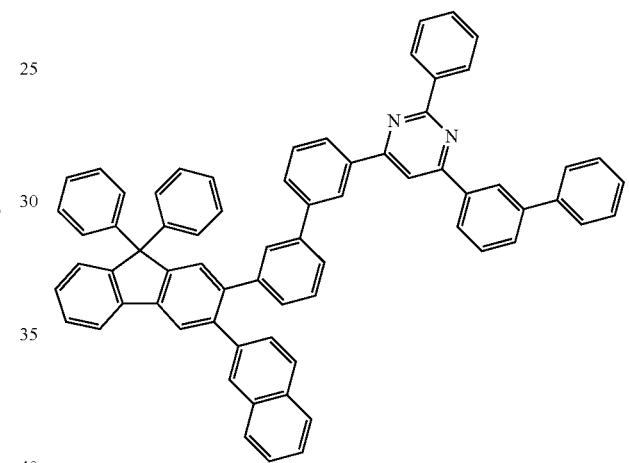
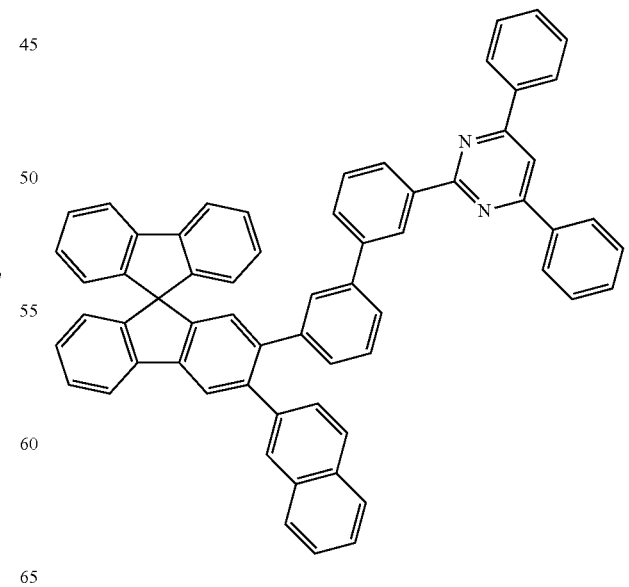

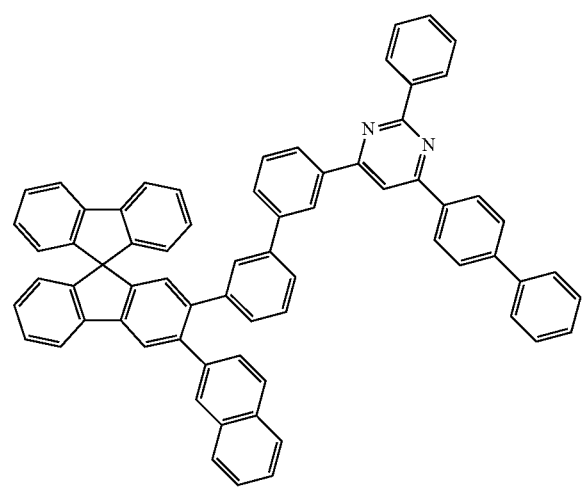
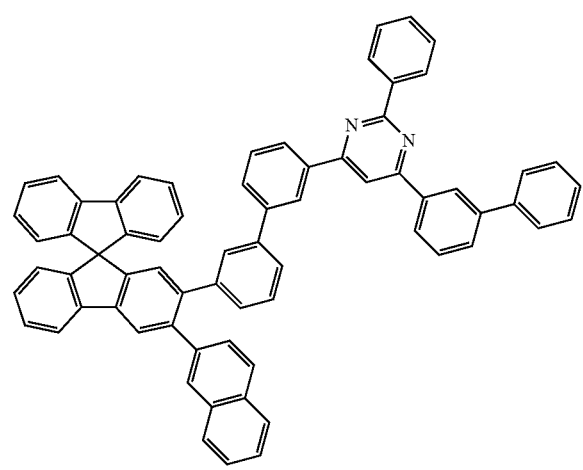
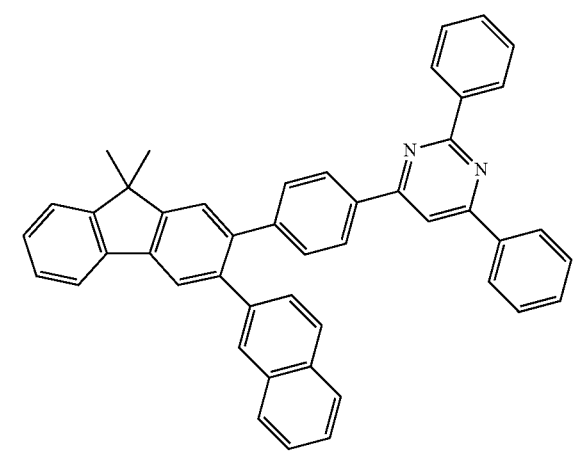
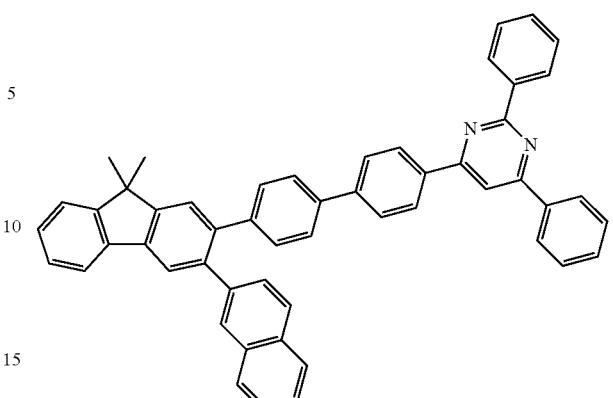
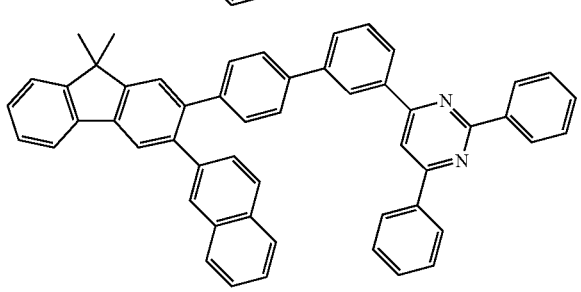
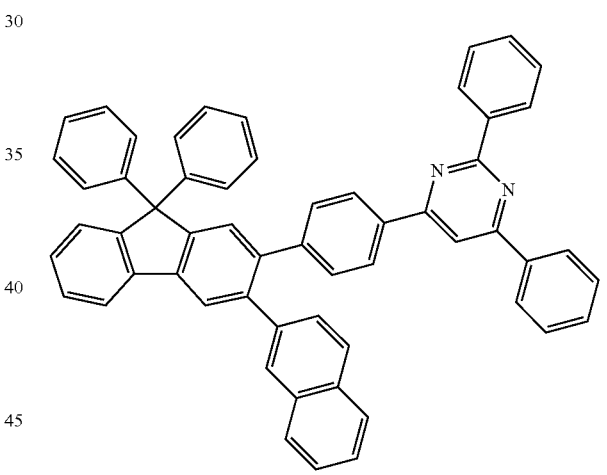
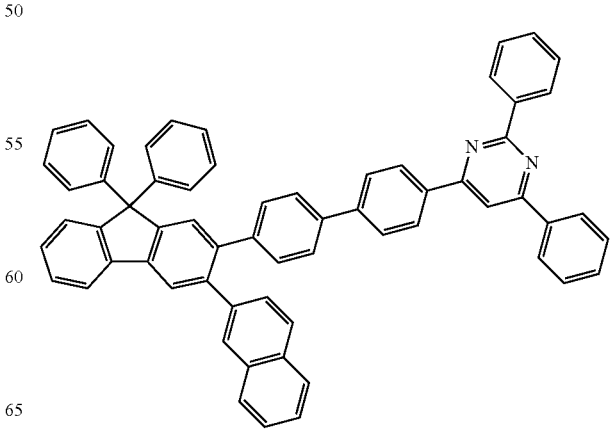

77
-continued
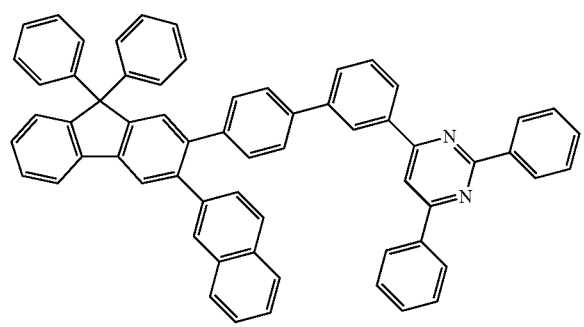
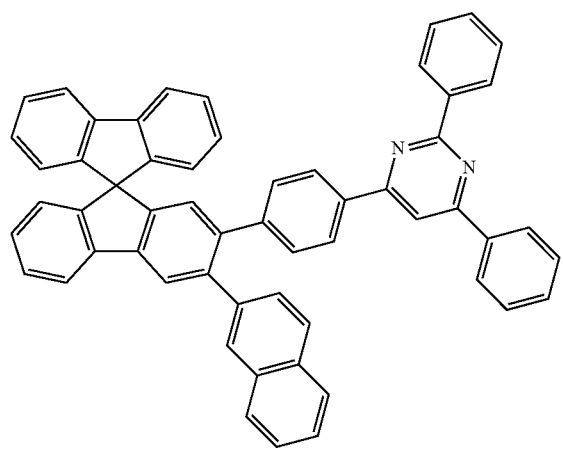
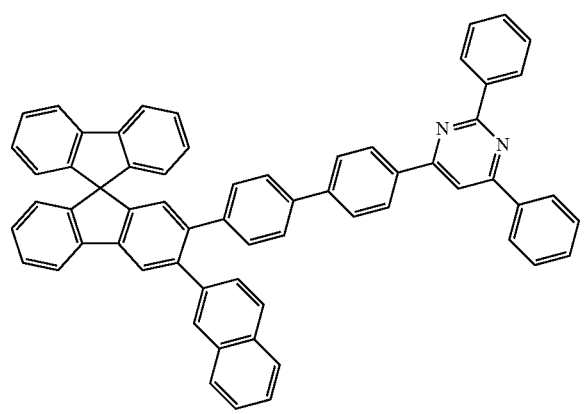
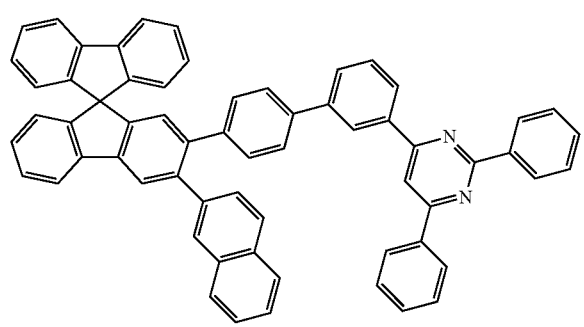
78
-continued
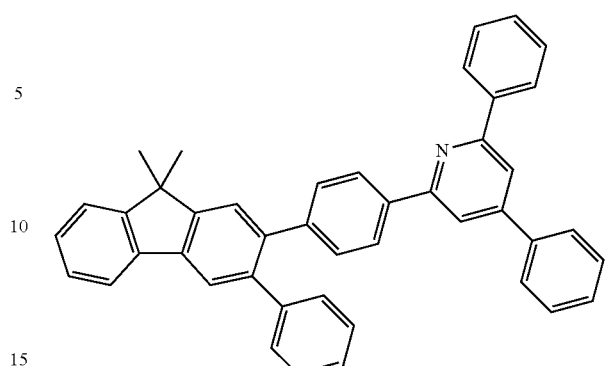
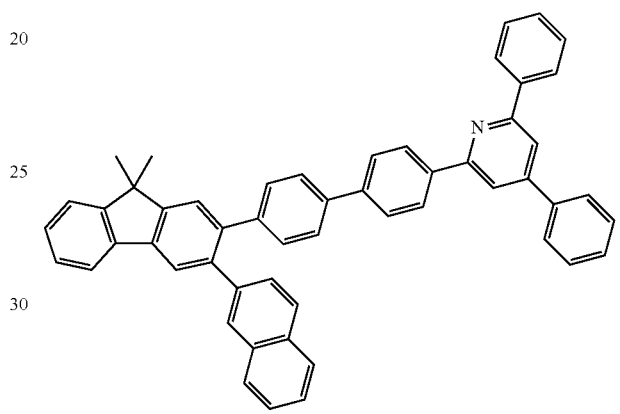
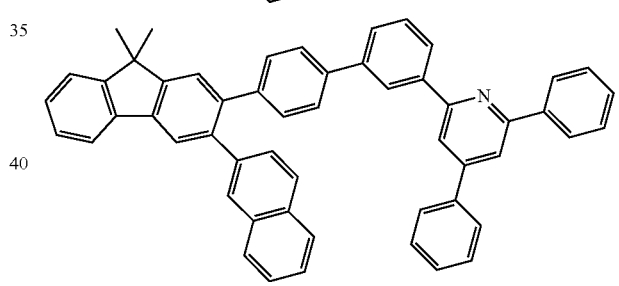
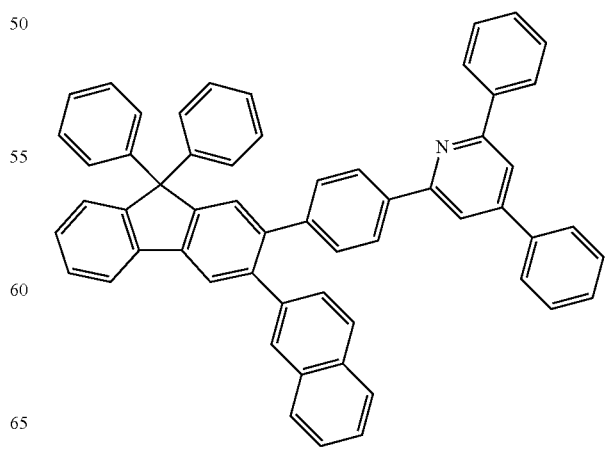

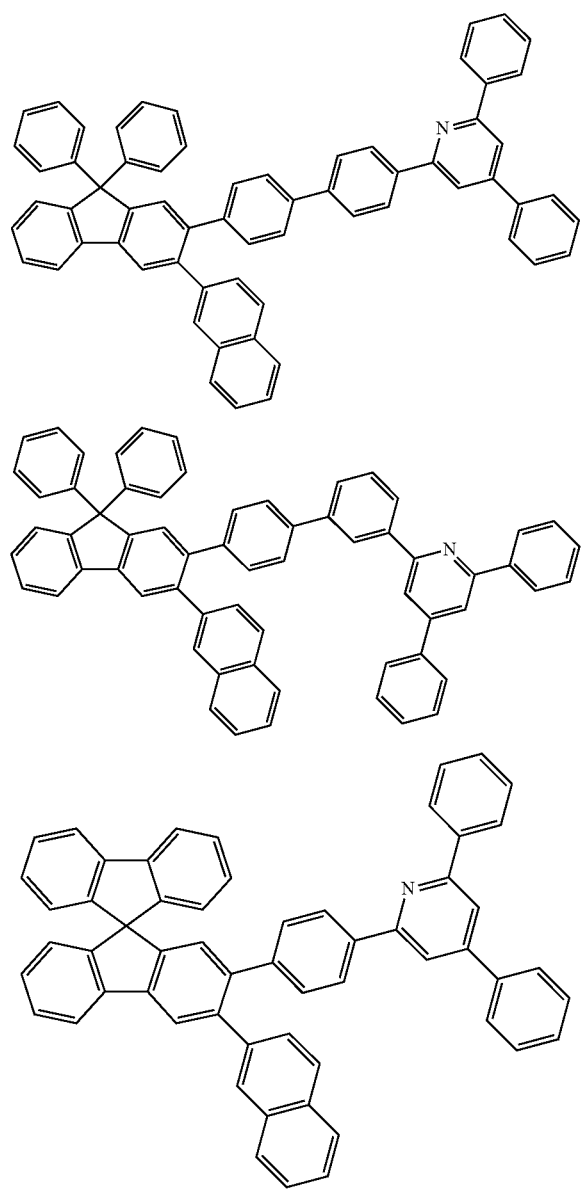
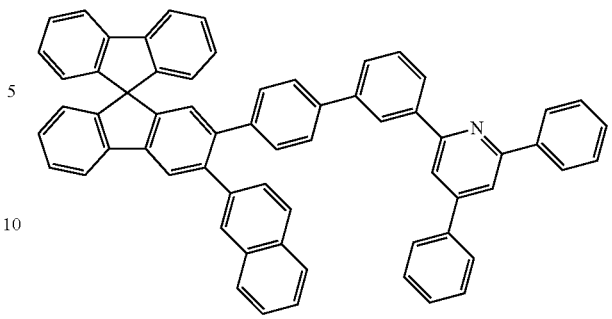
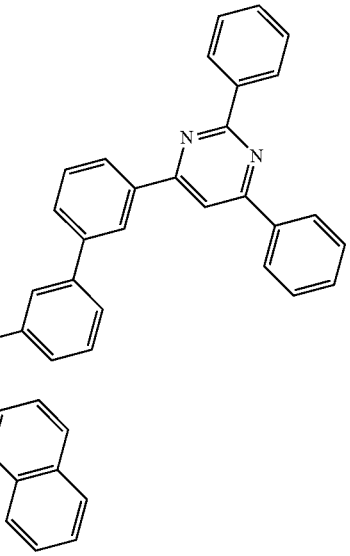
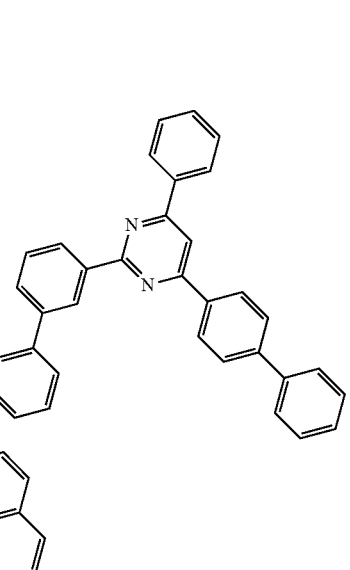

81
-continued
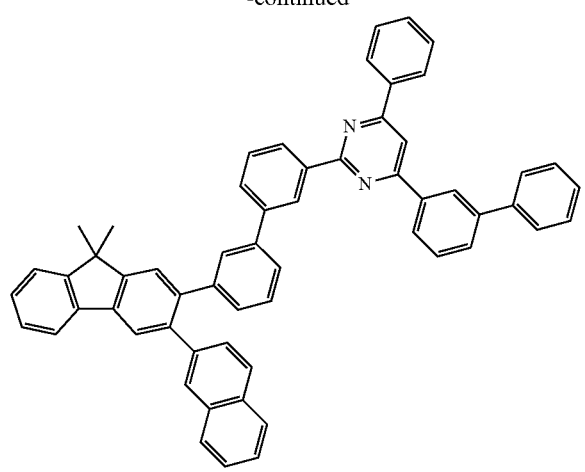
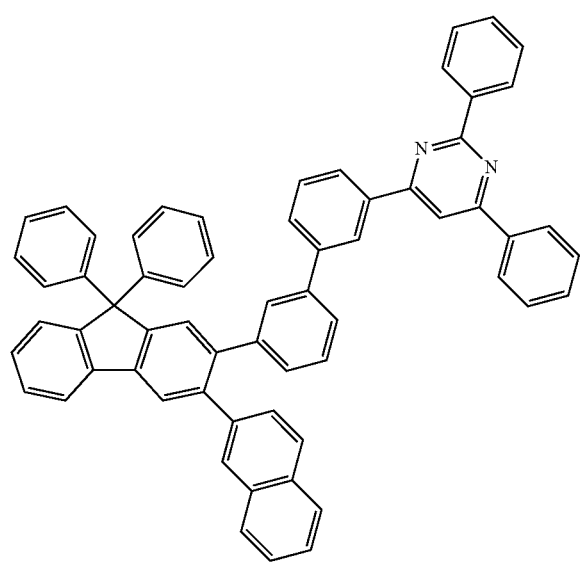
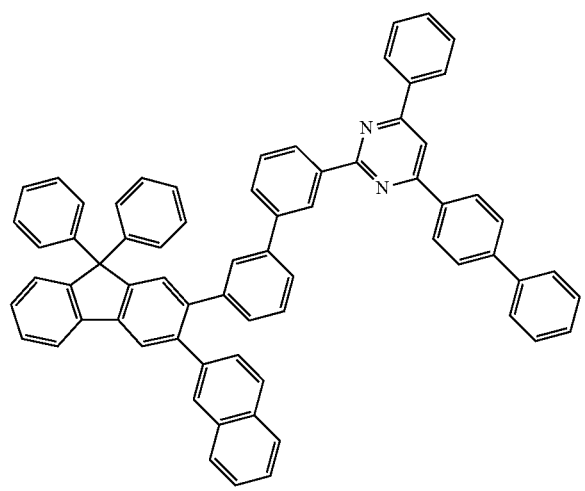
82
-continued
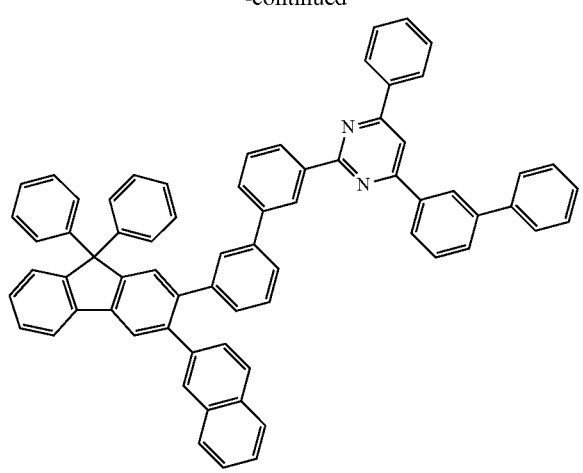
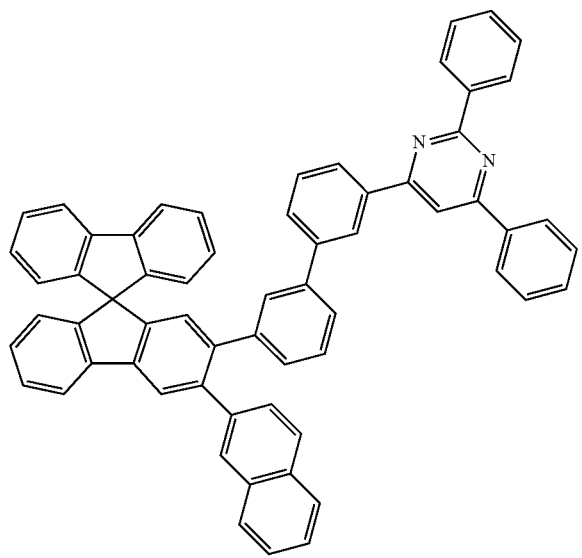
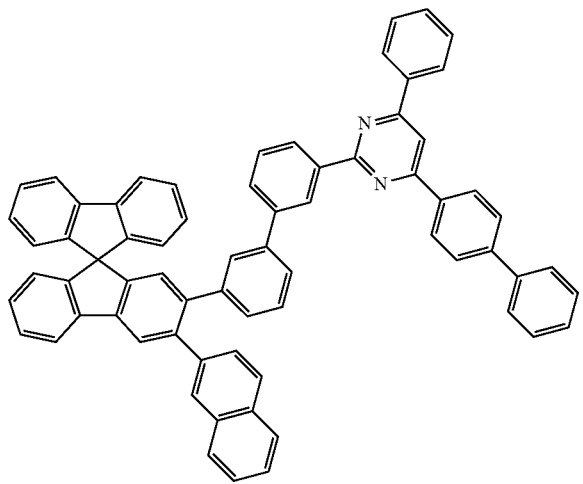

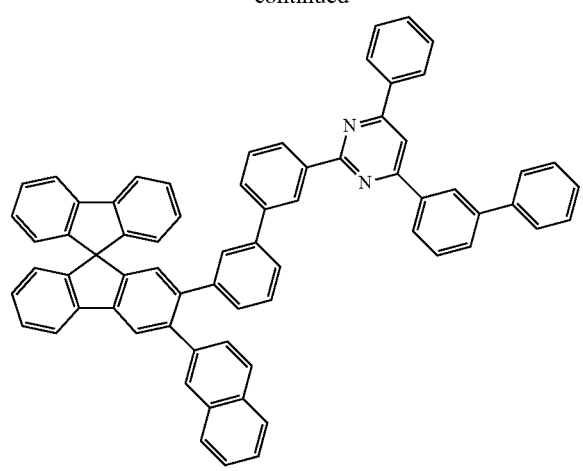
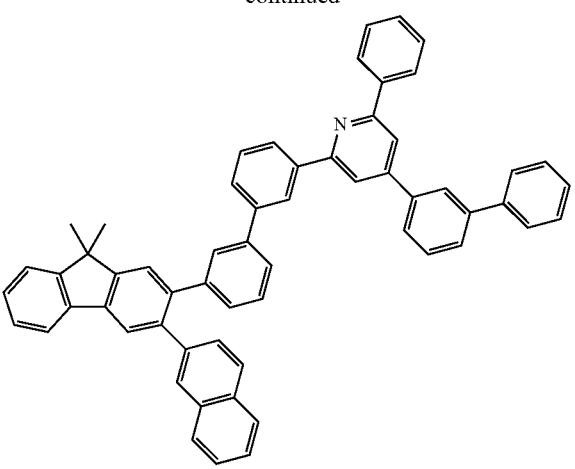
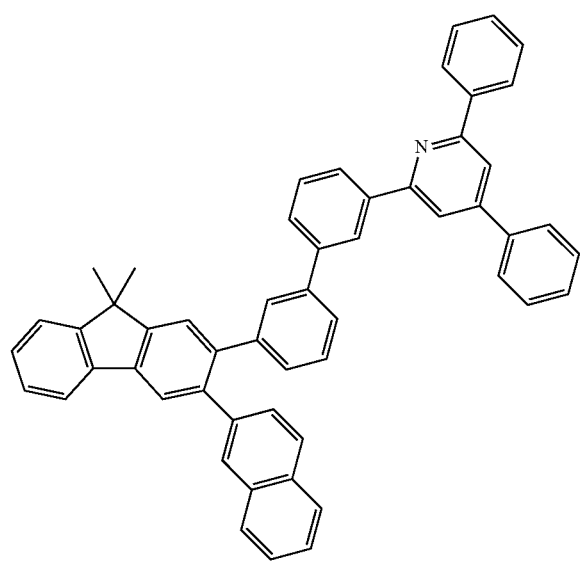
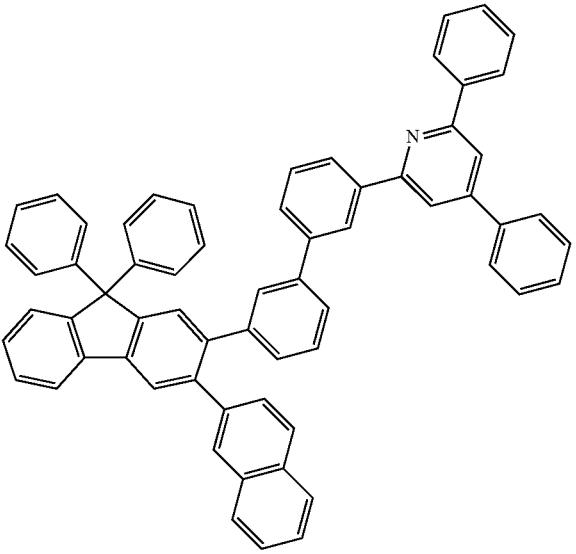
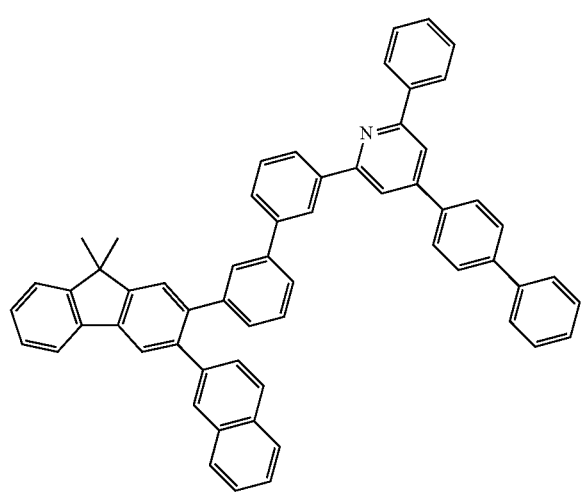
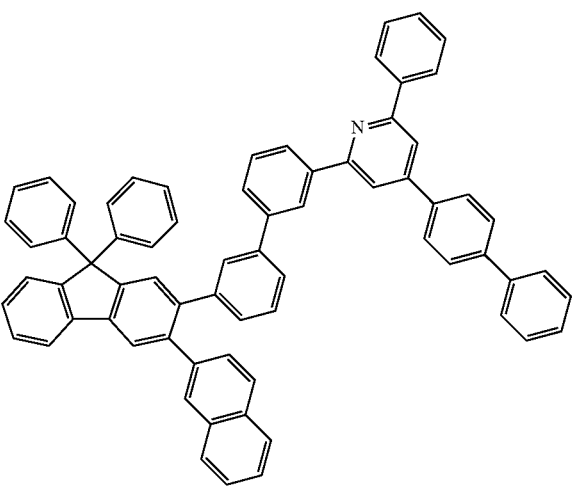

85
-continued
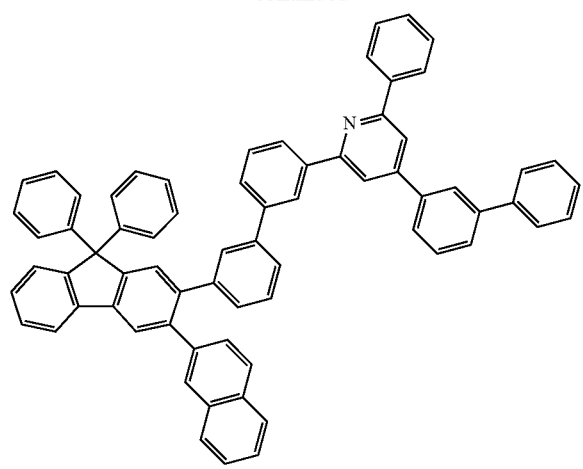
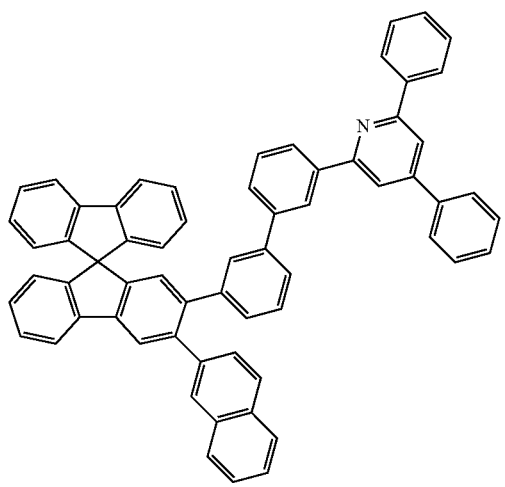
86
-continued
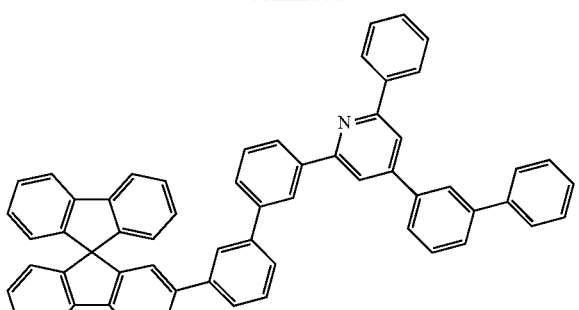
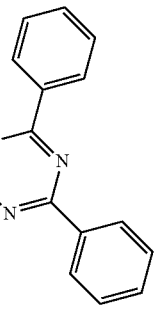
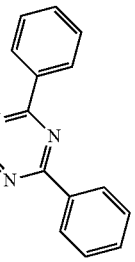
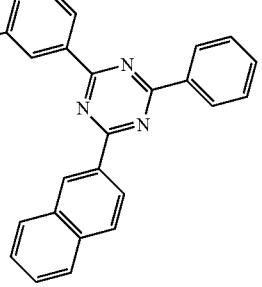

-continued
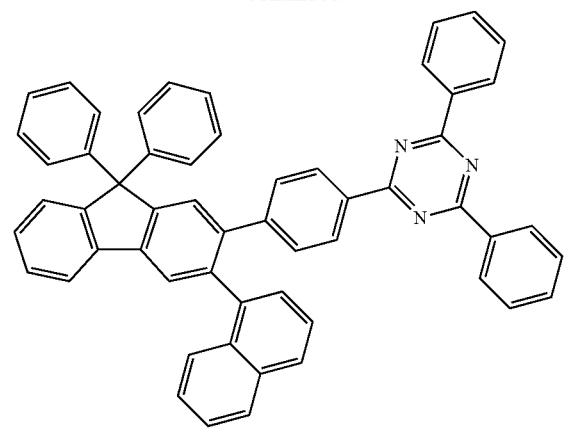
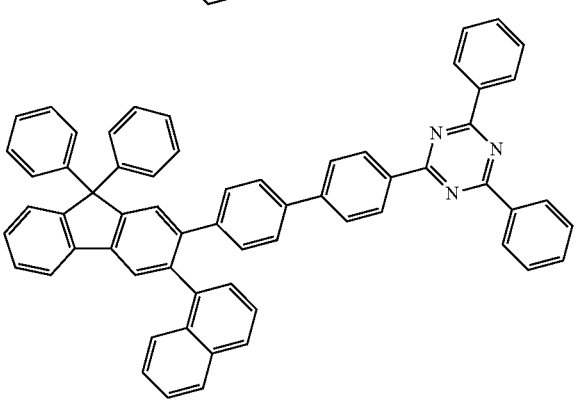
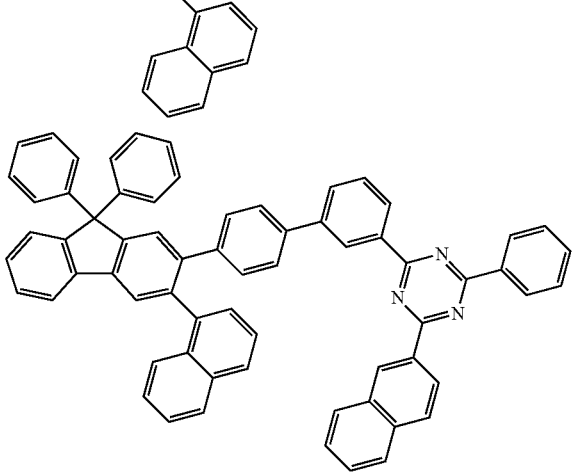
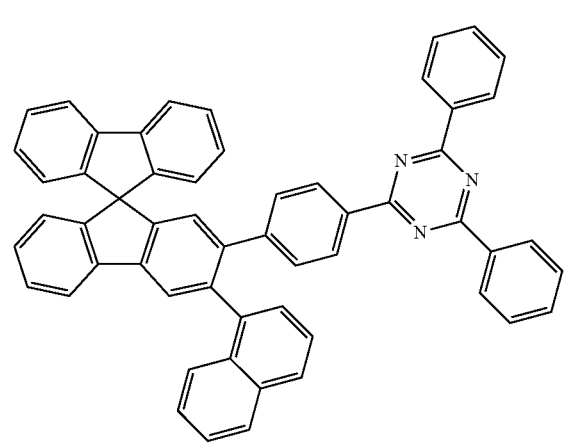
-continued
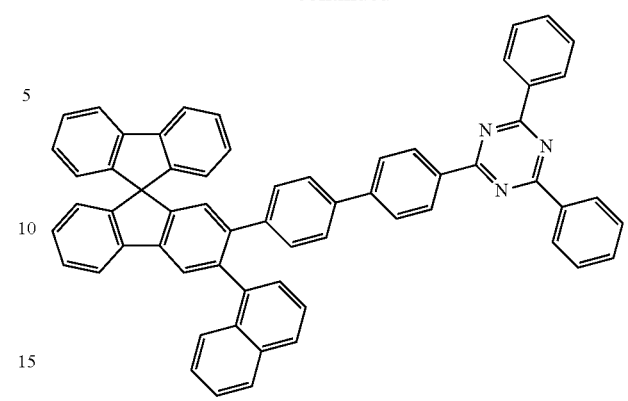
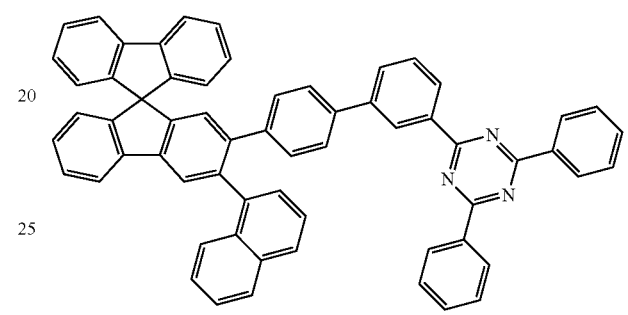
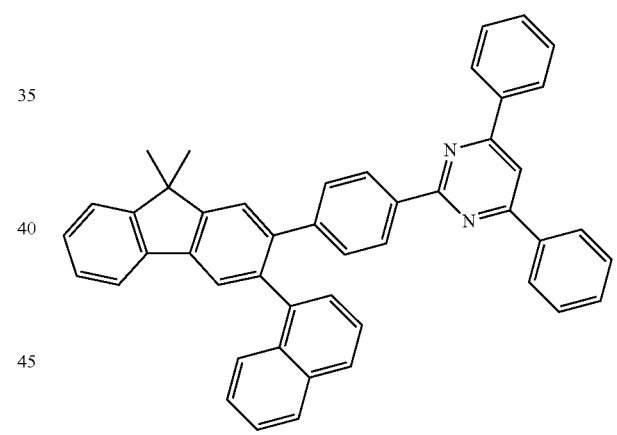
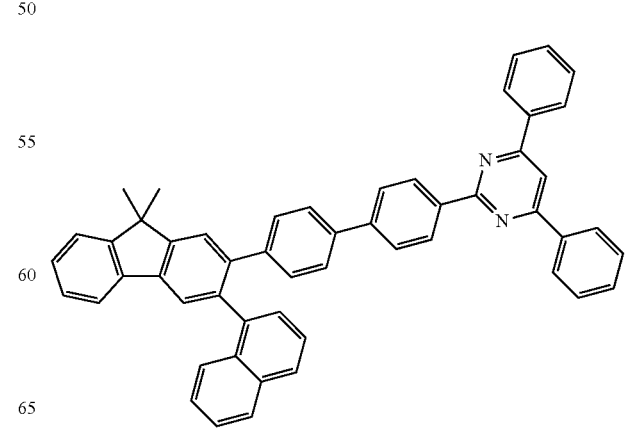

89
-continued
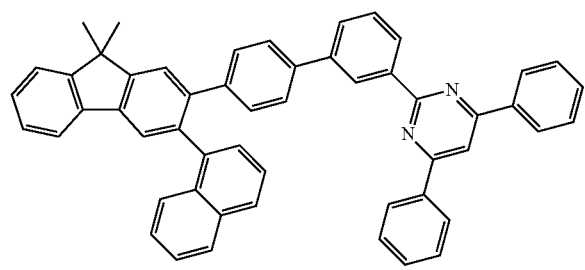
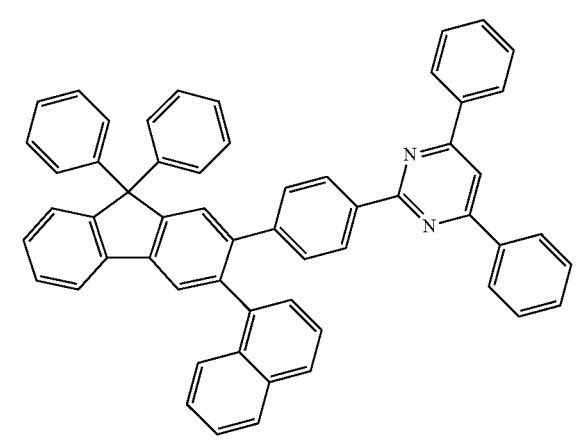
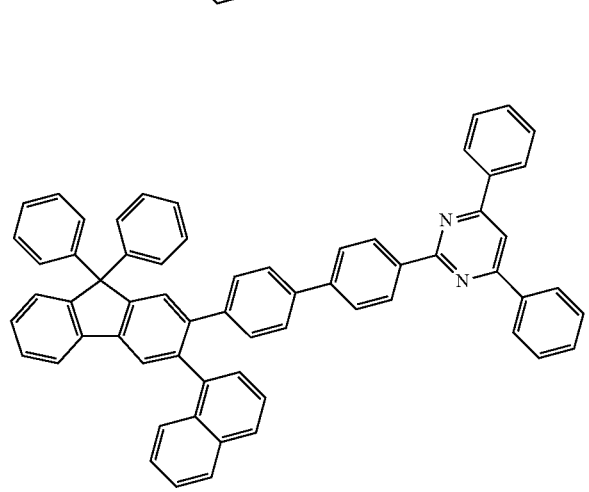
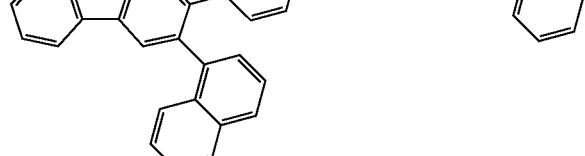
90
-continued
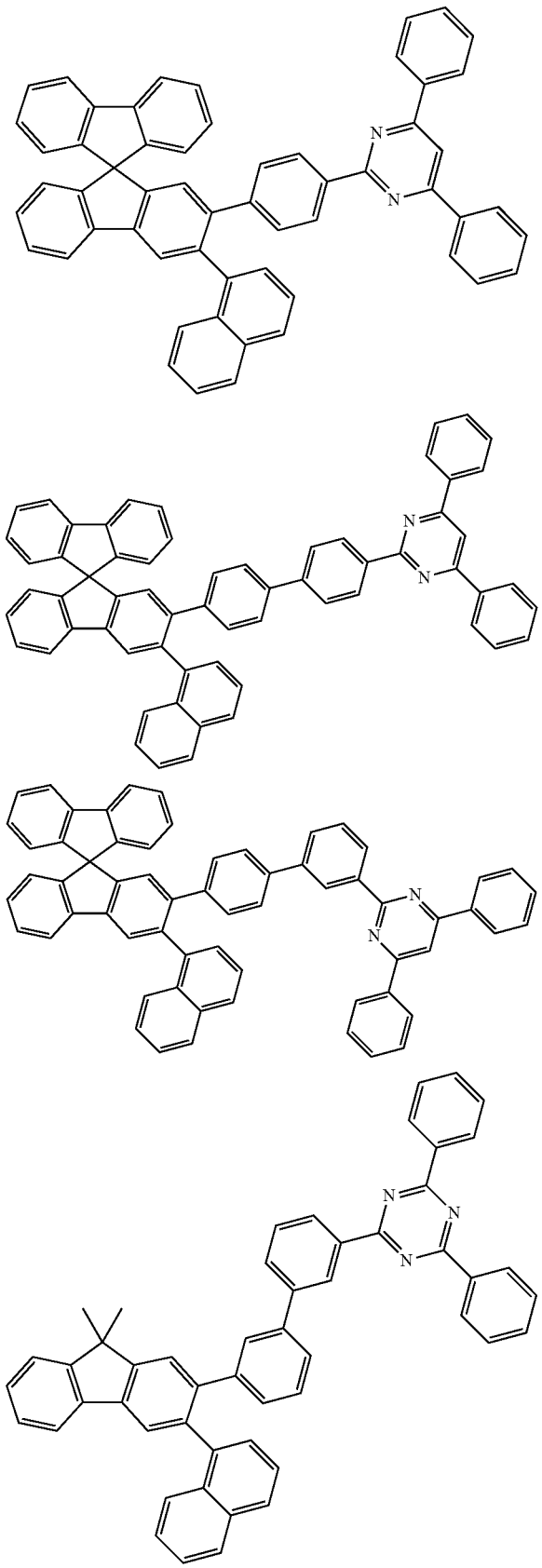

91
-continued
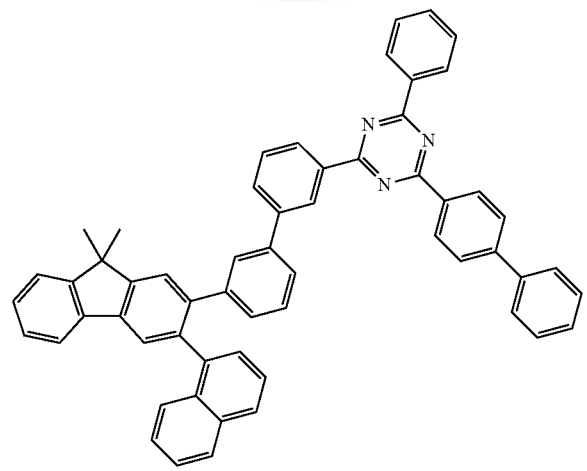
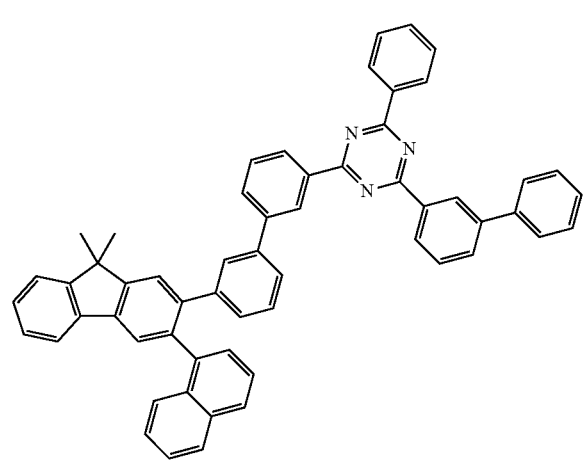
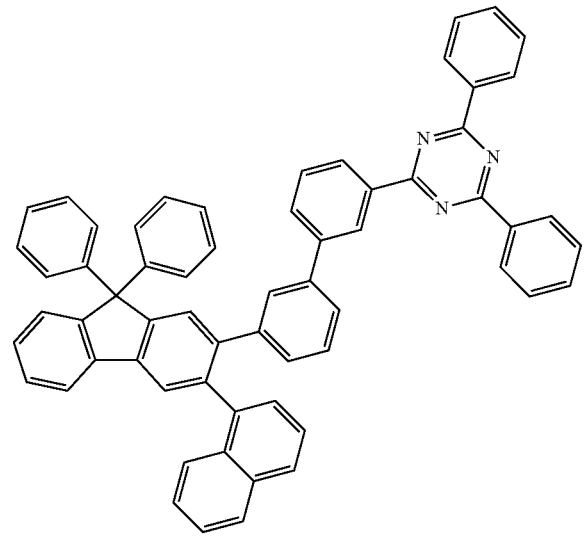
92
-continued
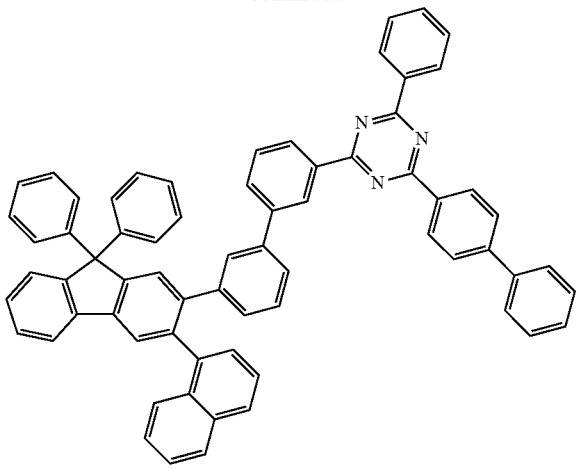
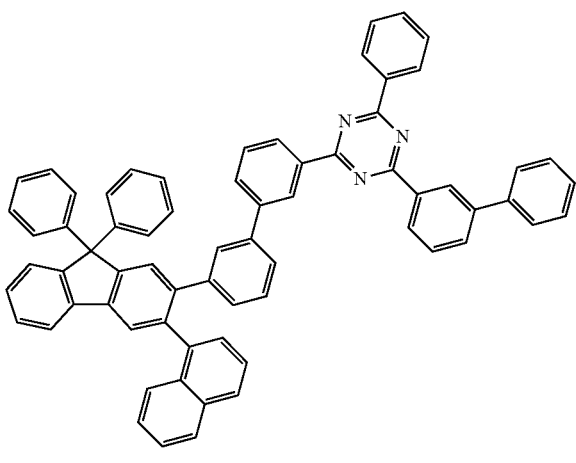
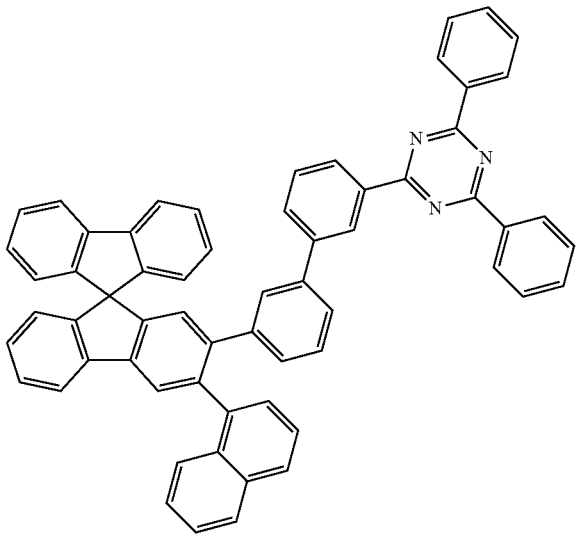

-continued
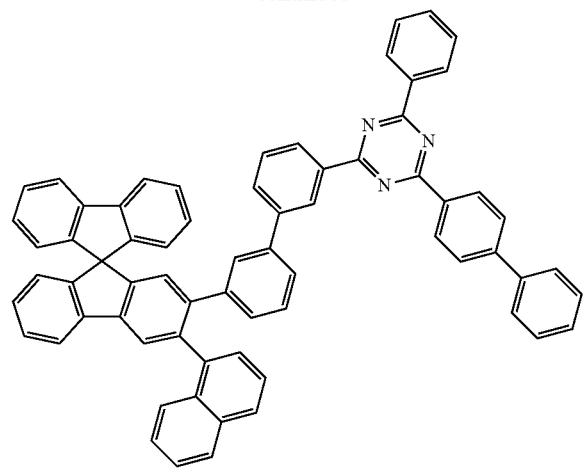
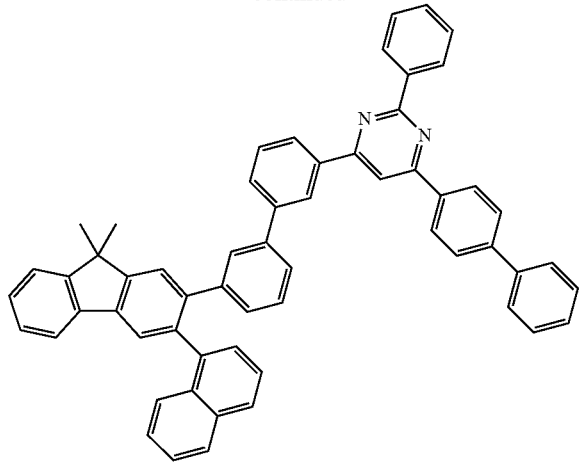
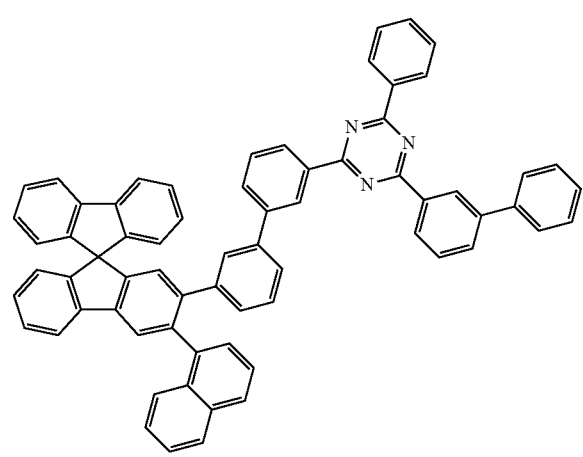
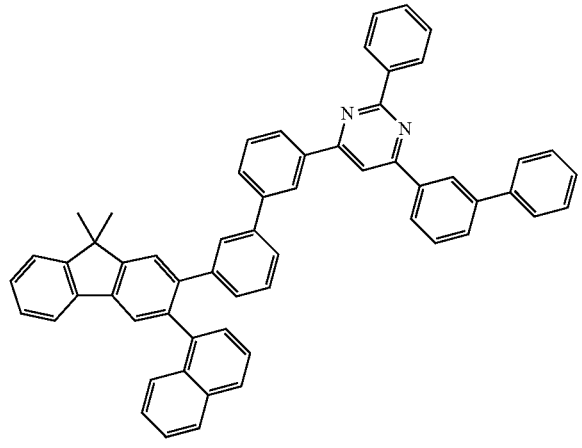
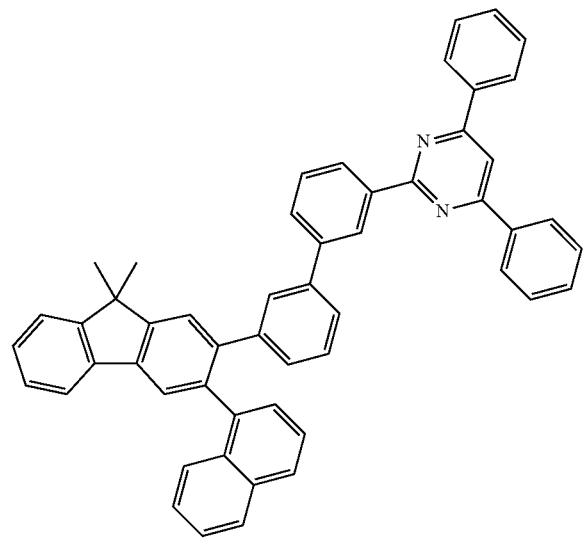
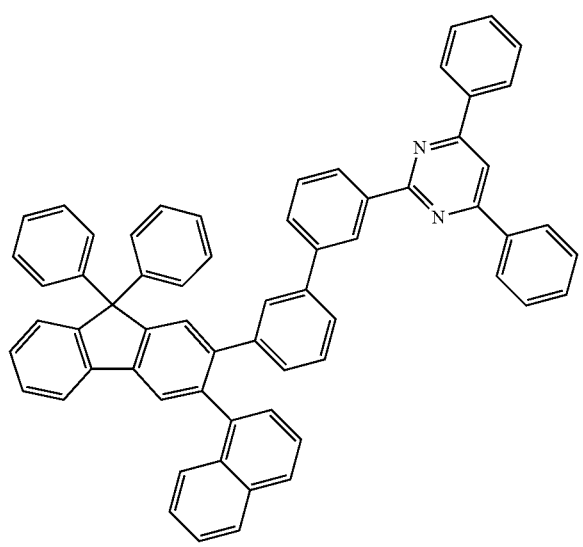

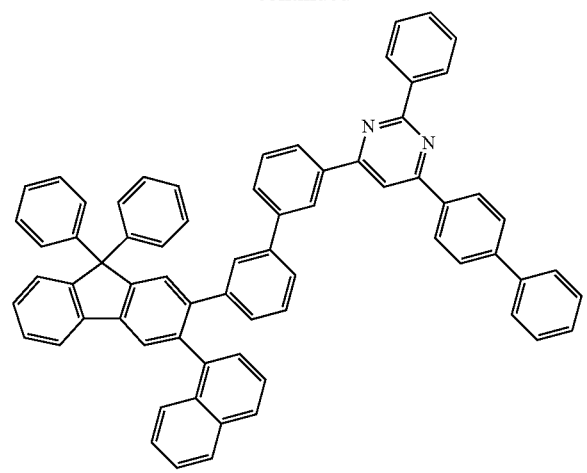
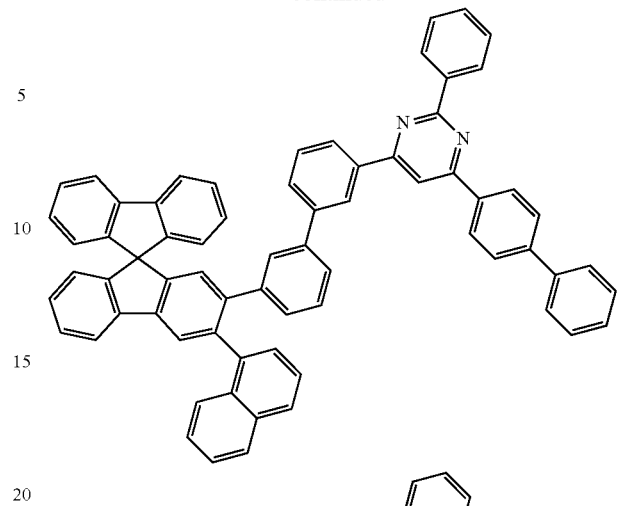
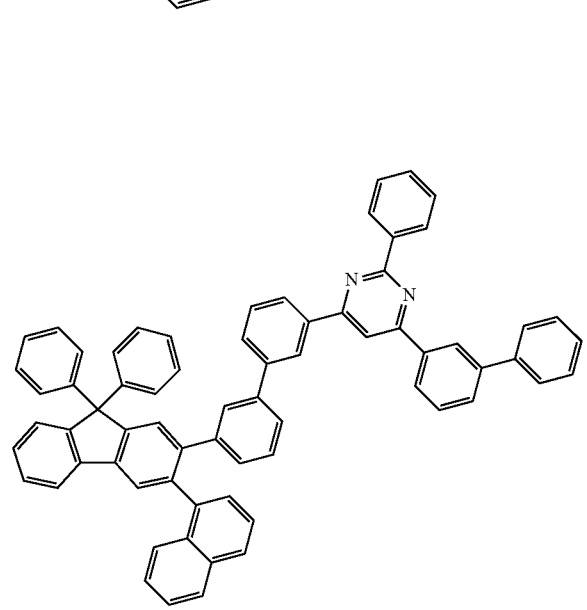
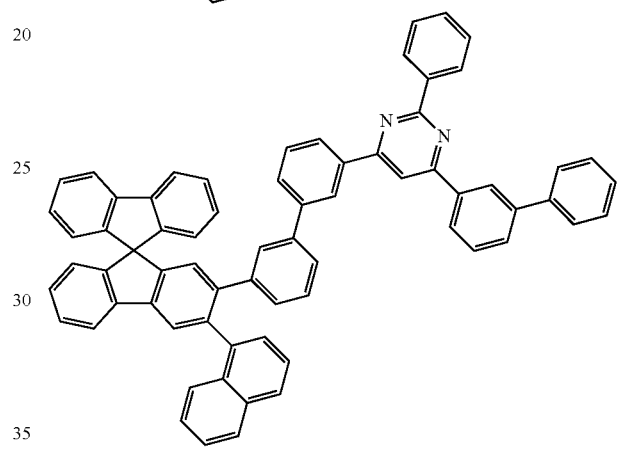
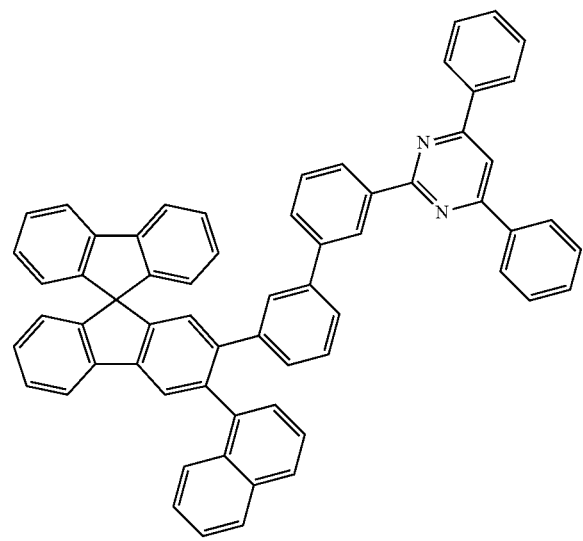
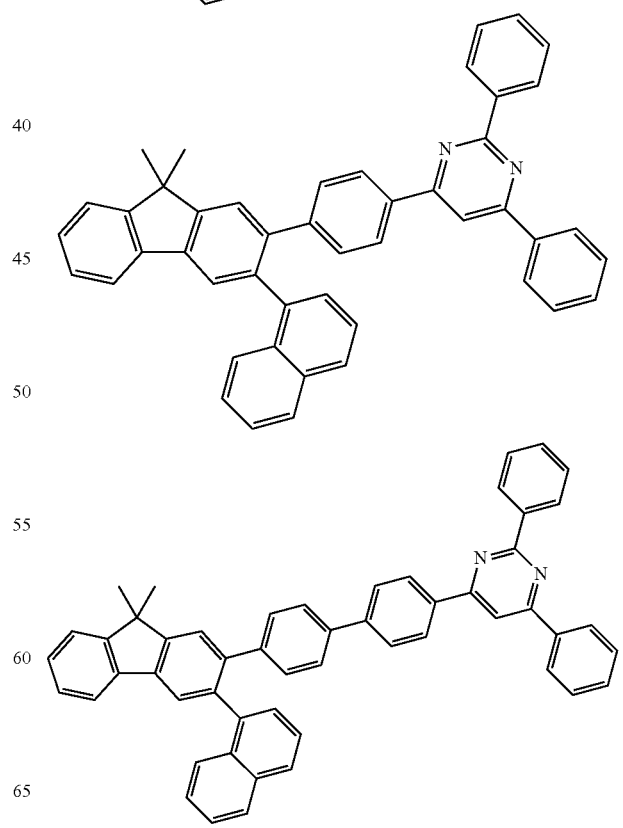

-continued
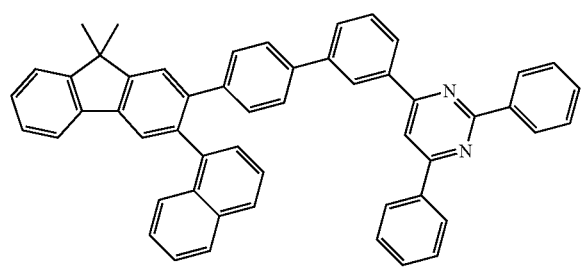
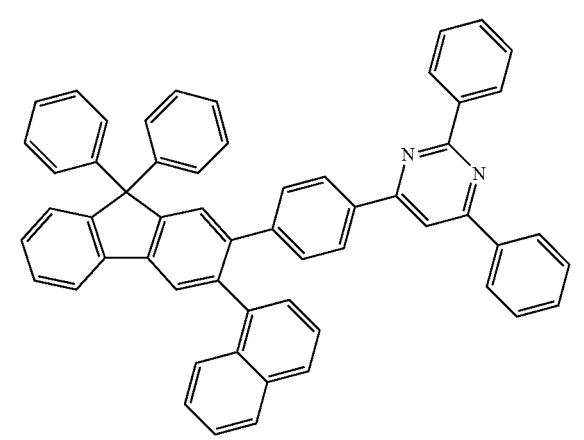
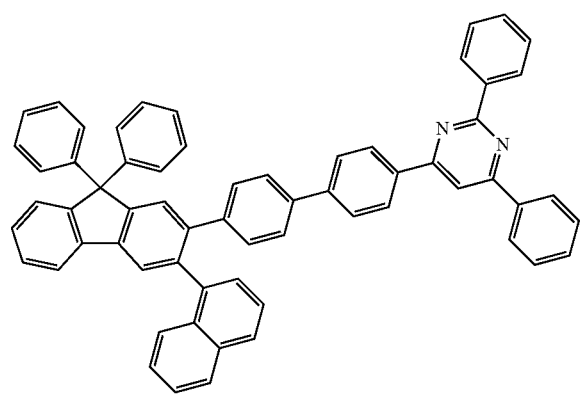
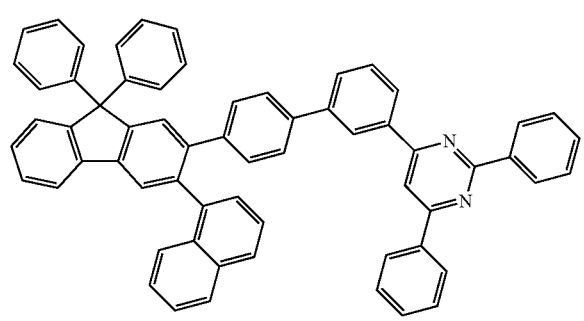
-continued
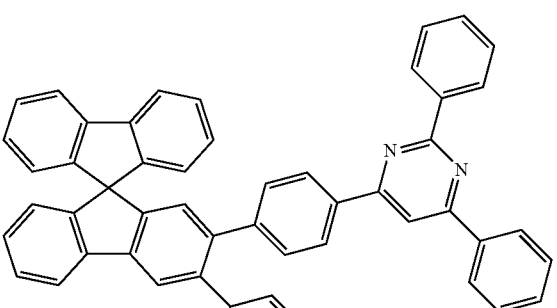
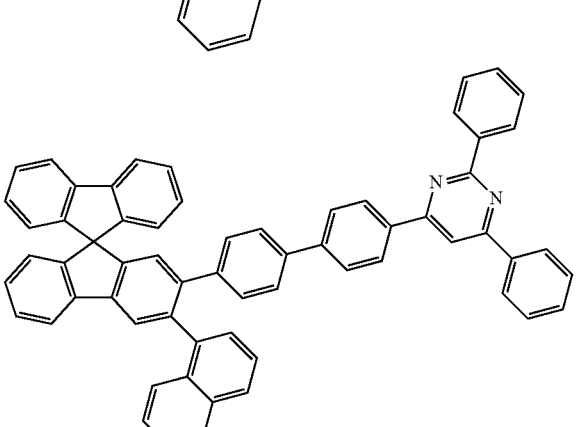
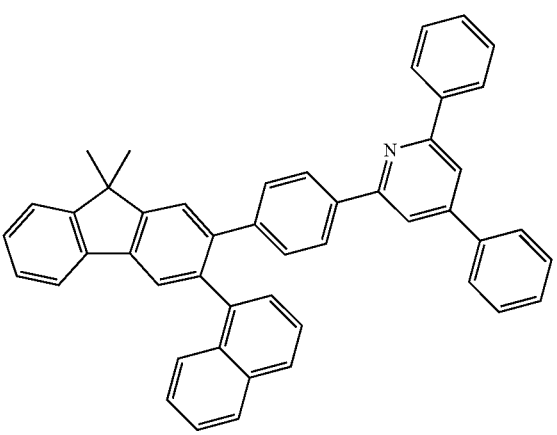

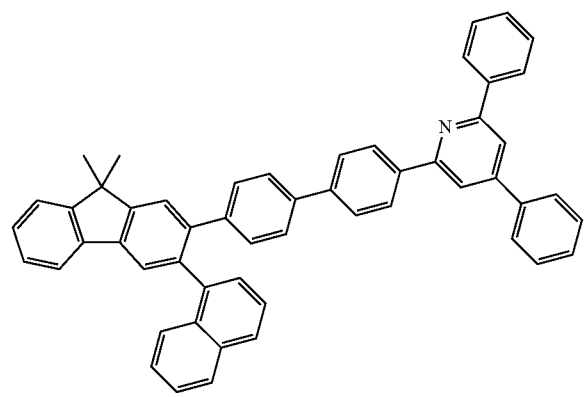
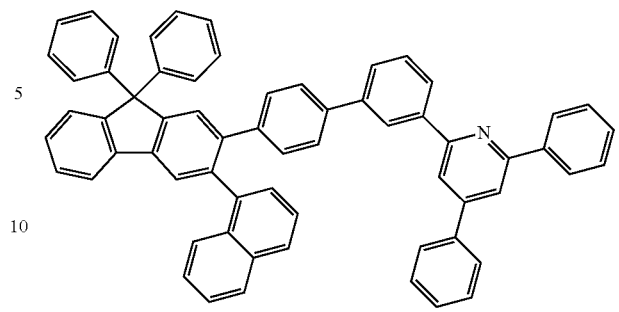
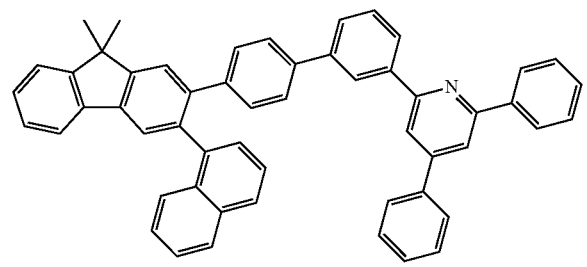
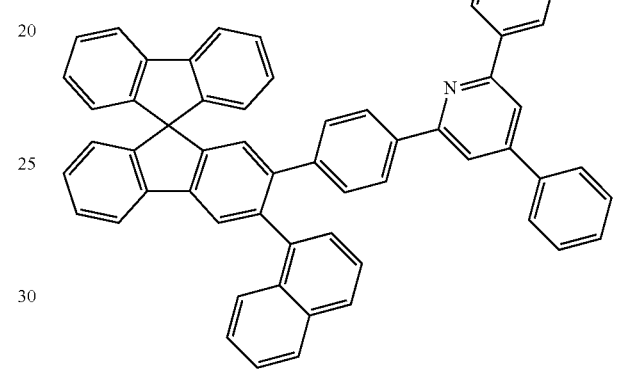
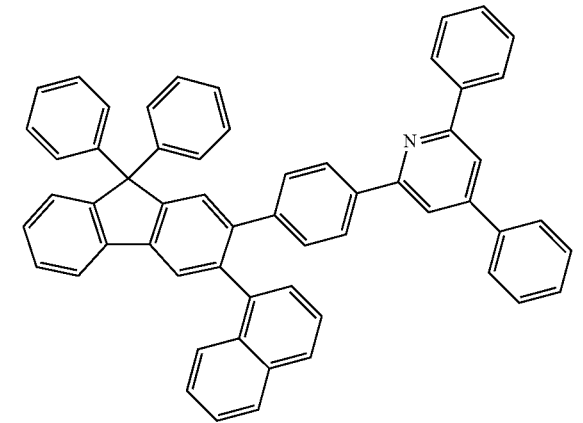
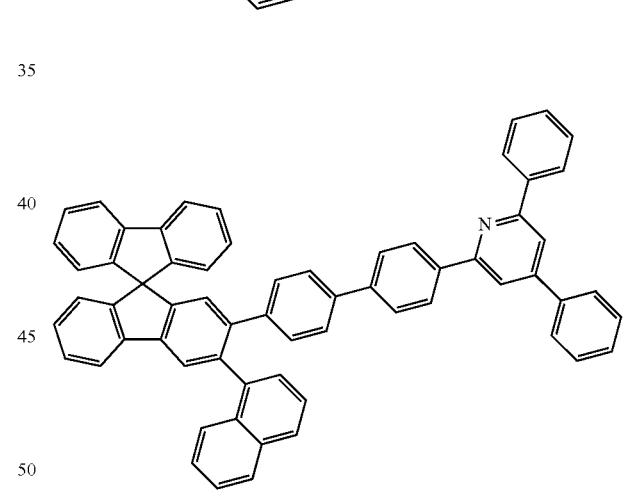
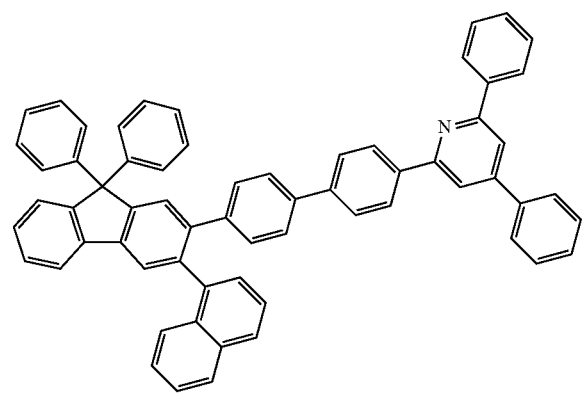
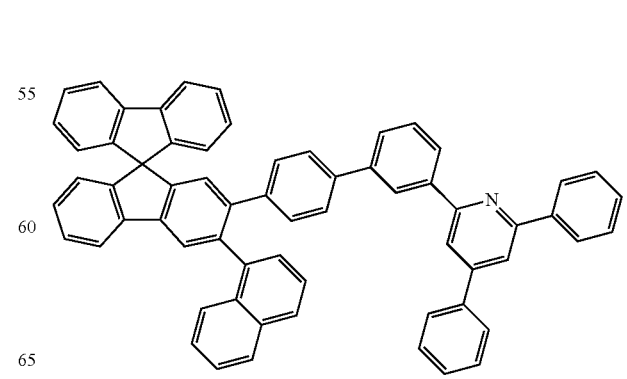

101
-continued
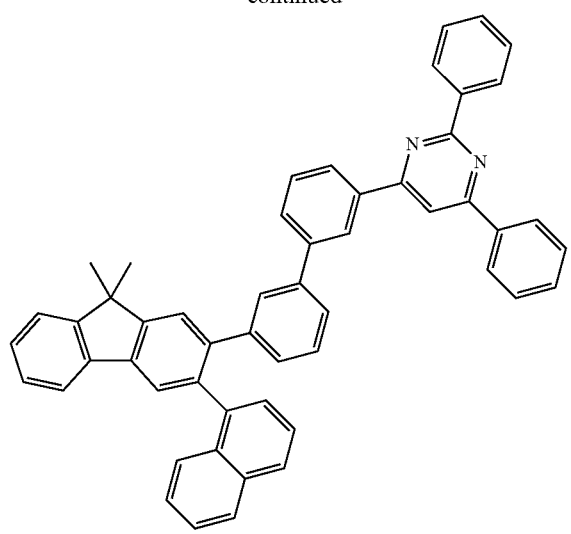
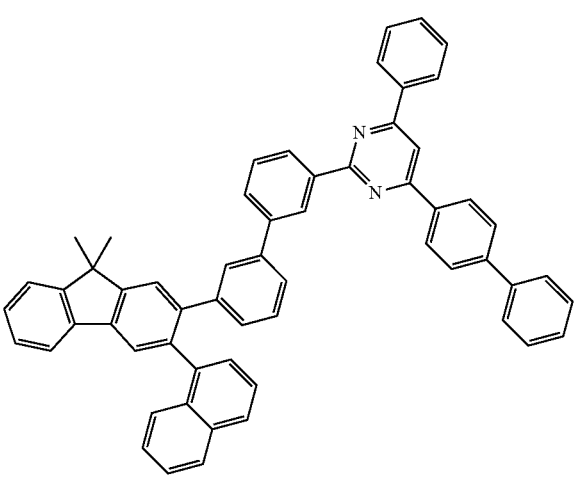
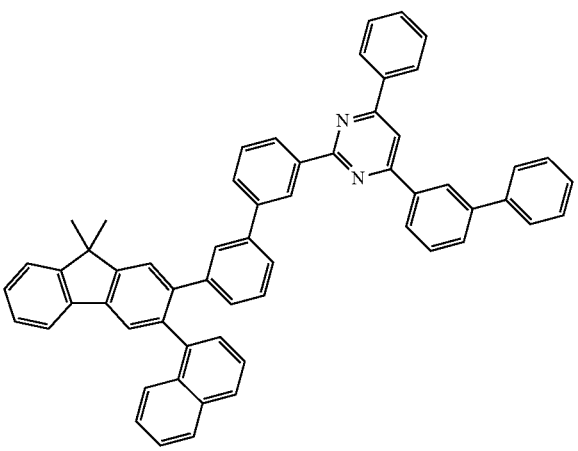
102
-continued
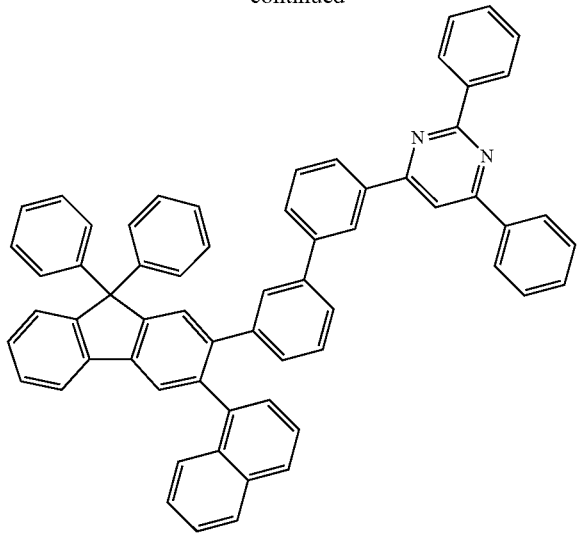
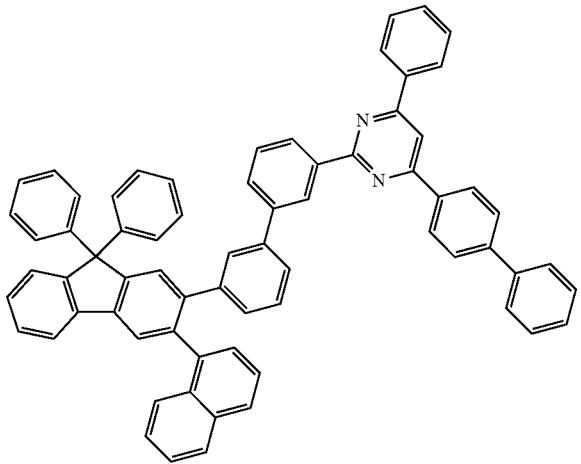
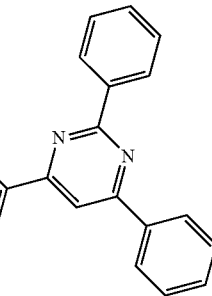

103
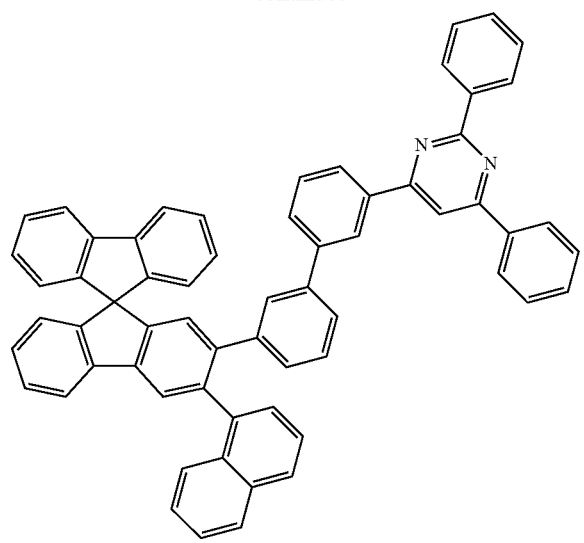
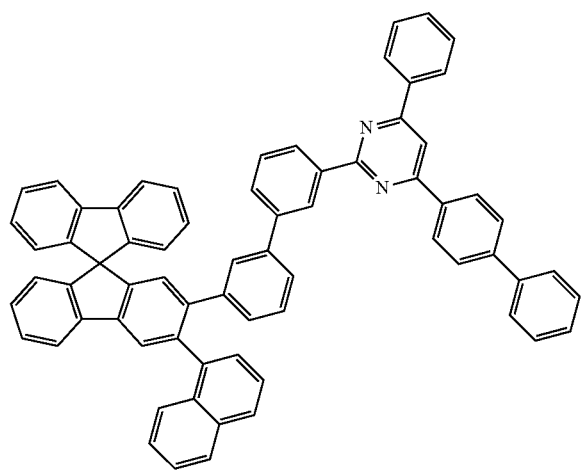
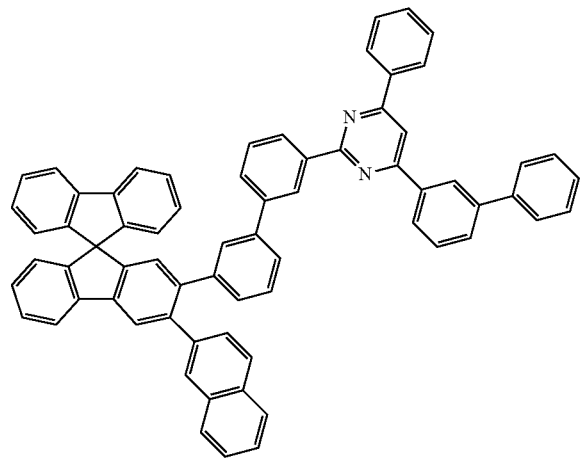
104
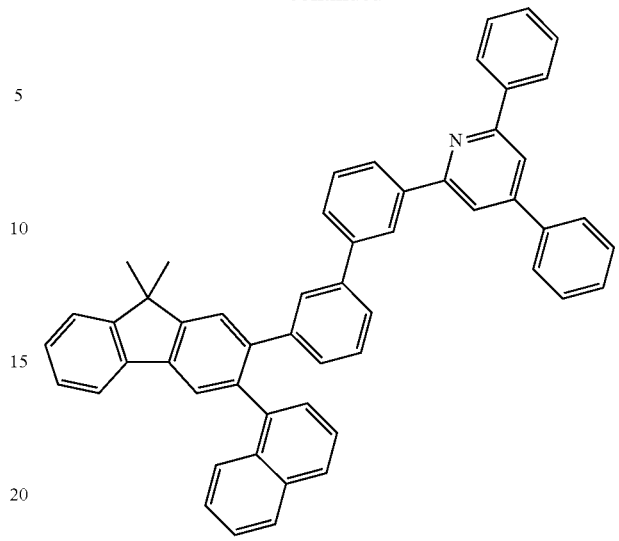

105
-continued
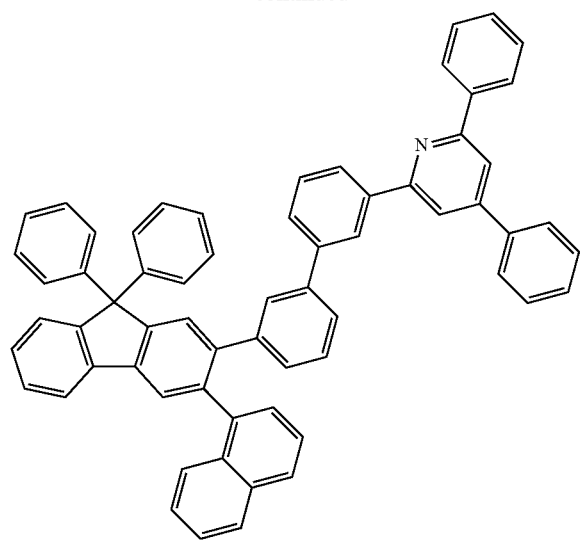
106
-continued
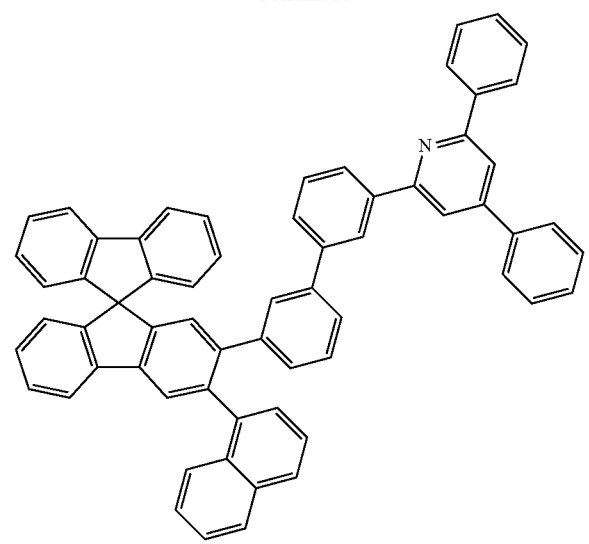
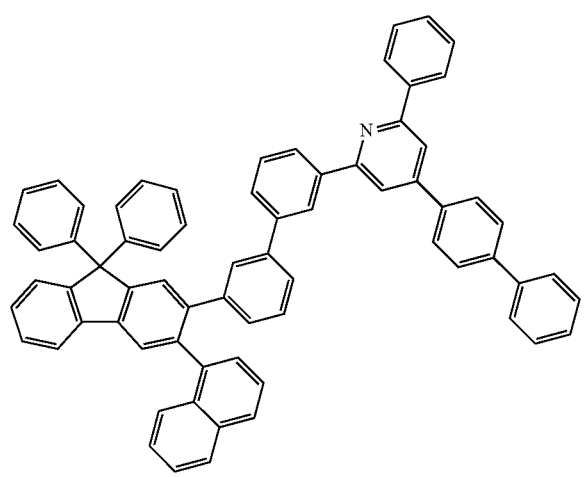
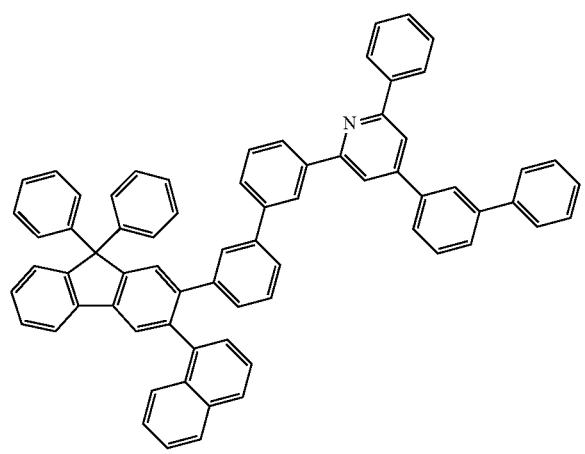
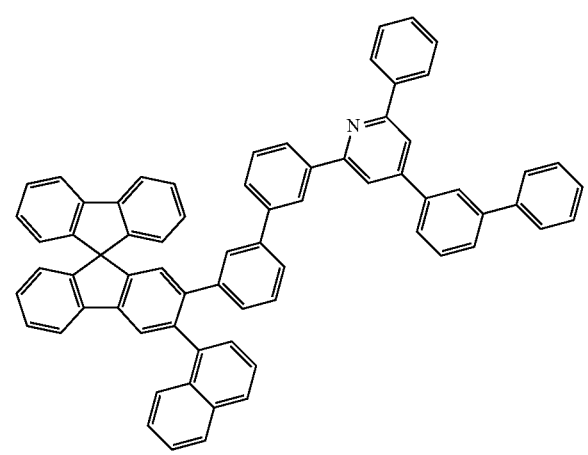

107
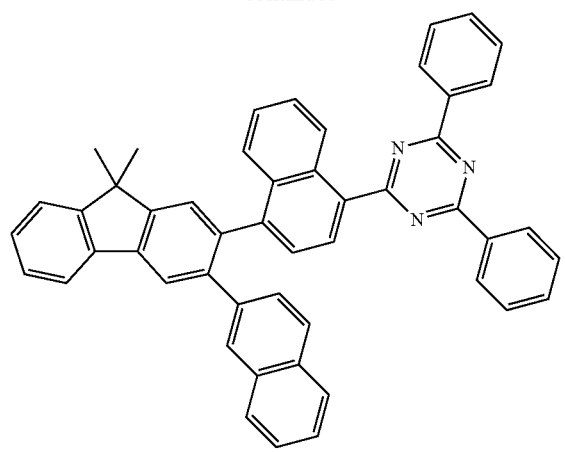
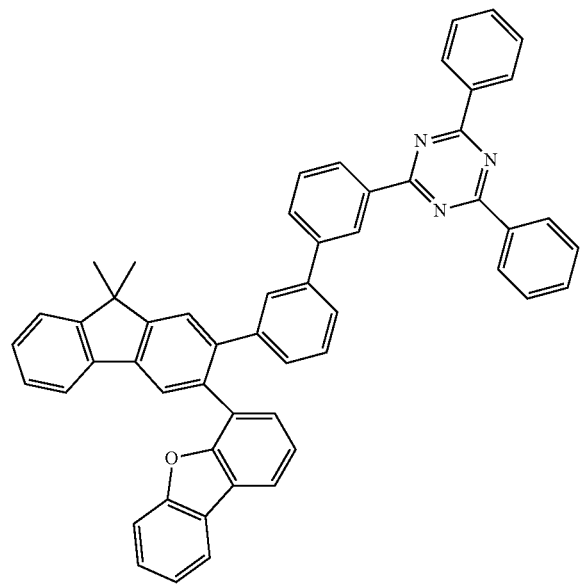
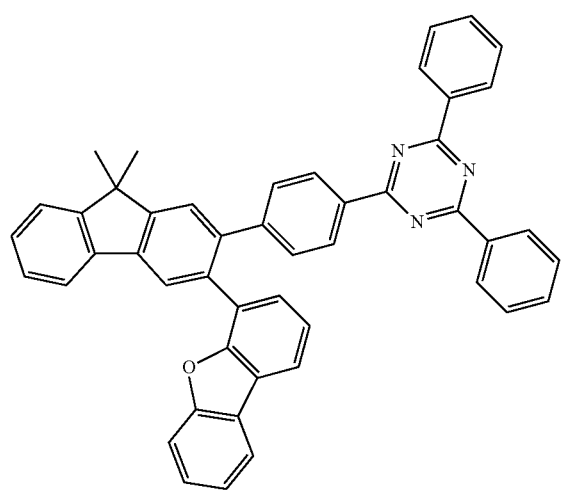
108
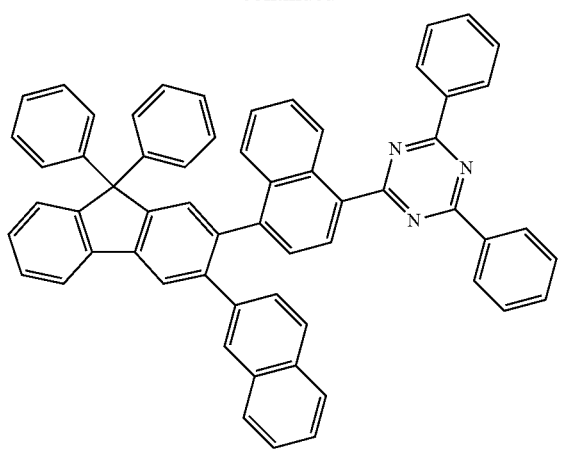
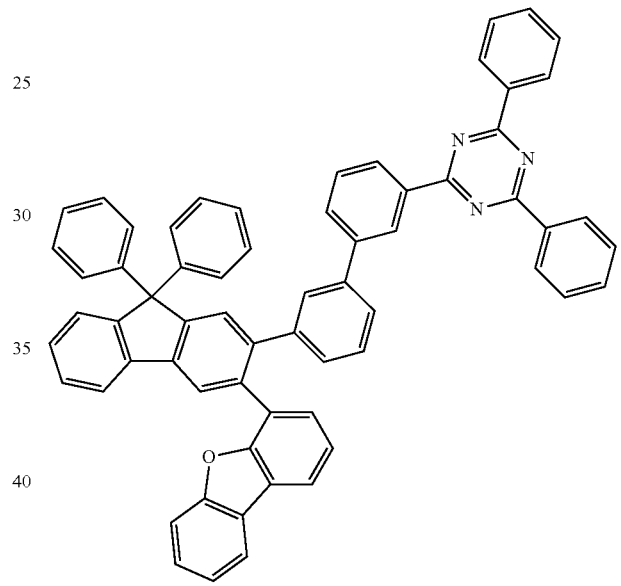
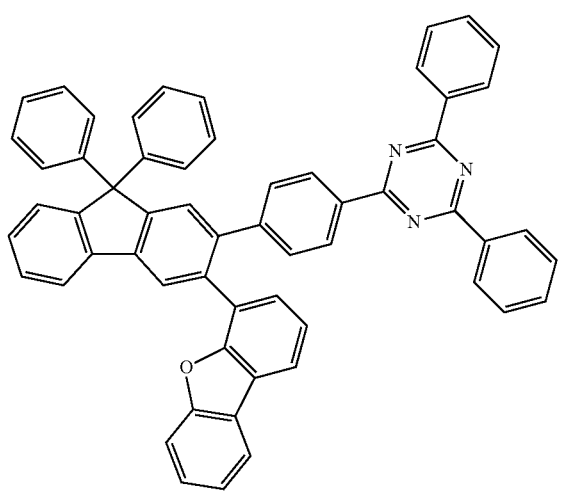

109
-continued
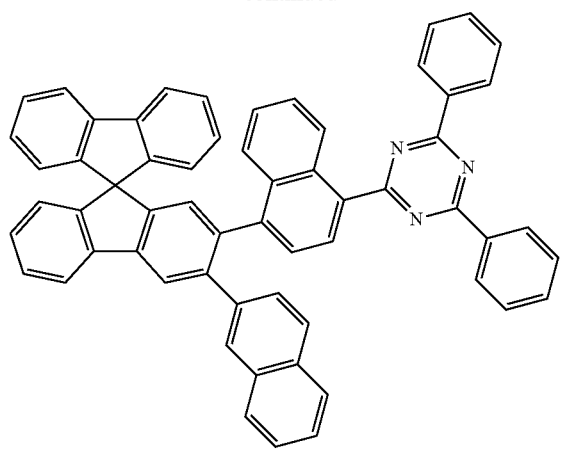
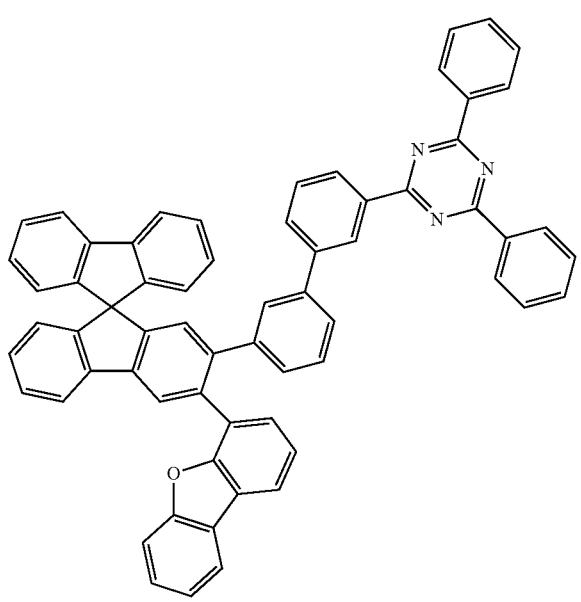
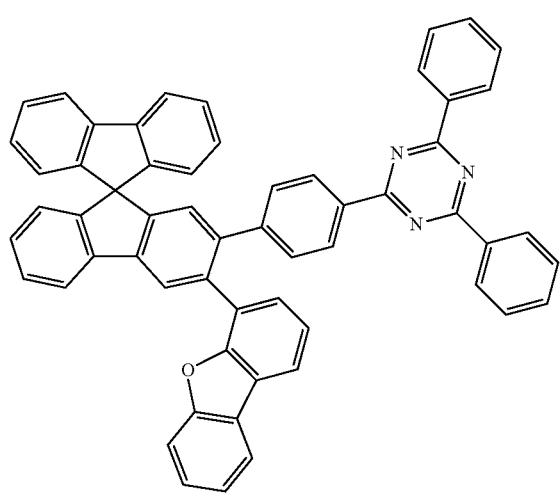
110
-continued
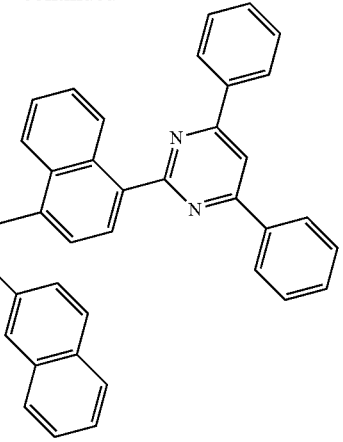
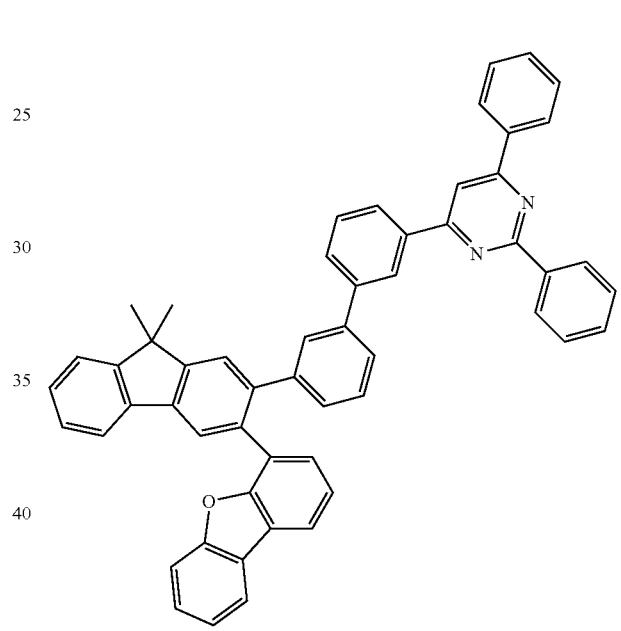
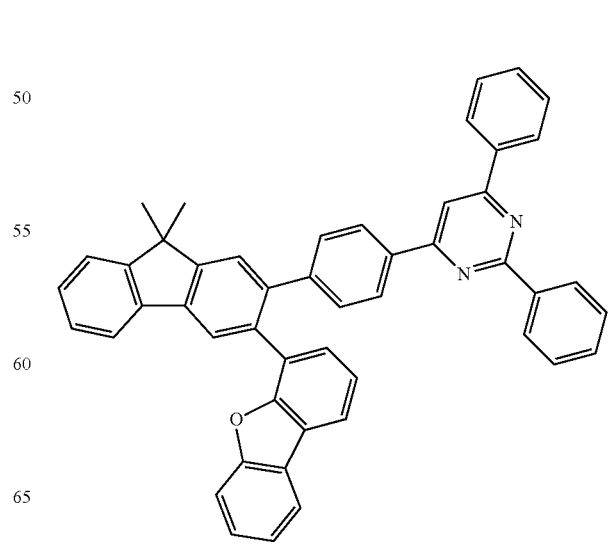

111
-continued
112
-continued
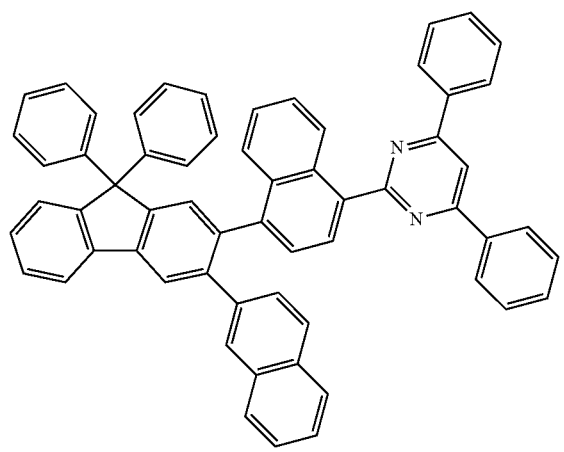
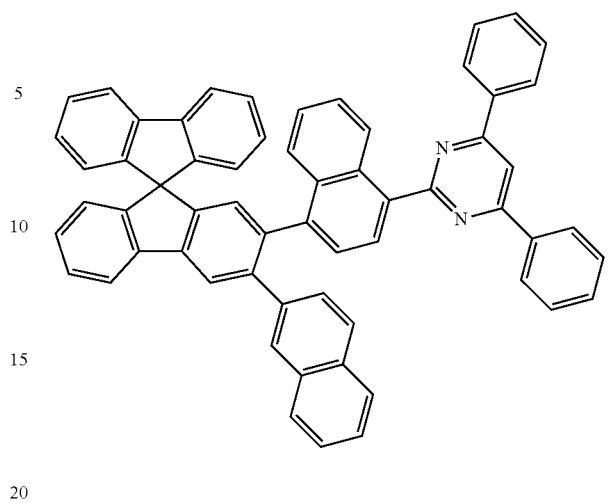
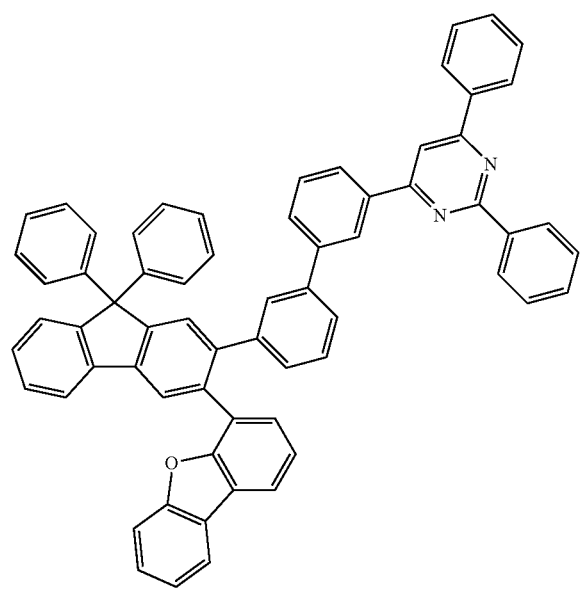
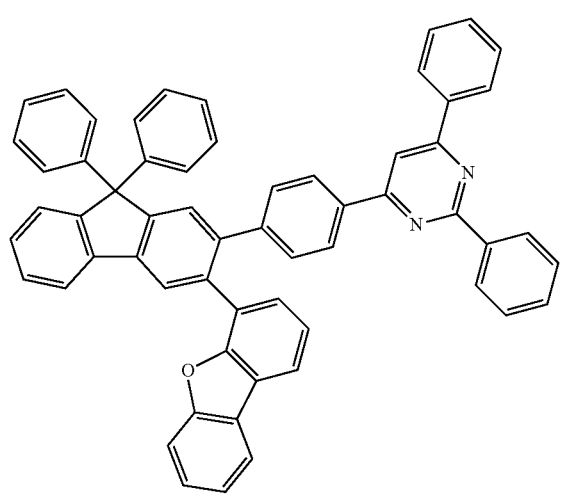

113
-continued
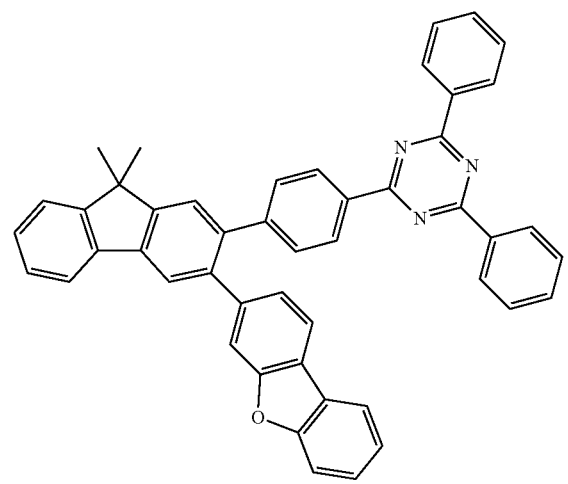
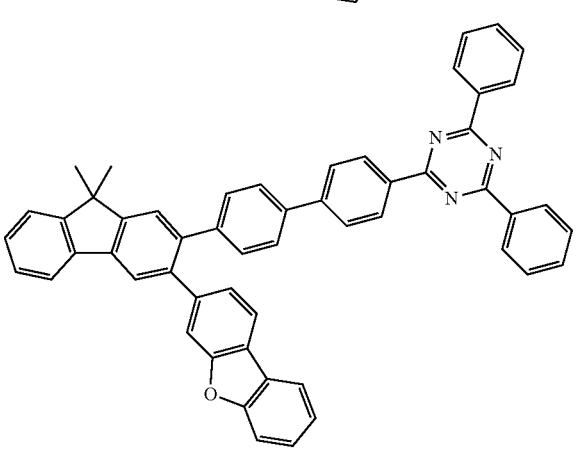
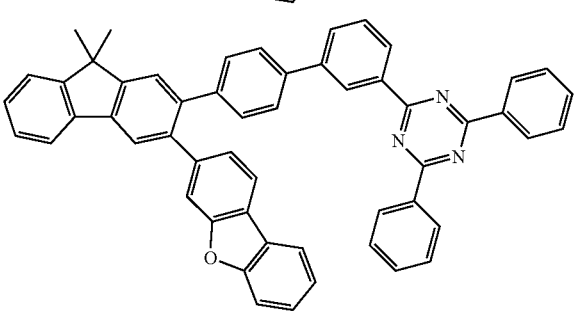
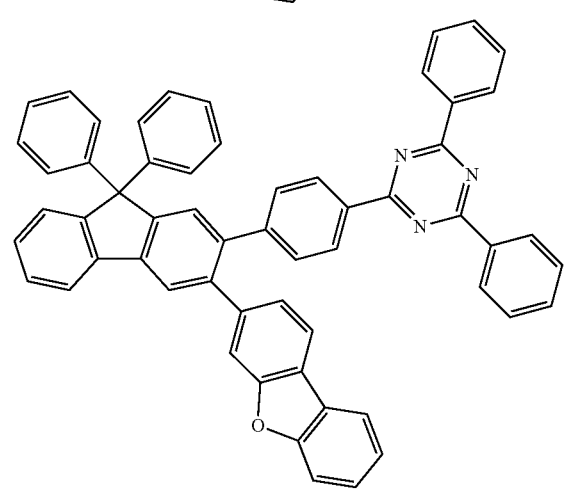
114
-continued
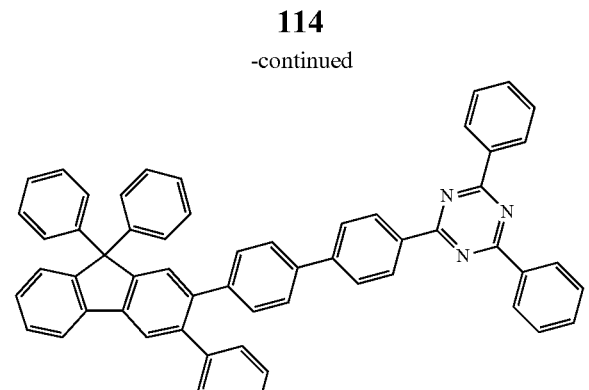
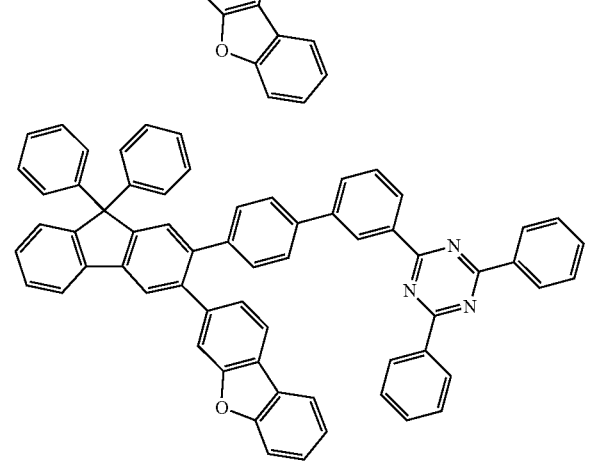
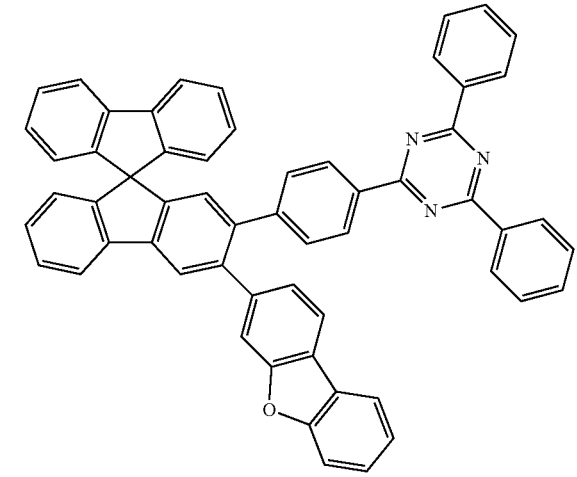
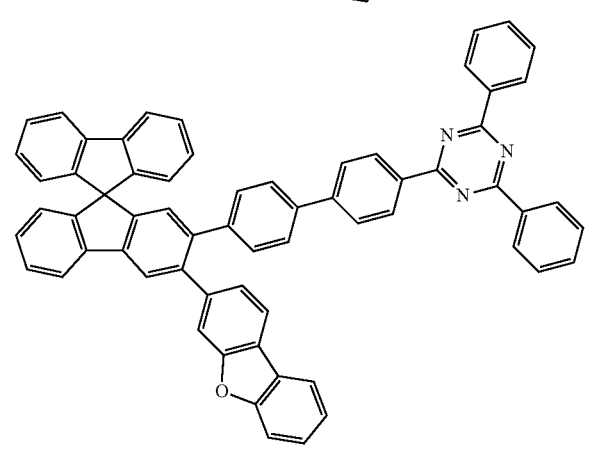

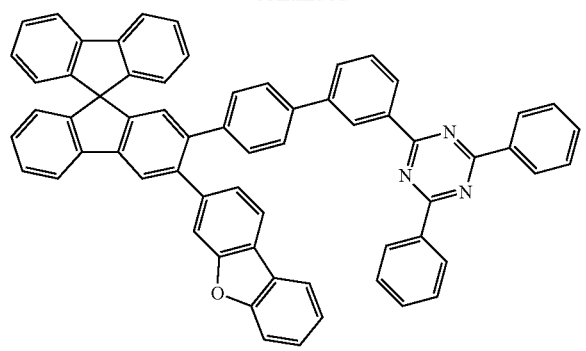
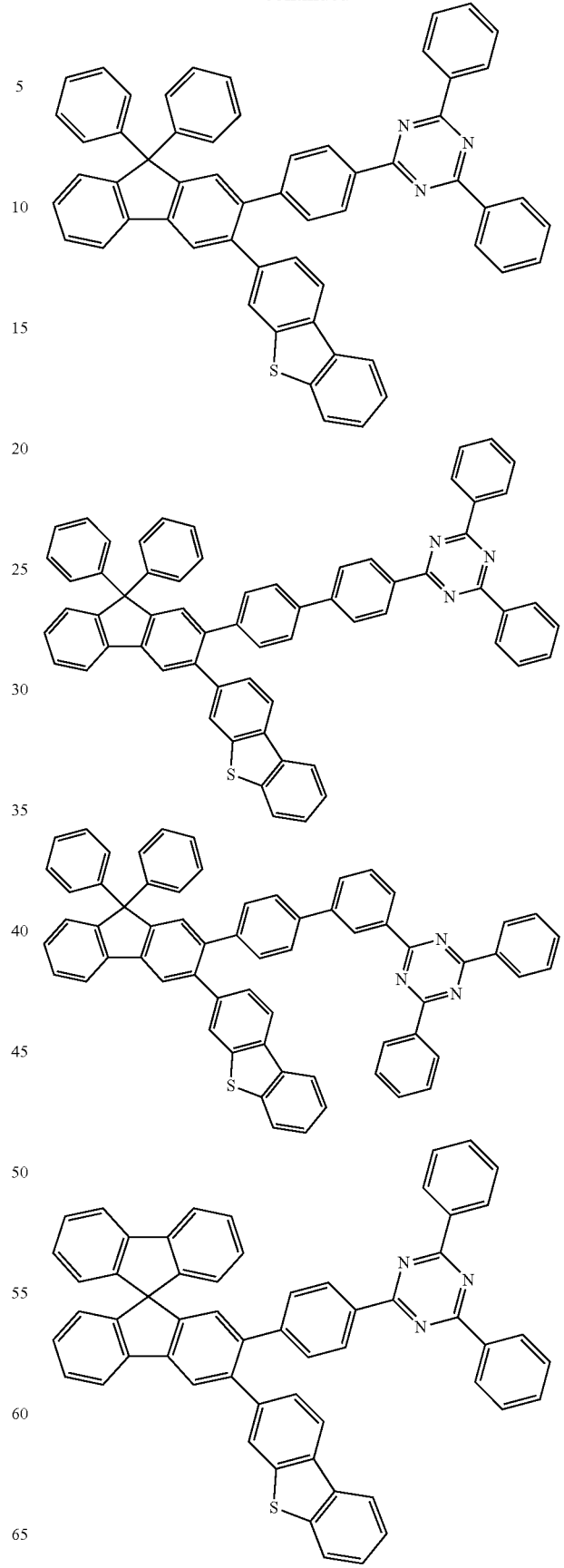

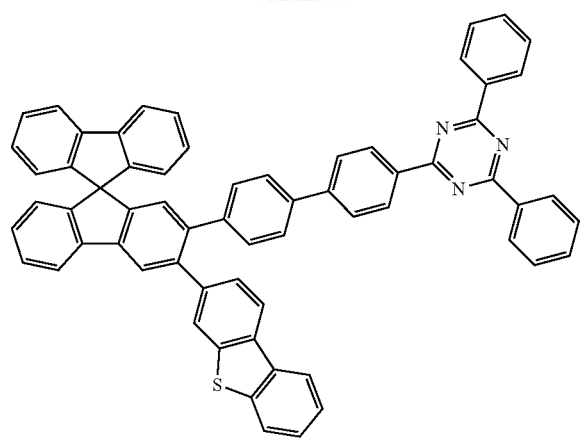
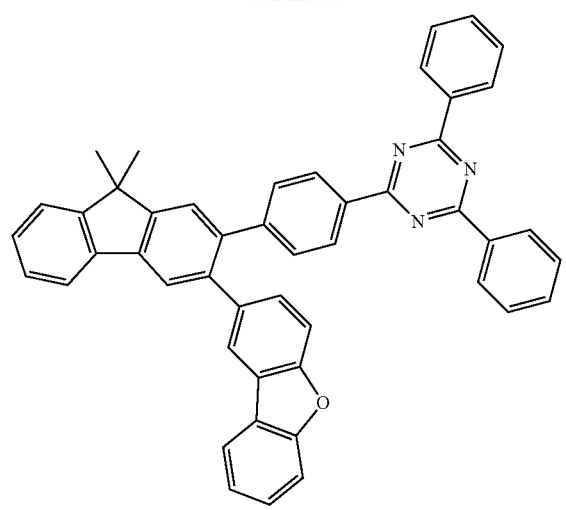
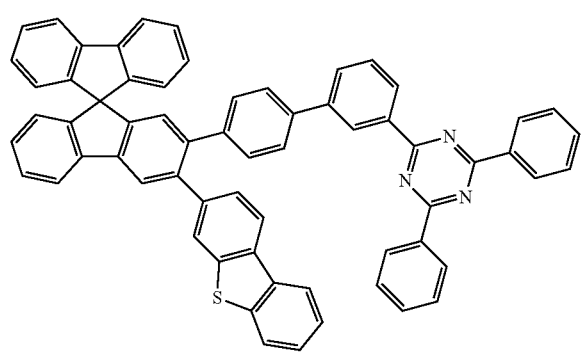
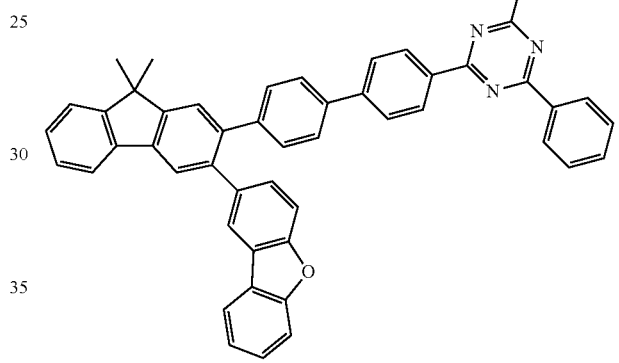
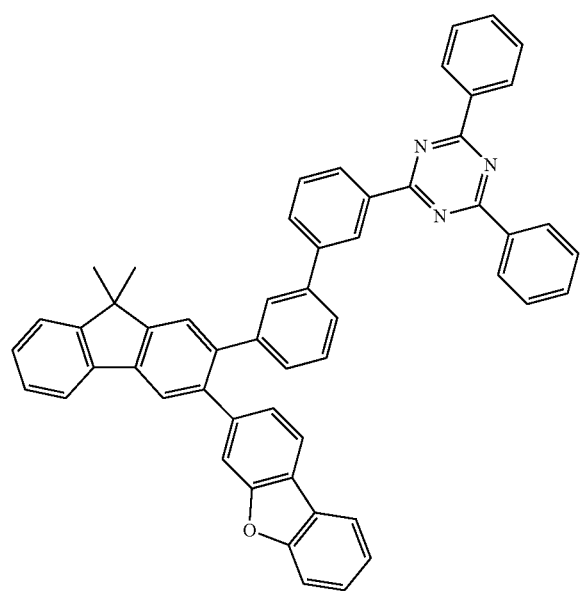
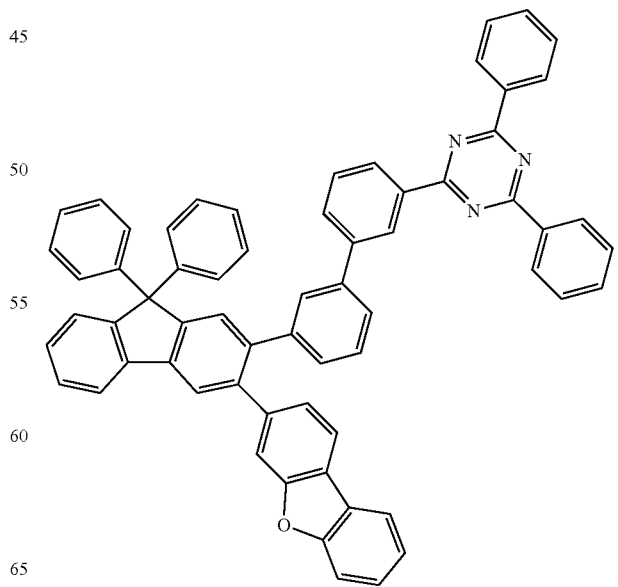

119
-continued
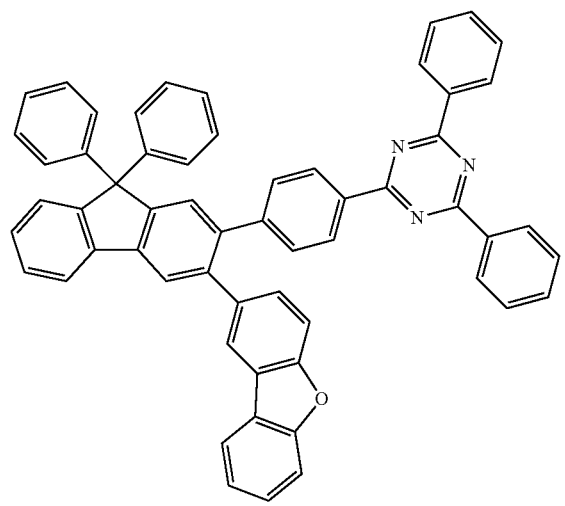
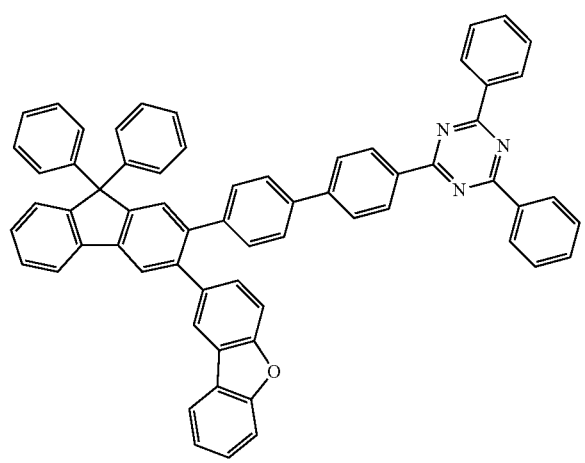
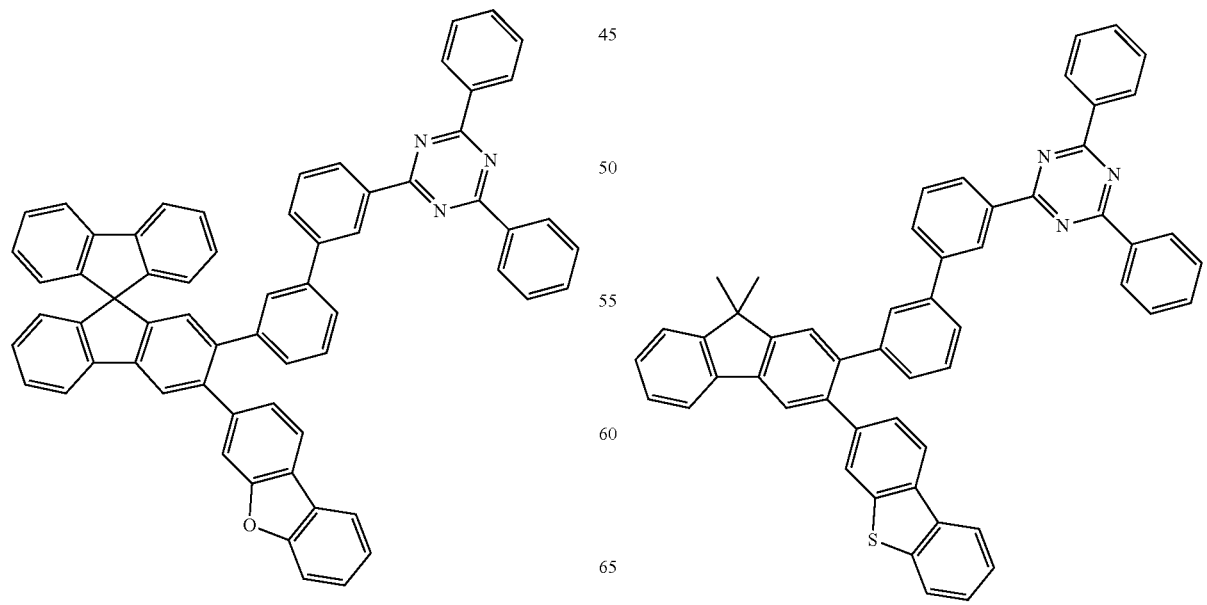
120
-continued
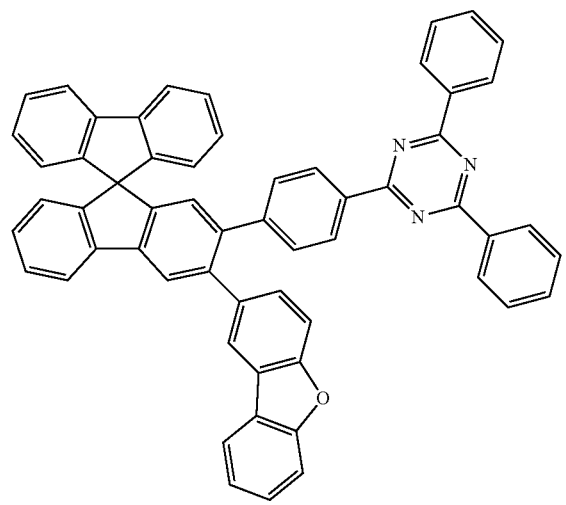
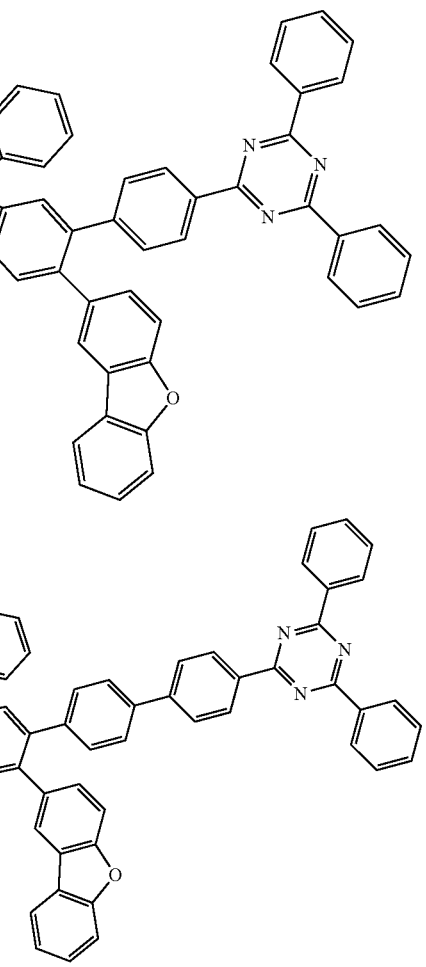

121
-continued
122
-continued
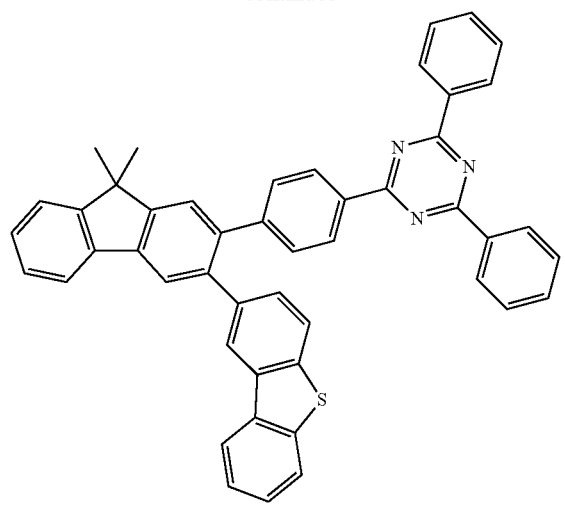
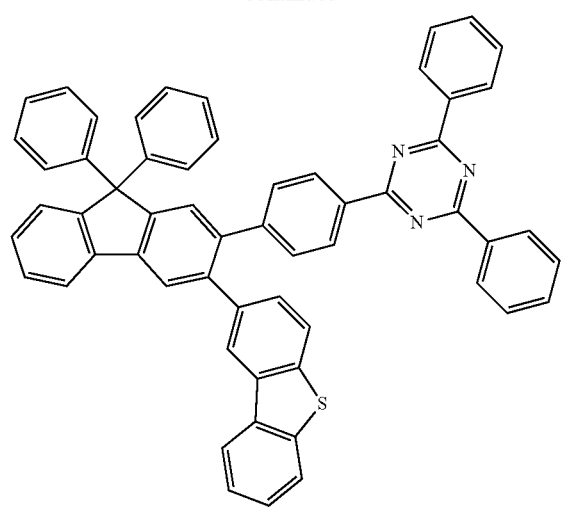
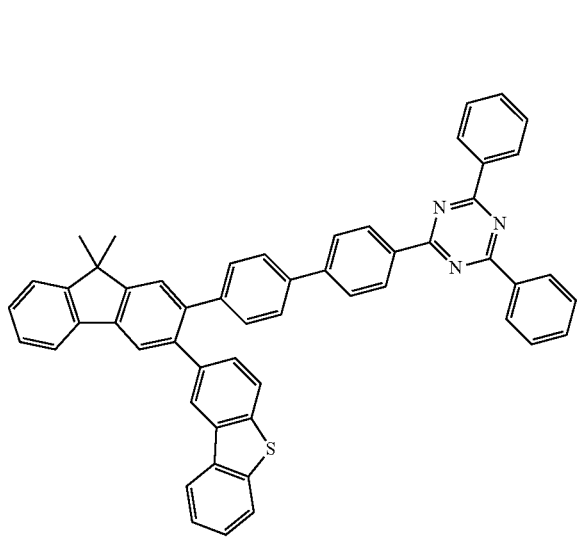
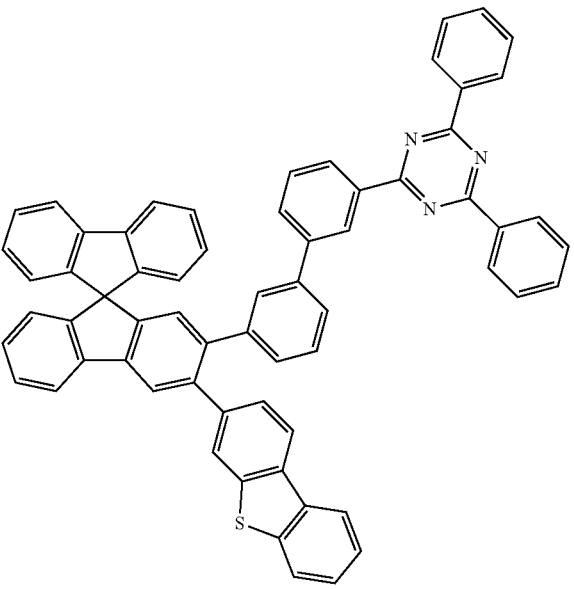

123
-continued
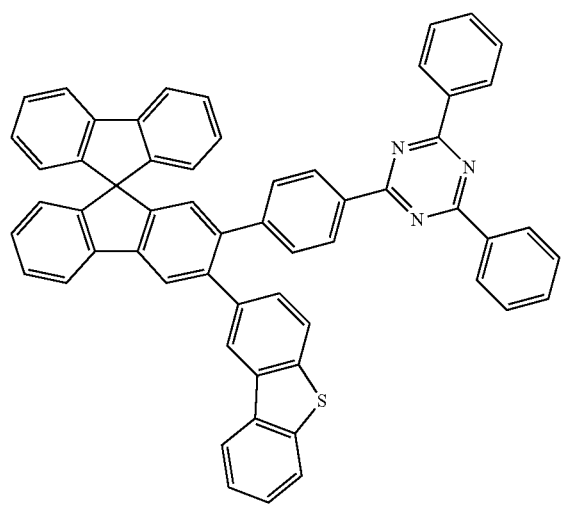
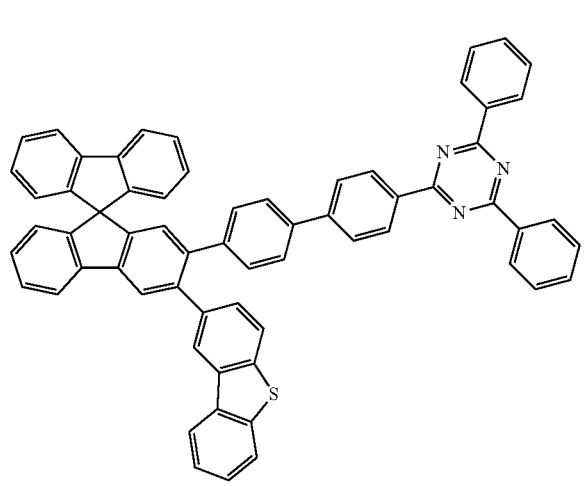
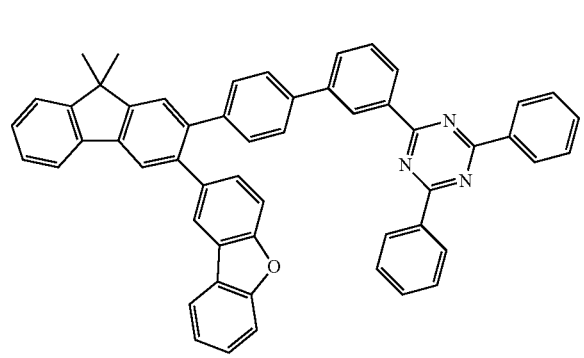
124
-continued
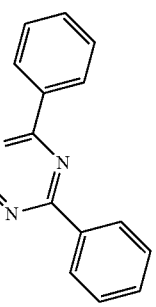
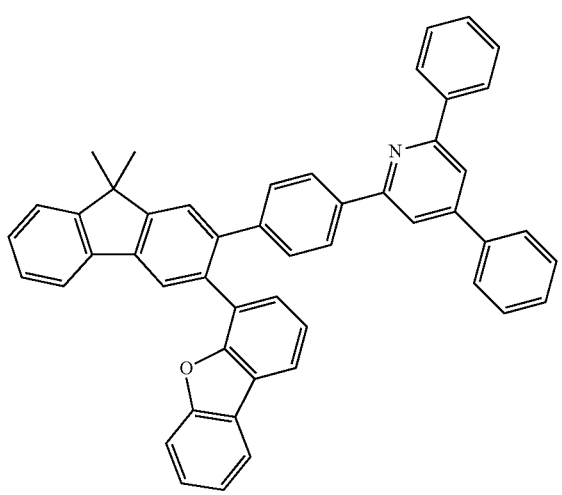
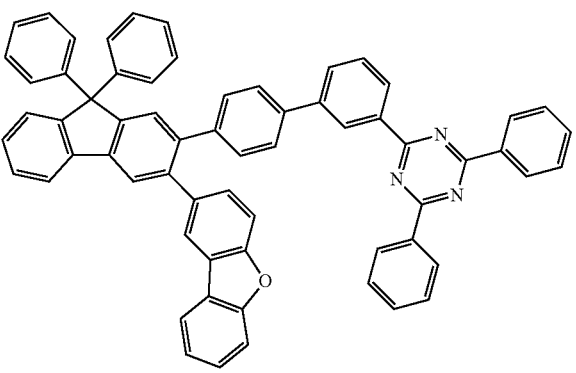

125
-continued
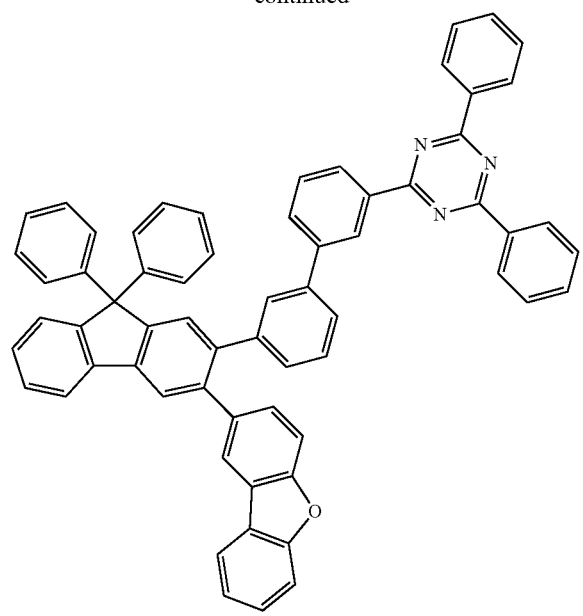
126
-continued
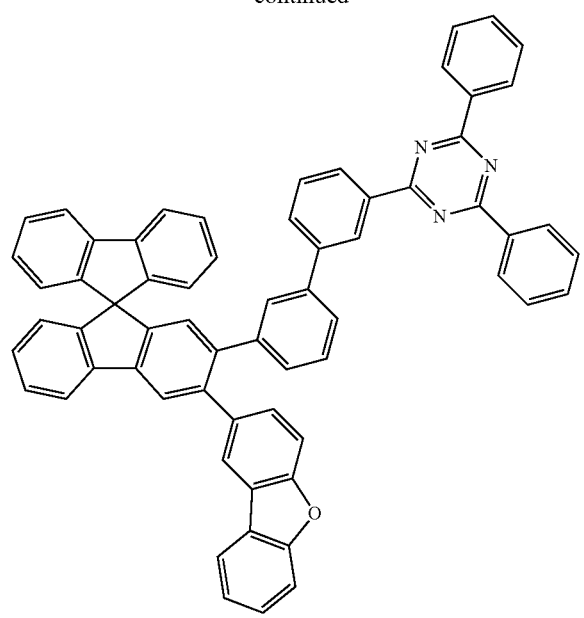

127
-continued
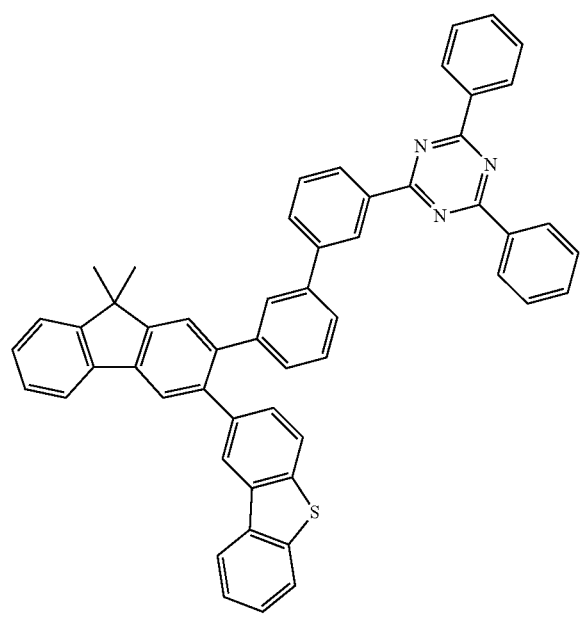
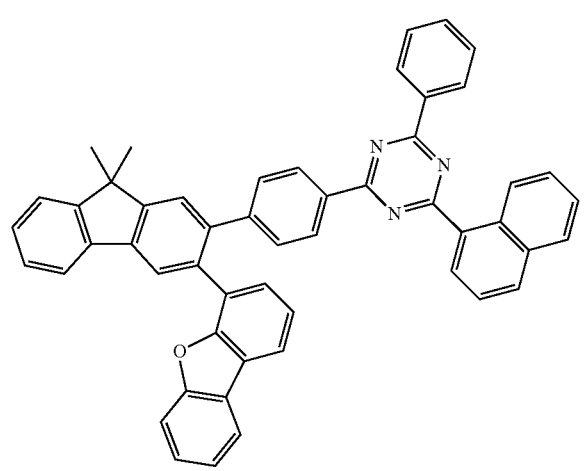
128
-continued
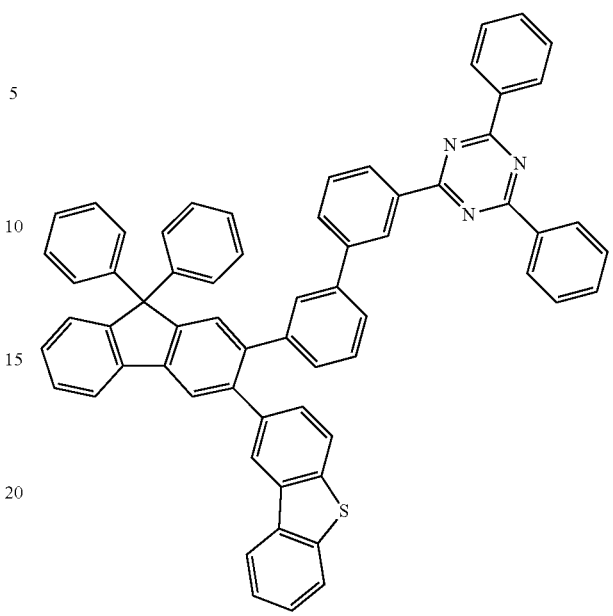
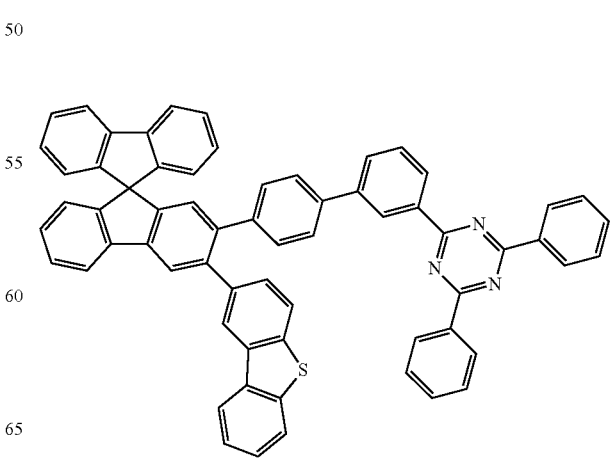

129
-continued
130
-continued
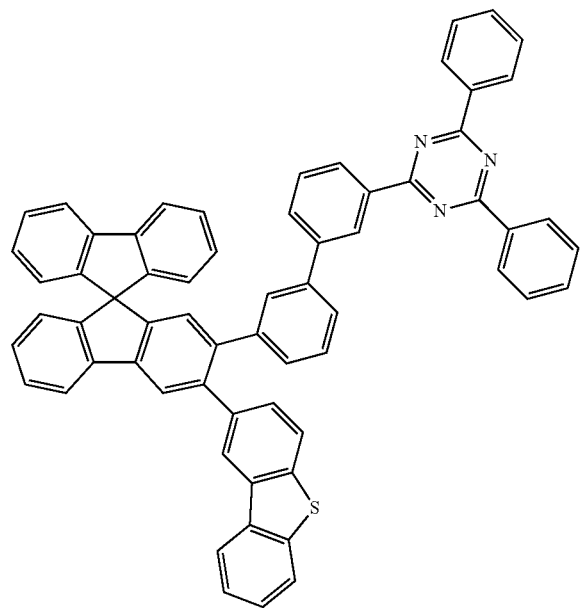
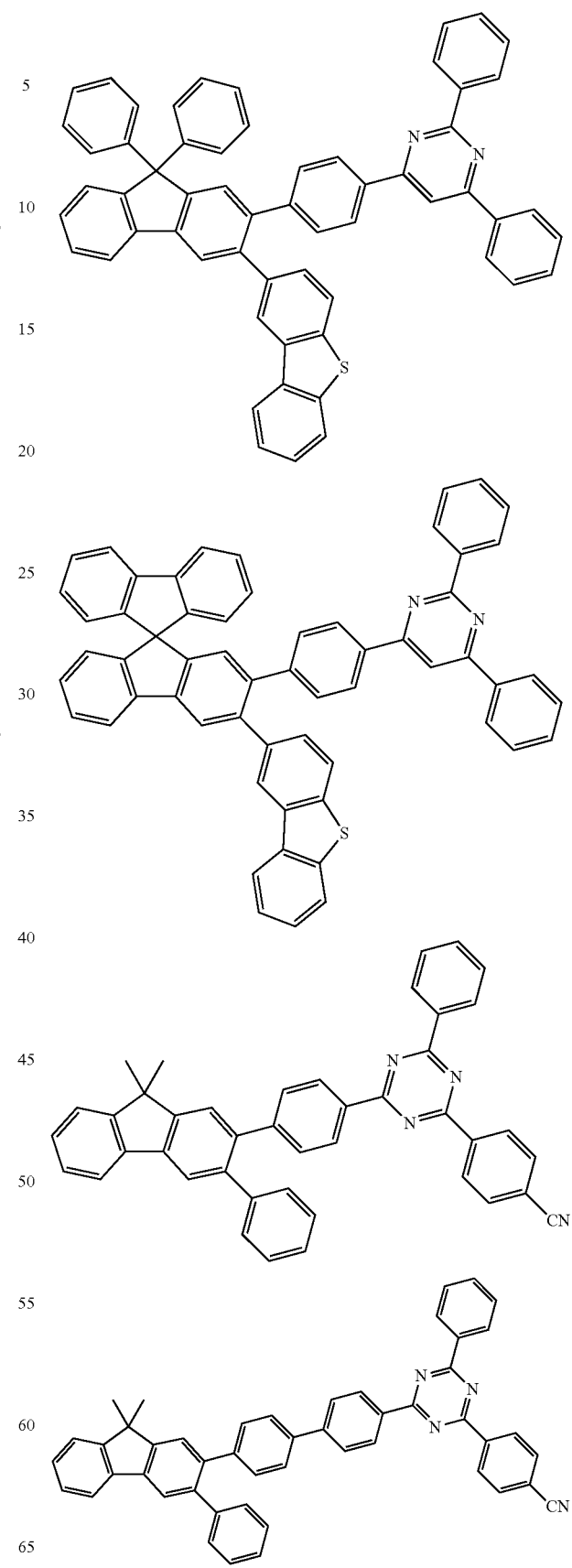

131
-continued
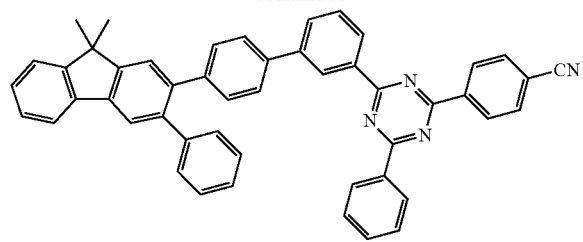
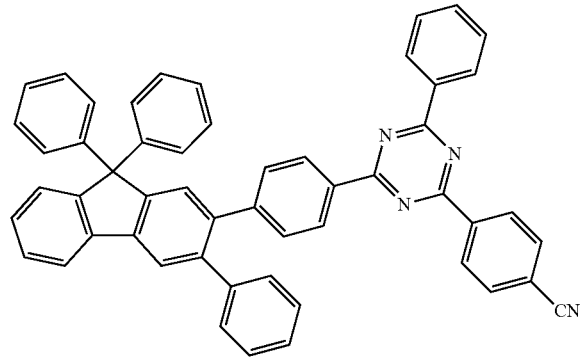
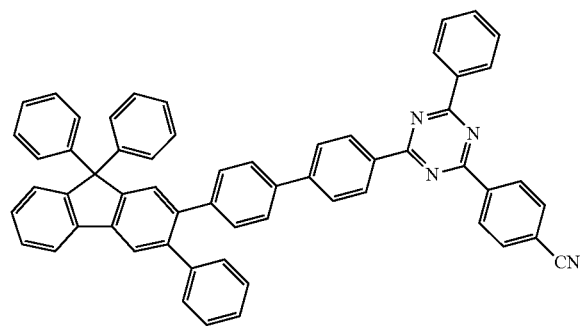
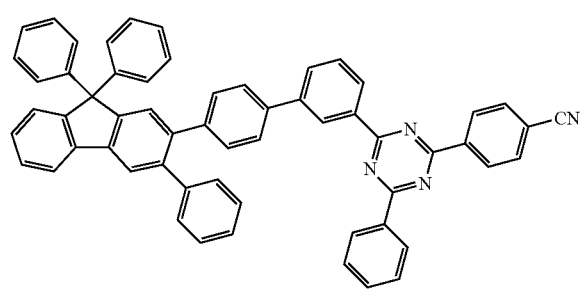
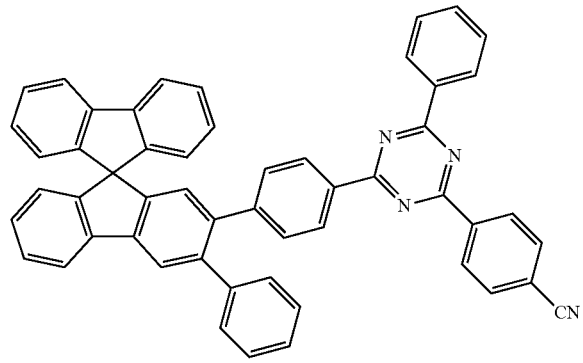
132
-continued
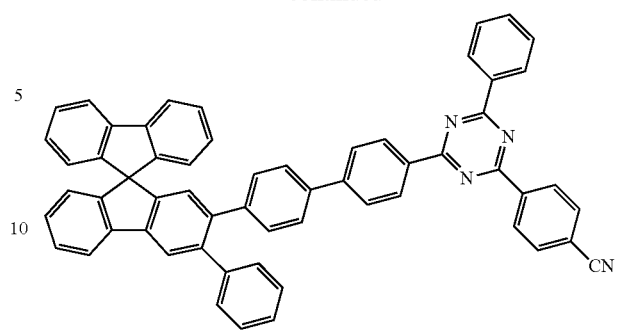
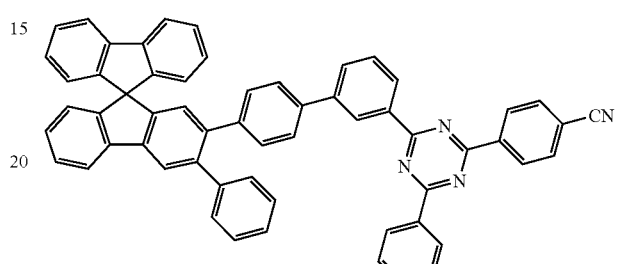
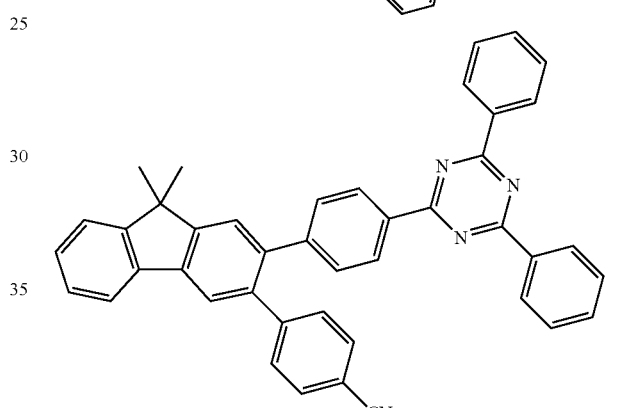
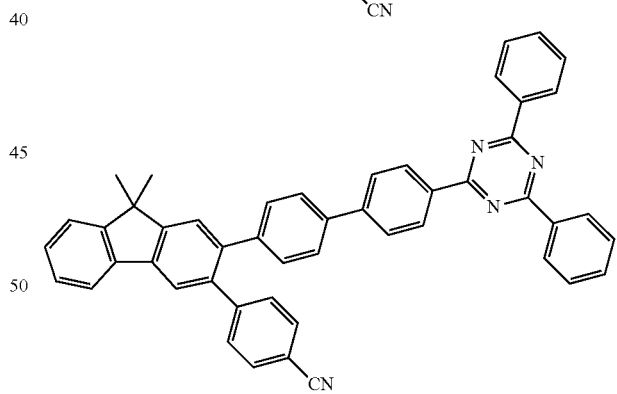
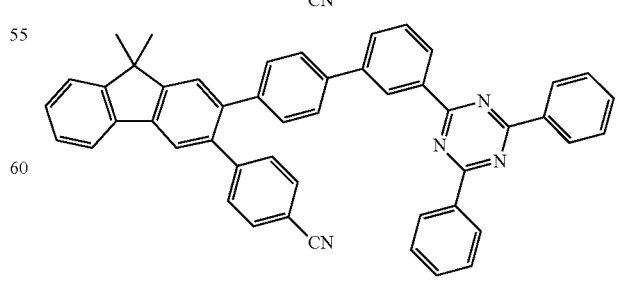

133
-continued
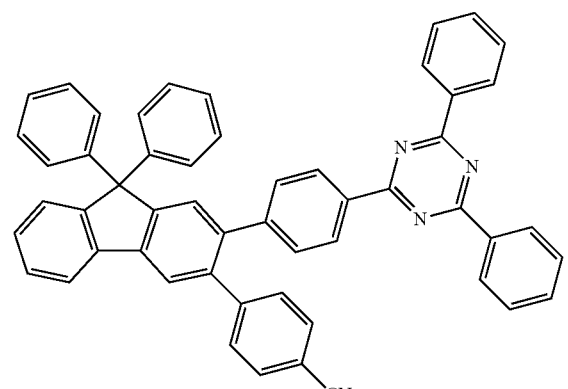
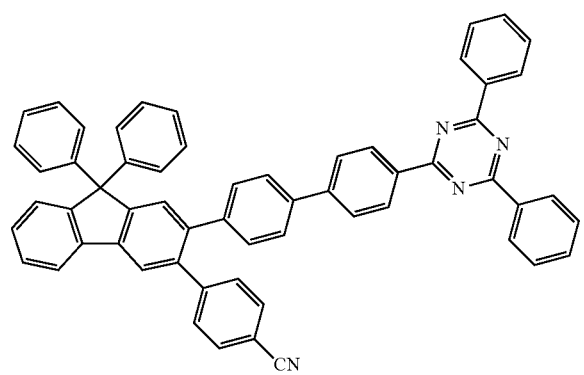
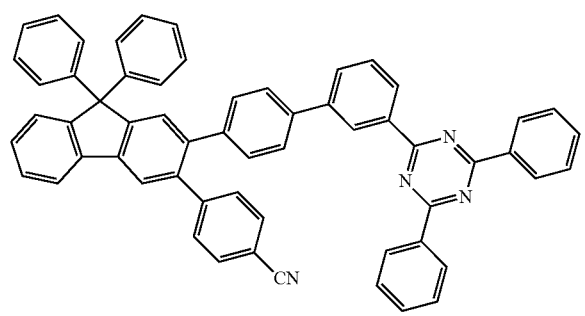
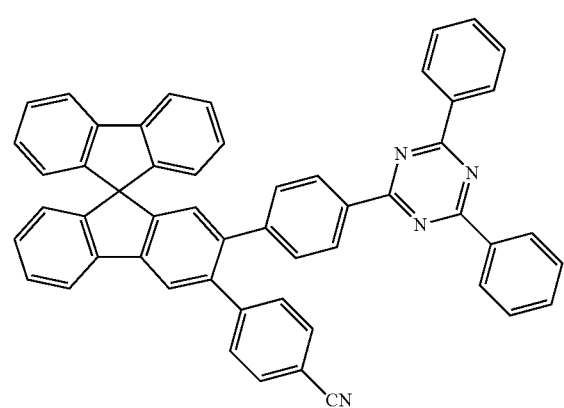
134
-continued
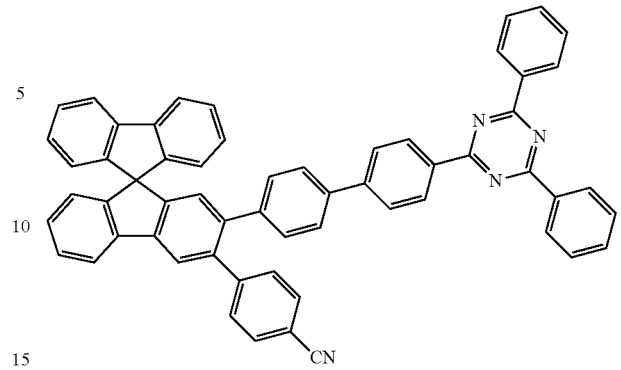
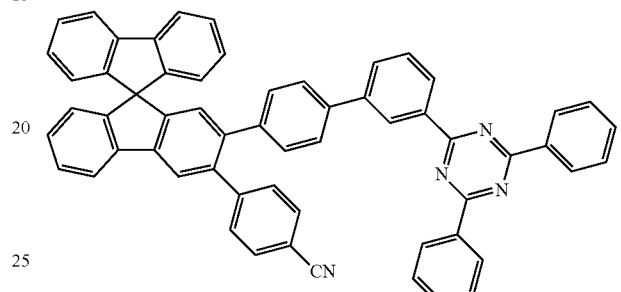
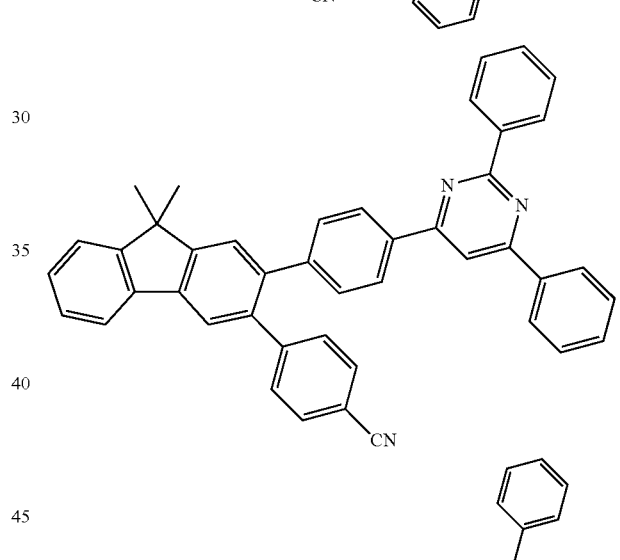
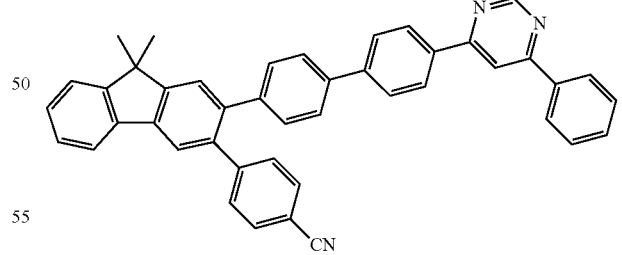
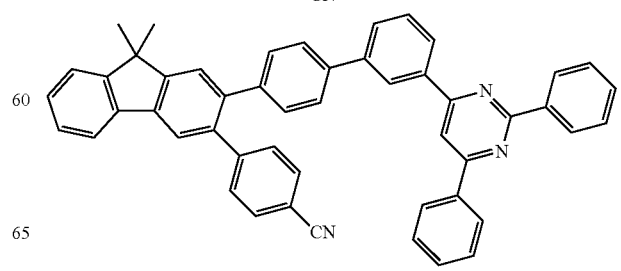

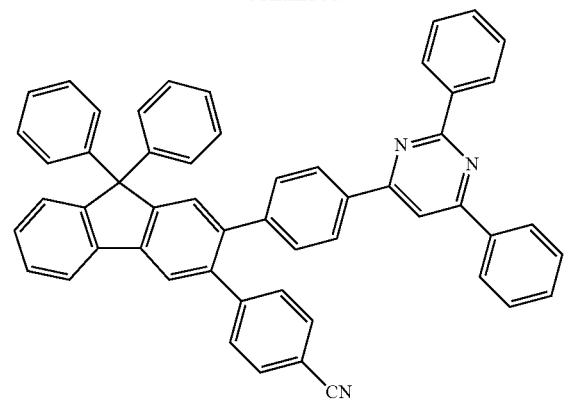
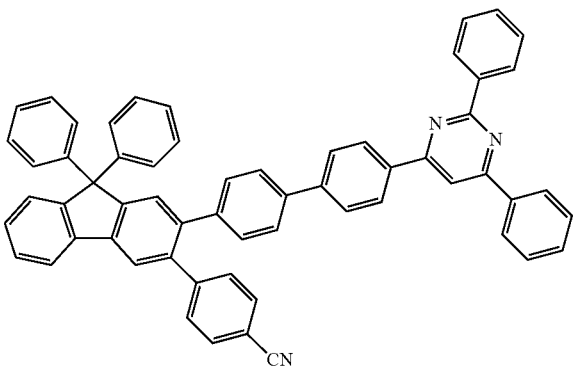
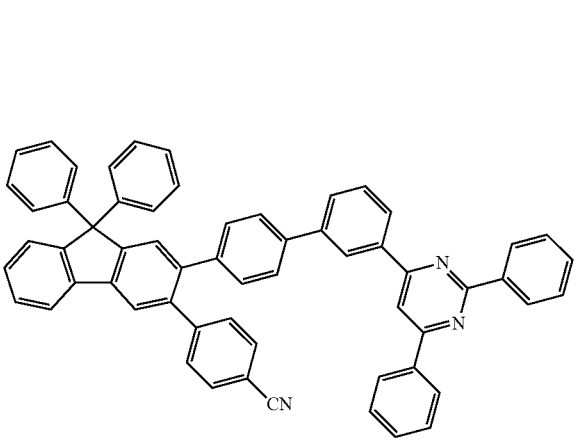
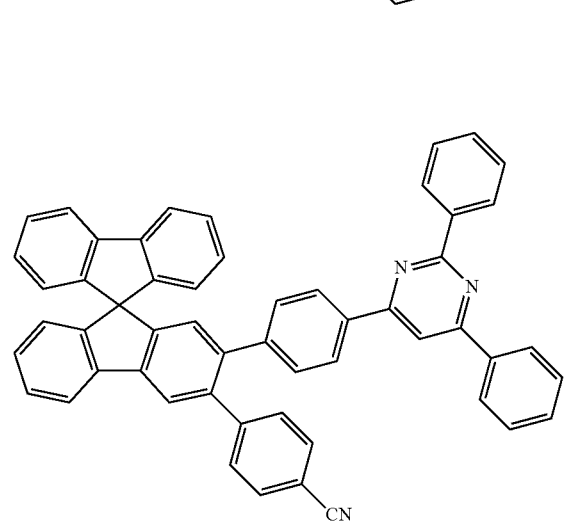
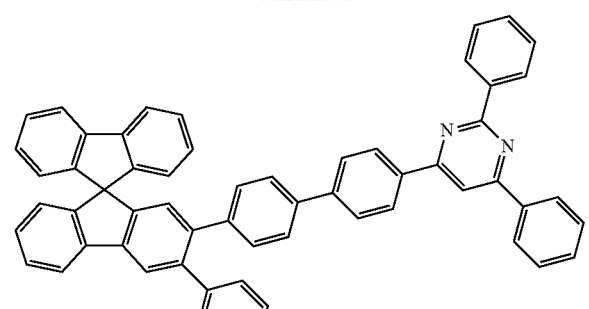
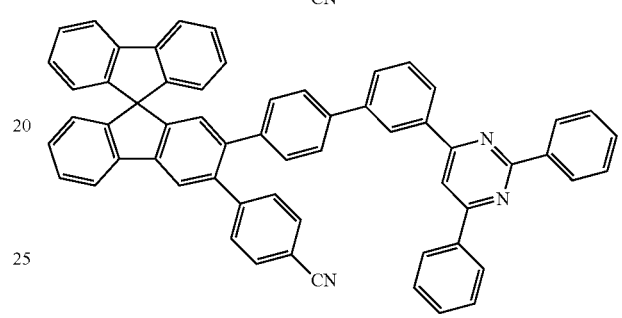
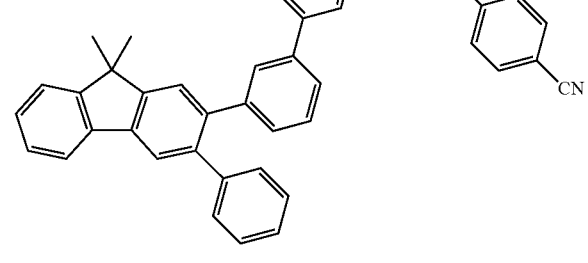
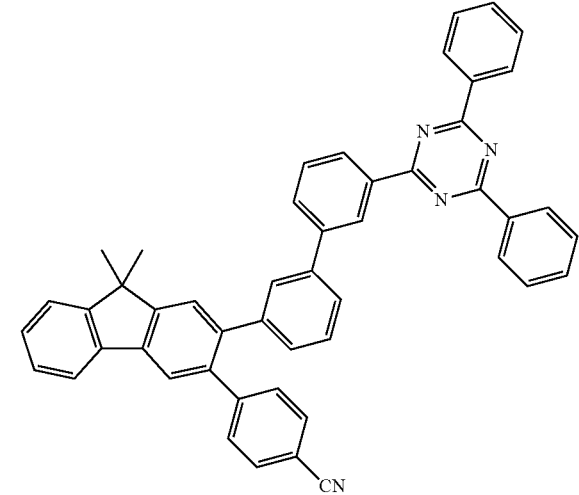

137
-continued
138
-continued
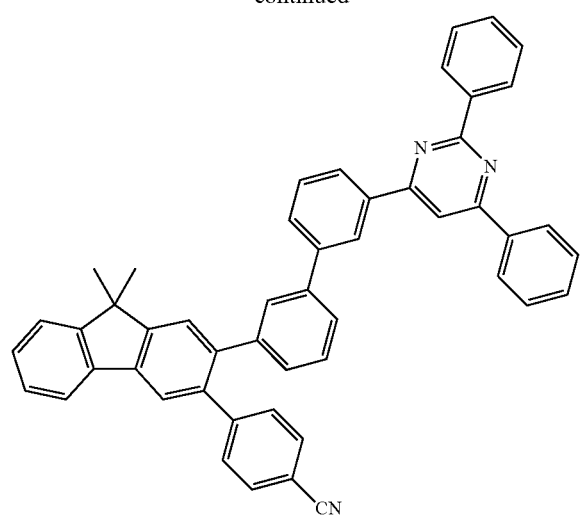
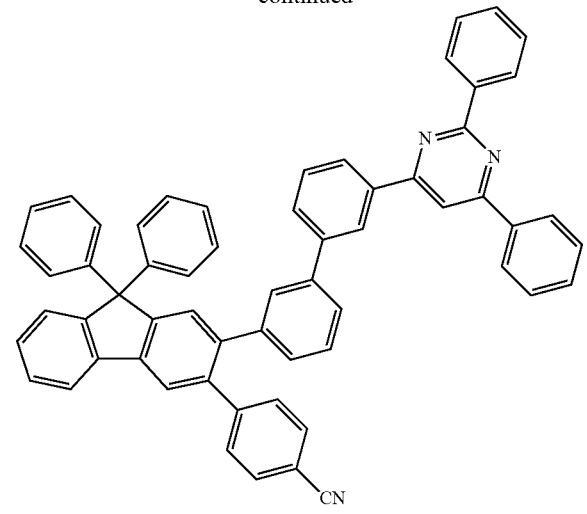

-continued

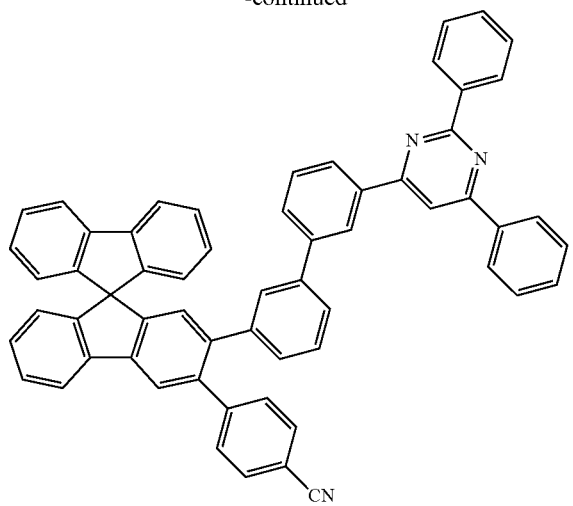

According to one embodiment of the present specification, the compound of Chemical Formula 1 described above can be prepared according to the following General Formula 1.

However, the method for preparing the compound of Chemical Formula 1 is not limited to the following General Formula 1, and methods known in the art can be used in the preparation, and types, positions or the number of substituents can vary depending on technologies known in the art.

General Formula 1

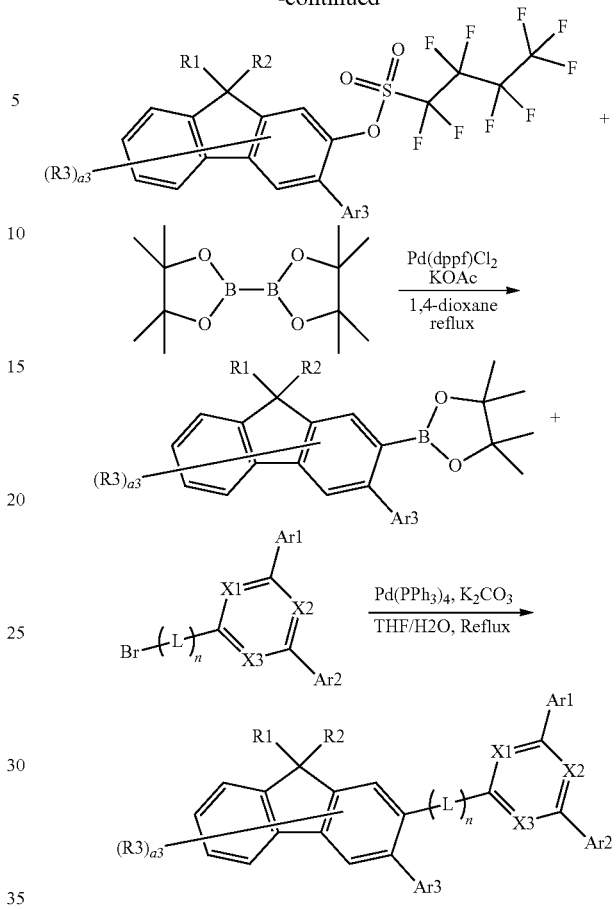

In General Formula 1, R1, R2, R3, X1, X2, X3, Ar1, Ar2, Ar3, L, a3 and n have the same definitions as in Chemical Formula 1.

Materials having a substituent substituting a 2, 3 or 4 carbon position alone of a fluorene-based core are known in organic light emitting devices, however, through the new synthesis method of General Formula 1, the present disclosure substitutes each of 2 and 3 carbon positions of fluorene with substituents. Through the synthesis method of General Formula 1, the present disclosure prepares a compound having a distorted molecular symmetry, and resultingly provides a compound enhancing efficiency and lifetime properties of a device when used in the device.

Another embodiment of the present specification provides an organic light emitting device comprising the compound of Chemical Formula 1.

One embodiment of the present specification provides an organic light emitting device comprising a first electrode, a second electrode, and one or more organic material layers disposed between the first electrode and the second electrode, wherein at least one of the organic material layers comprises the compound of Chemical Formula 1.

In one embodiment of the present specification, the first electrode is an anode, and the second electrode is a cathode.

In another embodiment, the first electrode is a cathode, and the second electrode is an anode.

The organic material layer of the organic light emitting device of the present specification can be formed in a single layer structure, but can also be formed in a multilayer structure in which two or more organic material layers are laminated. For example, the organic light emitting device of the present disclosure can have a structure including a hole injection layer, a hole transfer layer, a light emitting layer, an electron transfer layer, an electron injection layer and the like as the organic material layer. However, the structure of the organic light emitting device is not limited thereto, and can include less numbers of organic layers.

In one embodiment of the present specification, the organic material layer comprises at least one of an electron injection layer, an electron transfer layer and a layer carrying out electron injection and transfer at the same time, and at least one of the electron injection layer, the electron transfer layer and the layer carrying out electron injection and transfer at the same time comprises the compound.

In another embodiment, the organic material layer comprises a light emitting layer, and the light emitting layer comprises the compound of Chemical Formula 1.

In another embodiment, the organic material layer comprises a light emitting layer, and the light emitting layer comprises the compound of Chemical Formula 1 as a host.

In one embodiment of the present specification, the organic light emitting device is a green organic light emitting device, and the organic material layer comprises the compound of Chemical Formula 1 as a host of a light emitting layer.

In one embodiment of the present specification, when X1 to X3 are N, the compound of Chemical Formula 1 can be included in a light emitting layer of the organic material layer of the organic light emitting device as a host.

In one embodiment of the present specification, the organic material layer comprises a hole blocking layer, and the hole blocking layer comprises the compound of Chemical Formula 1.

In one embodiment of the present specification, the organic material layer comprises an electron control layer, and the electron control layer comprises the compound of Chemical Formula 1.

In another embodiment, the organic light emitting device can be an organic light emitting device having a structure in which an anode, one or more organic material layers and a cathode are consecutively laminated on a substrate (normal type).

In another embodiment, the organic light emitting device can be an organic light emitting device having a structure in a reverse direction in which a cathode, one or more organic material layers and an anode are consecutively laminated on a substrate (inverted type).

In addition thereto, the organic light emitting device of the present specification can have a lamination structure as follows, however, the structure is not particularly limited thereto.

(1) anode/hole transfer layer/light emitting layer/cathode
(2) anode/hole injection layer/hole transfer layer/light emitting layer/cathode
(3) anode/hole injection layer/hole buffer layer/hole transfer layer/light emitting layer/cathode
(4) anode/hole transfer layer/light emitting layer/electron transfer layer/cathode
(5) anode/hole transfer layer/light emitting layer/electron transfer layer/electron injection layer/cathode
(6) anode/hole injection layer/hole transfer layer/light emitting layer/electron transfer layer/cathode
(7) anode/hole injection layer/hole transfer layer/light emitting layer/electron transfer layer/electron injection layer/cathode
(8) anode/hole injection layer/hole buffer layer/hole transfer layer/light emitting layer/electron transfer layer/cathode
(9) anode/hole injection layer/hole buffer layer/hole transfer layer/light emitting layer/electron transfer layer/electron injection layer/cathode
(10) anode/hole transfer layer/electron blocking layer/light emitting layer/electron transfer layer/cathode
(11) anode/hole transfer layer/electron blocking layer/light emitting layer/electron transfer layer/electron injection layer/cathode
(12) anode/hole injection layer/hole transfer layer/electron blocking layer/light emitting layer/electron transfer layer/cathode
(13) anode/hole injection layer/hole transfer layer/electron blocking layer/light emitting layer/electron transfer layer/electron injection layer/cathode
(14) anode/hole transfer layer/light emitting layer/hole blocking layer/electron transfer layer/cathode
(15) anode/hole transfer layer/light emitting layer/hole blocking layer/electron transfer layer/electron injection layer/cathode
(16) anode/hole injection layer/hole transfer layer/light emitting layer/hole blocking layer/electron transfer layer/cathode
(17) anode/hole injection layer/hole transfer layer/light emitting layer/hole blocking layer/electron transfer layer/electron injection layer/cathode FIG. 1 illustrates an example of the organic light emitting device formed with a substrate (1), an anode (2), a light emitting layer (6) and a cathode (10). In such a structure, the compound can be included in the light emitting layer.

FIG. 2 illustrates an example of the organic light emitting device formed with a substrate (1), an anode (2), a hole injection layer (3), a hole transfer layer (4), an electron blocking layer (5), alight emitting layer (6), a hole blocking layer (7), an electron transfer layer (8), an electron injection layer (9) and a cathode (10). In such a structure, the compound can be included in at least one of the light emitting layer, the hole blocking layer, the electron transfer layer and the electron injection layer. In one embodiment, the compound of Chemical Formula 1 is included in the hole blocking layer.

The organic light emitting device of the present specification can be manufactured using materials and methods known in the art, except that one or more layers of the organic material layers include the compound of the present specification, that is, the compound of Chemical Formula 1.

When the organic light emitting device includes a plurality of organic material layers, the organic material layers can be formed with materials the same as or different from each other.

For example, the organic light emitting device of the present specification can be manufactured by consecutively laminating a first electrode, an organic material layer and a second electrode on a substrate. Herein, the organic light emitting device can be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device can also be manufactured by consecutively depositing a cathode material, an organic material layer and an anode material on a substrate.

In addition, the compound of Chemical Formula 1 can be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such a method, the organic light emitting device can also be manufactured by consecutively laminating a cathode material, an organic material layer and an anode material on a substrate (International Patent Application Publication No. WO2003/012890). However, the manufacturing method is not limited thereto.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The electron blocking layer is a layer capable of enhancing lifetime and efficiency of a device by preventing electrons injected from an electron injection layer from passing through a light emitting layer and entering a hole injection layer. The electron blocking layer can be formed in a proper part between the light emitting layer and the hole injection layer using known materials. As the electron blocking material, hole transfer materials can be used, however, the electron blocking material is not limited thereto. In one embodiment of the present specification, the electron blocking layer is formed using arylamine-based organic materials.

The hole blocking layer is a layer capable of enhancing lifetime and efficiency of a device by preventing holes injected from a hole injection layer from passing through a light emitting layer and entering an electron injection layer, and can be formed as necessary in a proper part between the light emitting layer and the electron injection layer using known materials. The hole blocking layer can be formed by vacuum thermal depositing and spin coating a hole blocking material using common methods, and as the hole blocking material, oxadiazole derivatives, triazole derivatives, phenanthroline derivatives, BCP, aluminum complexes and the like can be specifically used, however, the hole blocking material is not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$), carbazole-based compounds, dimerized styryl compounds, BAlq, 10-hydroxybenzoquinoline-metal compounds, benzoxazole-, benzthiazole- and benzimidazole-based compounds, poly(p-phenylenevinylene) (PPV)-based polymers, spiro compounds, polyfluorene, rubrene, and the like, but are not limited thereto.

The light emitting layer can include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline, complexes including Alq₃, organic radical compounds, hydroxyflavon-metal complexes, and the like, but are not limited thereto. The electron transfer layer can be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition thereto, has an excellent thin film forming ability. Specific examples thereof include fluorenone, anthraquino-dimethane, diphenoquinone, thiopyran dioxide, oxazole, oxadiazole, triazole, imidazole, perylene tetracarboxylic acid, fluorenylidene methane, anthrone or the like, and derivatives thereof, triazine derivatives, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxy-quinolinato)copper, bis(8-hydroxyquinolinato)manganese, tris(8-hydroxyquinolinato)aluminum, tris(2-methyl-8-hydroxy-quinolinato)aluminum, tris(8-hydroxyquinolinato)gallium, bis(10-hydroxybenzo[h]quinolinato)berylium, bis(10-hydroxybenzo[h]quinolinato) zinc, bis(2-methyl-8-quinolinato)-chloro-gallium, bis(2-methyl-8-quinolinato)(o-cresolato)-gallium, bis(2-methyl-8-quinolinato)(1-naphtholato)aluminum, bis(2-methyl-8-quinolinato) (2-naphtholato)gallium and the like, but is not limited thereto.

The organic light emitting device according to the present specification can be a top-emission type, a bottom-emission type or a dual-emission type depending on the materials used.

EXAMPLES

Hereinafter, preparation methods and characteristics of the compound of the present disclosure and the organic light emitting device including the same will be described in order to illuminate the present disclosure in detail.

Preparation Examples of A to D

Preparation Example of A

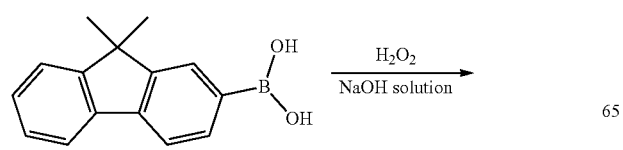

-continued

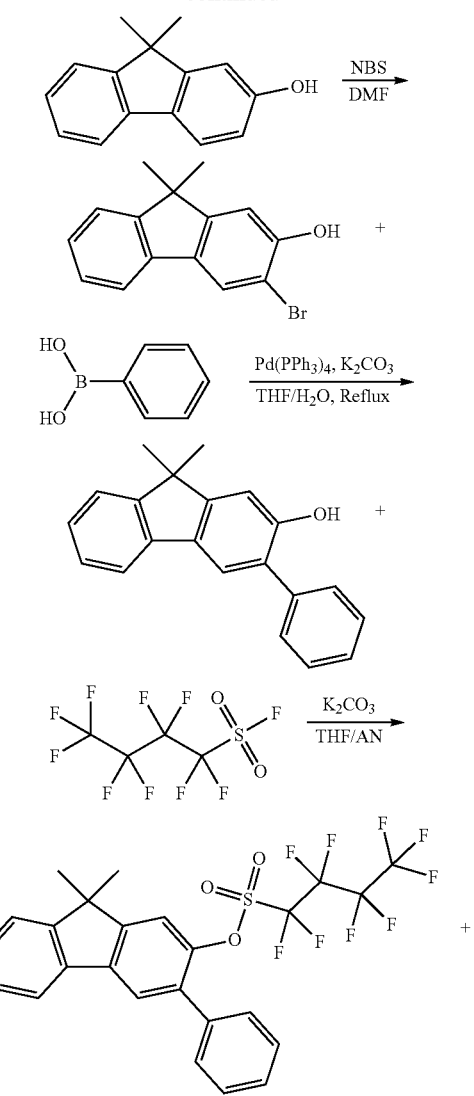

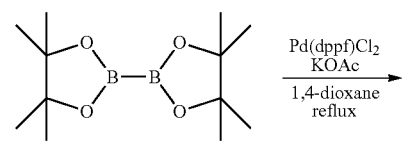

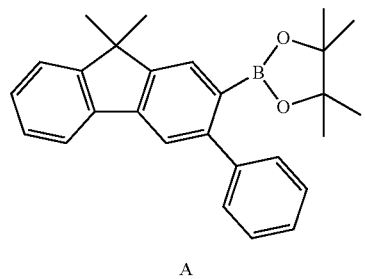

A

147
Preparation Example of B

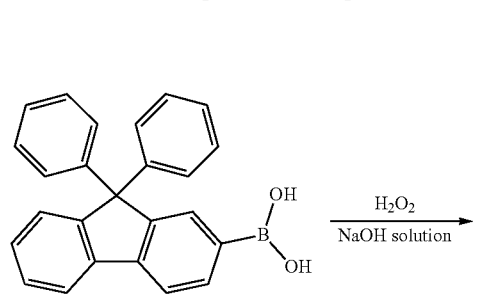

$\xrightarrow{\text{H}_2\text{O}_2}{\text{NaOH solution}}$

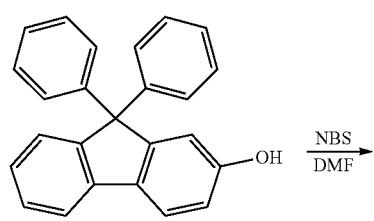

$\xrightarrow{\text{NBS}}{\text{DMF}}$

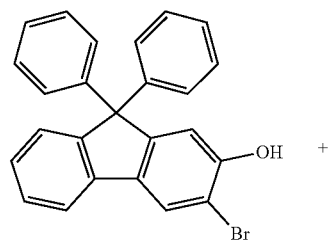

+

$\xrightarrow[\text{THF/H}_2\text{O, Reflux}]{\text{Pd(PPh}_3)_4, \text{K}_2\text{CO}_3}$

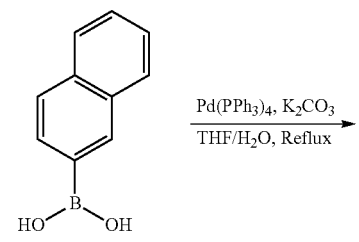

+

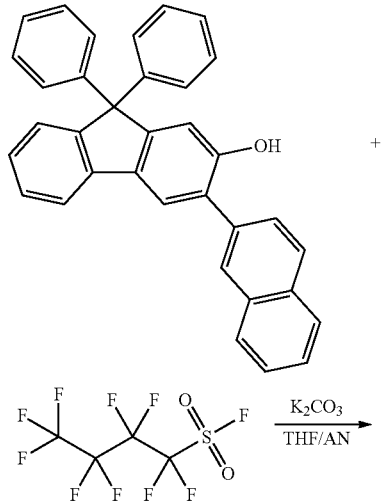

$\xrightarrow[\text{THF/AN}]{\text{K}_2\text{CO}_3}$

148
-continued

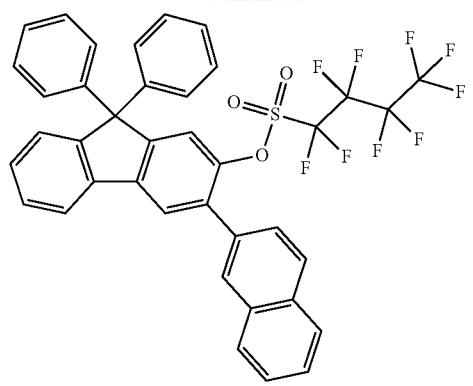

+

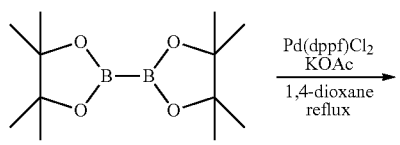

$\xrightarrow[\substack{\text{KOAc}\\\text{1,4-dioxane}\\\text{reflux}}]{\text{Pd(dppf)Cl}_2}$

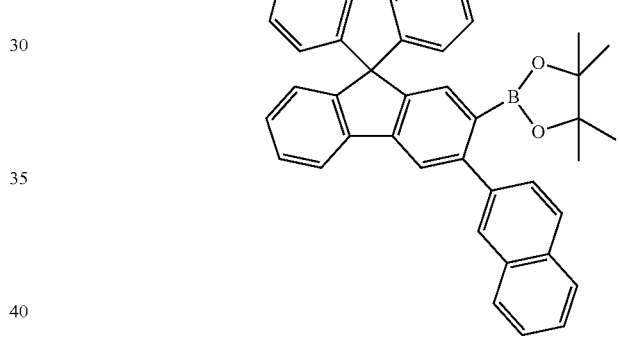

B

Preparation Example of C

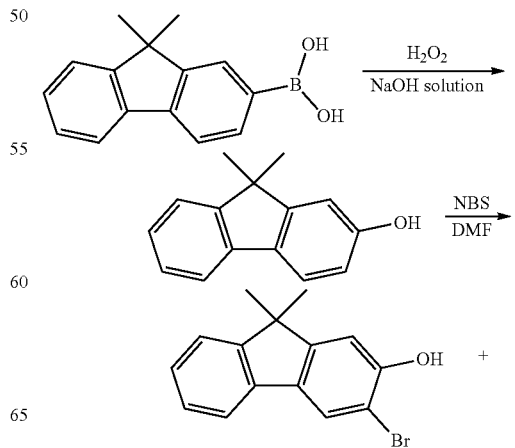

$\xrightarrow{\text{H}_2\text{O}_2}{\text{NaOH solution}}$ $\xrightarrow{\text{NBS}}{\text{DMF}}$

+

149
-continued
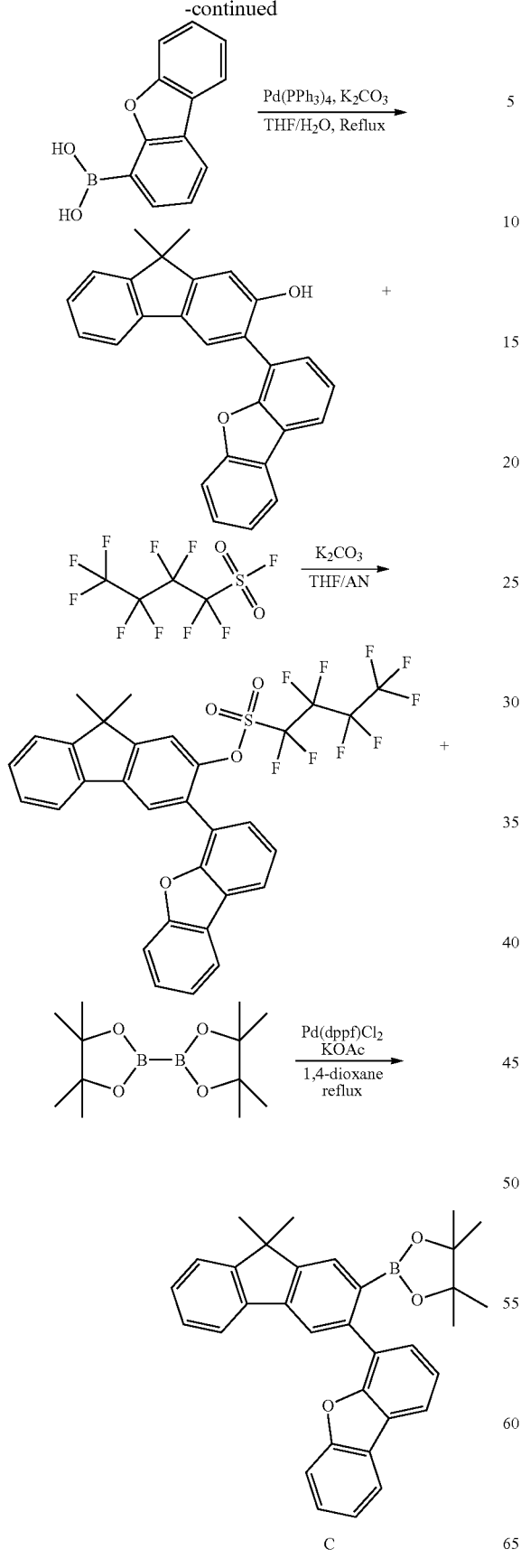
C
150
Preparation Example of D
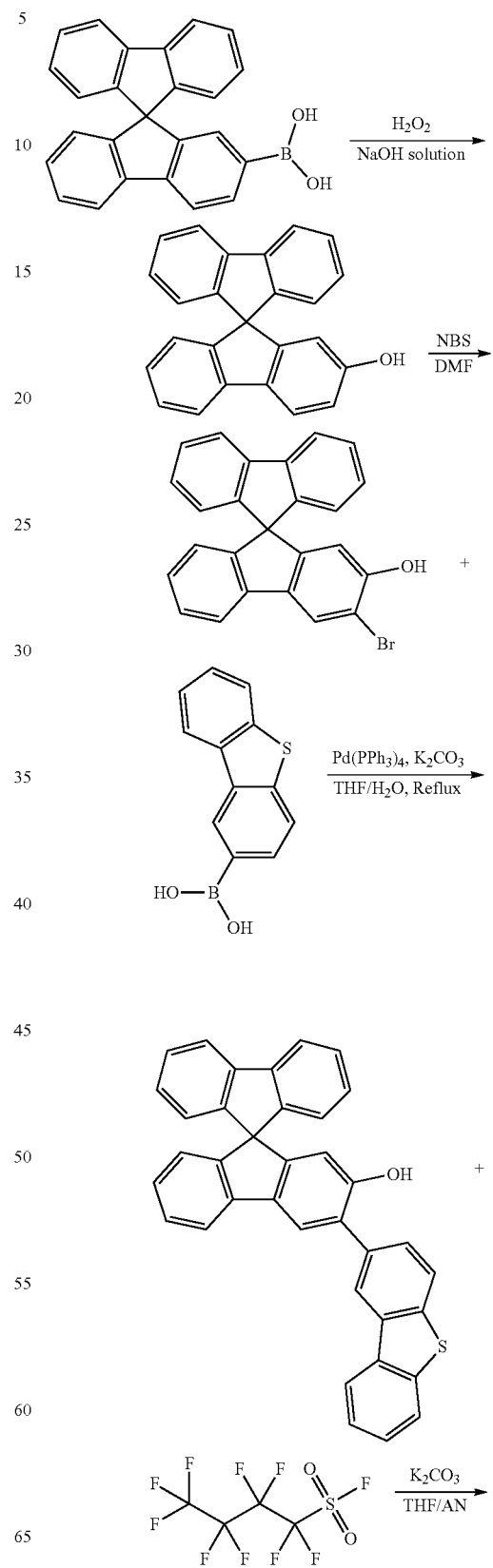

151
-continued

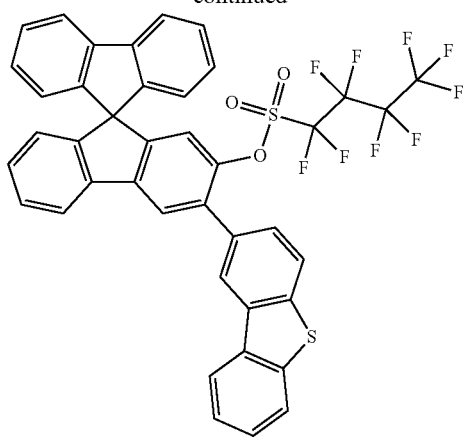

Preparation Example 1

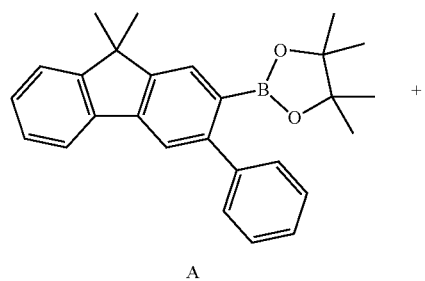

152
-continued

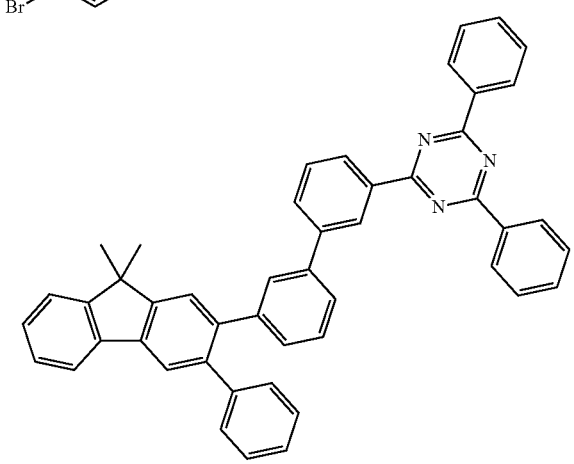

compound 1

After completely dissolving Compound A (10.33 g, 26.08 mmol) and 2-(3'-bromo-[1,1'-biphenyl]-3-yl)-4,6-diphenyl-1,3,5-triazine (10.5 g, 22.68 mmol) in tetrahydrofuran (300 ml) in a 500 ml round bottom flask under the nitrogen atmosphere, a 2 M aqueous potassium carbonate solution (150 ml) was added thereto and then tetrakis-(triphenylphosphine)palladium (0.79 g, 0.68 mmol) was introduced thereto, and the result was stirred for 3 hours while heating. The temperature was lowered to room temperature, the water layer was removed, and after drying the result with anhydrous magnesium sulfate, the result was vacuum concentrated and recrystallized with ethyl acetate (300 ml) to prepare Compound 1 (10.67 g, 72%). (MS [M+H]$^+$=654)

Preparation Example 2

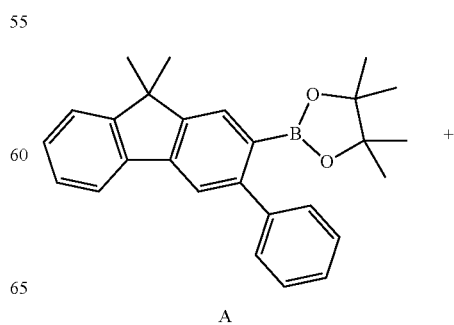

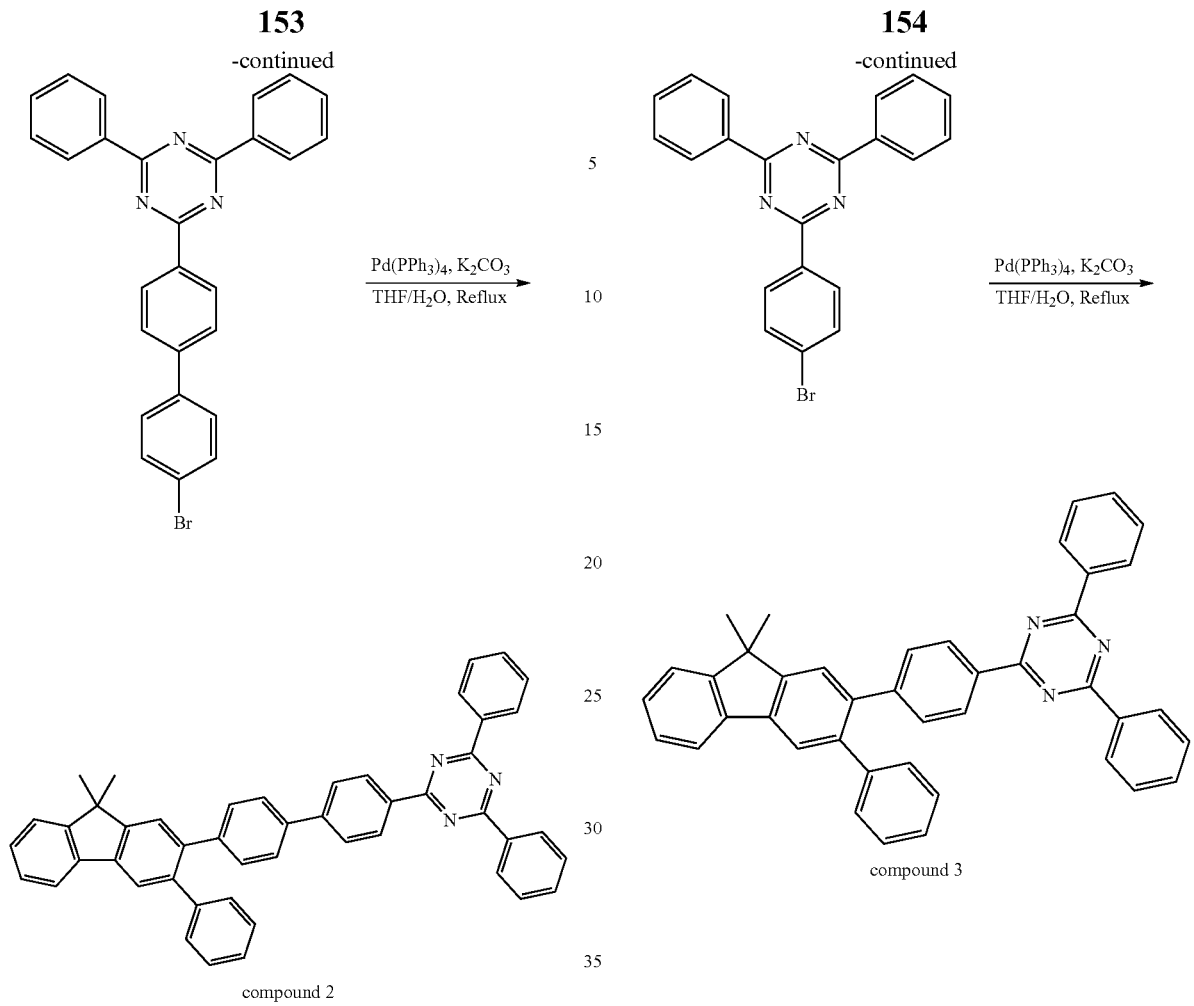

compound 2 compound 3

After completely dissolving Compound A (9.34 g, 23.6 mmol) and 2-(4'-bromo-[1,1'-biphenyl]-4-yl)-4,6-diphenyl-1,3,5-triazine (9.5 g, 20.52 mmol) in tetrahydrofuran (240 ml) in a 500 ml round bottom flask under the nitrogen atmosphere, a 2 M aqueous potassium carbonate solution (120 ml) was added thereto and then tetrakis-(triphenylphosphine)palladium (0.71 g, 0.62 mmol) was introduced thereto, and the result was stirred for 5 hours while heating. The temperature was lowered to room temperature, the water layer was removed, and after drying the result with anhydrous magnesium sulfate, the result was vacuum concentrated and recrystallized with ethyl acetate (240 ml) to prepare Compound 2 (8.67 g, 65%). (MS[M+H]$^+$=654)

After completely dissolving Compound A (10 g, 25.26 mmol) and 2-(4-bromophenyl)-4,6-diphenyl-1,3,5-triazine (8.5 g, 21.96 mmol) in tetrahydrofuran (220 ml) in a 500 ml round bottom flask under the nitrogen atmosphere, a 2 M aqueous potassium carbonate solution (110 ml) was added thereto and then tetrakis-(triphenylphosphine)palladium (0.76 g, 0.66 mmol) was introduced thereto, and the result was stirred for 5 hours while heating. The temperature was lowered to room temperature, the water layer was removed, and after drying the result with anhydrous magnesium sulfate, the result was vacuum concentrated and recrystallized with ethyl acetate (210 ml) to prepare Compound 3 (7.76 g, 61%). (MS[M+H]$^+$=578)

Preparation Example 3

Preparation Example 4

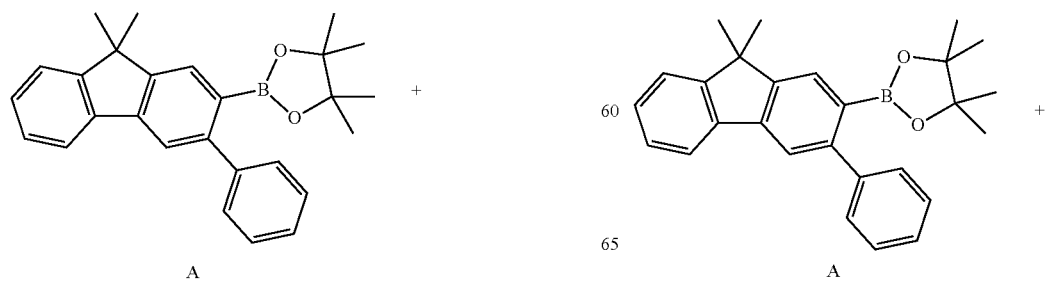

A

A

-continued

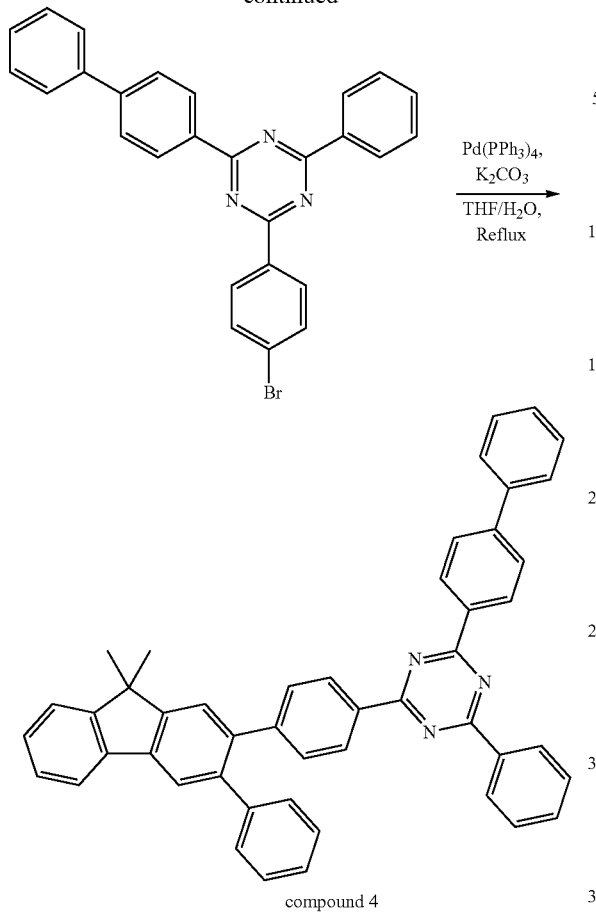

compound 4

-continued

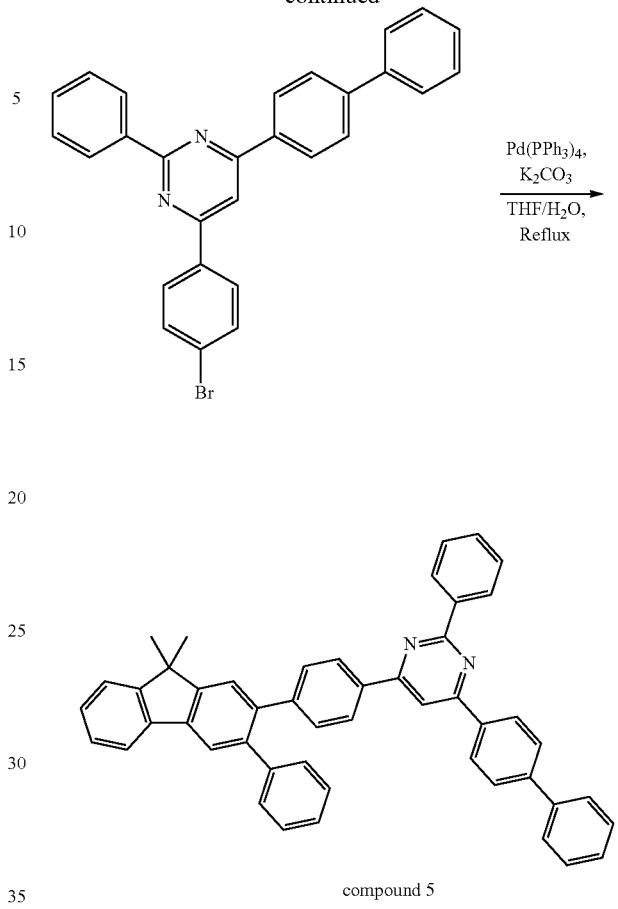

compound 5

After completely dissolving Compound A (8.95 g, 22.60 mmol) and 2-([1,1'-biphenyl]-4-yl)-4-(4-bromophenyl)-6-phenyl-1,3,5-triazine (9.1 g, 19.65 mmol) in tetrahydrofuran (220 ml) in a 500 ml round bottom flask under the nitrogen atmosphere, a 2 M aqueous potassium carbonate solution (110 ml) was added thereto and then tetrakis-(triphenylphosphine)palladium (0.68 g, 0.59 mmol) was introduced thereto, and the result was stirred for 5 hours while heating. The temperature was lowered to room temperature, the water layer was removed, and after drying the result with anhydrous magnesium sulfate, the result was vacuum concentrated and recrystallized with ethyl acetate (220 ml) to prepare Compound 4 (6.47 g, 50%). (MS[M+H]$^+$=654)

After completely dissolving Compound A (7.69 g, 19.42 mmol) and 4-([1,1'-biphenyl]-4-yl)-6-(4-bromophenyl)-2-pinelpyrimidine (7.8 g, 16.88 mmol) in tetrahydrofuran (200 ml) in a 500 ml round bottom flask under the nitrogen atmosphere, a 2 M aqueous potassium carbonate solution (100 ml) was added thereto and then tetrakis-(triphenylphosphine)palladium (0.59 g, 0.51 mmol) was introduced thereto, and the result was stirred for 6 hours while heating. The temperature was lowered to room temperature, the water layer was removed, and after drying the result with anhydrous magnesium sulfate, the result was vacuum concentrated and recrystallized with ethyl acetate (180 ml) to prepare Compound 5 (5.17 g, 47%). (MS [M+H]$^+$=653)

Preparation Example 5

Preparation Example 6

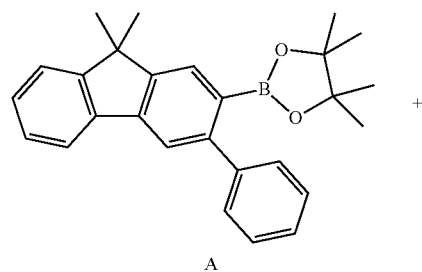

A

+

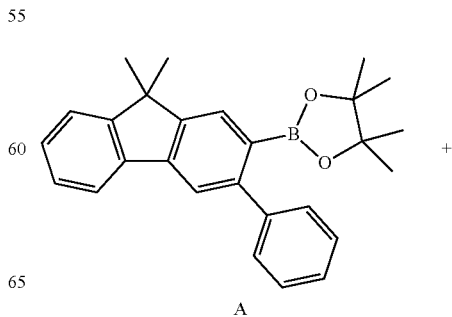

A

+

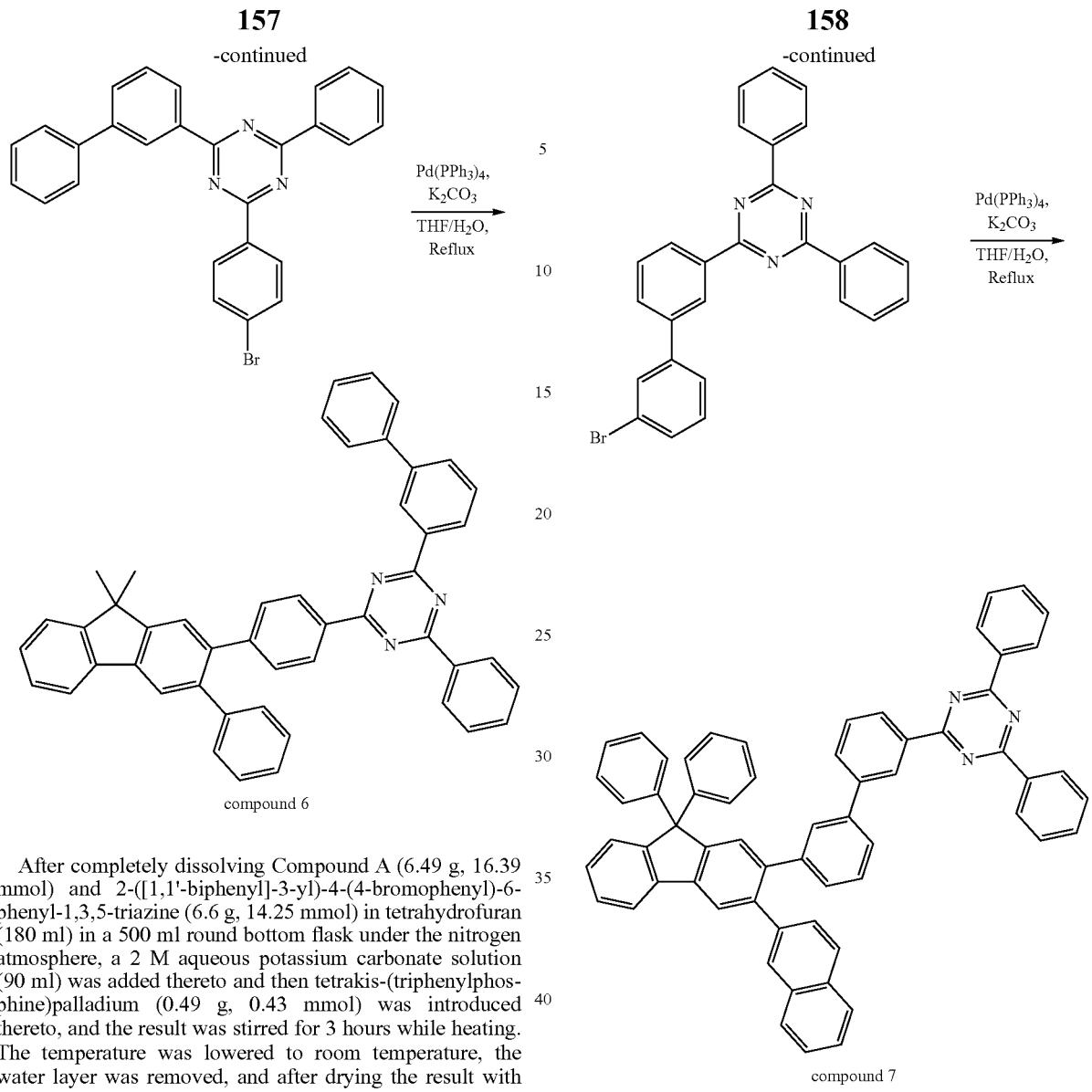

After completely dissolving Compound A (6.49 g, 16.39 mmol) and 2-([1,1'-biphenyl]-3-yl)-4-(4-bromophenyl)-6-phenyl-1,3,5-triazine (6.6 g, 14.25 mmol) in tetrahydrofuran (180 ml) in a 500 ml round bottom flask under the nitrogen atmosphere, a 2 M aqueous potassium carbonate solution (90 ml) was added thereto and then tetrakis-(triphenylphosphine)palladium (0.49 g, 0.43 mmol) was introduced thereto, and the result was stirred for 3 hours while heating. The temperature was lowered to room temperature, the water layer was removed, and after drying the result with anhydrous magnesium sulfate, the result was vacuum concentrated and recrystallized with ethyl acetate (220 ml) to prepare Compound 6 (7.21 g, 62%). (MS[M+H]$^+$=654)

Preparation Example 7

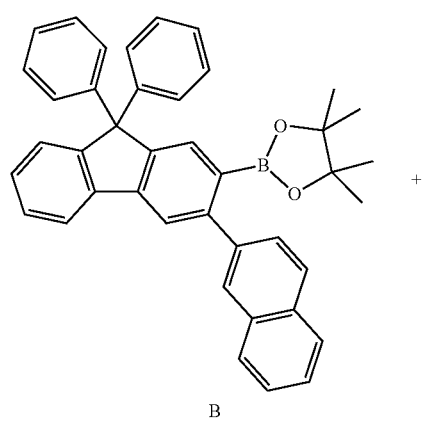

B

After completely dissolving Compound B (8.35 g, 14.65 mmol) and 2-(3'-bromo-[1,1'-biphenyl]-3-yl)4,6-diphenyl-1,3,5-triazine (5.9 g, 12.74 mmol) in tetrahydrofuran (300 ml) in a 500 ml round bottom flask under the nitrogen atmosphere, a 2 M aqueous potassium carbonate solution (150 ml) was added thereto and then tetrakis-(triphenylphosphine)palladium (0.44 g, 0.38 mmol) was introduced thereto, and the result was stirred for 3 hours while heating. The temperature was lowered to room temperature, the water layer was removed, and after drying the result with anhydrous magnesium sulfate, the result was vacuum concentrated and recrystallized with ethanol (300 ml) to prepare Compound 7 (8.12 g, 77%). (MS[M+H]$^+$=828)

Preparation Example 8

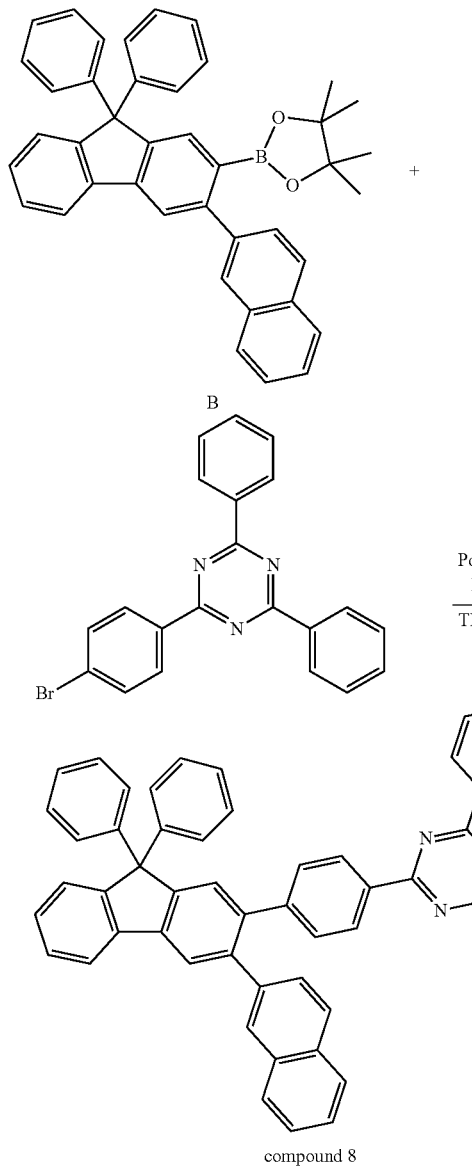

compound 8

Preparation Example 9

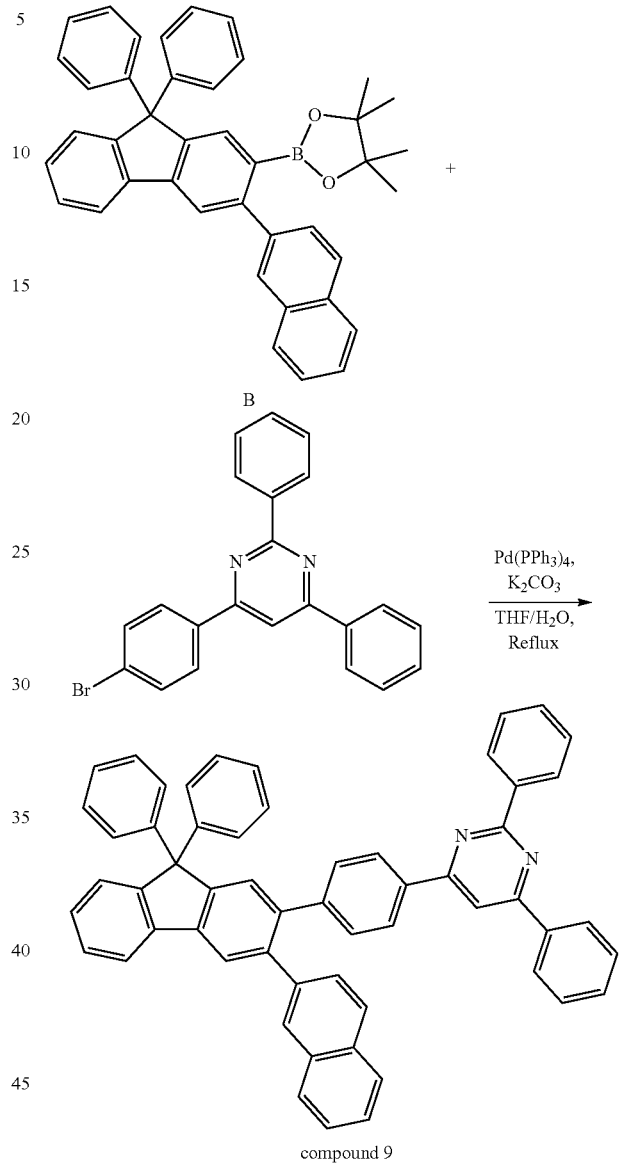

compound 9

After completely dissolving Compound B (10.5 g, 18.42 mmol) and 2-(4-bromophenyl)-4,6-diphenyl-1,3,5-triazine (6.2 g, 16.02 mmol) in tetrahydrofuran (240 ml) in a 500 ml round bottom flask under the nitrogen atmosphere, a 2 M aqueous potassium carbonate solution (120 ml) was added thereto and then tetrakis-(triphenylphosphine)palladium (0.56 g, 0.48 mmol) was introduced thereto, and the result was stirred for 5 hours while heating. The temperature was lowered to room temperature, the water layer was removed, and after drying the result with anhydrous magnesium sulfate, the result was vacuum concentrated and recrystallized with ethyl acetate (260 ml) to prepare Compound 8 (9.23 g, 77%). (MS [M+H]$^+$=752)

After completely dissolving Compound B (9.82 g, 17.24 mmol) and 4-(4-bromophenyl)-2,6-diphenylpyrimidine (5.8 g, 14.99 mmol) in tetrahydrofuran (260 ml) in a 500 ml round bottom flask under the nitrogen atmosphere, a 2 M aqueous potassium carbonate solution (130 ml) was added thereto and then tetrakis-(triphenylphosphine)palladium (0.52 g, 0.45 mmol) was introduced thereto, and the result was stirred for 3 hours while heating. The temperature was lowered to room temperature, the water layer was removed, and after drying the result with anhydrous magnesium sulfate, the result was vacuum concentrated and recrystallized with ethyl acetate (220 ml) to prepare Compound 9 (5.67 g, 50%). (MS [M+H]$^+$=751)

Preparation Example 10

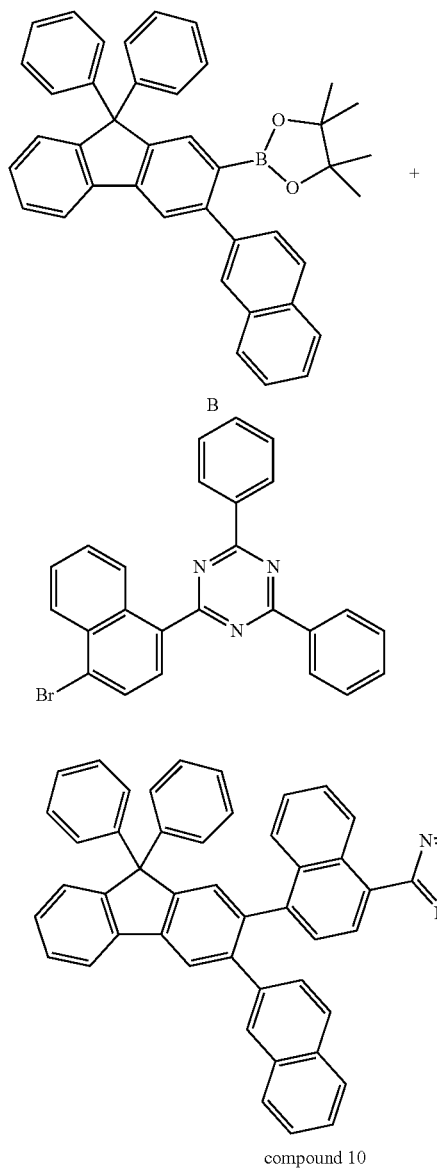

compound 10

Preparation Example 11

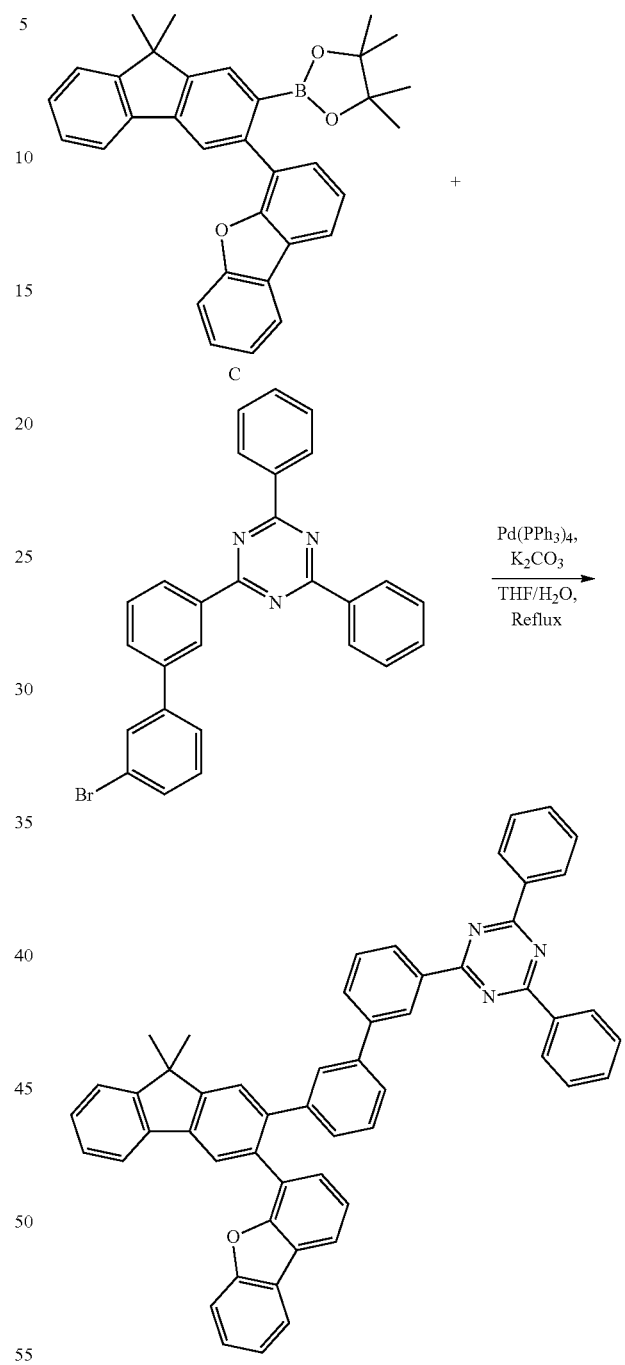

compound 11

After completely dissolving Compound B (9.45 g, 16.58 mmol) and 2-(4-bromonaphthalen-1-yl)-4,6-diphenyl-1,3,5-triazine (6.3 g, 14.42 mmol) in tetrahydrofuran (220 ml) in a 500 ml round bottom flask under the nitrogen atmosphere, a 2 M aqueous potassium carbonate solution (110 ml) was added thereto and then tetrakis-(triphenylphosphine)palladium (0.5 g, 0.43 mmol) was introduced thereto, and the result was stirred for 9 hours while heating. The temperature was lowered to room temperature, the water layer was removed, and after drying the result with anhydrous magnesium sulfate, the result was vacuum concentrated and recrystallized with ethyl acetate (320 ml) to prepare Compound 10 (8.11 g, 70%). (MS[M+H]$^+$=802)

After completely dissolving Compound C (8.59 g, 17.68 mmol) and 2-(3'-bromo-[1,1'-biphenyl]-3-yl)-4,6-diphenyl-1,3,5-triazine (7.12 g, 15.38 mmol) in tetrahydrofuran (300 ml) in a 500 ml round bottom flask under the nitrogen atmosphere, a 2 M aqueous potassium carbonate solution (150 ml) was added thereto and then tetrakis-(triphenylphosphine)palladium (0.53 g, 0.46 mmol) was introduced thereto, and the result was stirred for 3 hours while heating. The temperature was lowered to room temperature, the water layer was removed, and after drying the result with anhydrous magnesium sulfate, the result was vacuum concentrated and recrystallized with tetrahydrofuran (210 ml) to prepare Compound 11 (8.36 g, 73%). (MS[M+H]⁺=744)

Preparation Example 12

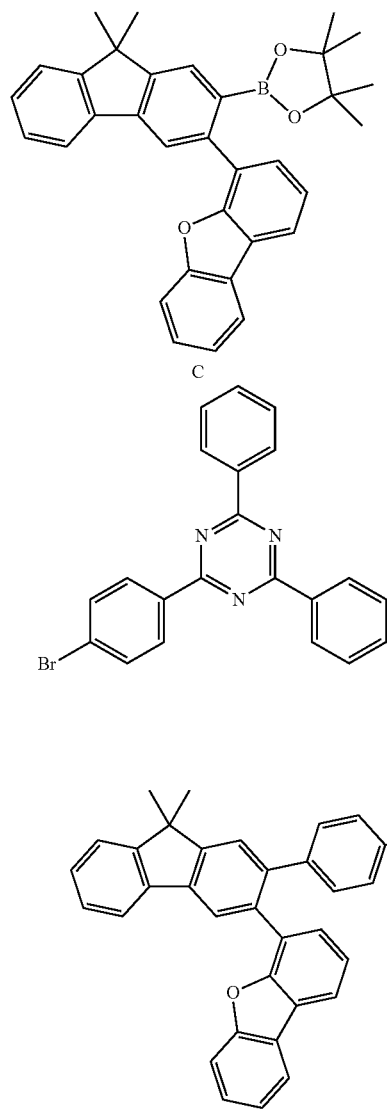

compound 12

Preparation Example 13

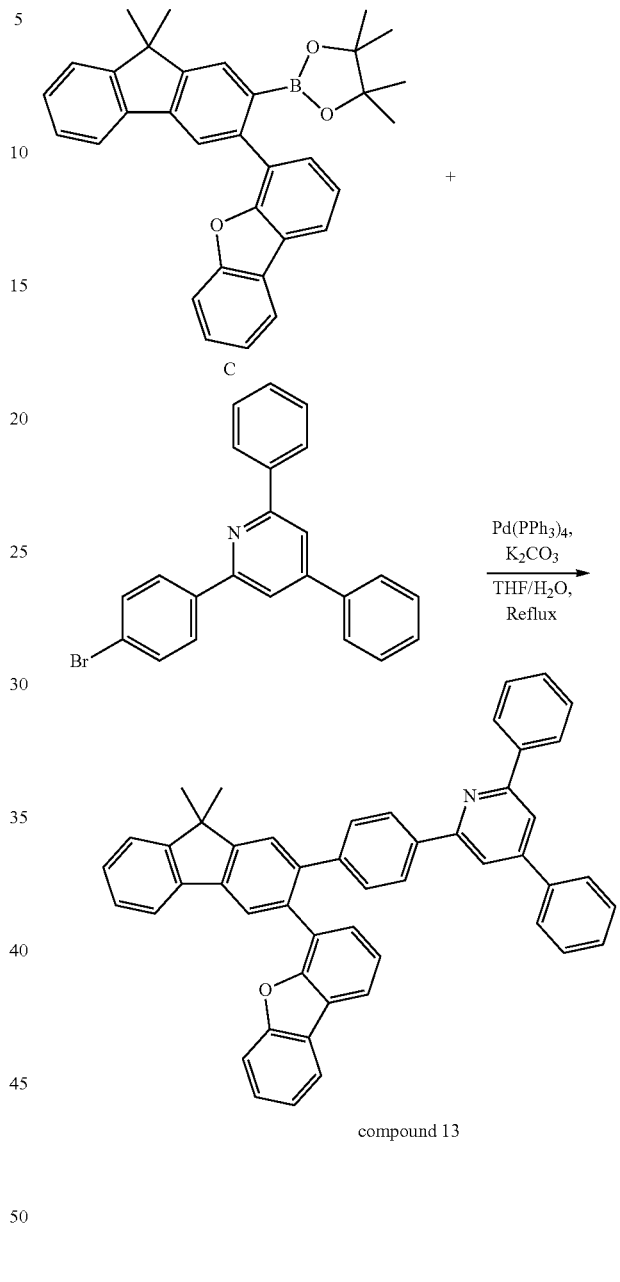

compound 13

After completely dissolving Compound C (9.21 g, 18.96 mmol), and 2-(3'-bromo-[1,1'-biphenyl]-3-yl)-4,6-diphenyl-1,3,5-triazine (6.38 g, 16.49 mmol) in tetrahydrofuran (260 ml) in a 500 ml round bottom flask under the nitrogen atmosphere, a 2 M aqueous potassium carbonate solution (130 ml) was added thereto and then tetrakis-(triphenylphosphine)palladium (0.57 g, 0.49 mmol) was introduced thereto, and the result was stirred for 4 hours while heating. The temperature was lowered to room temperature, the water layer was removed, and after drying the result with anhydrous magnesium sulfate, the result was vacuum concentrated and recrystallized with ethyl acetate (260 ml) to prepare Compound 12 (6.95 g, 63%). (MS[M+H]⁺=668)

After completely dissolving Compound C (8.51 g, 17.5 mmol) and 2-(4-bromophenyl)-4,6-diphenylpyridine (5.86 g, 15.22 mmol) in tetrahydrofuran (220 ml) in a 500 ml round bottom flask under the nitrogen atmosphere, a 2 M aqueous potassium carbonate solution (110 ml) was added thereto and then tetrakis-(triphenylphosphine)palladium (0.53 g, 0.46 mmol) was introduced thereto, and the result was stirred for 3 hours while heating. The temperature was lowered to room temperature, the water layer was removed, and after drying the result with anhydrous magnesium sulfate, the result was vacuum concentrated and recrystallized with ethyl acetate (240 ml) to prepare Compound 13 (5.76 g, 57%). (MS[M+H]⁺=666)

Preparation Example 14

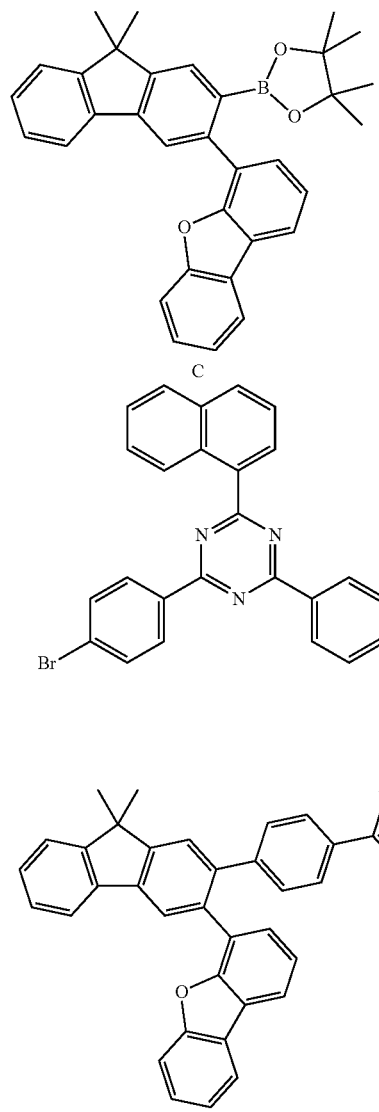

compound 14

Preparation Example 15

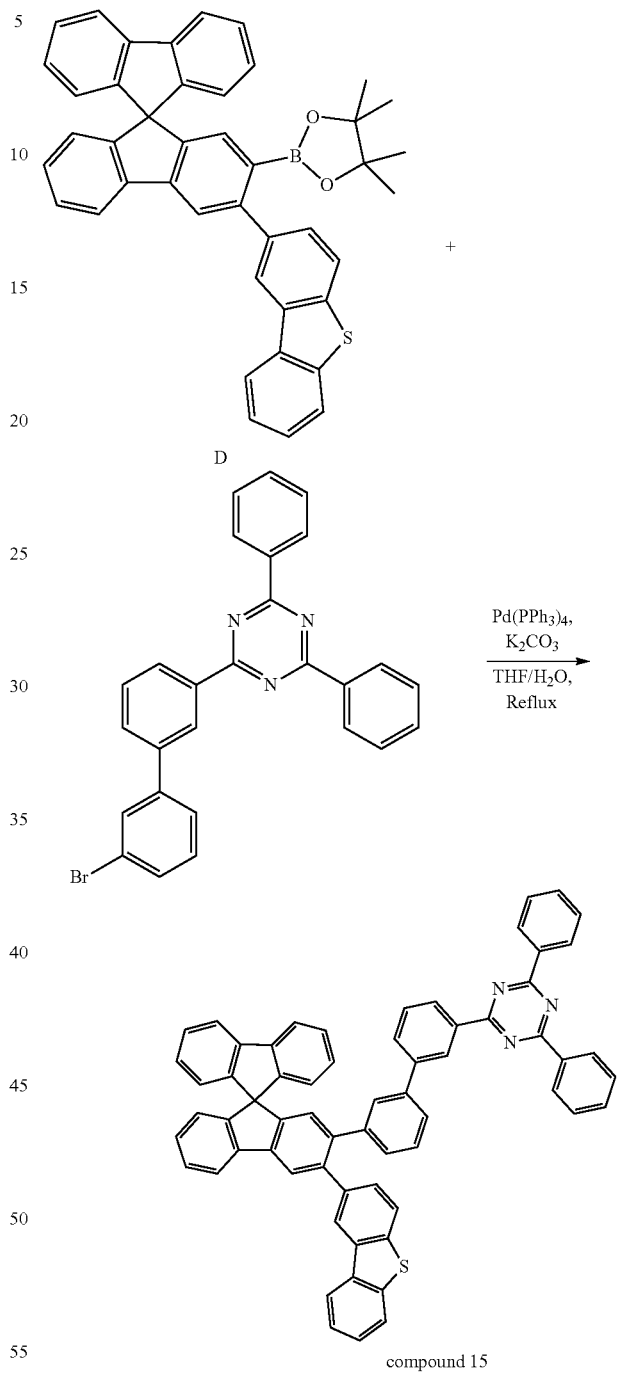

compound 15

After completely dissolving Compound C (9.39 g, 19.32 mmol) and 2-(4-bromophenyl)-4-(naphthalen-1-yl)6-phenyl-1,3,5-triazine (7.34 g, 16.8 mmol) in tetrahydrofuran (260 ml) in a 500 ml round bottom flask under the nitrogen atmosphere, a 2 M aqueous potassium carbonate solution (130 ml) was added thereto and then tetrakis-(triphenylphosphine)palladium (0.58 g, 0.5 mmol) was introduced thereto, and the result was stirred for 4 hours while heating. The temperature was lowered to room temperature, the water layer was removed, and after drying the result with anhydrous magnesium sulfate, the result was vacuum concentrated and recrystallized with ethyl acetate (280 ml) to prepare Compound 14 (8.85 g, 73%). (MS[M+H]$^+$=718)

After completely dissolving Compound D (9.08 g, 14.56 mmol) and 2-(3'-bromo-[1,1'-biphenyl]-3-yl)-4,6-diphenyl-1,3,5-triazine (5.86 g, 12.66 mmol) in tetrahydrofuran (240 ml) in a 500 ml round bottom flask under the nitrogen atmosphere, a 2 M aqueous potassium carbonate solution (120 ml) was added thereto and then tetrakis-(triphenylphosphine)palladium (0.44 g, 0.38 mmol) was introduced thereto, and the result was stirred for 3 hours while heating. The temperature was lowered to room temperature, the water layer was removed, and after drying the result with anhydrous magnesium sulfate, the result was vacuum concentrated and recrystallized with ethyl acetate (240 ml) to prepare Compound 15 (6.85 g, 61%). (MS[M+H]⁺=882)

Preparation Example 16

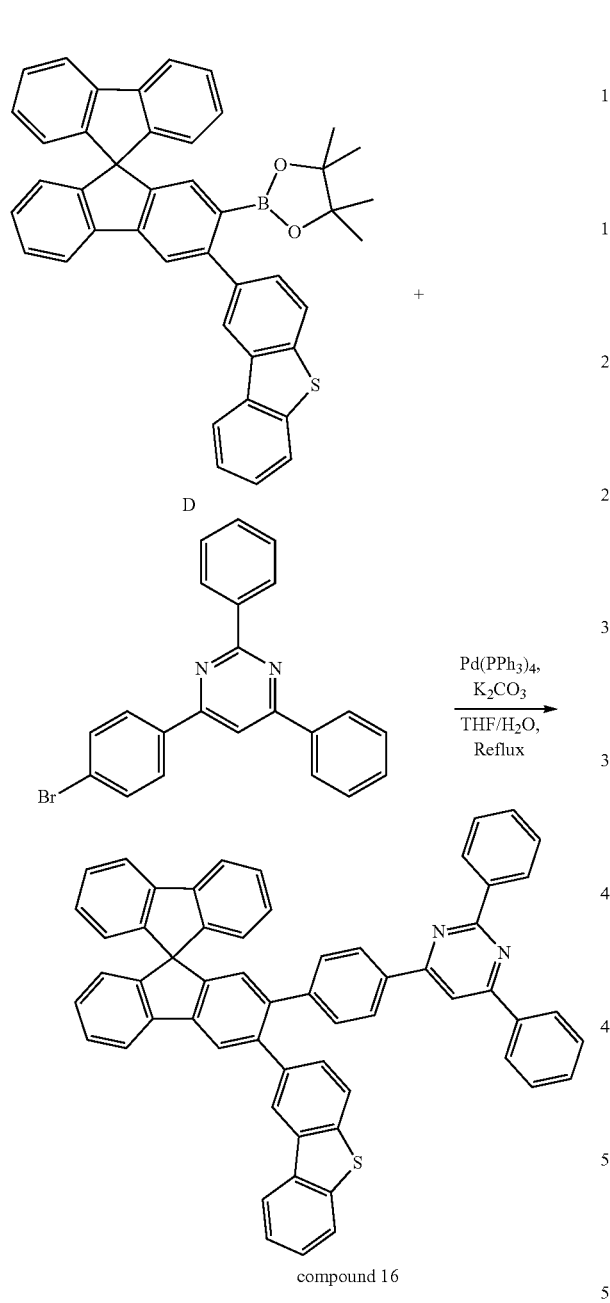

compound 16

After completely dissolving Compound D (7.24 g, 11.60 mmol) and 4-(4-bromophenyl)-2,6-diphenylpyrimidine (4.67, 10.09 mmol) in tetrahydrofuran (220 ml) in a 500 ml round bottom flask under the nitrogen atmosphere, a 2 M aqueous potassium carbonate solution (110 ml) was added thereto and then tetrakis-(triphenylphosphine) palladium (0.35 g, 0.3 mmol) was introduced thereto, and the result was stirred for 5 hours while heating. The temperature was lowered to room temperature, the water layer was removed, and after drying the result with anhydrous magnesium sulfate, the result was vacuum concentrated and recrystallized with ethyl acetate (230 ml) to prepare Compound 16 (4.67 g, 58%). (MS [M+H]⁺=805)

Preparation Example 17

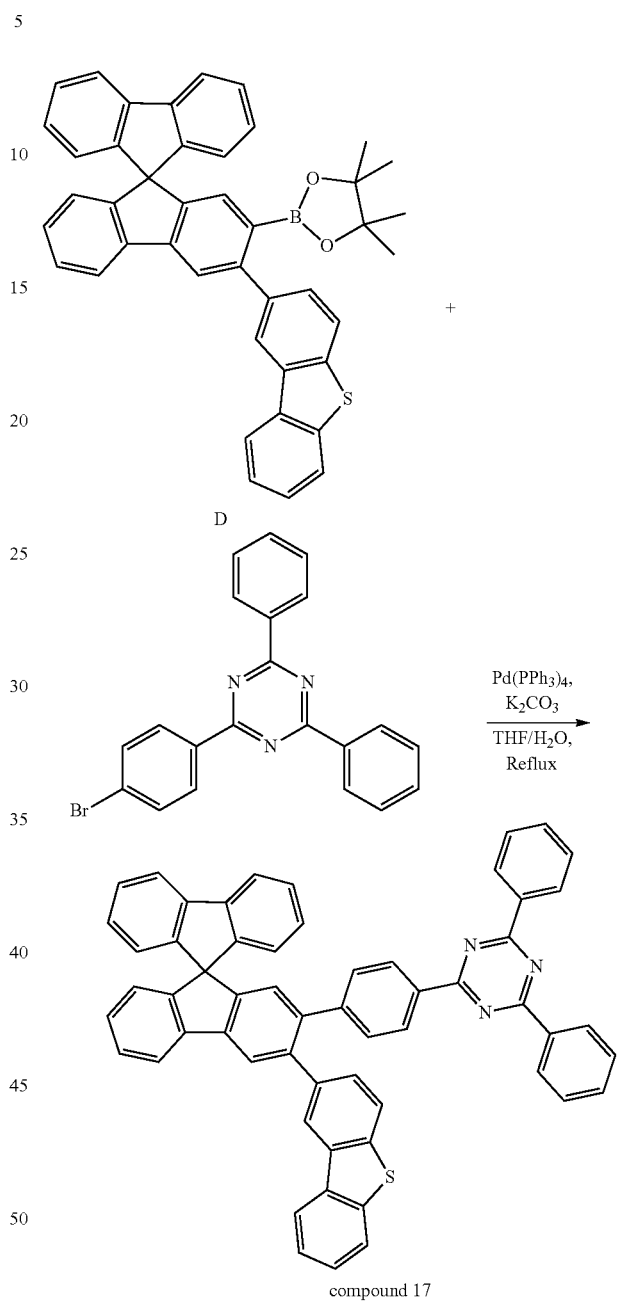

compound 17

After completely dissolving Compound D (10.29 g, 16.49 mmol) and 2-(4-bromophenyl)-4,6-diphenyl-1,3,5-triazine (5.55 g, 14.34 mmol) in tetrahydrofuran (220 ml) in a 500 ml round bottom flask under the nitrogen atmosphere, a 2 M aqueous potassium carbonate solution (110 ml) was added thereto and then tetrakis-(triphenylphosphine) palladium (0.5 g, 0.43 mmol) was introduced thereto, and the result was stirred for 5 hours while heating. The temperature was lowered to room temperature, the water layer was removed, and after drying the result with anhydrous magnesium sulfate, the result was vacuum concentrated and recrystallized with ethyl acetate (240 ml) to prepare Compound 17 (7.62 g, 66%). (MS[M+H]⁺=806)

Preparation Example 18

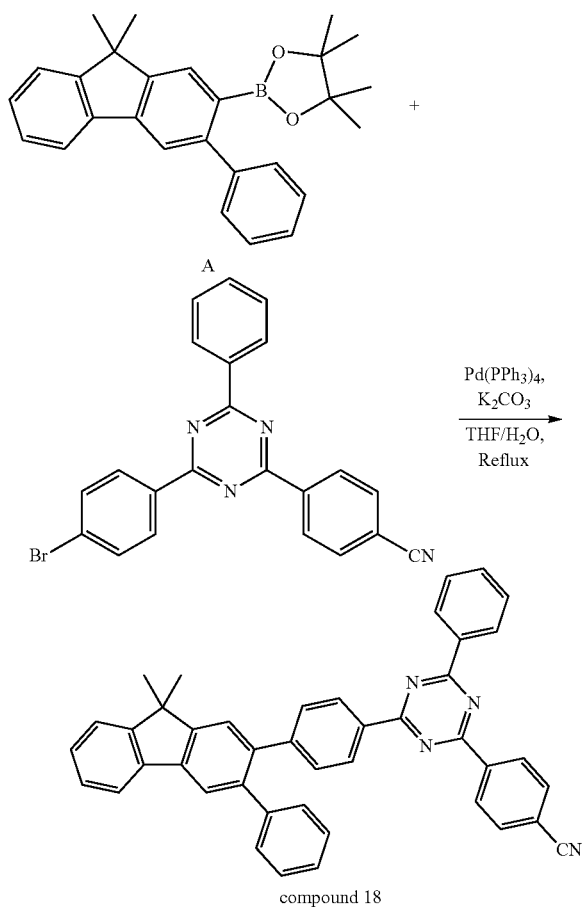

compound 18

After completely dissolving Compound A (8.68 g, 21.92 mmol) and 4-(4-(4-bromophenyl)-6-phenyl-1,3,6-triazin-2-yl)benzo-nitrile (8.21 g, 19.93 mmol) in tetrahydrofuran (220 ml) in a 500 ml round bottom flask under the nitrogen atmosphere, a 2 M aqueous potassium carbonate solution (110 ml) was added thereto and then tetrakis-(triphenylphosphine)palladium (0.69 g, 0.6 mmol) was introduced thereto, and the result was stirred for 4 hours while heating. The temperature was lowered to room temperature, the water layer was removed, and after drying the result with anhydrous magnesium sulfate, the result was vacuum concentrated and recrystallized with ethyl acetate (260 ml) to prepare Compound 18 (7.76 g, 65%). (MS[M+H]$^+$=603)

Example 1-1

A glass substrate on which indium tin oxide (ITO) was coated as a thin film to a thickness of 1,000 Å was placed in detergent-dissolved distilled water and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum deposition apparatus.

On the transparent ITO electrode, an anode, prepared as above, a hole injection layer was formed by thermal vacuum depositing compounds of the following Compound HI1 and the following Compound HI2 in a ratio of 98:2 (molar ratio) to a thickness of 100 Å. On the hole injection layer, a hole transfer layer was formed by vacuum depositing a compound of the following Chemical Formula HT1 (1150 Å). Subsequently, an electron blocking layer was formed on the hole transfer layer by vacuum depositing a compound of EB1 shown below to a film thickness of 50 Å. Then, a light emitting layer was formed on the electron blocking layer by vacuum depositing a compound of the following Chemical Formula BH and a compound of the following Chemical Formula BD in a weight ratio of 50:1 to a film thickness of 200 Å. On the light emitting layer, a hole blocking layer was formed by vacuum depositing Compound 1 to a film thickness of 50 Å. Then, an electron injection and transfer layer was formed on the hole blocking layer to a thickness of 30 Å by vacuum depositing a compound of the following Chemical Formula ET1 and a compound of the following Chemical Formula LiQ in a weight ratio of 1:1. On the electron injection and transfer layer, a cathode was formed by consecutively depositing lithium fluoride (LiF) to a thickness of 12 Å and aluminum to a thickness of 1,000 Å.

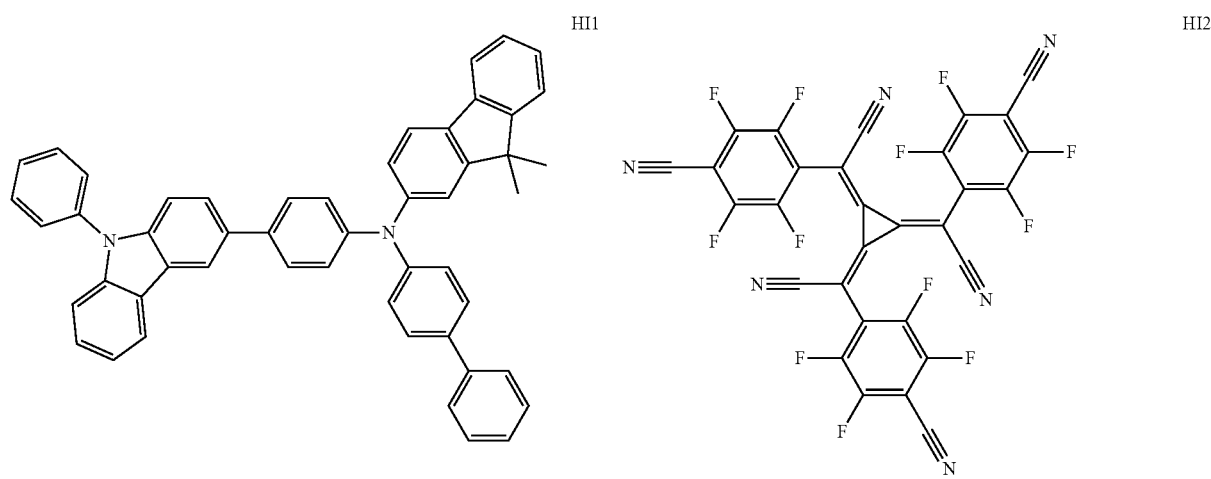

-continued
HT1
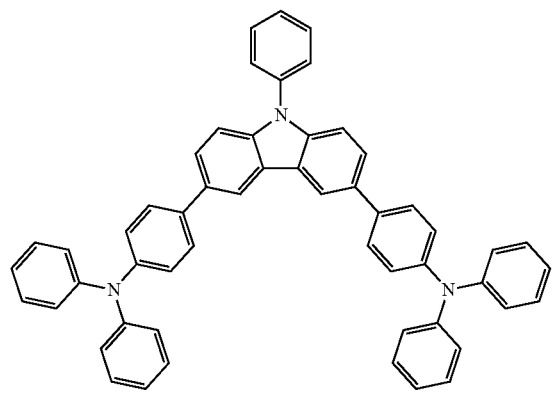
EB1
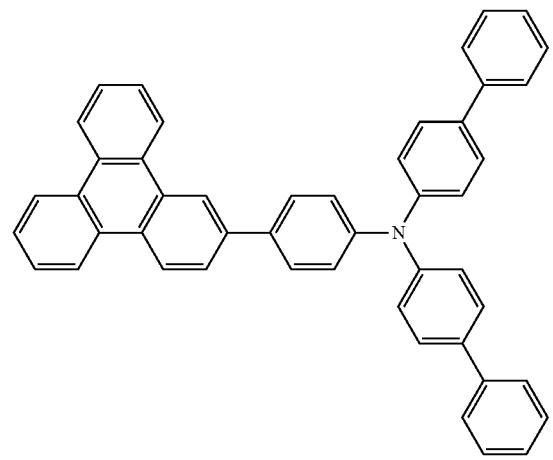
BH
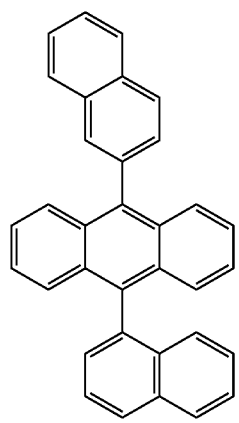
BD
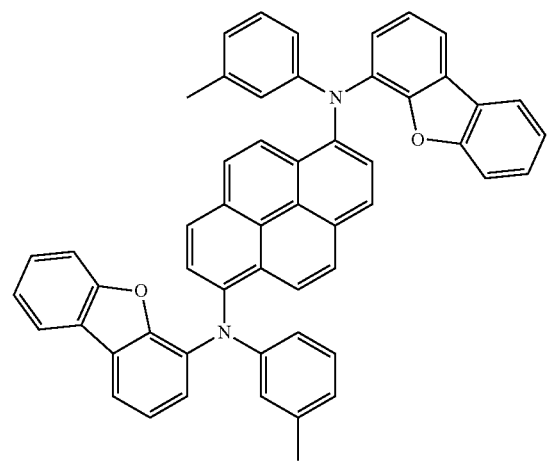
ET1
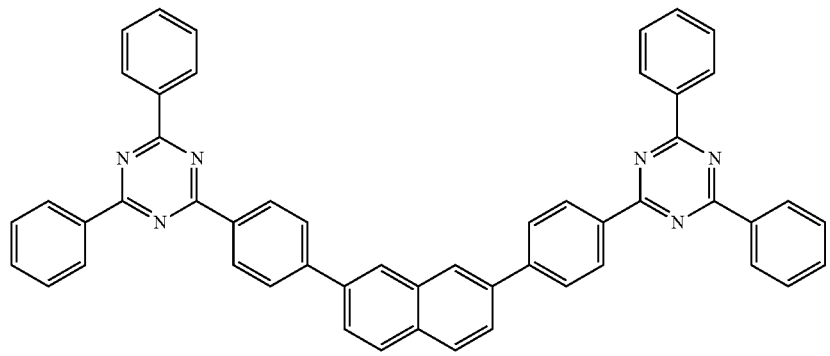
LiQ
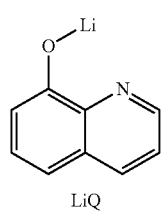

In the above-mentioned process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum during the deposition was maintained at $2 \times 10^{-7}$ torr to $5 \times 10^{-6}$ torr to manufacture an organic light emitting device.

Example 1-2 to Example 1-18

Organic light emitting devices were manufactured in the same manner as in Example 1-1 except that compounds described in the following Table 1 were used as the hole blocking layer instead of Compound 1.

Comparative Examples 1-1 to 1-4

Organic light emitting devices were manufactured in the same manner as in Example 1-1 except that compounds described in the following Table 1 were used as the hole blocking layer instead of Compound 1. Compounds of HB1, HB2, HB3 and HB4 used in the following Table 1 are as follows:

HB1

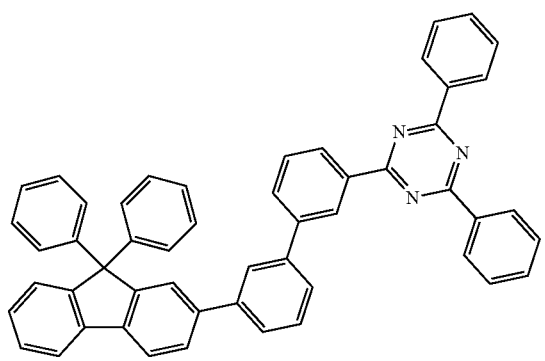

HB2

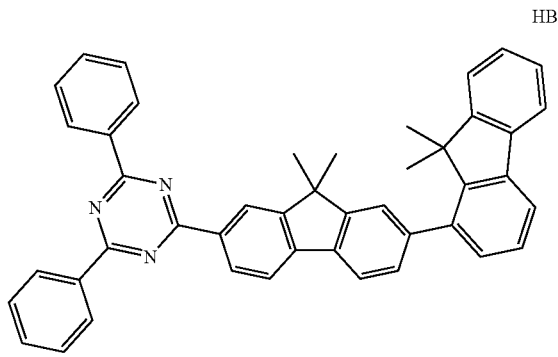

HB3

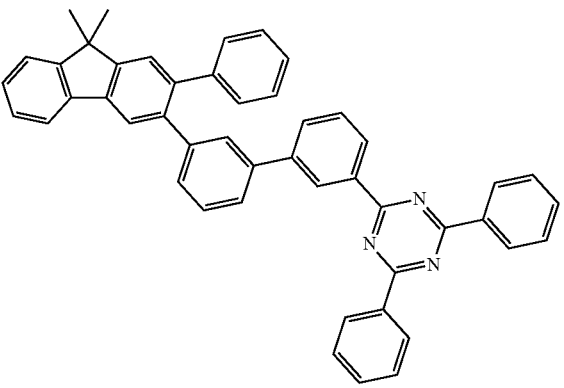

HB4

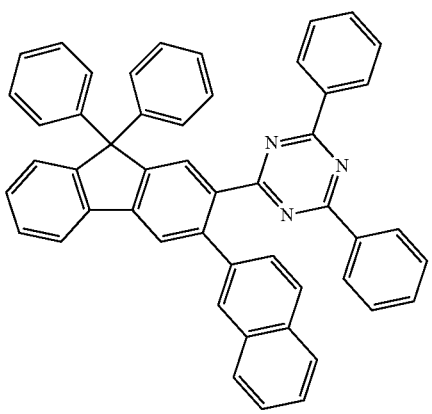

Experimental Example 1

A voltage, efficiency, a color coordinate and a lifetime were measured when applying a current to each of the organic light emitting devices manufactured in the examples and the comparative examples, and the results are shown in the following Table 1. T95 means time taken for luminance decreasing to 95% from initial luminance (1600 nit).

TABLE 1

| | Compound (Hole Blocking Layer) | Voltage (V@10 mA/cm²) | Efficiency (cd/A@10 mA/cm²) | Color Coordinate (x, y) | T95 (hr) |
|---|---|---|---|---|---|
| Example 1-1 | Compound 1 | 4.26 | 6.35 | (0.140, 0.045) | 300 |
| Example 1-2 | Compound 2 | 4.33 | 6.23 | (0.141, 0.045) | 275 |
| Example 1-3 | Compound 3 | 4.38 | 6.24 | (0.143, 0.046) | 275 |
| Example 1-4 | Compound 4 | 4.39 | 6.25 | (0.142, 0.045) | 280 |
| Example 1-5 | Compound 5 | 4.32 | 6.26 | (0.140, 0.046) | 265 |
| Example 1-6 | Compound 6 | 4.36 | 6.27 | (0.141, 0.047) | 290 |
| Example 1-7 | Compound 7 | 4.25 | 6.39 | (0.140, 0.046) | 305 |
| Example 1-8 | Compound 8 | 4.33 | 6.18 | (0.141, 0.047) | 290 |

TABLE 1-continued

| | Compound (Hole Blocking Layer) | Voltage (V@10 mA/cm²) | Efficiency (cd/A@10 mA/cm²) | Color Coordinate (x, y) | T95 (hr) |
|---|---|---|---|---|---|
| Example 1-9 | Compound 9 | 4.43 | 6.17 | (0.141, 0.046) | 260 |
| Example 1-10 | Compound 10 | 4.37 | 6.19 | (0.140, 0.047) | 285 |
| Example 1-11 | Compound 11 | 4.26 | 6.38 | (0.142, 0.045) | 280 |
| Example 1-12 | Compound 12 | 4.31 | 6.14 | (0.140, 0.046) | 270 |
| Example 1-13 | Compound 13 | 4.48 | 6.17 | (0.141, 0.047) | 250 |
| Example 1-14 | Compound 14 | 4.43 | 6.16 | (0.142, 0.047) | 275 |
| Example 1-15 | Compound 15 | 4.25 | 6.31 | (0.141, 0.046) | 300 |
| Example 1-16 | Compound 16 | 4.42 | 6.10 | (0.141, 0.046) | 260 |
| Example 1-17 | Compound 17 | 4.45 | 6.15 | (0.142, 0.048) | 270 |
| Example 1-18 | Compound 18 | 4.52 | 6.16 | (0.141, 0.046) | 325 |
| Comparative Example 1-1 | HB1 | 4.73 | 5.78 | (0.142, 0.047) | 160 |
| Comparative Example 1-2 | HB2 | 5.06 | 5.52 | (0.143, 0.048) | 135 |
| Comparative Example 1-3 | HB3 | 4.66 | 5.87 | (0.143, 0.048) | 220 |
| Comparative Example 1-4 | HB4 | 4.94 | 5.61 | (0.143, 0.048) | 185 |

As shown in Table 1, the organic light emitting device using the compound of the present disclosure as a hole blocking layer exhibited superior properties in terms of efficiency, driving voltage and stability of the organic light emitting device.

In Examples 1-1 to 1-18, as shown in Table 1, it was seen that, when using a material in which the No. 2 carbon position of the fluorene core was substituted with triazine, pyrimidine or pyridine through an aryl group as a hole blocking layer, the device had properties of low voltage, high efficiency and long lifetime. The compound according to the present disclosure has an excellent hole blocking ability, and is usable in an organic light emitting device.

Furthermore, when referring to the results of Examples 1-1, 1-7, 1-11 and 1-15, it was identified that, when using a compound in which an N-including heteroring bonds to the fluorene core by being linked through

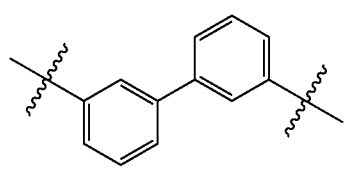 [SMILES: *c1cccc(-c2cccc(*)c2)c1]

as a hole blocking layer, the device had a lower driving voltage and higher efficiency.

In Example 1-18 of Table 1, it was identified that the lifetime was the longest when using a compound in which a triazine group including a CN group as substituent bonds to the fluorene core as a hole blocking layer. The CN group in the compound greatly enhances a device lifetime by slightly slowing electron injection into a light emitting layer in a hole blocking layer.

Hereinbefore, preferred embodiments (hole blocking layer) of the present disclosure have been described, however, the present disclosure is not limited thereto, and various modifications can be made within the scope of the claims and the detailed descriptions of the disclosure, and these also fall within the category of the disclosure.

REFERENCE NUMERALS

1: Substrate
2: Anode
3: Hole Injection Layer
4: Hole Transfer Layer
5: Electron Blocking Layer
6: Light Emitting Layer
7: Hole Blocking Layer
8: Electron Transfer Layer
9: Electron Injection Layer
10: Cathode

The invention claimed is:

1. A compound of Chemical Formula 1:

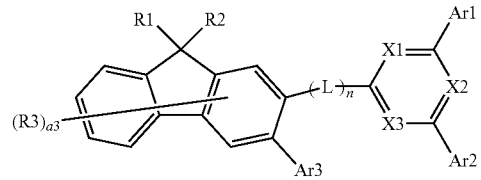

Chemical Formula 1 wherein, in Chemical Formula 1:
X1 to X3 are N;
Ar1 and Ar2 are the same as or different from each other, and each independently is an unsubstituted phenyl group, a phenyl group substituted with CN, an unsubstituted biphenyl group, or an unsubstituted naphthyl group;
Ar3 is phenyl group, a phenyl group substituted with CN, a biphenyl group, a naphthyl group, a dibenzofuran group, or a dibenzothiophene group;
L is a phenylene group;
R1 and R2 are the same as or different from each other, and each independently is hydrogen, deuterium, a C1-C6 alkyl group, or a phenyl group, or bond to each other to form a fluorene group;
each R3 is the same as or different from each other, and each independently is hydrogen or deuterium;
Ra to Rc are hydrogen;
a3 is 6; and
n is an integer of 1 to 2.

2. The compound of claim 1, wherein Chemical Formula 1 is any one of the following Chemical Formulae 1-A to 1-C:

Chemical Formula 1-A

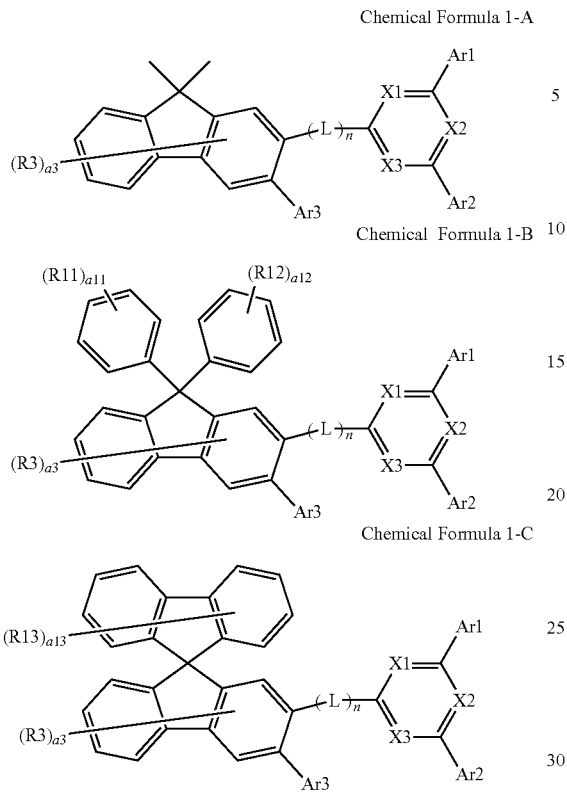

Chemical Formula 1-B

Chemical Formula 1-C wherein in Chemical Formulae 1-A to 1-C:

R3, Ar1 to Ar3, X1 to X3, L, n and a3 have the same definitions as in Chemical Formula 1;

R11 to R13 are the same as or different from each other, and each independently is hydrogen or deuterium;

a11 and a12 are each 5; and a13 is 8.

3. The compound of claim 1, wherein Chemical Formula 1 is Chemical Formula 2:

Chemical Formula 2

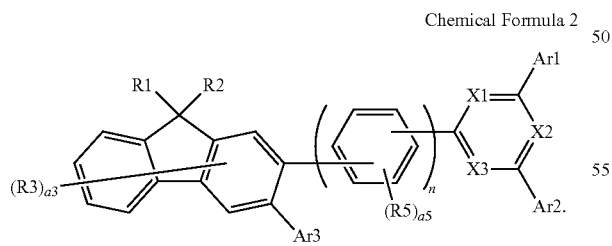

wherein in Chemical Formula 2, R1, R2, R3, X1, X2, X3, Ar1, Ar2, Ar3, a3 and n have the same definitions as in Chemical Formula 1;

R5 is hydrogen or deuterium; and a5 is 4.

4. The compound of claim 1, wherein Chemical Formula 1 is Chemical Formula 3:

Chemical Formula 3

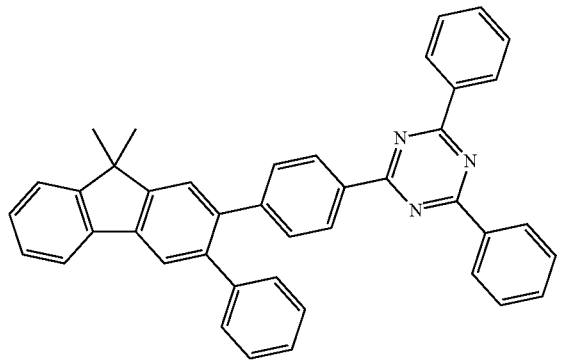

wherein in Chemical Formula 3:

R1 to R3, Ar1 to Ar3, X1 to X3 and a3 have the same definitions as in Chemical Formula 1;

R6 and R7 are deuterium; and a6 and a7 are each 4.

5. The compound of claim 1, wherein the compound of Chemical Formula 1 is any one compound selected from among the following compounds:

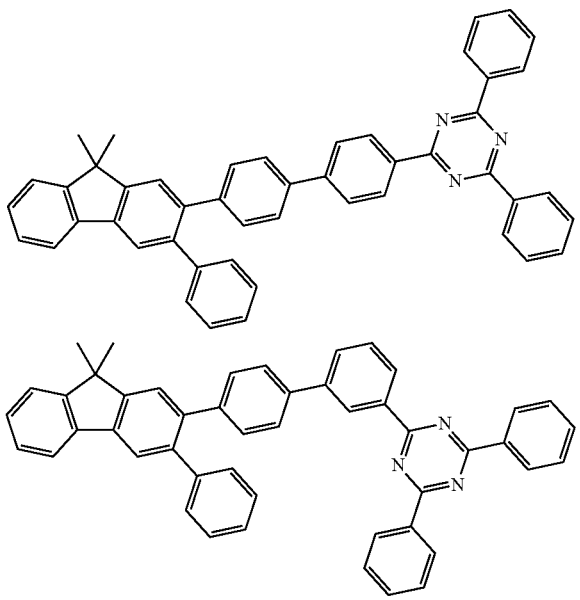

179
-continued
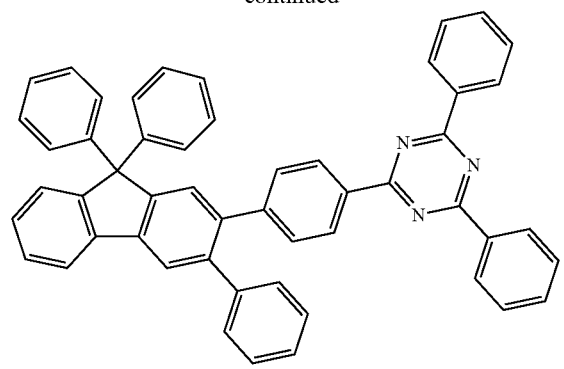
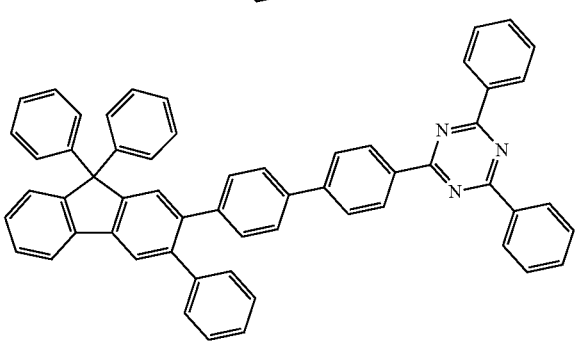
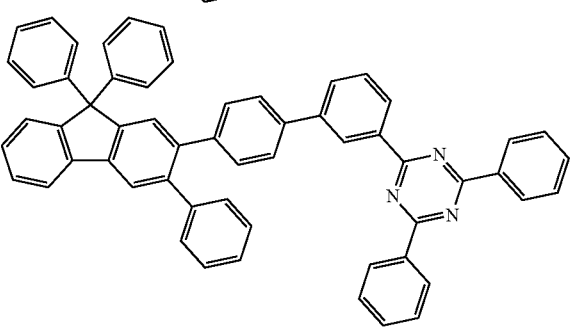
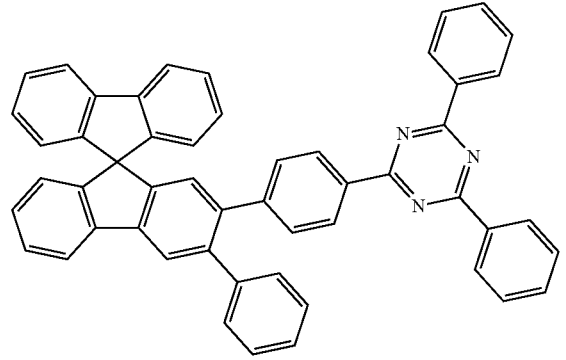
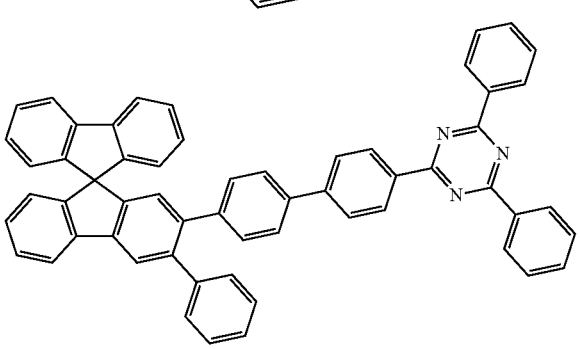
180
-continued
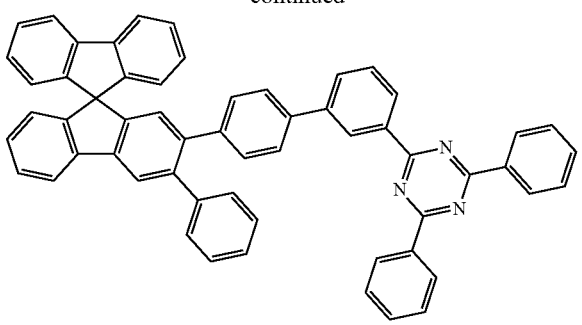
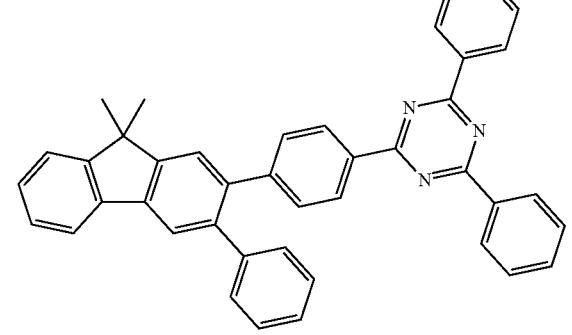
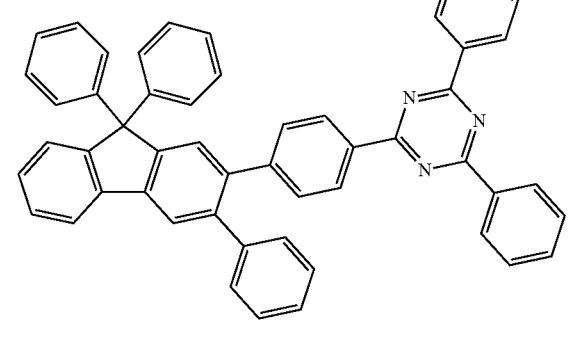

181
-continued
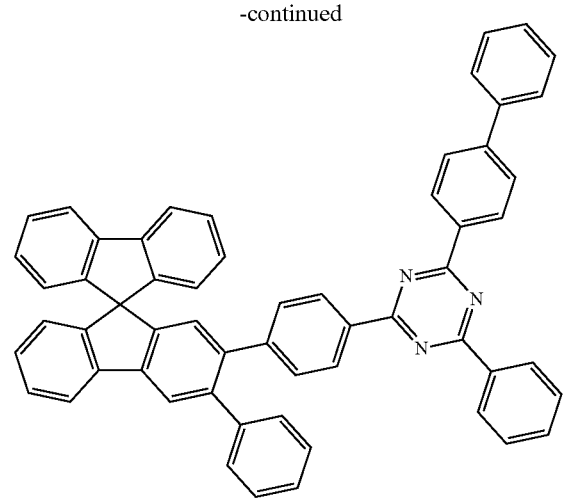
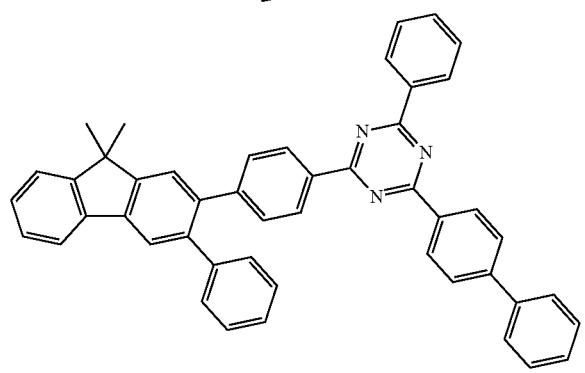
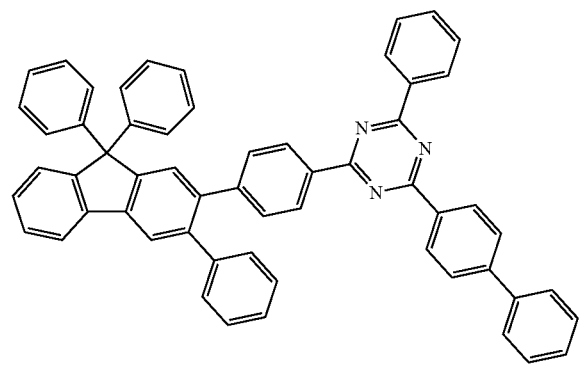
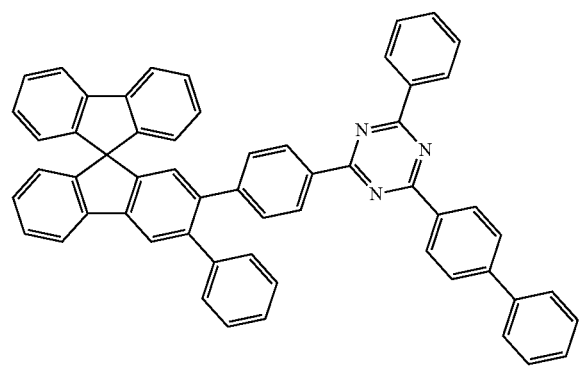
182
-continued
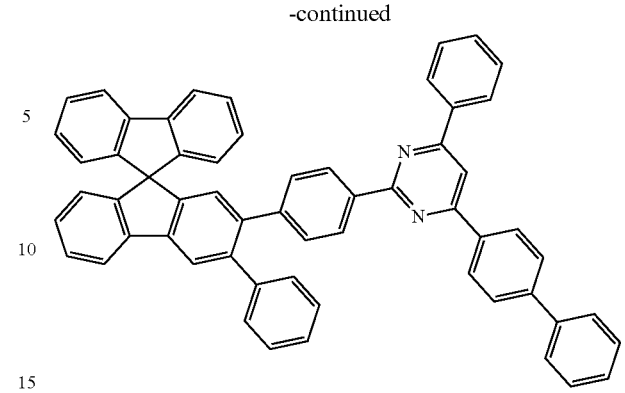
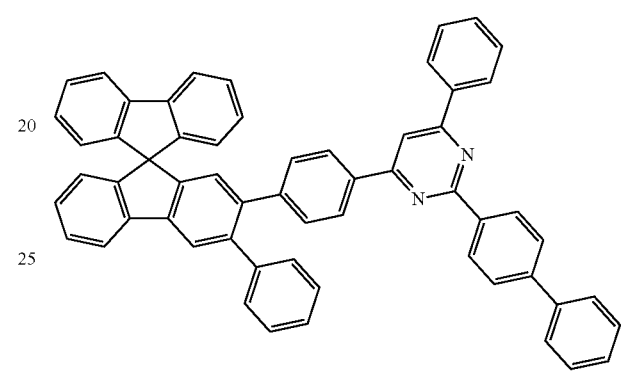
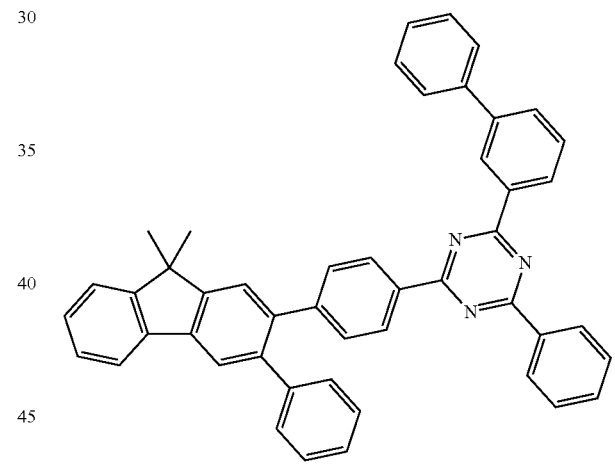
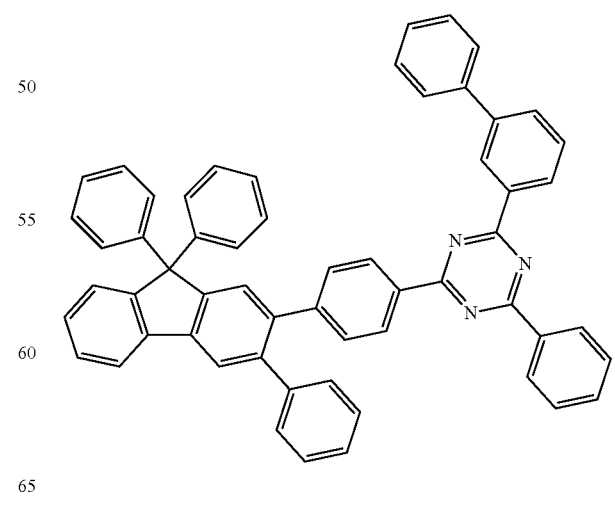

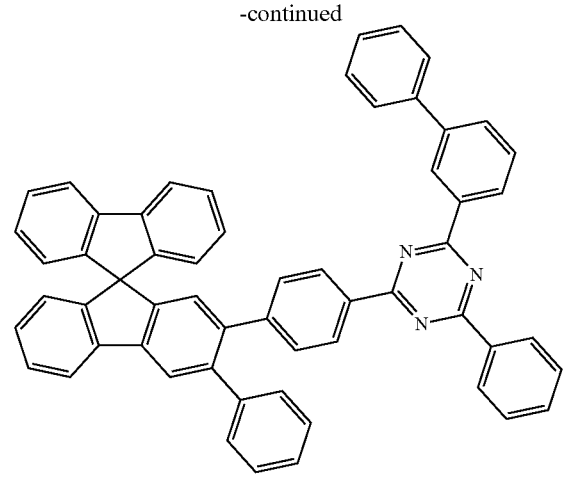
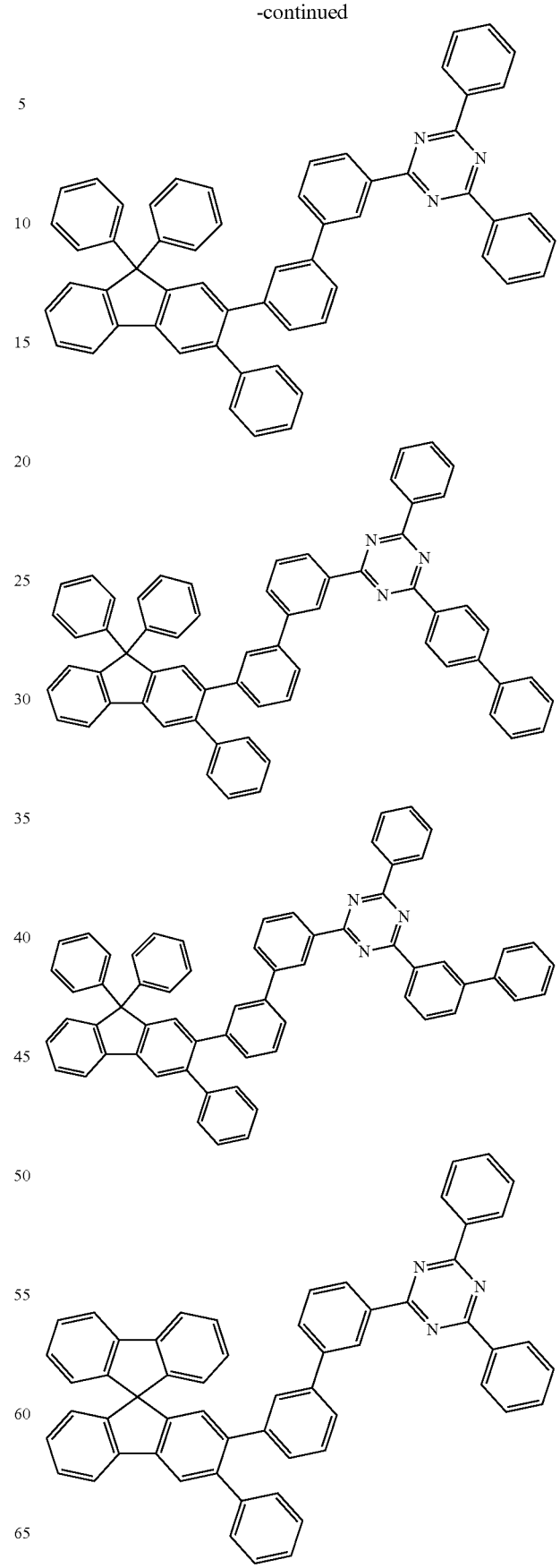

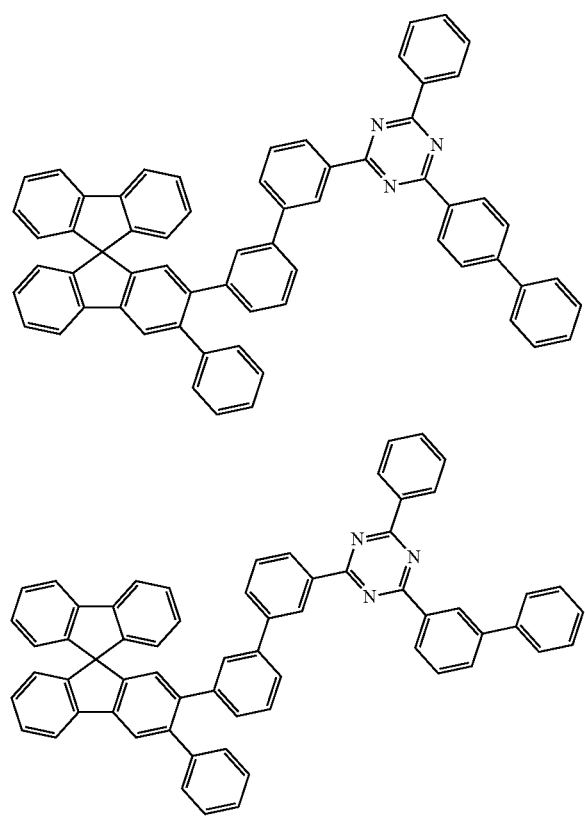
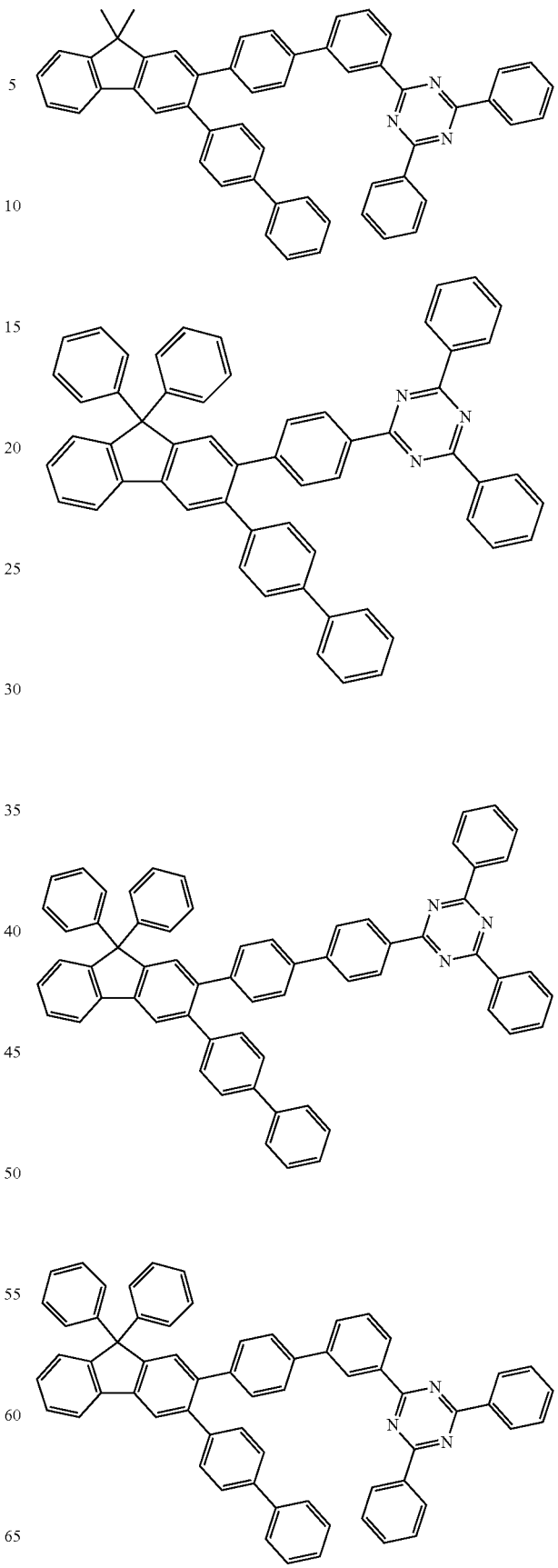

187
-continued
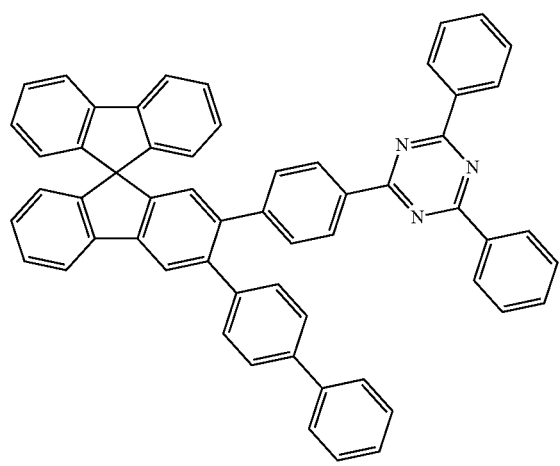
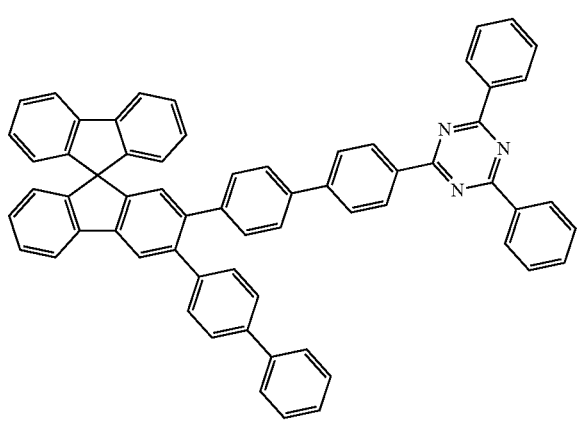
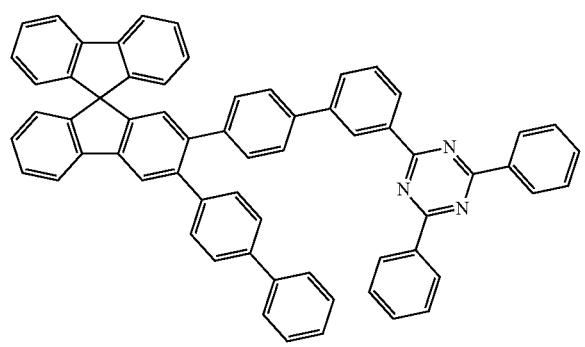
188
-continued
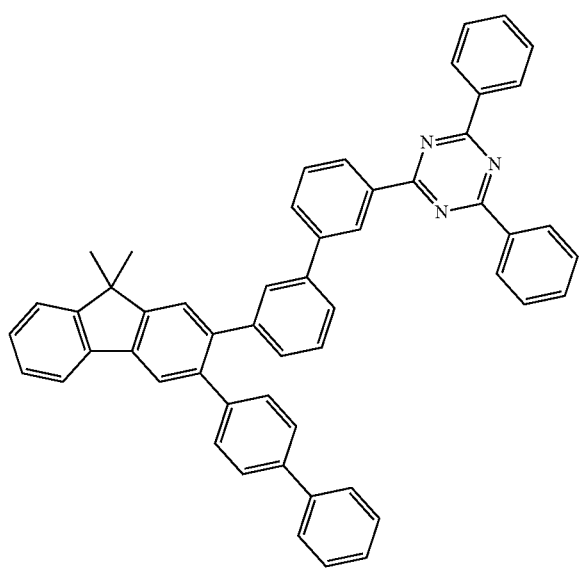
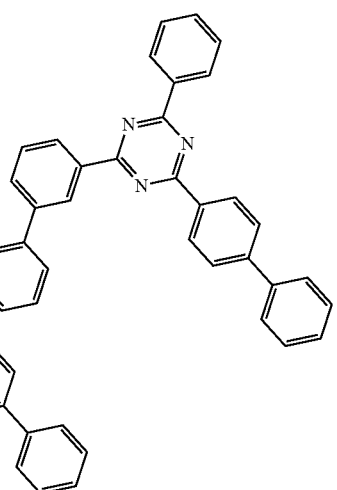
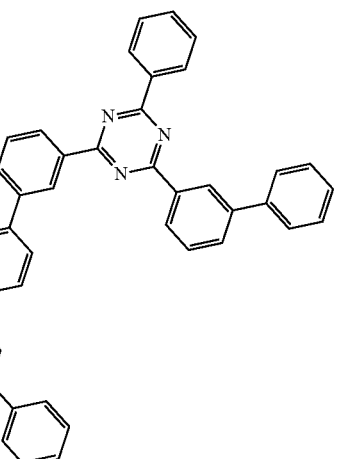

189
-continued
190
-continued
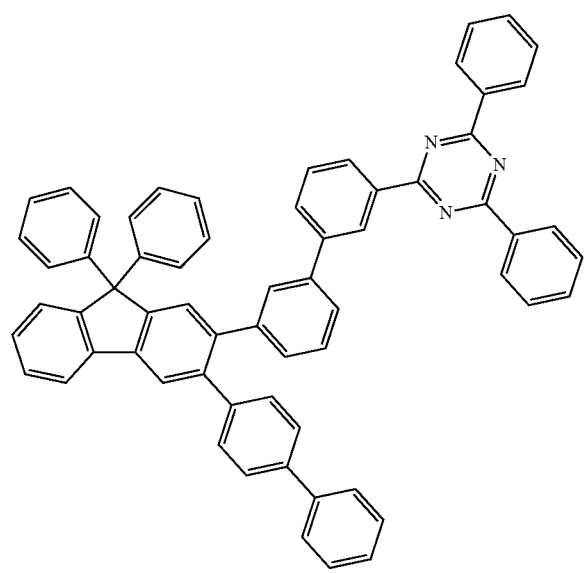
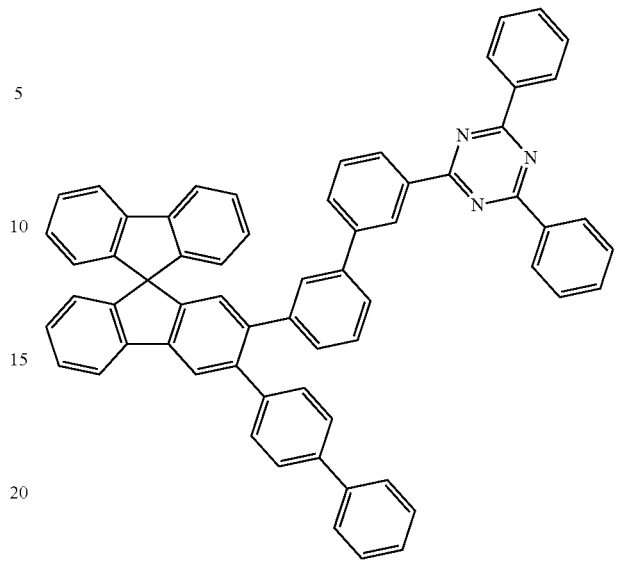
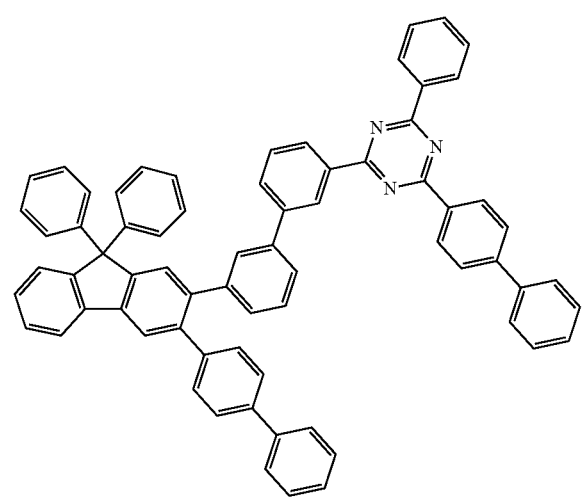
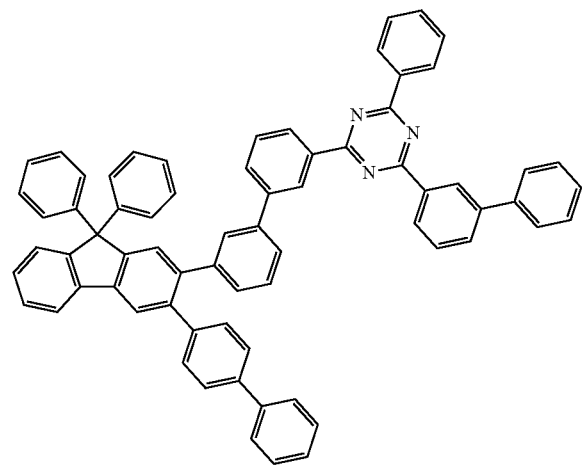

191
-continued
192
-continued
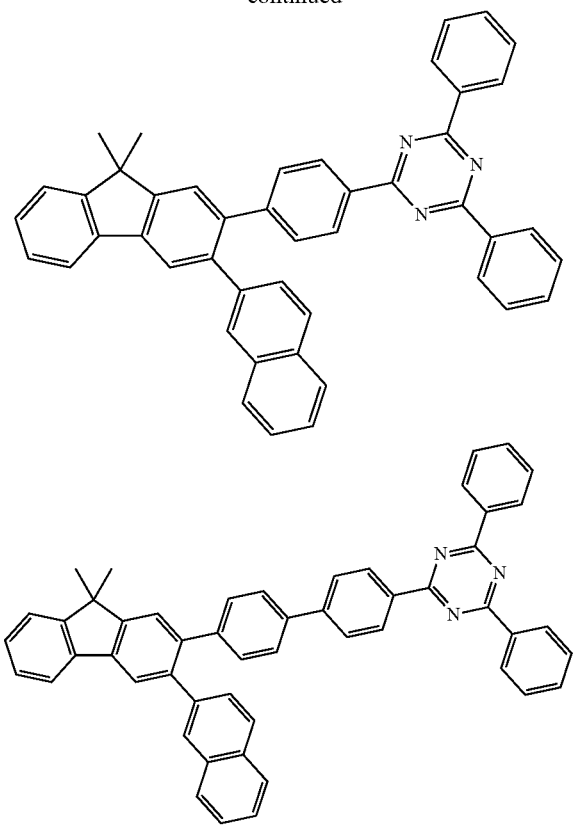
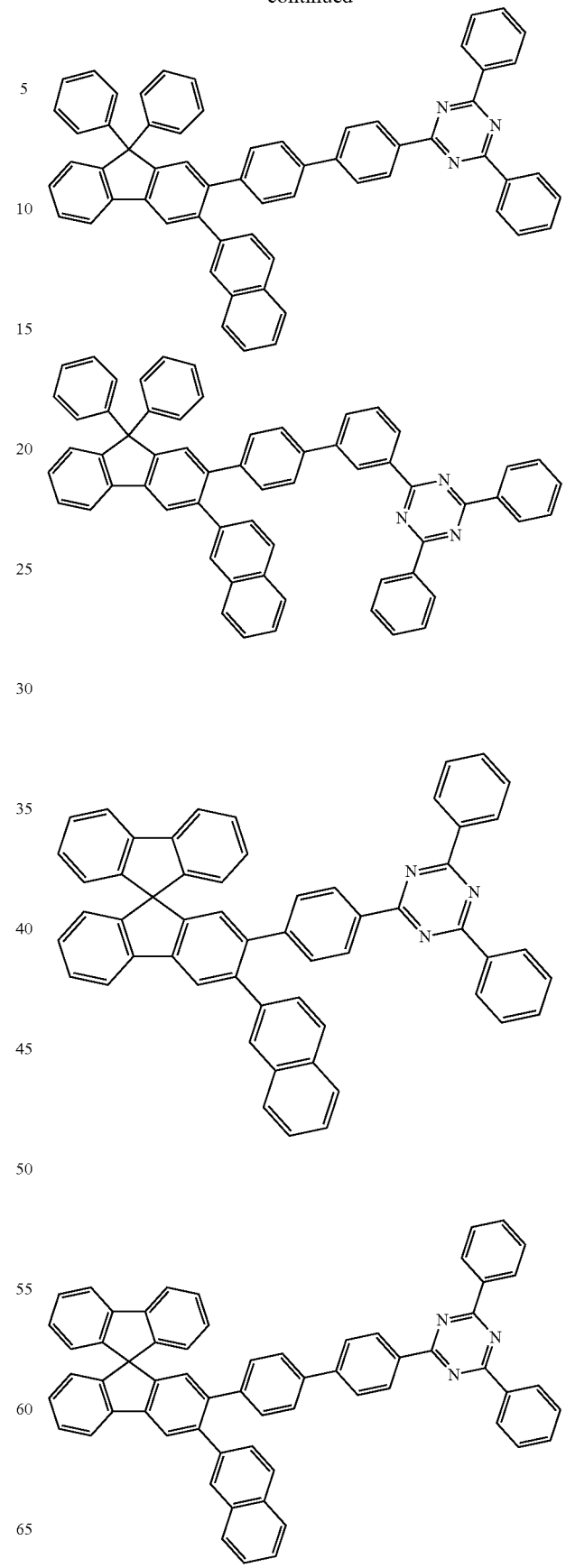

193
-continued
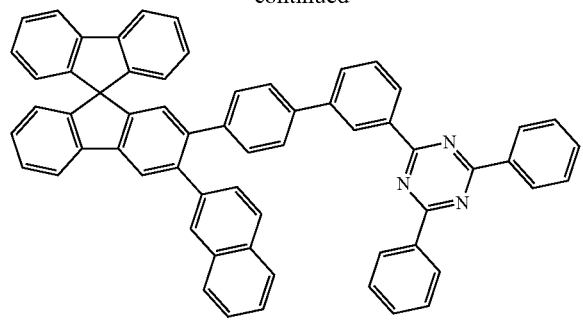
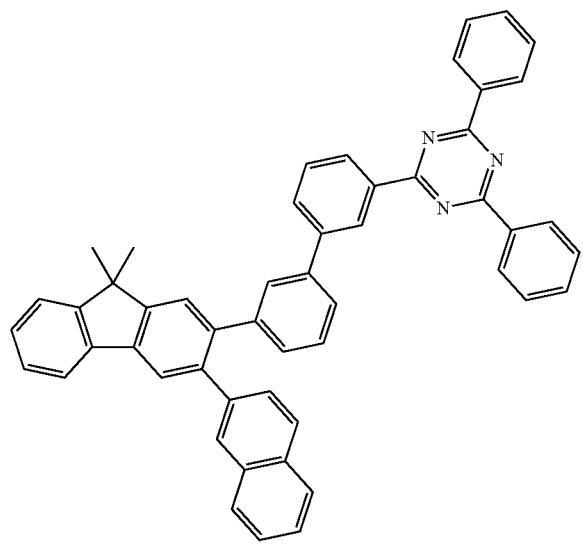
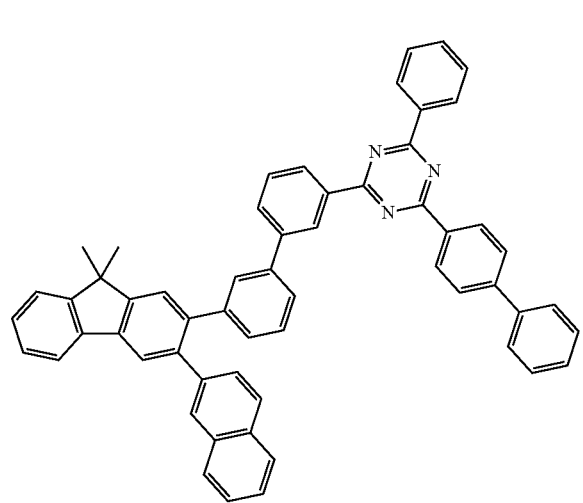
194
-continued
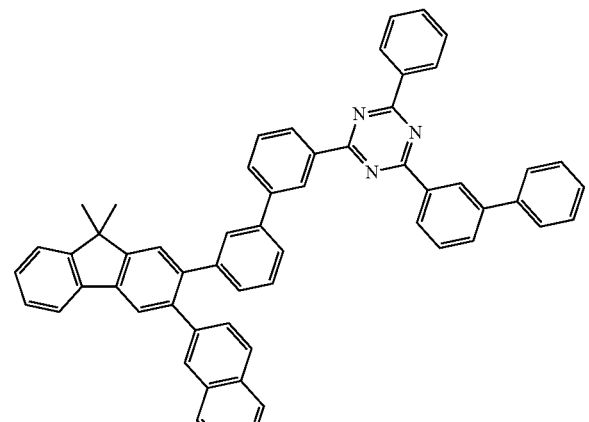
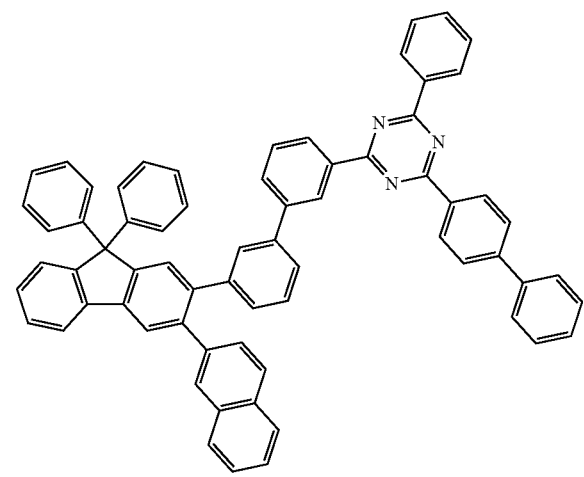

-continued
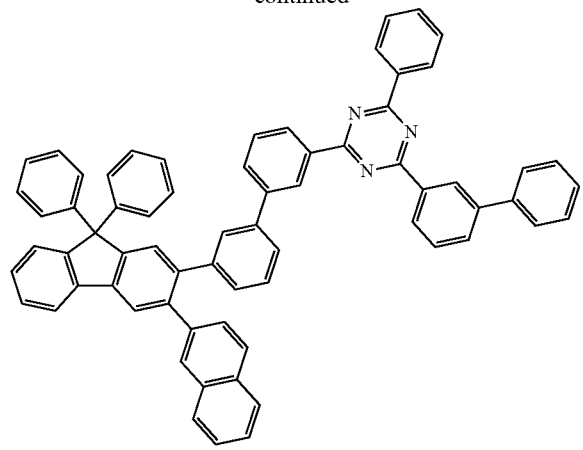
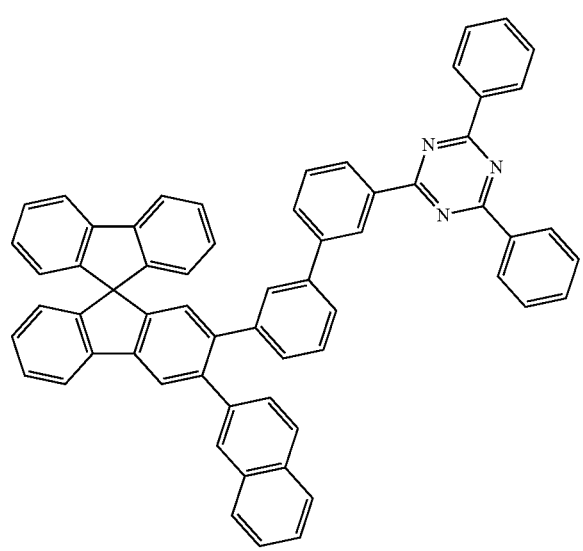
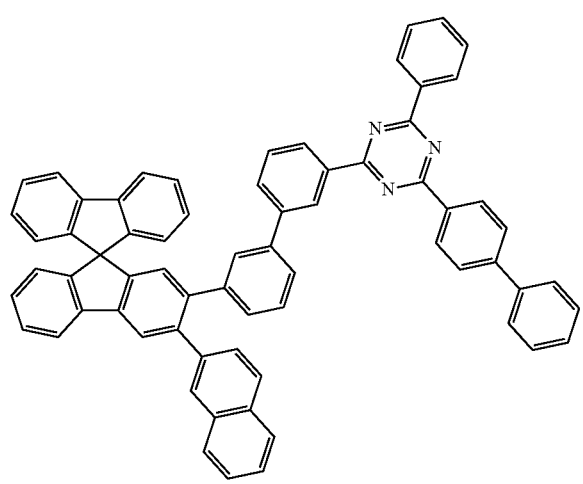
-continued
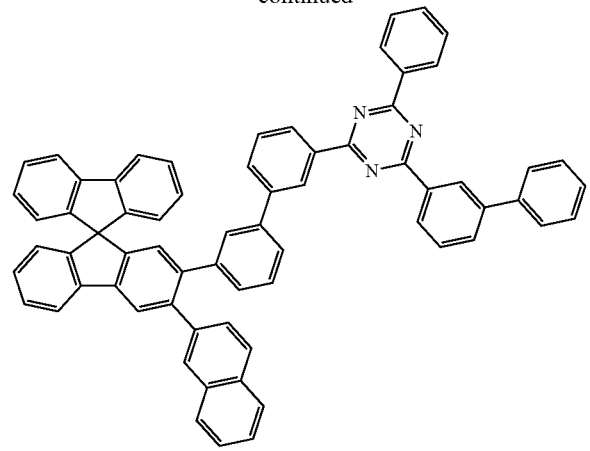
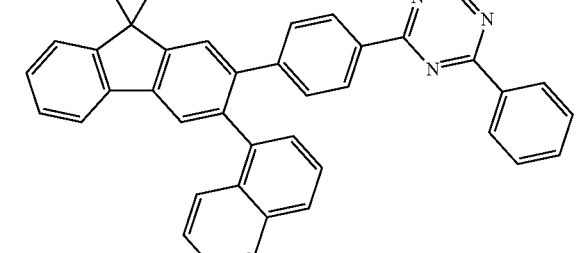
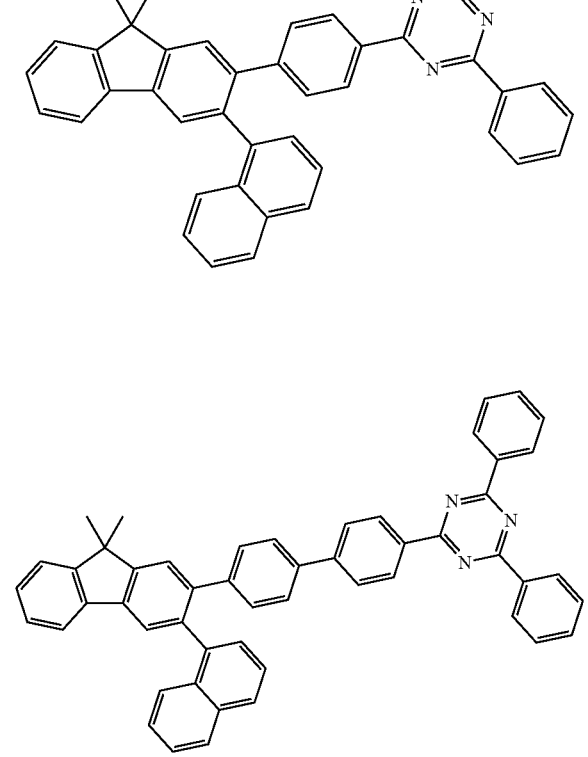
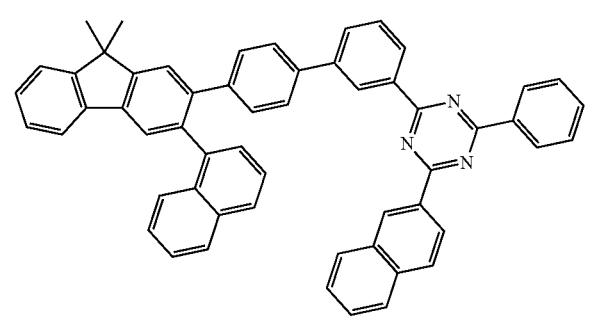

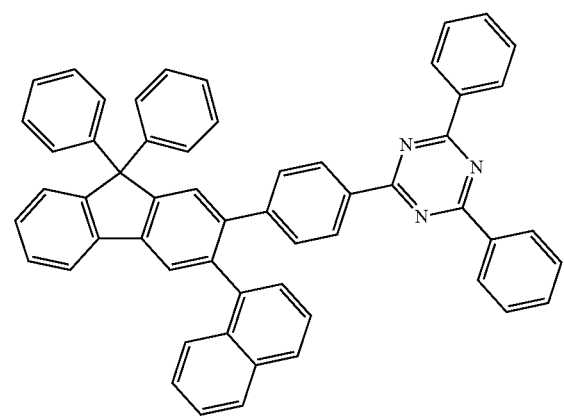
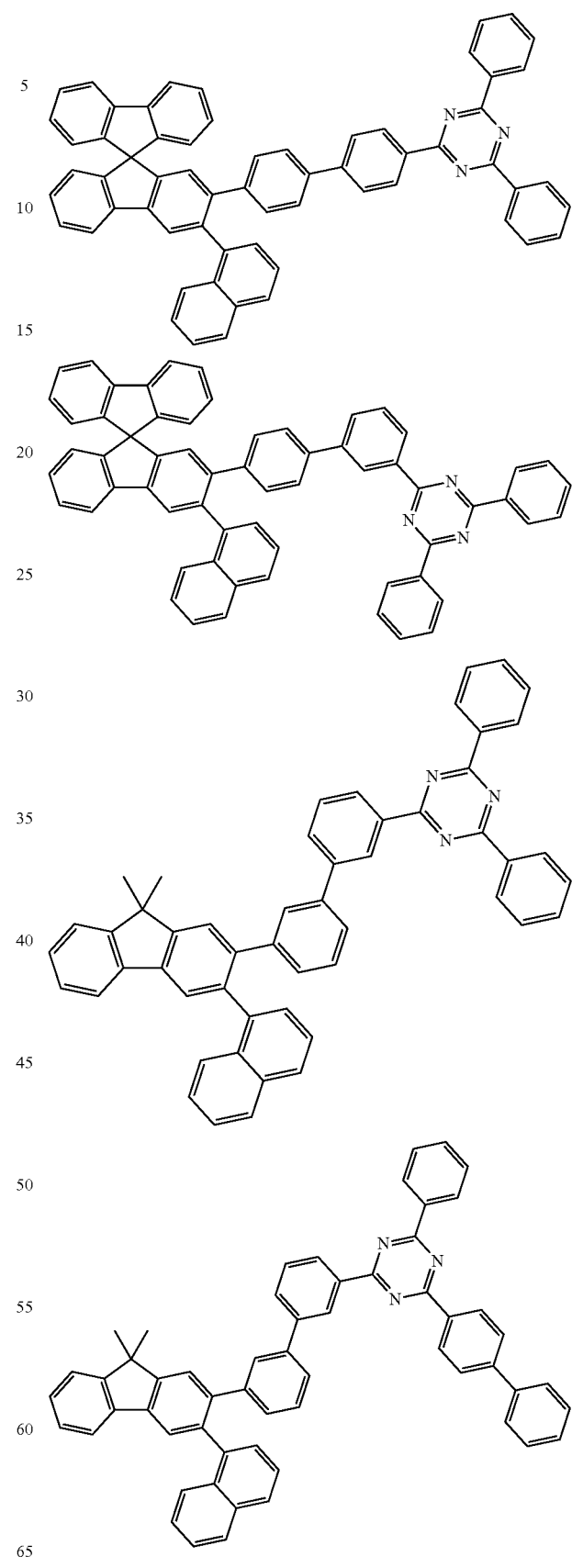

199
-continued
200
-continued
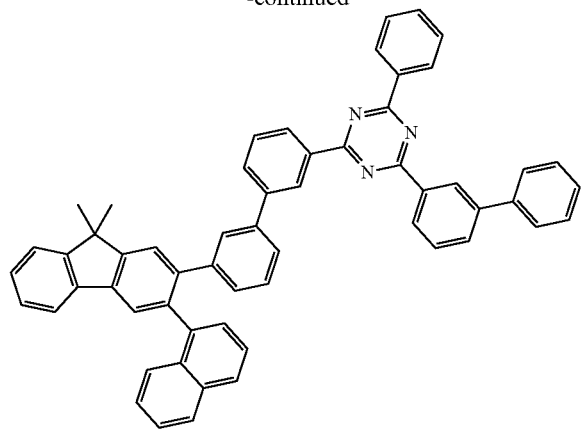
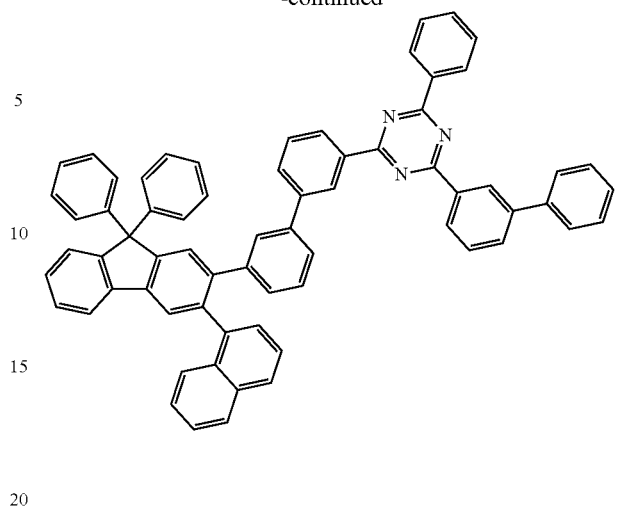
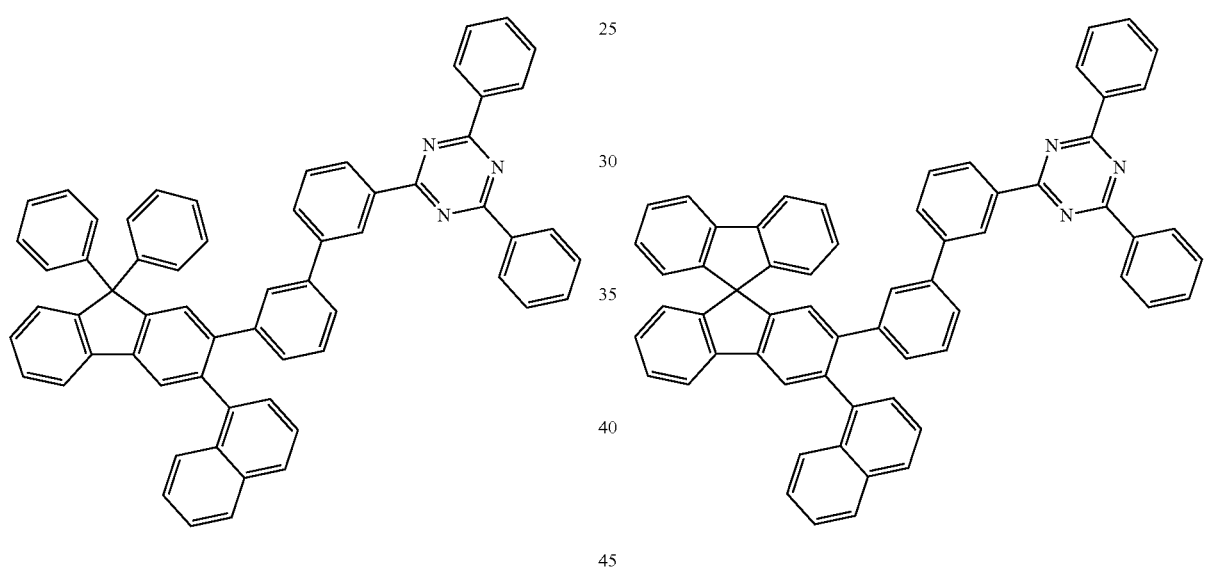
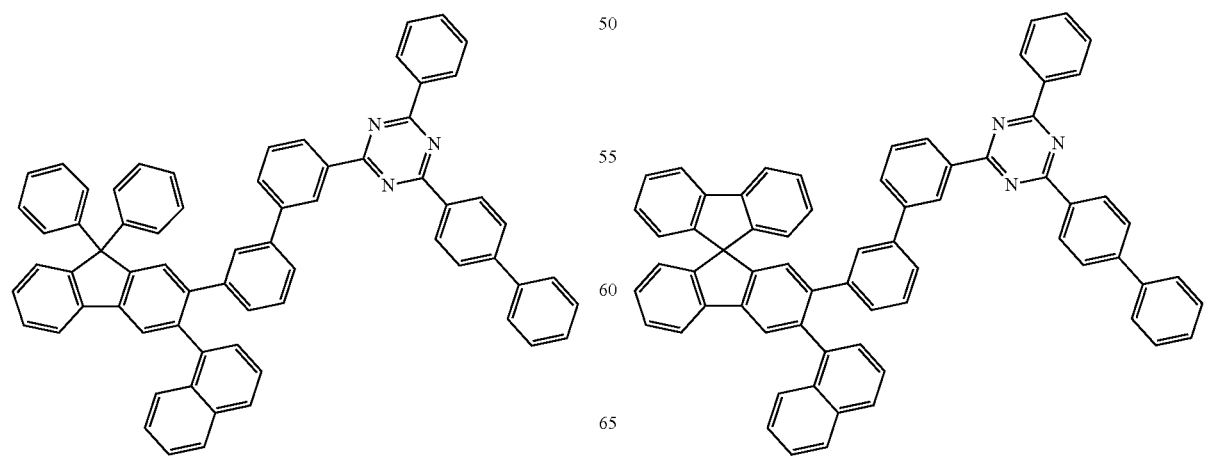

201
-continued
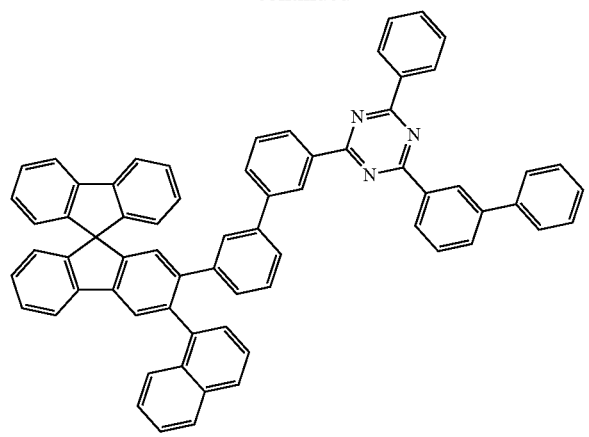
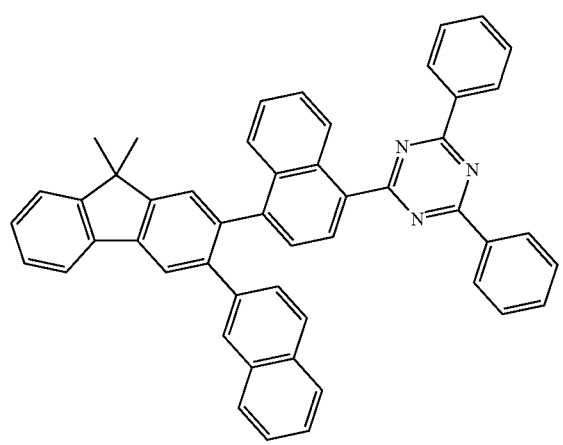
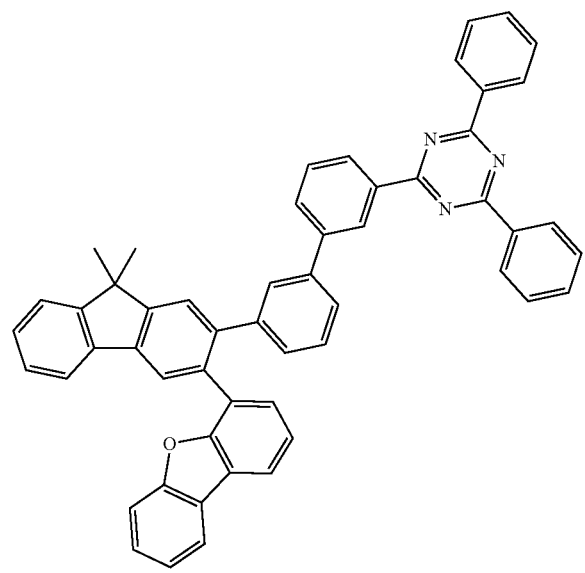
202
-continued
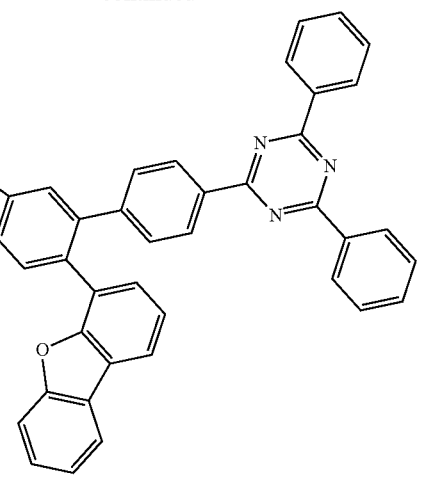
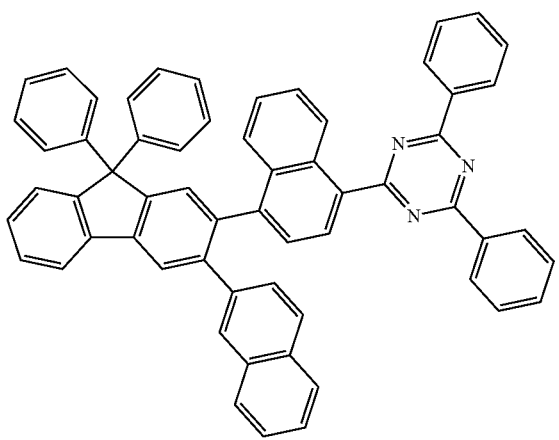
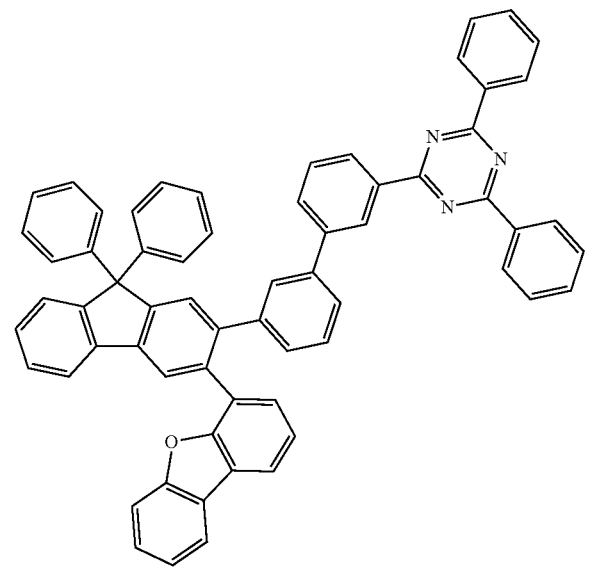

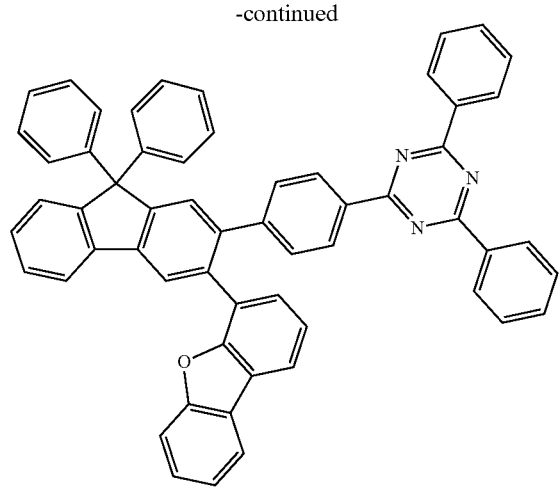
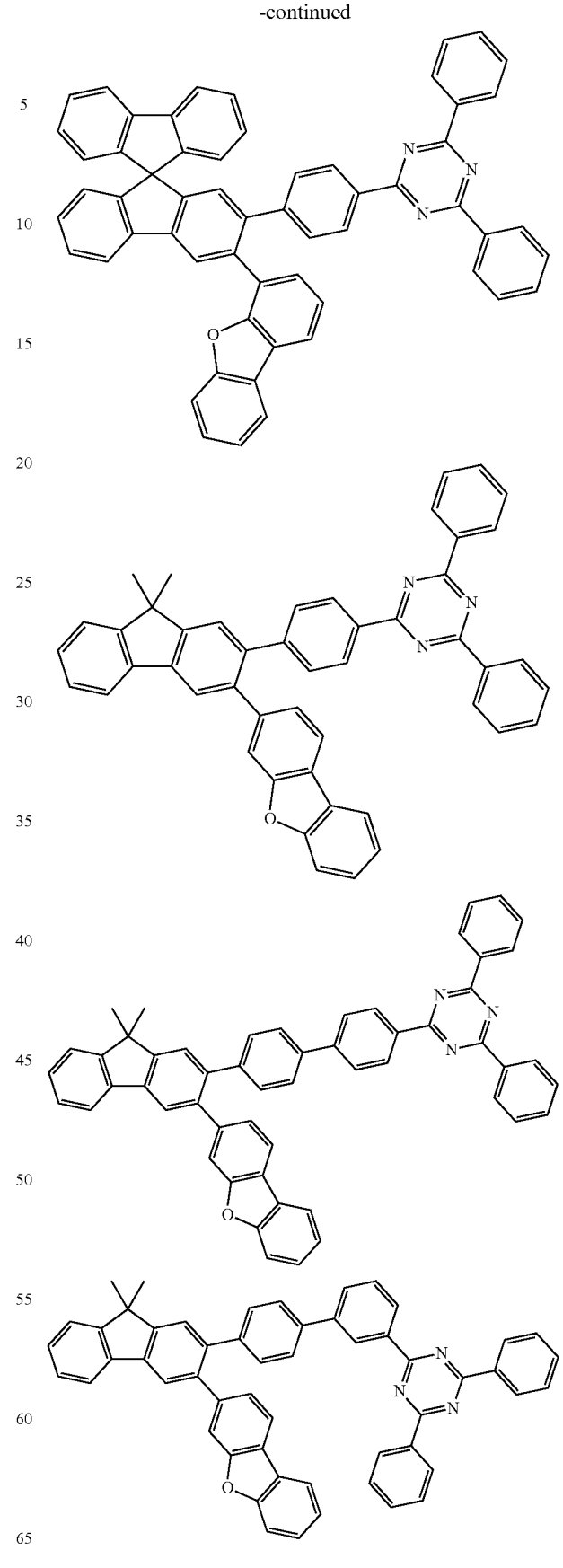

205
-continued
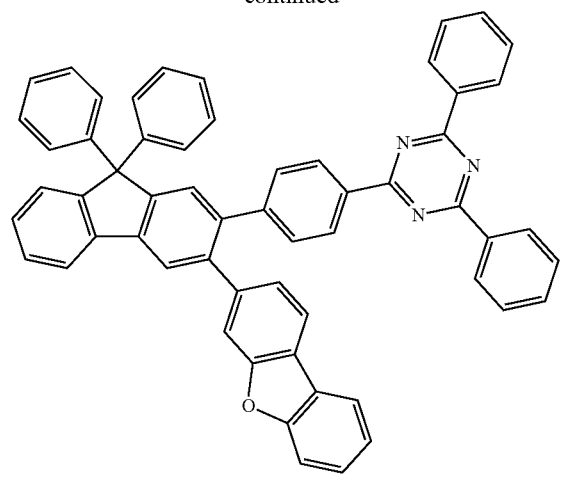
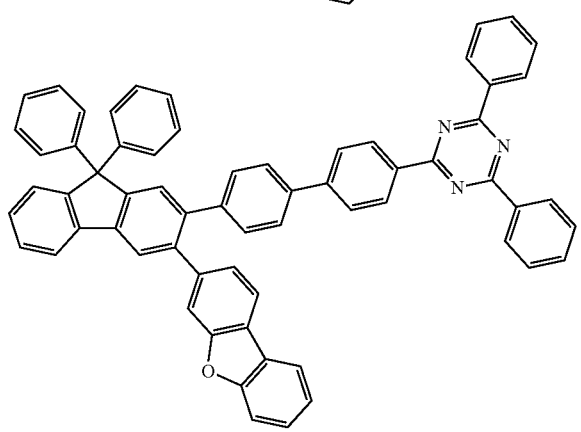
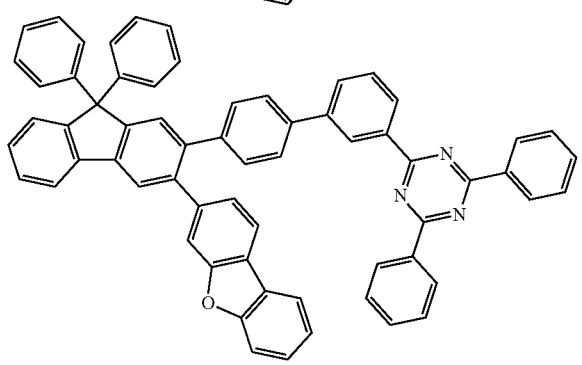
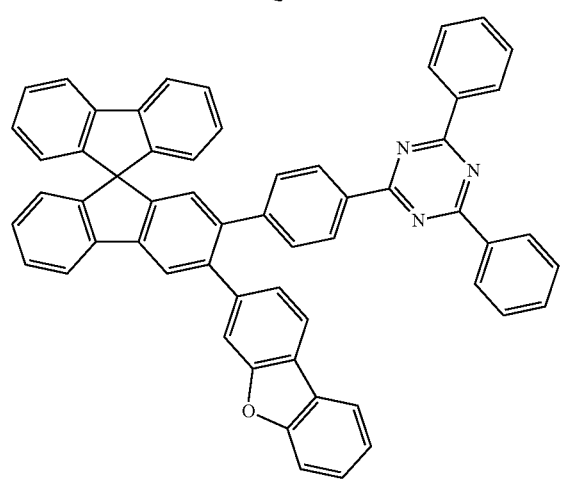
206
-continued
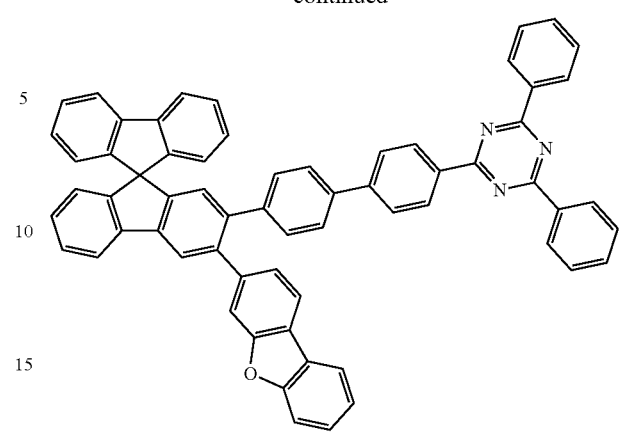
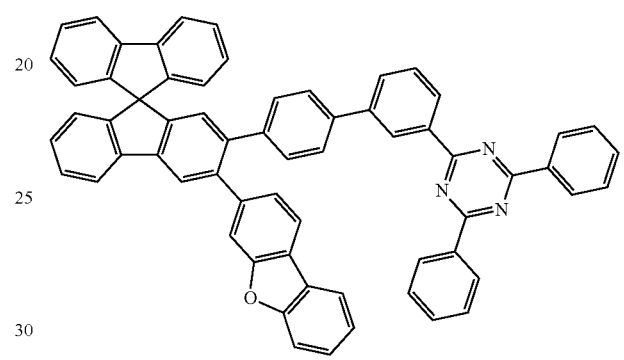
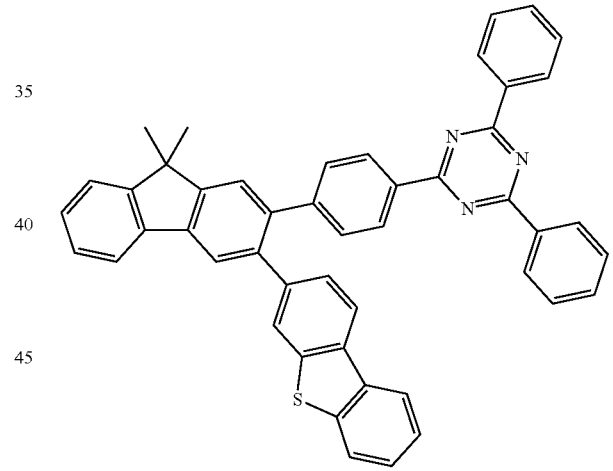
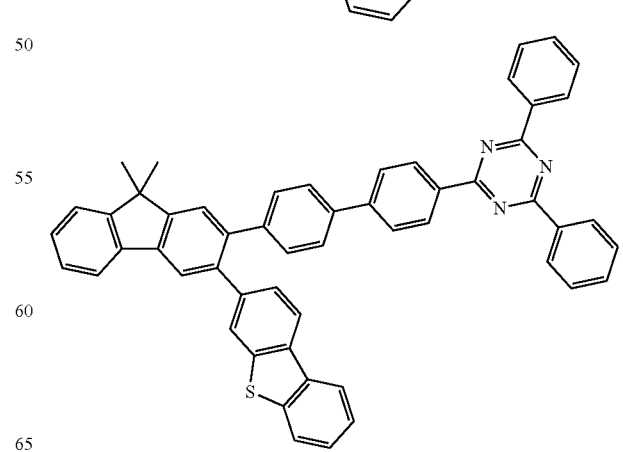

207
-continued
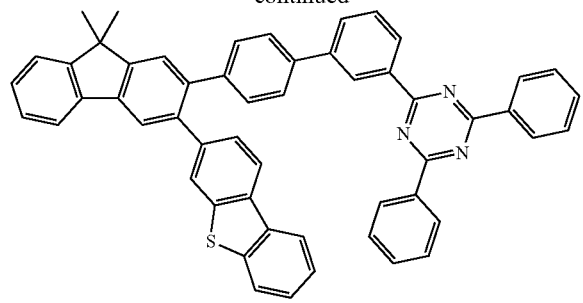
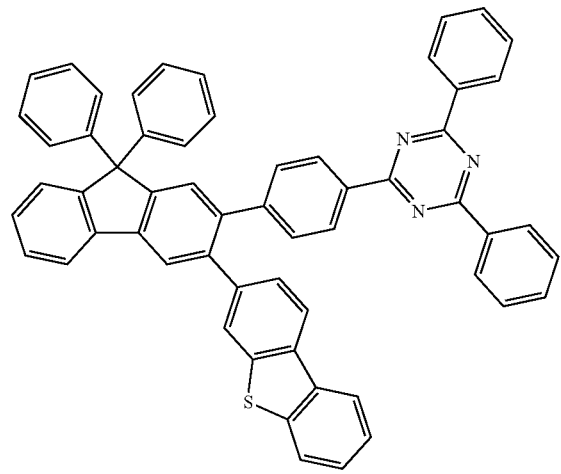
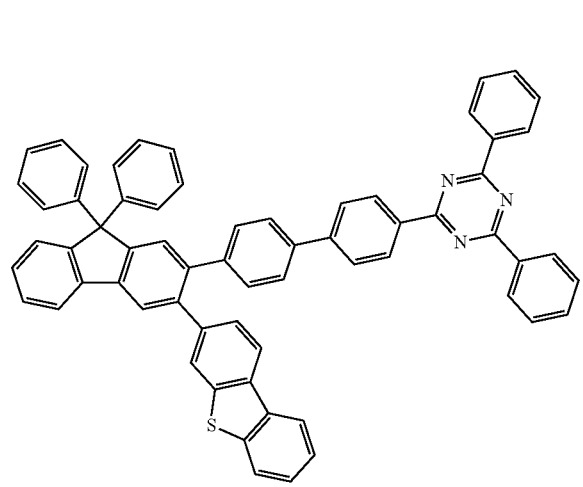
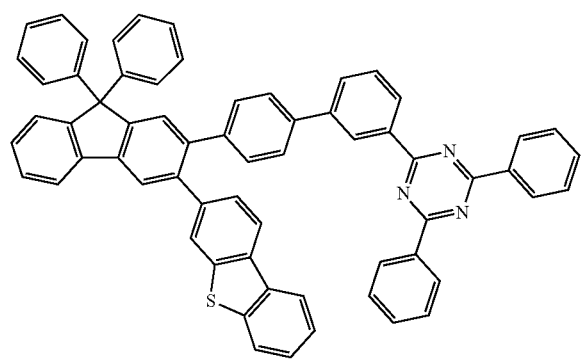
208
-continued
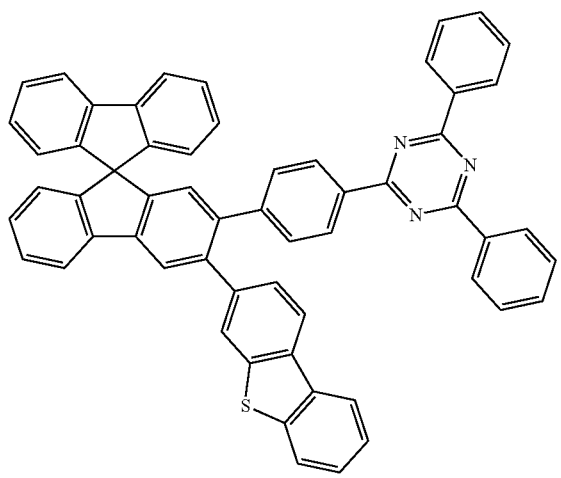
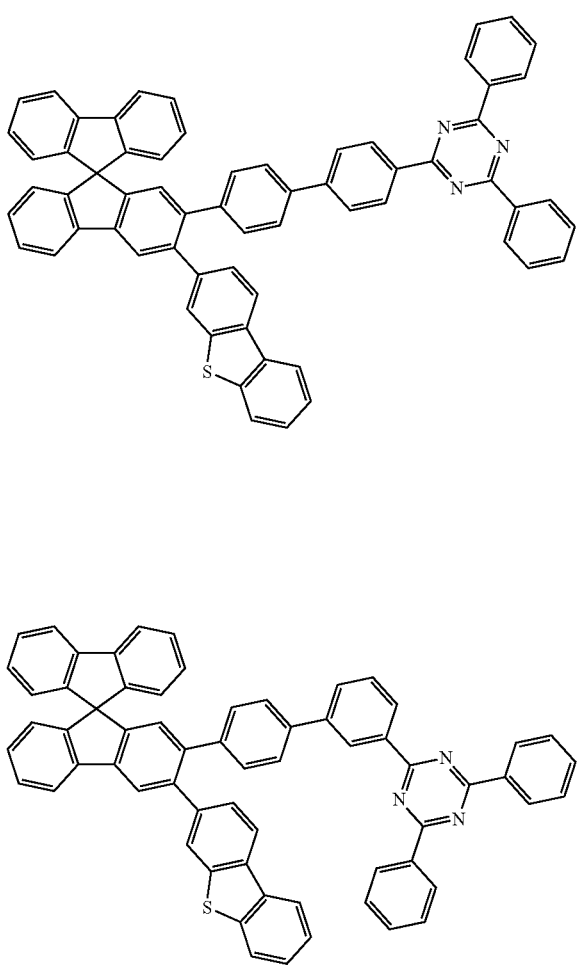

209
-continued
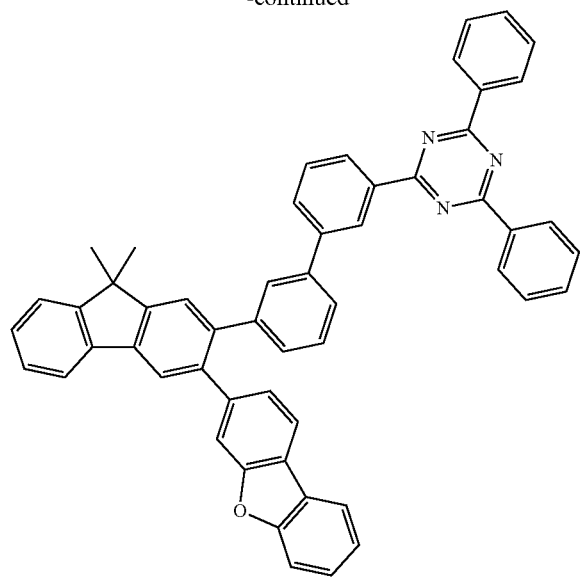
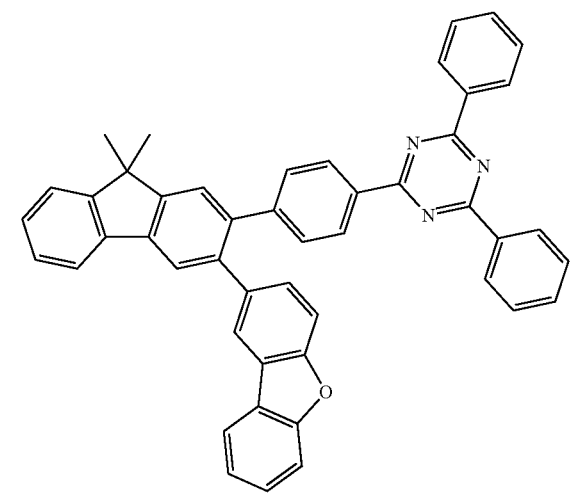
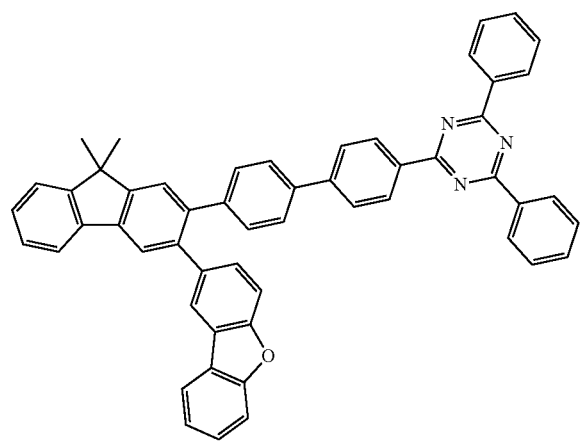
210
-continued
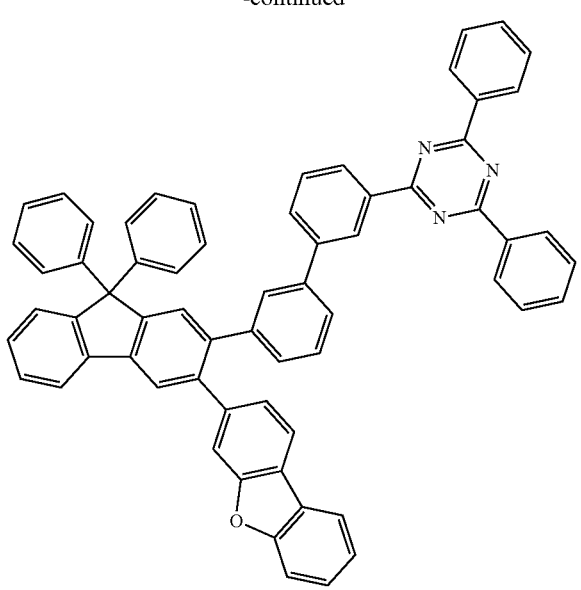
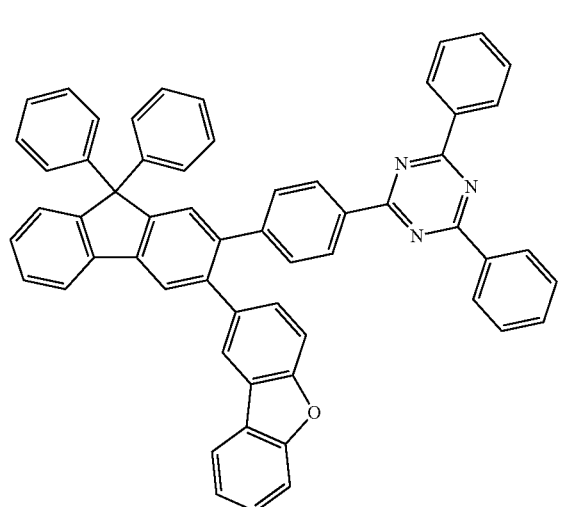
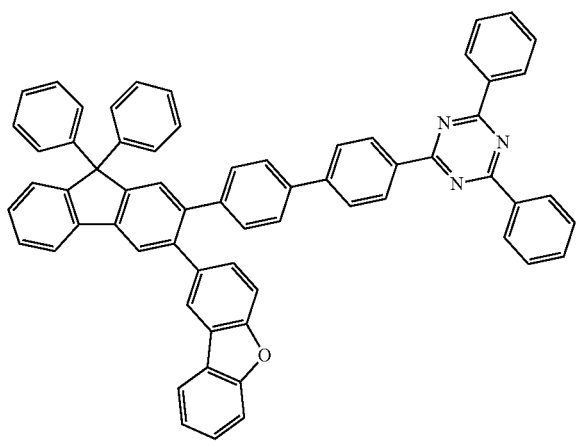

211
-continued
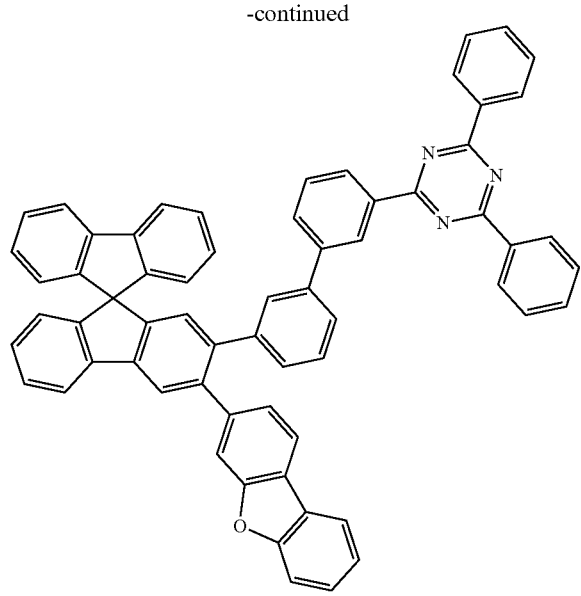
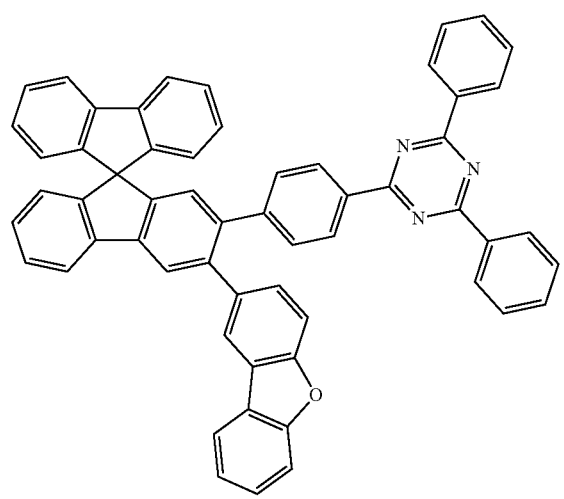
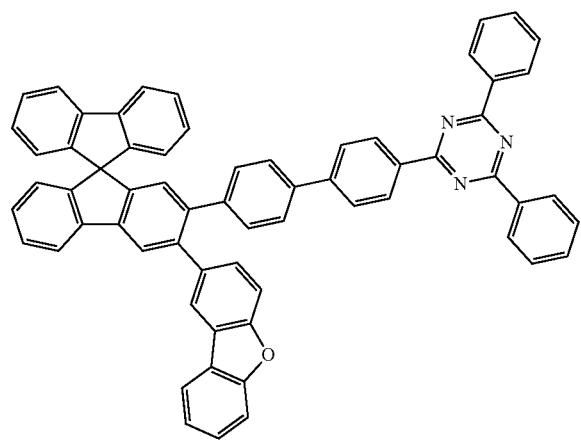
212
-continued
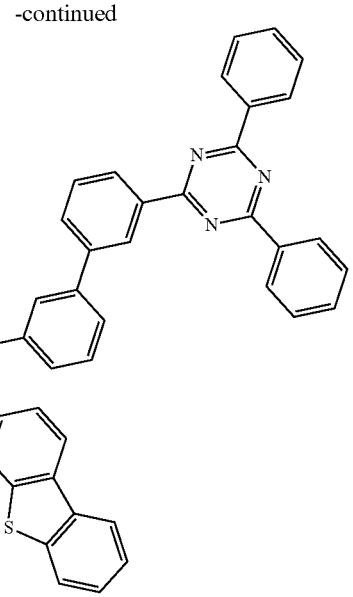
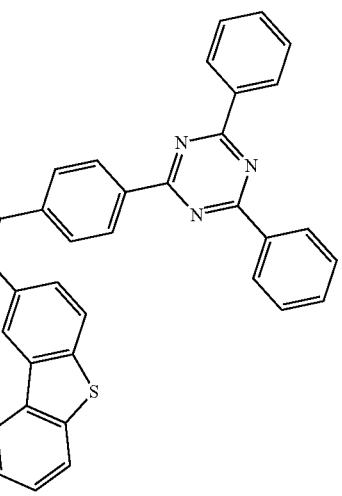
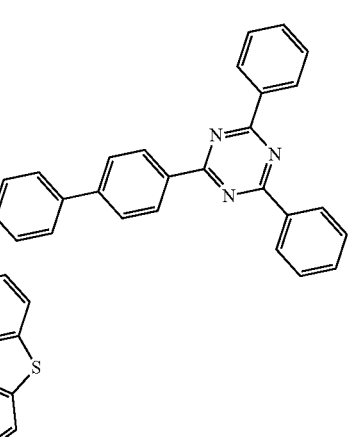

213
-continued
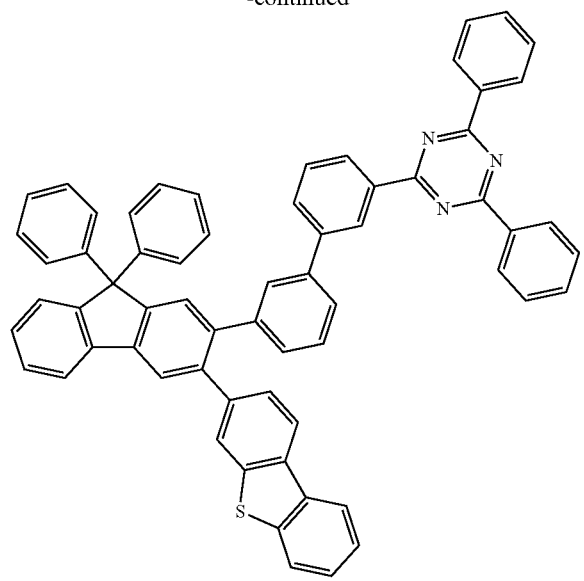
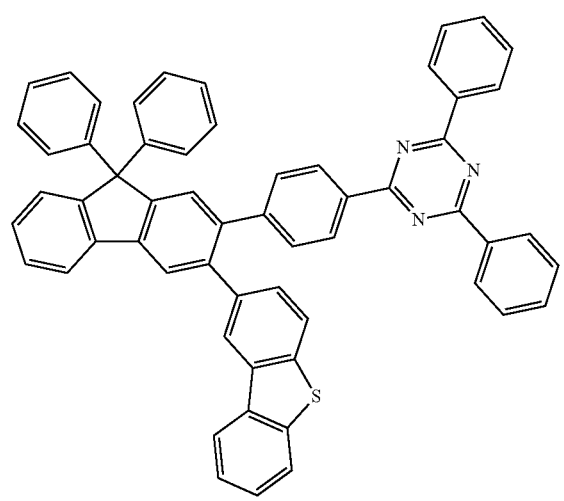
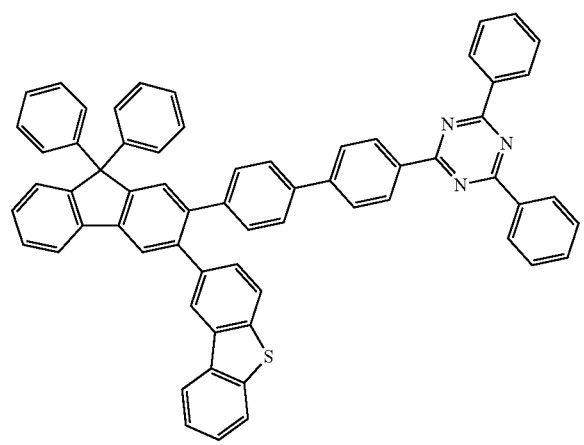
214
-continued
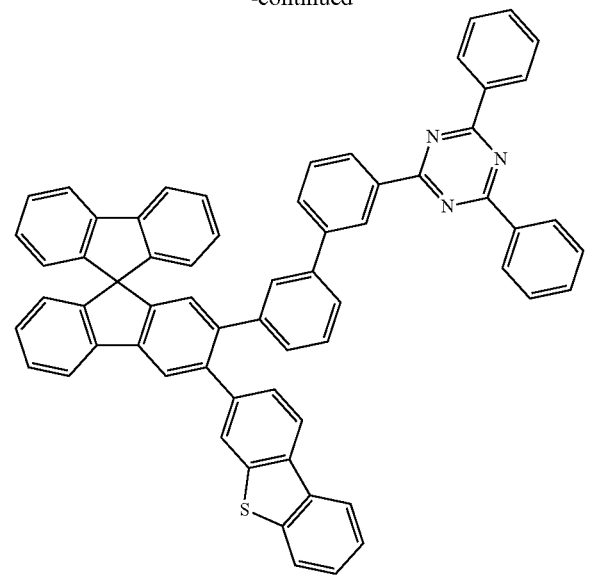
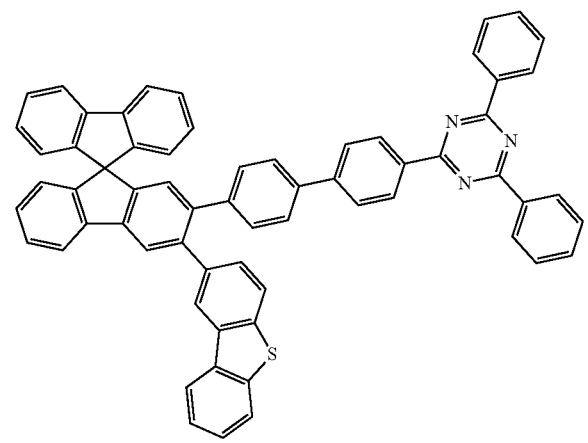

215
-continued
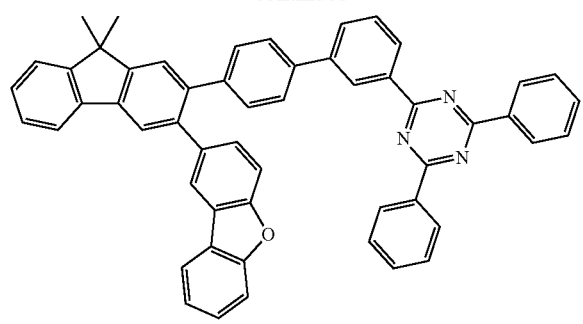
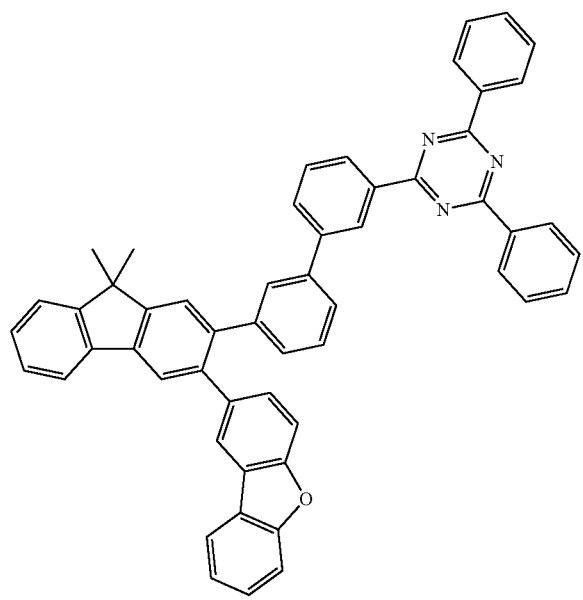
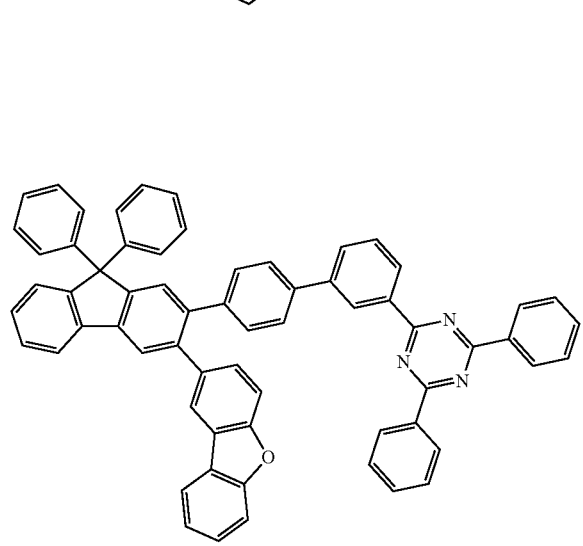
216
-continued
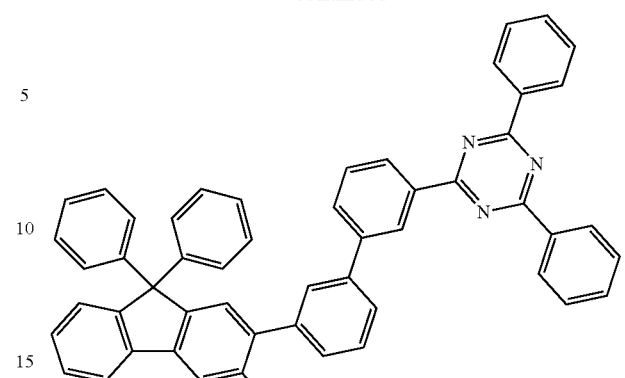
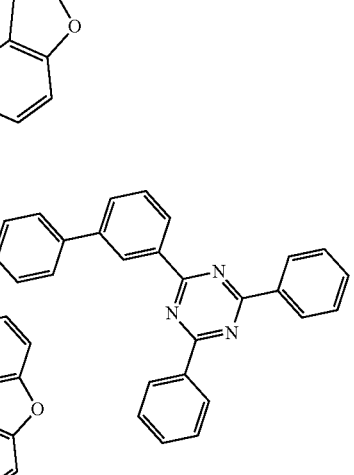
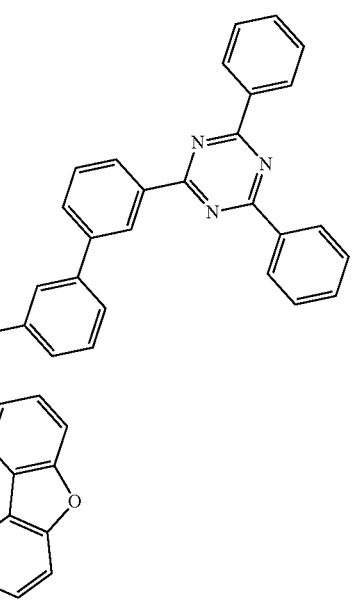

217
-continued
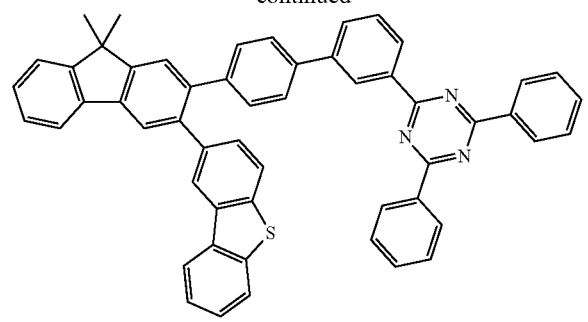
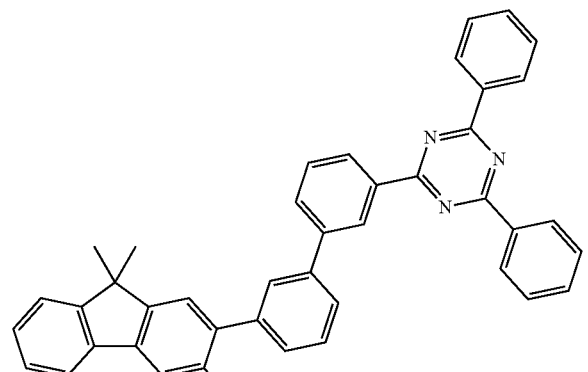
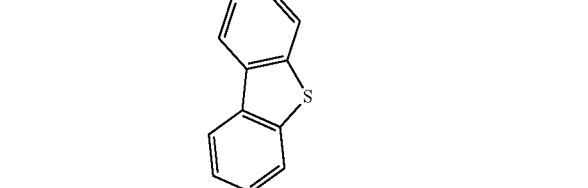
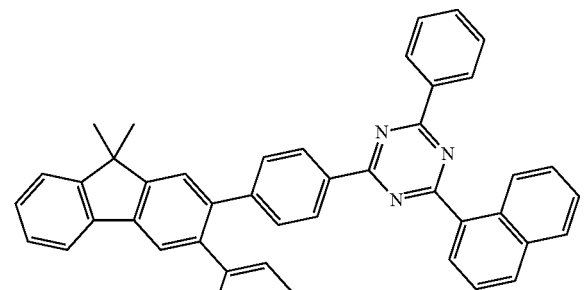
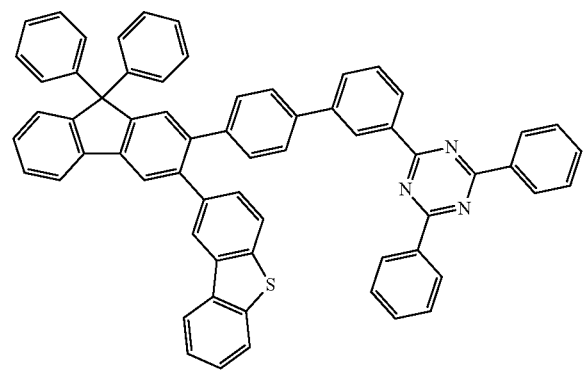
218
-continued
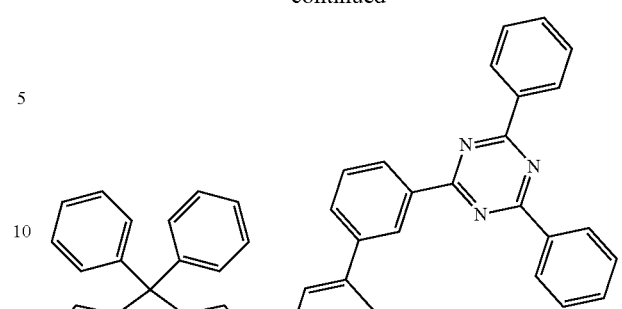

219
-continued
220
-continued
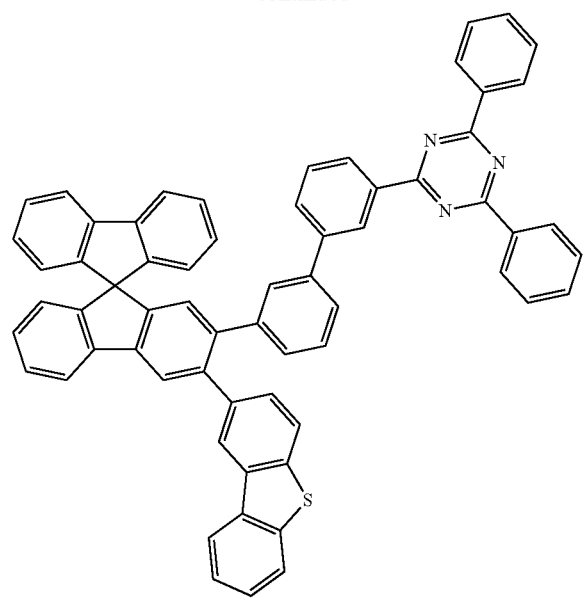
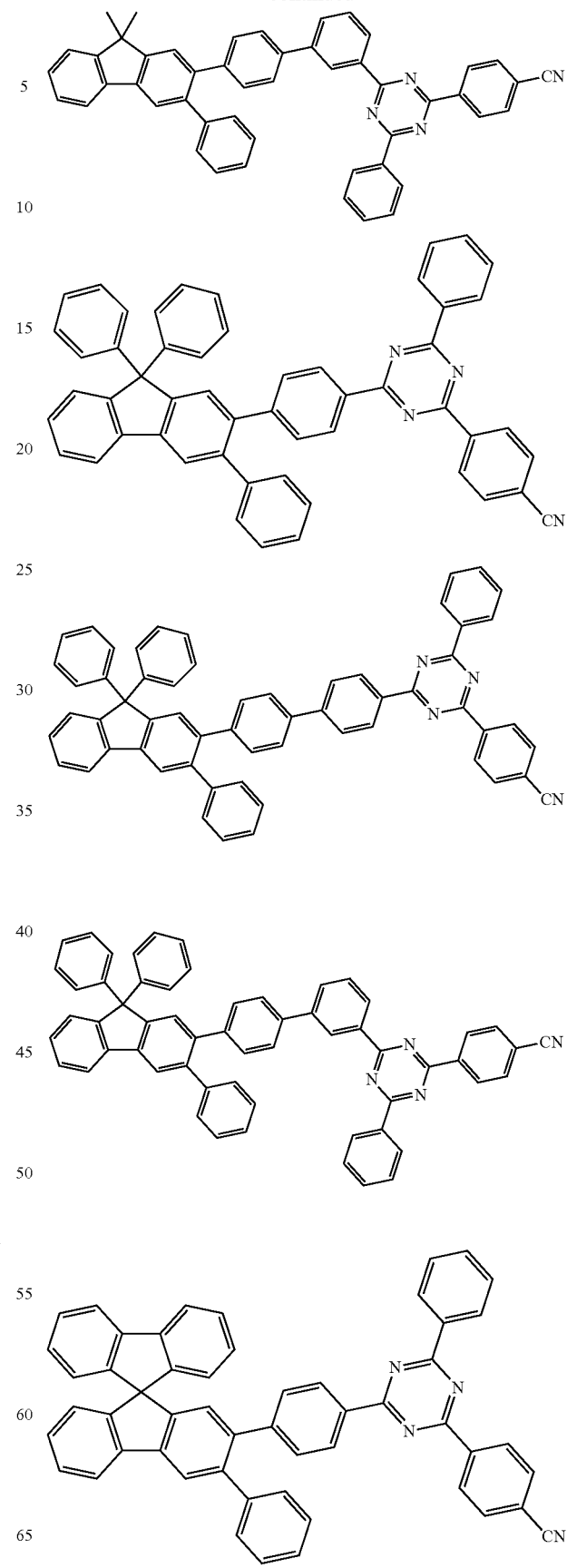

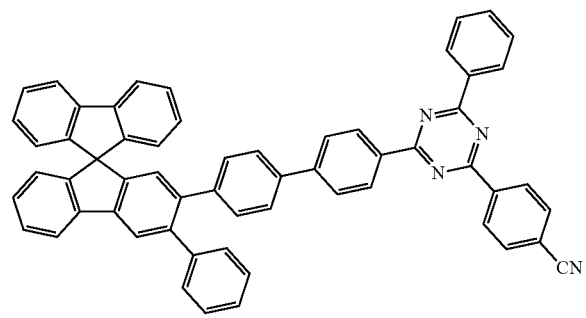
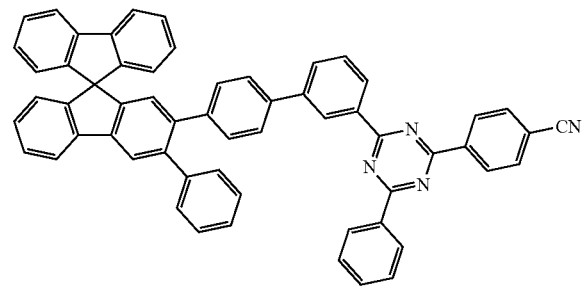
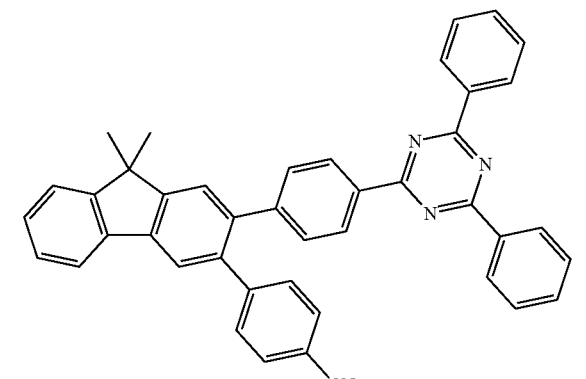
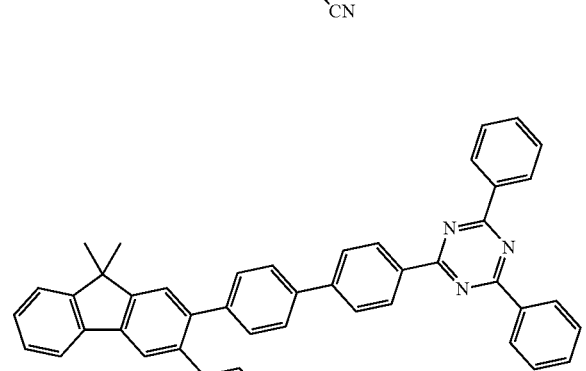
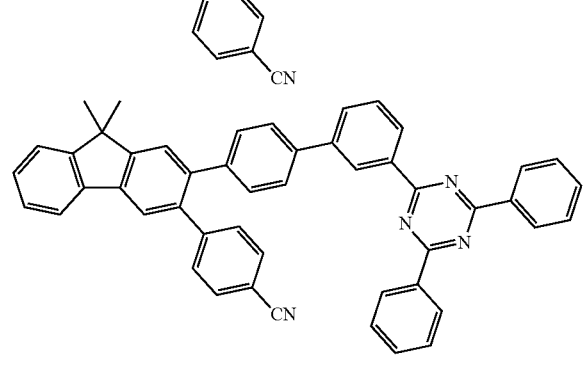
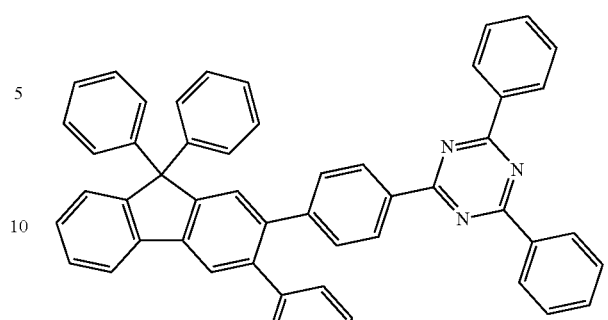
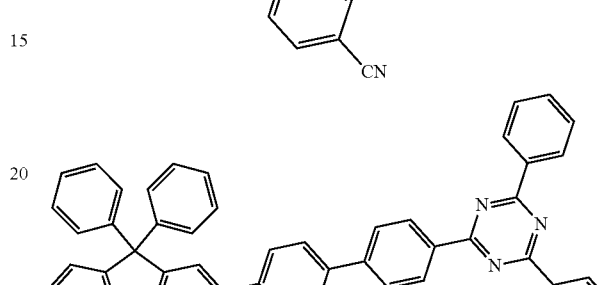
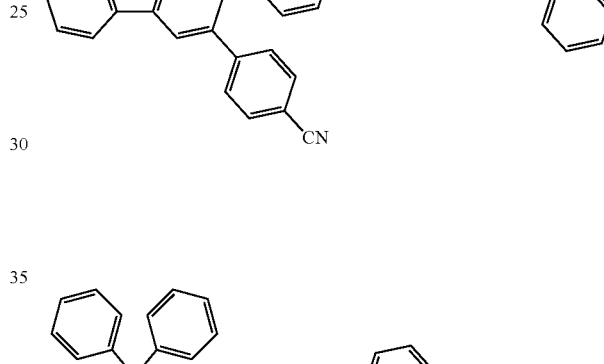
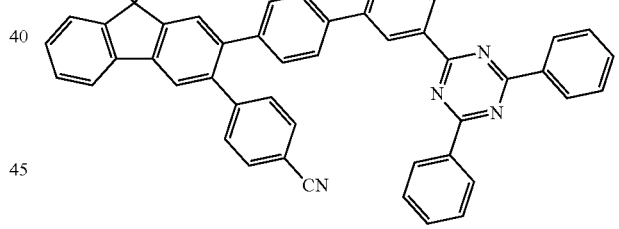
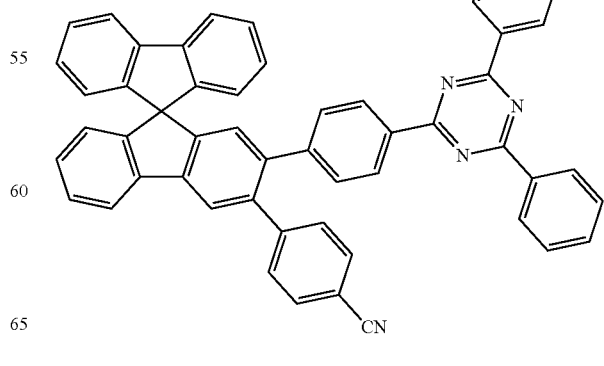

223
-continued
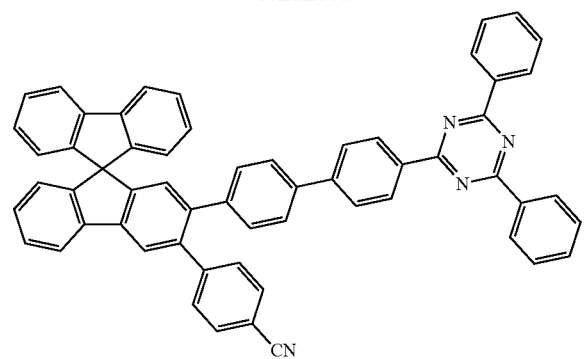
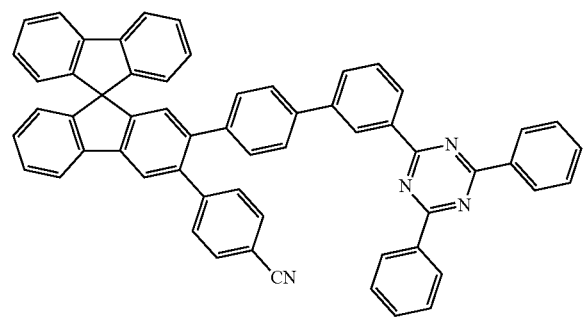
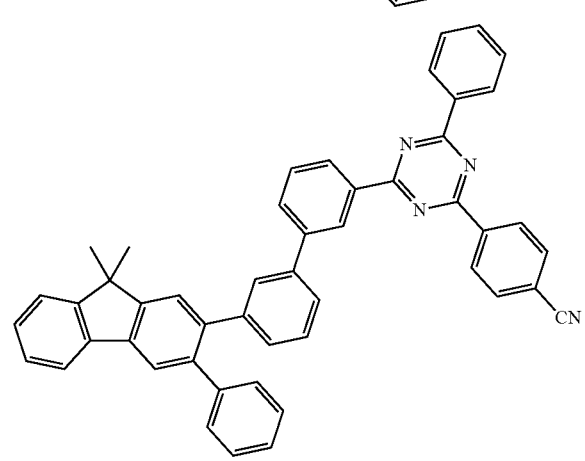
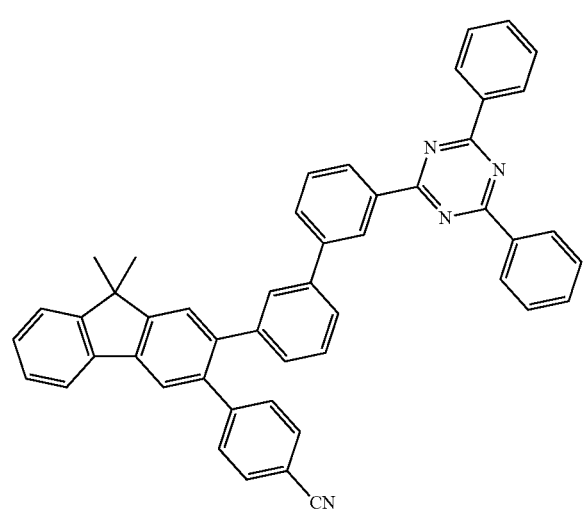
224
-continued
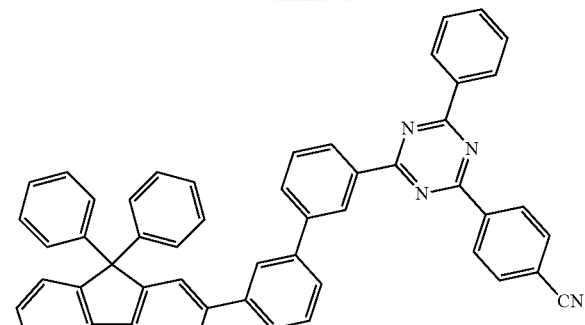
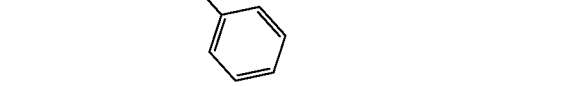
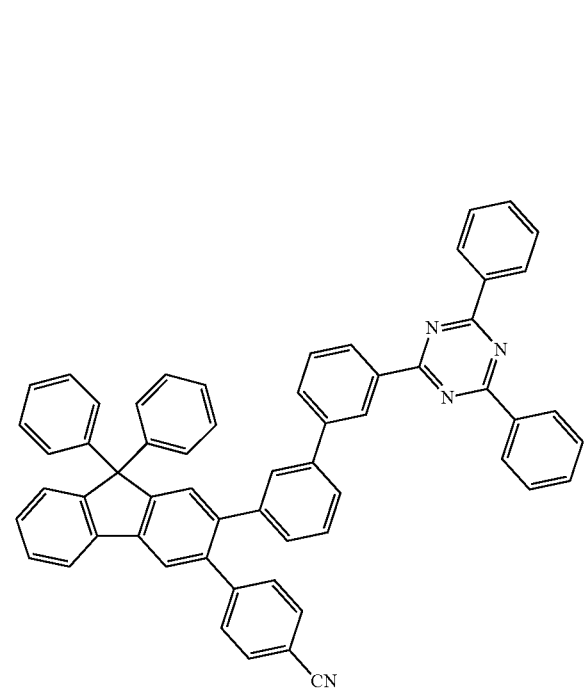
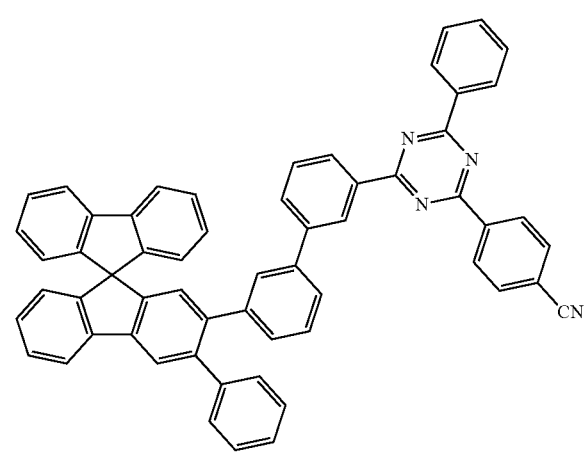

-continued

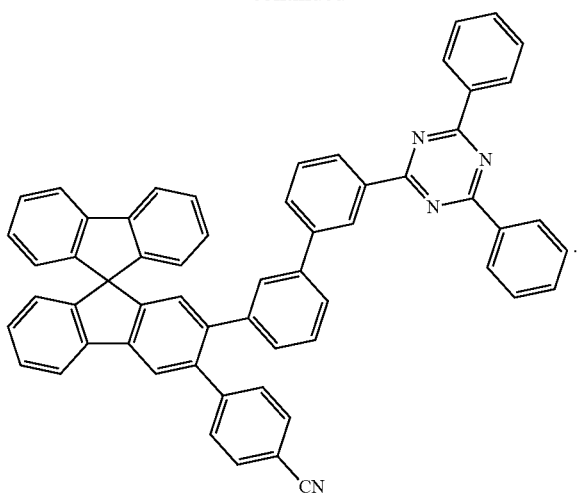

6. An organic light emitting device comprising:
a first electrode;
a second electrode; and
one or more organic material layers provided between the first electrode and the second electrode,
wherein one or more layers of the one or more organic material layers comprise the compound of claim 1.

7. The organic light emitting device of claim 6, wherein the one or more organic material layers comprise at least one of an electron injection layer, an electron transfer layer, or a layer carrying out electron injection and transfer at the same time, and at least one of the electron injection layer, the electron transfer layer, or the layer carrying out electron injection and transfer at the same time comprises the compound.

8. The organic light emitting device of claim 6, wherein the organic material layer comprises a hole blocking layer, and the hole blocking layer comprises the compound.

9. The organic light emitting device of claim 6, wherein the organic material layer comprises a light emitting layer, and the light emitting layer comprises the compound as a host of the light emitting layer.

\* \* \* \* \*